(12) United States Patent
El-Sayed et al.

(10) Patent No.: US 9,345,781 B2
(45) Date of Patent: May 24, 2016

(54) TARGETED DENDRIMER-DRUG CONJUGATES

(75) Inventors: Mohamed E. H. El-Sayed, Dexter, MI (US); William Ensminger, Ann Arbor, MI (US); Donna Shewach, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 87 days.

(21) Appl. No.: 13/493,691

(22) Filed: Jun. 11, 2012

(65) Prior Publication Data

US 2013/0004427 A1 Jan. 3, 2013

Related U.S. Application Data

(63) Continuation-in-part of application No. PCT/US2010/060093, filed on Dec. 13, 2010.

(60) Provisional application No. 61/285,811, filed on Dec. 11, 2009.

(51) Int. Cl.
*A61K 47/48* (2006.01)
*A61K 49/00* (2006.01)
*A61K 51/06* (2006.01)
*C08G 83/00* (2006.01)

(52) U.S. Cl.
CPC ..... *A61K 47/48192* (2013.01); *A61K 47/48176* (2013.01); *A61K 47/48207* (2013.01); *A61K 47/48215* (2013.01); *A61K 49/0043* (2013.01); *A61K 49/0054* (2013.01); *A61K 51/06* (2013.01); *C08G 83/003* (2013.01)

(58) Field of Classification Search
CPC ............... A61K 47/48215; A61K 47/48207
See application file for complete search history.

(56) References Cited

U.S. PATENT DOCUMENTS

| 4,315,857 | A | 2/1982 | Buecheler |
| 6,471,968 | B1* | 10/2002 | Baker et al. ............. 424/280.1 |
| 2004/0030031 | A1* | 2/2004 | Martin et al. ............. 524/502 |
| 2004/0228831 | A1 | 11/2004 | Belinka et al. |
| 2005/0153913 | A1 | 7/2005 | Kosak |
| 2006/0194218 | A1* | 8/2006 | Cook et al. ............. 435/6 |
| 2007/0060499 | A1 | 3/2007 | Kosak |
| 2007/0166281 | A1* | 7/2007 | Kosak ............. 424/85.1 |
| 2008/0051323 | A1* | 2/2008 | Kosak ............. 514/8 |

OTHER PUBLICATIONS

Aromatic Azo (https://en.wikipedia.org/wiki/Azo_compound (downloaded on Jul. 19, 2013)).*
McGrath et al, Effect of Covalently Incorporated Azobenzenes on Dendrimers, Mat. Res. Soc. Symp. Proc., 1999, vol. 543, pp. 319-326.*
Majoros et al, Poly(amidoamine) Dendrimer-Based Multifunctional Engineered Nanodevice for Cancer Therapy, J. Med. Chem., 2005, vol. 48, pp. 5892-5899.*
Wu et al. Frontiers in Bioscience 7, p. 717-725, 2002.*

(Continued)

*Primary Examiner* — Nissa Westerberg
(74) *Attorney, Agent, or Firm* — Marshall, Gerstein & Borun LLP

(57) ABSTRACT

The invention provides for dendrimer conjugates useful for liver-specific delivery of therapeutic agents. The therapeutic agent is associated to the dendrimer through a enzyme-cleavable covalent linkage.

15 Claims, 57 Drawing Sheets

(56) References Cited

OTHER PUBLICATIONS

Patri et al. Advanced Drug delivery Reviews 57, p. 2203-2214, 2005.*
Ozawa et al. Organic Letters 10(16), p. 3531-3533, 2008.*
Adam et al., Differentiation of spontaneous canine breast tumors using dynamic magnetic resonance imaging with 24-gadolinium-DTPA-cascade-polymer, A new blood-pool agent: Preliminary experience, Invest. Rad., 31(5):267-74 (1996).
Bailey et al., *Polymeric Drugs and Drug Delivery Systems*, Chapter 25, pp. 285-300, American Chemical Society (1991).
Balogh et al., Poly(Amidoamine) dendrimer-templated nanocomposites. 1. Synthesis of zerovalent copper nanoclusters, J. Am. Chem. Soc., 120(29):7355-6 (1998).
Balogh et al., Proceedings of the American Chemical Society PMSE, 77:118—(1997).
Bishop et al., Single stable reagent for creatine kinase assay, Clin. Chem., 17(6):548-50 (1971).
Carey et al., *Advanced Organic Chemistry*, 3rd ed., New York: Plenum Press (1990).
Chan et al., Quantum dot bioconjugates for ultrasensitive nonisotopic detection, Science, 281(5385):2016-8 (1998).
Cook et al., Viability measurements in mammalian cell systems, Anal. Biochem., 179(1):1-7 (1989).
D'Emanuele et al., Dendrimer-drug interactions, Adv. Drug Deliv. Rev., 57(15):2147-62 (2005).
Darlington et al., Growth and hepatospecific gene expression of human hepatoma cells in a defined medium, In Vitro Cell Dev. Biol., 23(5):349-54 (1987).
El-Sayed et al., Extravasation of poly(amidoamine) (PAMAM) dendrimers across microvascular network endothelium, Pharm. Res., 18(1):23-8 (2001).
Erdi, The use of PET for radiotherapy, Curr. Med. Imag. Rev., 3:3-16 (2007).
Farkas et al., Microscopic and mesoscopic spectral bio-imaging, SPIE, 2678:200-9 (1997).
Gao et al., Colon-specific 9-aminocamptothecin-HPMA copolymer conjugates containing a 1,6-elimination spacer, J. Control. Release, 110(2):323-31 (2006).
Grirrane et al., Gold-catalyzed synthesis of aromatic azo compounds from anilines and nitroaromatics, Science, 322(5908):1661-4 (2008).
Heindryckx et al., Experimental mouse models for hepatocellular carcinoma research, Int. J. Exp. Pathol., 90(4):367-86 (2009).
International Preliminary Report on Patentability for corresponding international application No. PCT/US2010/060093, dated Jun. 12, 2012.
International Search Report and Written Opinion for corresponding international application No. PCT/US2010/060093, mailing date Sep. 28, 2011.
Karvinen et al., Homogeneous time-resolved fluorescence quenching assay (LANCE) for caspase-3, J. Biomol. Screen., 7(3):223-31 (2002).
Kovar et al., HPMA copolymers containing doxorubicin bound by a proteolytically or hydrolytically cleavable bond: comparison of biological properties in vitro, J. Control. Release, 99(2):301-14 (2004).
Krikova et al., Synthesis of some azo compounds and a study of their properties, Chem. Heterocyclic Compounds, 3(4):244-8 (1967).
Lee et al., Synthesis of symmetrical and unsymmetrical PAMAM dendrimers by fusion between azide- and alkyne-functionalized PAMAM dendrons, Bioconjug. Chem., 18(2):579-84 (2007).
Lester et al., Infrared microspectroscopic imaging of the cerebellum of normal and cytarabine treated rats, Cell Mol. Biol. (Noisy-le-grand), 44(1):29-38 (1998).
Lowry et al., *Mechanism and Theory in Organic Chemistry*, 3rd ed., New York: Harper Collins (1987).
Majoros et al., Poly(amidoamine) dendrimer-based multifunctional engineered nanodevice for cancer therapy, J. Med. Chem., 48(19):5892-9 (2005).
Mannucci, Hemostatic drugs, N. Engl. J. Med., 339(4):245-53 (1998).
March, *Advanced Organic Chemistry: Reactions, Mechanisms and Structure*, 5th ed., New York: Wiley-InterScience (2001).
Medina et al., N-acetylgalactosamine-functionalized dendrimers as hepatic cancer cell-targeted carriers, Biomaterials, 32(17):4118-29 (2011).
Medina et al., Dendrimers as carriers for delivery of chemotherapeutic agents, Chem. Rev., 109(7):3147-57 (2009).
Medintz et al., Quantum dot bioconjugates for imaging, labelling and sensing, Nat. Mater., 4(6):435-46 (2005).
Mocharla et al., A novel, sensitive fluorometric staining technique for the detection of DNA in RNA preparations, Nucleic Acids Res., 15(24):10589 (1987).
Mullis et al., Specific synthesis of DNA in vitro via a polymerase-catalyzed chain reaction, Methods Enzymol., 155:335-50 (1987).
Negoescu et al., In situ apoptotic cell labeling by the TUNEL method: improvement and evaluation on cell preparations, J. Histochem. Cytochem., 44(9):959-68 (1996).
Priewisch et al., Efficient preparation of nitrosoarenes for the synthesis of azobenzenes, J. Org. Chem., 70(6):2350-2 (2005).
Reers et al., J-aggregate formation of a carbocyanine as a quantitative fluorescent indicator of membrane potential, Biochemistry, 30(18):4480-6 (1991).
Reers et al., Mitochondrial membrane potential monitored by JC-1 dye, Methods Enzymol., 260:406-17 (1995).
Saiki et al., Primer-directed enzymatic amplification of DNA with a thermostable DNA polymerase, Science, 239(4839):487-91 (1988).
Seymour et al., The pharmacokinetics of polymer-bound adriamycin, Biochem. Pharmacol., 39(6):1125-31 (1990).
Shen et al., cis-Aconityl spacer between daunomycin and macromolecular carriers: a model of pH-sensitive linkage releasing drug from a lysosomotropic conjugate, Biochem. Biophys. Res. Commun., 102(3):1048-54 (1981).
Shortreed et al., Directed energy transfer funnels in dendrimeric antenna supermolecules, J. Phys. Chem. B, 101(33):6318-22 (1997).
Singh et al., "Antibody-cytotoxic agent conjugates: preparation and characterization", in: Dimitrov (ed.), *Therapeutic Antibodies: Methods and Protocols*, vol. 525, pp. 445-467 (2009).
Sooklal et al., A Blue-Emitting CdS/Dendrimer Nanocomposite, Adv. Mater., 10(14):1083-7 (1998).
Sterzel et al., Automated determination of DNA using the fluorochrome Hoechst 33258, Anal. Biochem., 147(2):462-7 (1985).
Symon et al., Selective radioprotection of hepatocytes by systemic and portal vein infusions of amifostine in a rat liver tumor model, Int. J. Radiat. Oncol. Biol. Phys., 50(2):473-8 (2001).
Tomalia et al., Starburst dendrimers: Molecular-level control of size, shape, surface chemistry, topology, and flexibility from atoms to macroscopic matter, Adv. Mater., 29(2):138-75 (1990).
Tomalia, Starburst/Cascade Dendrimers: Fundamental building blocks for a new nanoscopic chemistry set, Adv. Mater., 6(7-8):529-39 (1994).
van Asperen et al., Determination of doxorubicin and metabolites in murine specimens by high-performance liquid chromatography, J. Chromatograph B, 712(1-2 (129-43 (1998).
van Engeland et al., A novel assay to measure loss of plasma membrane asymmetry during apoptosis of adherent cells in culture, Cytometry, 24(2):131-9 (1996).
Wiener et al., Dendrimer-based metal chelates: a new class of magnetic resonance imaging contrast agents, Magn. Reson. Med., 31(1):1-8 (1994).
Yin et al., Architectural copolymers: Rod-shaped, cylindrical dendrimers, J. Am. Chem. Soc., 120(11):2678-9 (1998).

* cited by examiner

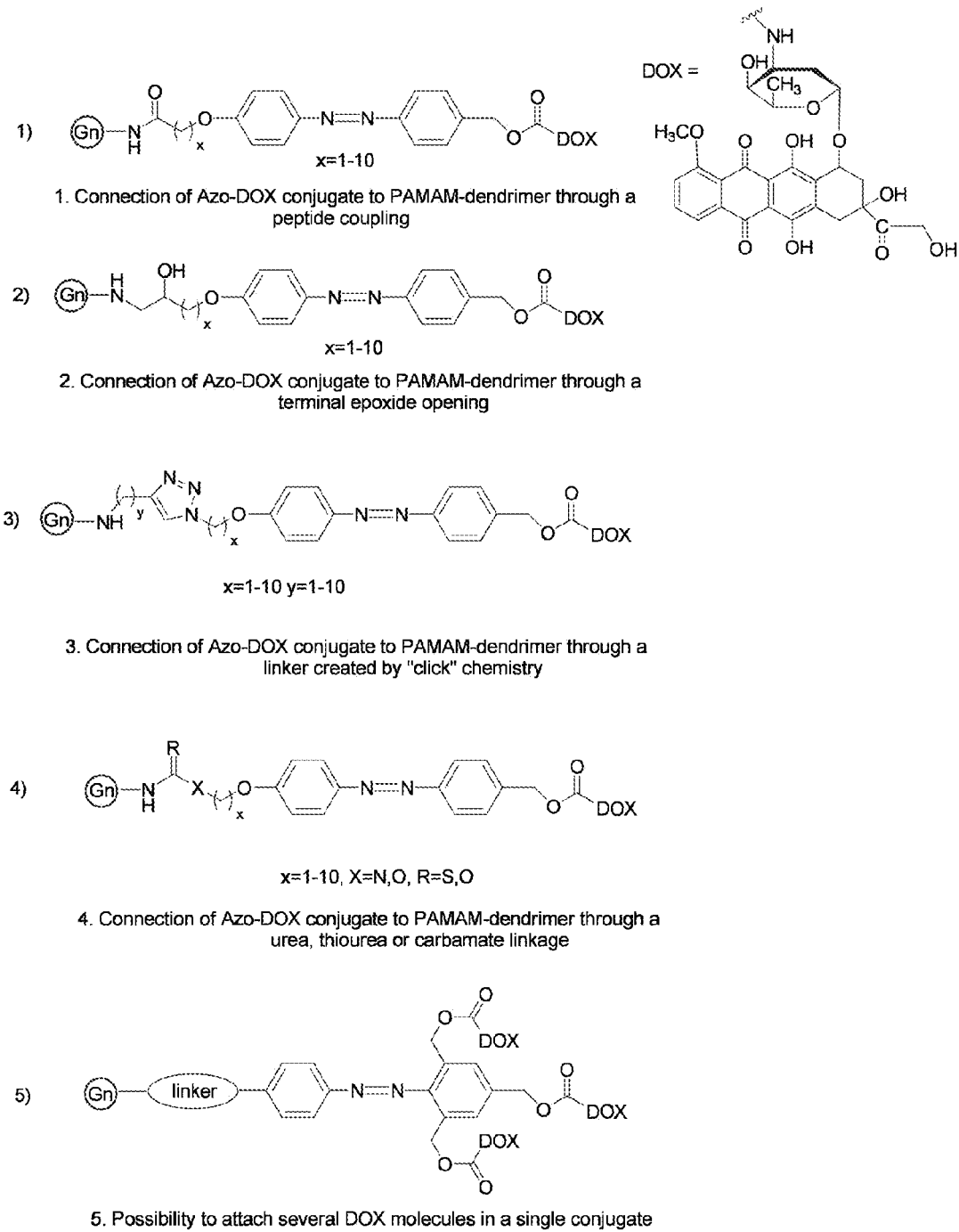

Figure 2

Summary of different linkages that conjugate Azo-DOX to a PAMAM dendrimer

1. Connection of Azo-DOX conjugate to PAMAM-dendrimer through a peptide coupling 2. Connection of Azo-DOX conjugate to PAMAM-dendrimer through a terminal epoxide opening 3. Connection of Azo-DOX conjugate to PAMAM-dendrimer through a linker created by "click" chemistry 4. Connection of Azo-DOX conjugate to PAMAM-dendrimer through a urea, thiourea or carbamate linkage 5. Possibility to attach several DOX molecules in a single conjugate

Figure 3

Summary of different linkages that conjugate a NAcGal to a PAMAM dendrimer

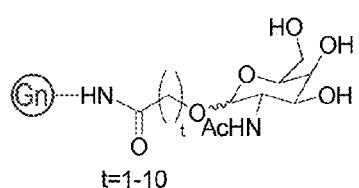

t=1-10

1. NAcGal is attached to the PAMAM-dendrimer through a peptide linker

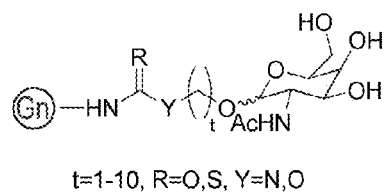

t=1-10, R=O,S, Y=N,O

2. NAcGal is attached to the PAMAM-dendrimer through a urea, thiourea or carbamate linker

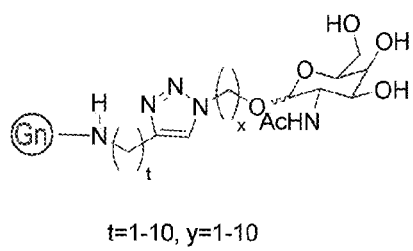

t=1-10, y=1-10

3. NAcGal is attached to the PAMAM-dendrimer linker created by "click" chemistry

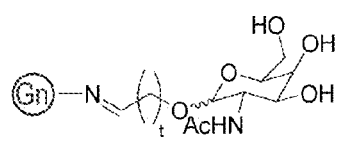

t=1-10

4. NAcGal is attached to the PAMAM-dendrimer through a Shiff-base formation

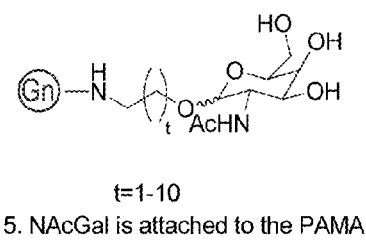

t=1-10

5. NAcGal is attached to the PAMAM-dendrimer through a Shiff-base reduction

Formation of Fluorescein-labeled PAMAM-dendrimers.

Acetylation of PAMAM dendrimers.

y=0-100%

Figure 4C: Radio-labeling of PAMAM dendrimers with ¹⁴C-Iodoacetamide (IAC).
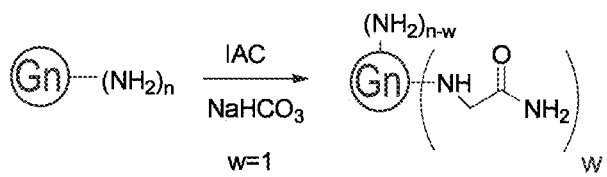
w=1
Figure 4D: Conjugation of PEG chains to PAMAM dendrimers.
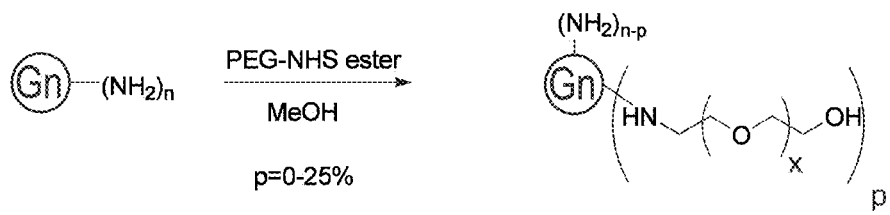
p=0-25%
Figure 4E: Composition of Gn-(Fl)$_z$-(Ac)$_y$-(NAcGal)$_x$-(PEG)$_p$-(DOX)$_D$ conjugates.
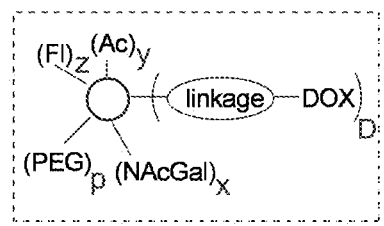
Gn-(Fl)$_z$-(Ac)$_y$-(NAcGal)$_x$-(PEG)$_p$-(DOX)$_D$ conjugates

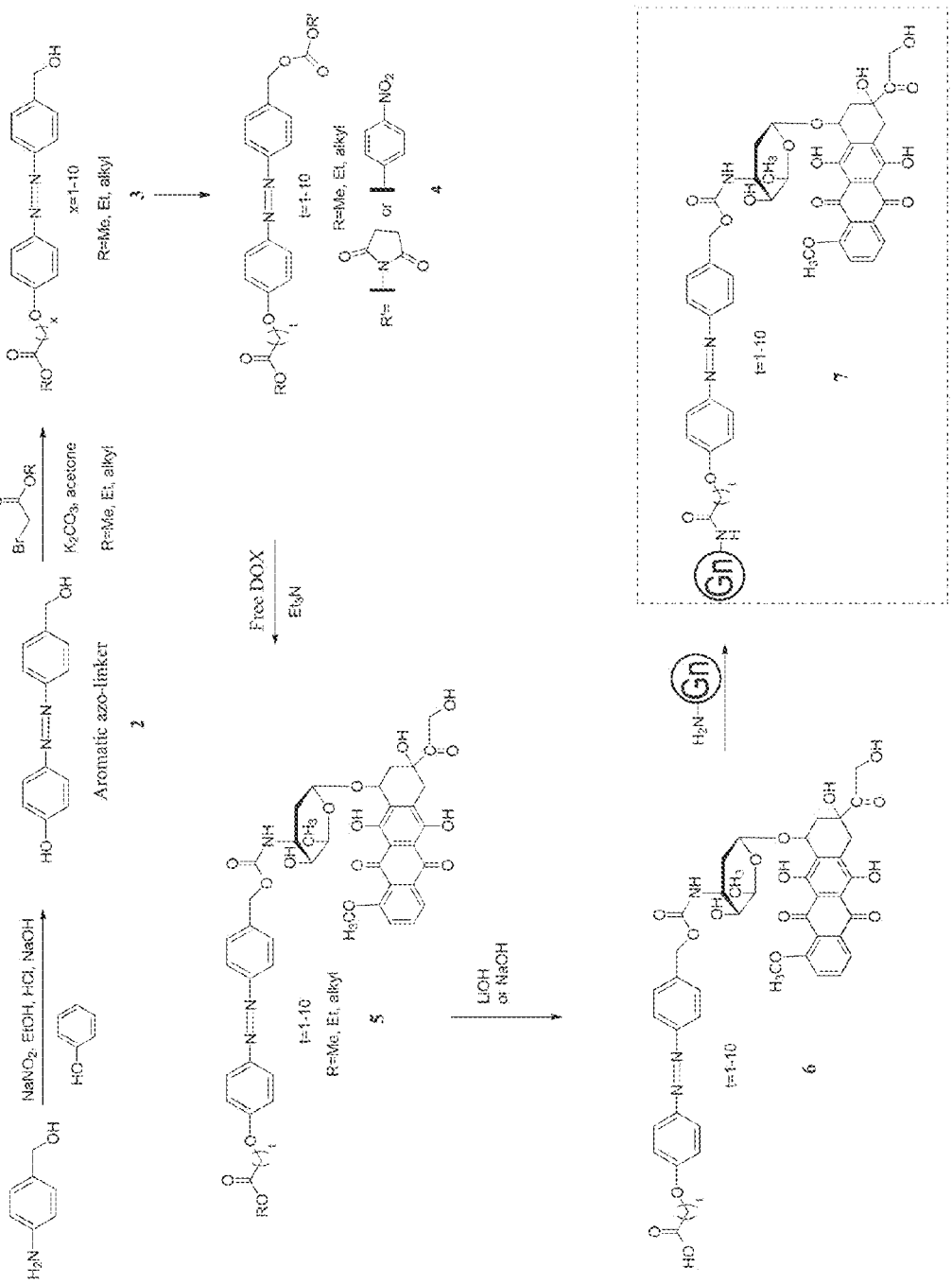
Figure 5A: Summary of synthetic strategies for coupling of DOX to PAMAM dendrimer

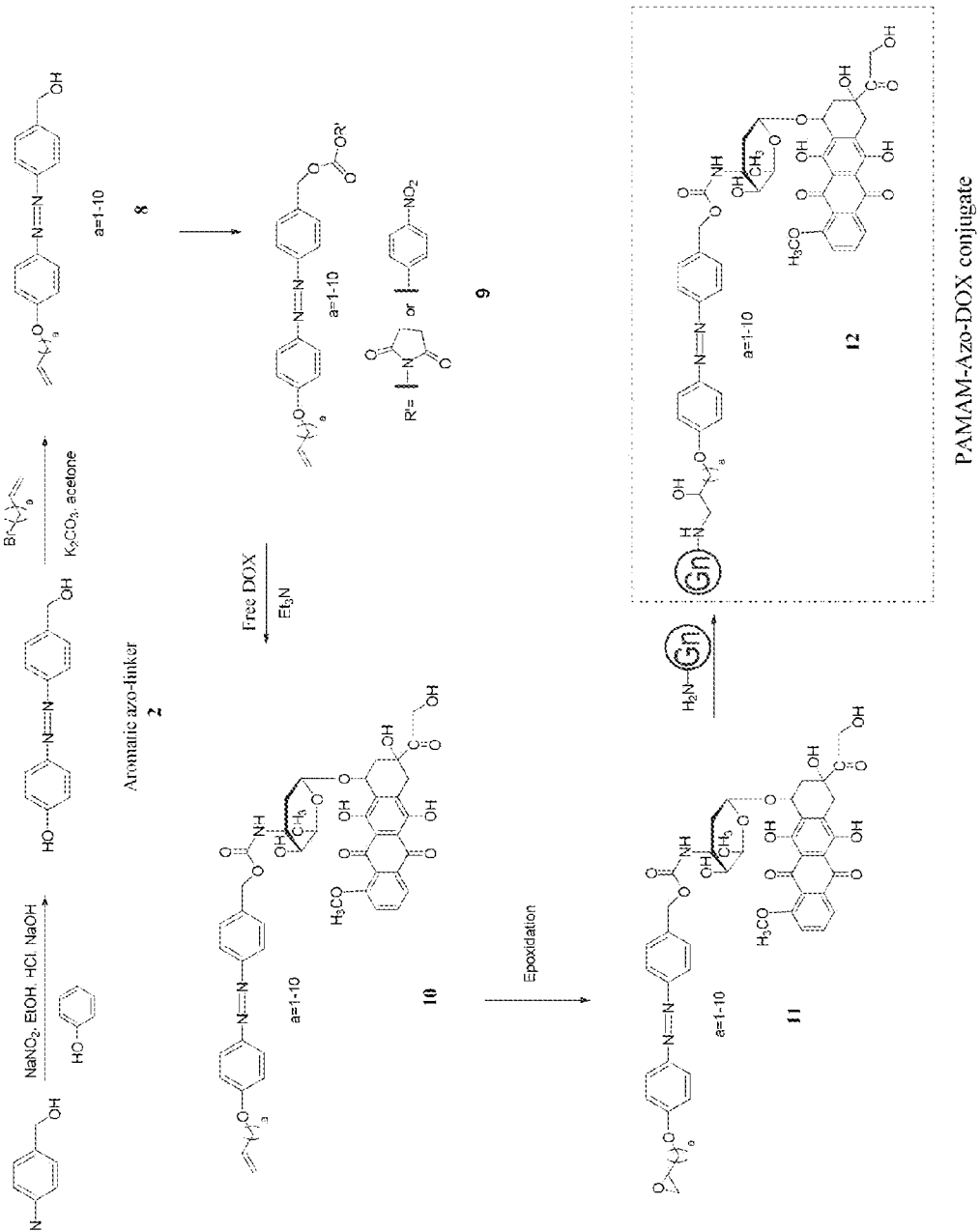
Figure 5B: Synthesis of PAMAM-Azo-DOX conjugate through opening of a terminal epoxide group.

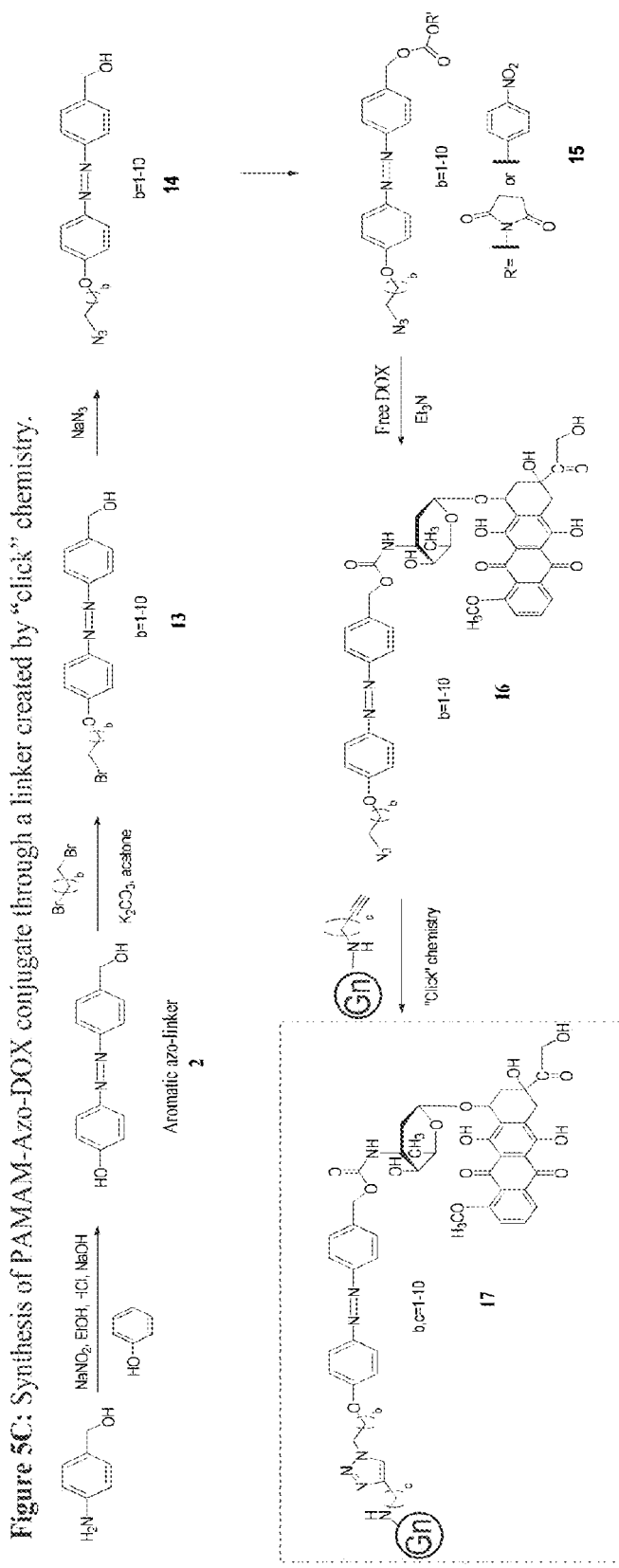
Figure 5C: Synthesis of PAMAM-Azo-DOX conjugate through a linker created by "click" chemistry.

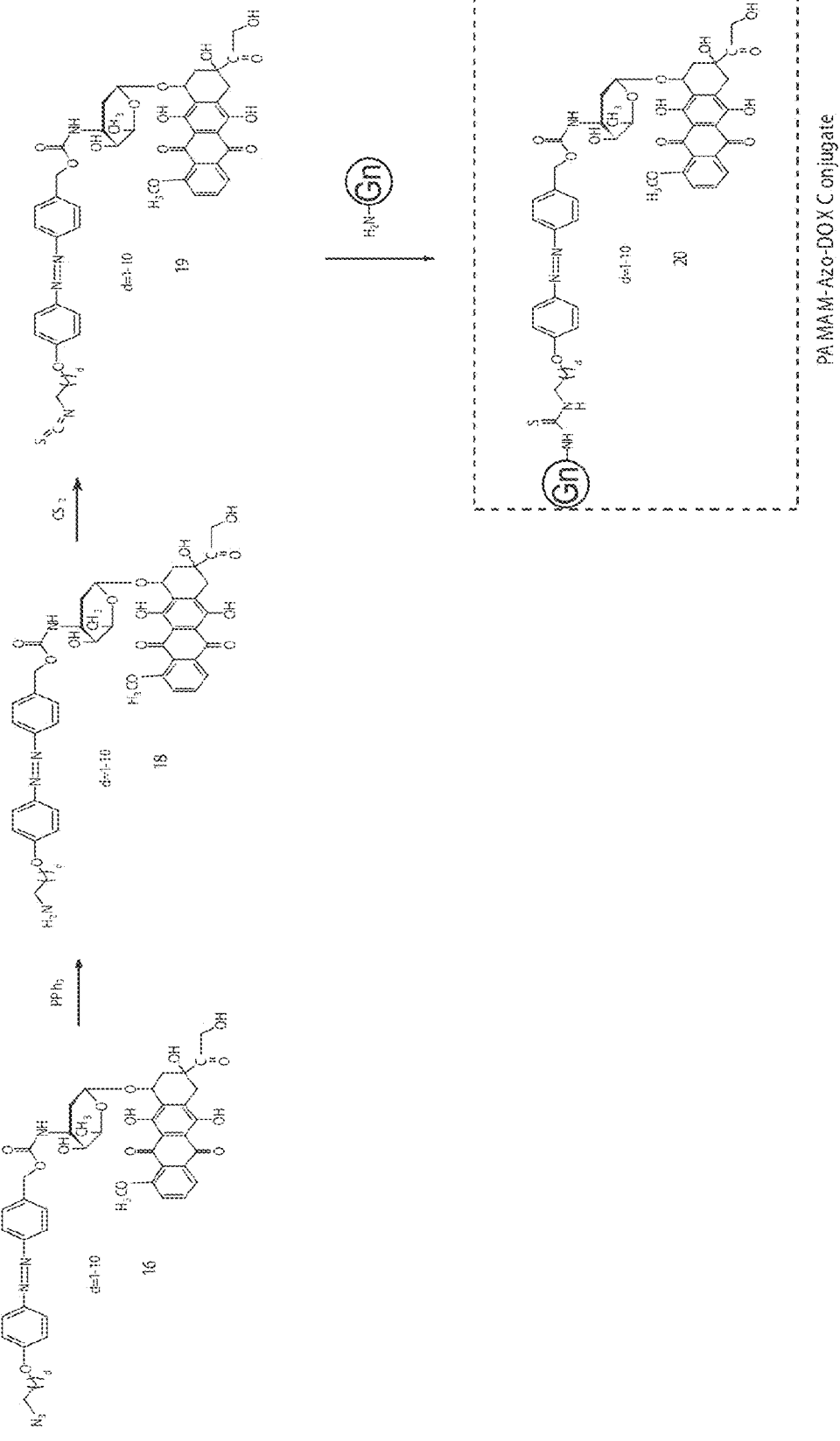
Figure 5D: Synthesis of PAMAM-Azo-DOX conjugate through a thiourea linkage.

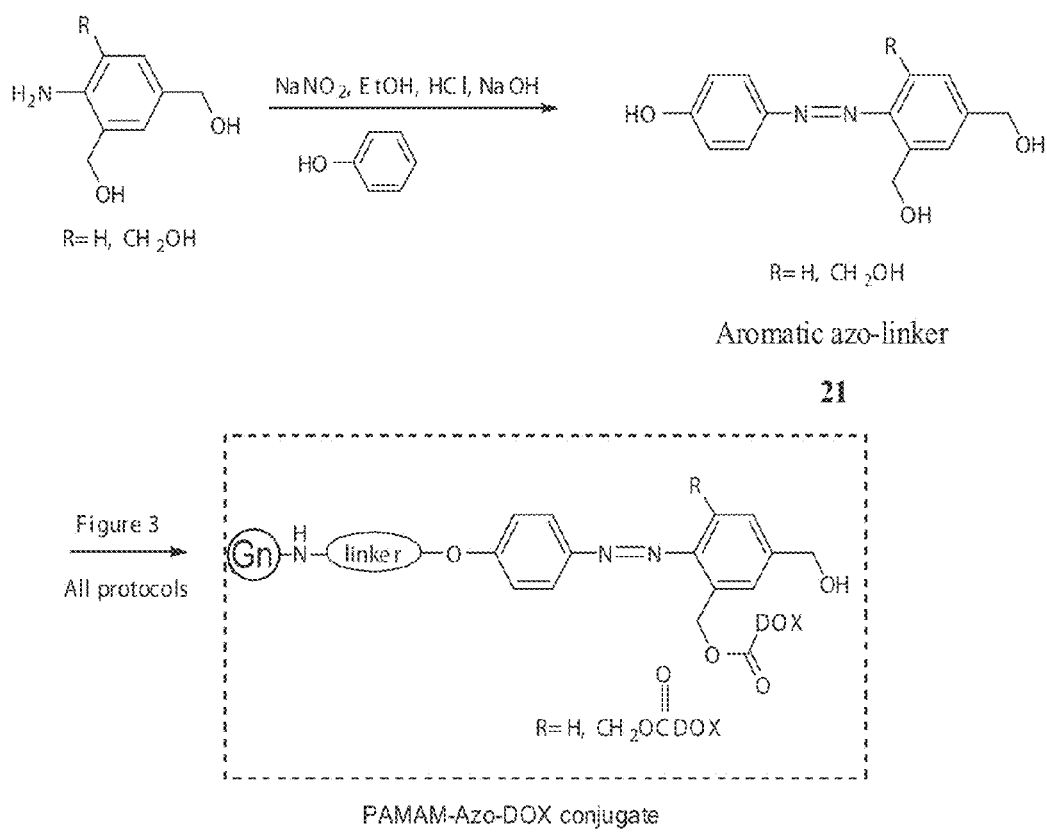
Figure 5E: Synthesis of PAMAM-Azo-DOX conjugate bearing several DOX molecules in a single conjugate.

Figure 6A: Attachment of targeting NAcGal-ligand through a short peptide linker.
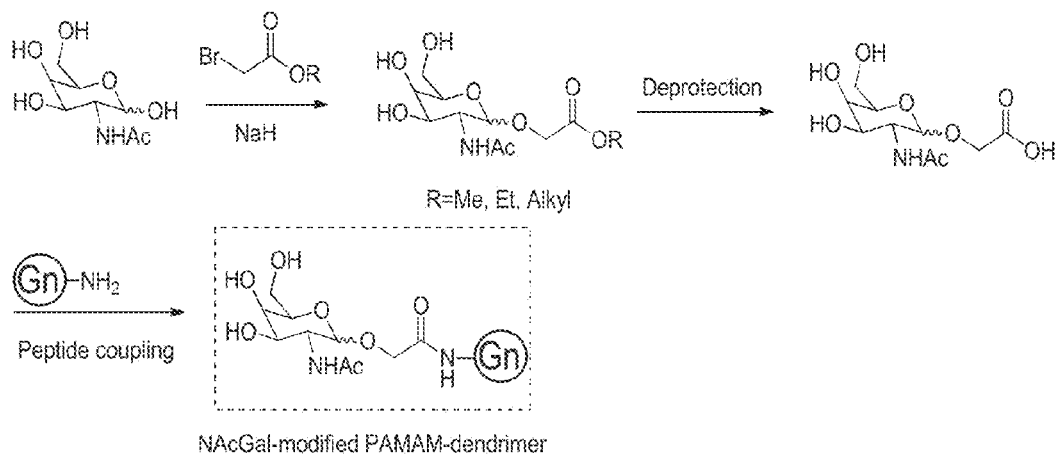
Figure 6B: Attachment of targeting NAcGal-ligand through a long peptide linker.
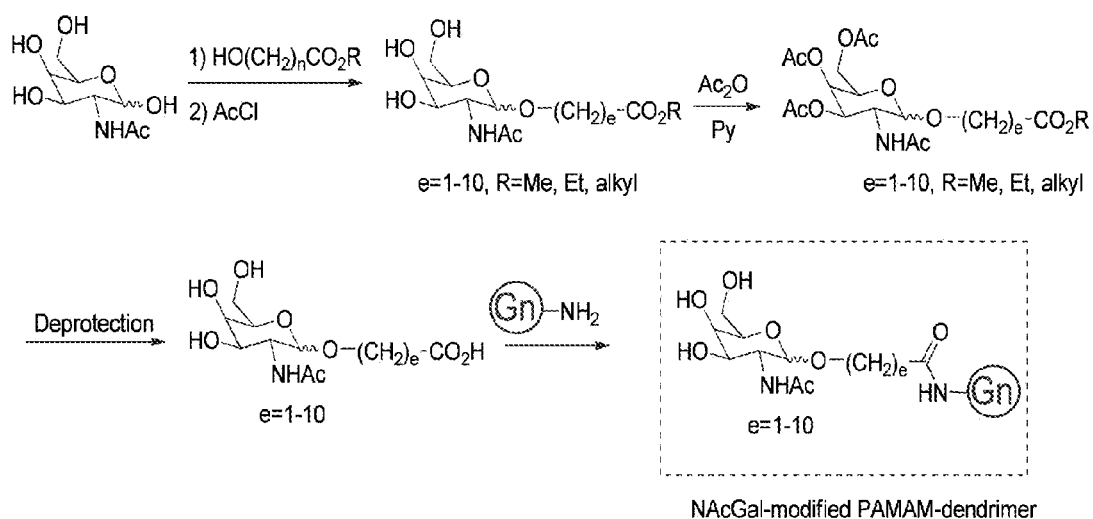

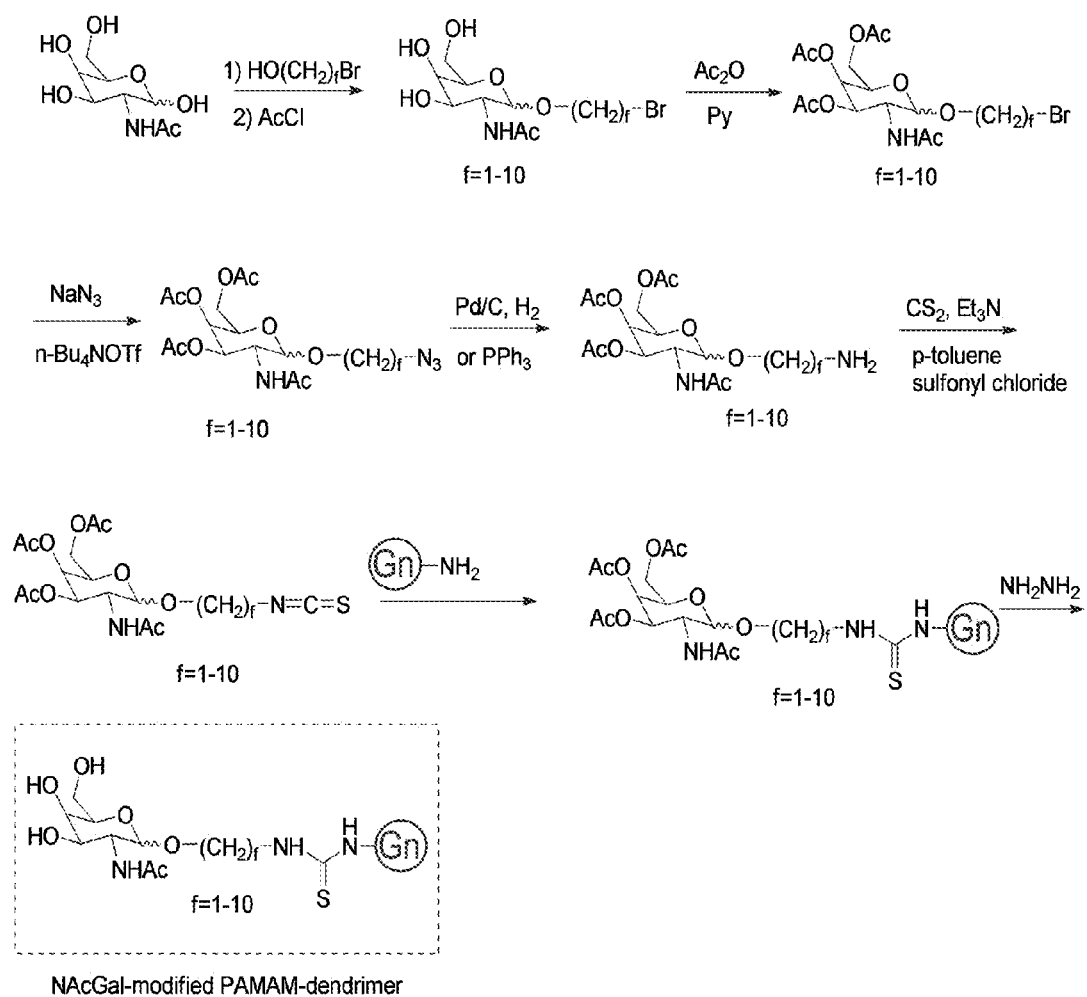
Figure 6C: Attachment of targeting NAcGal-ligand through a thiourea linkage.
NAcGal-modified PAMAM-dendrimer

Figure 6D: Attachment of targeting NAcGal-ligand through a linkage created using "click" chemistry.
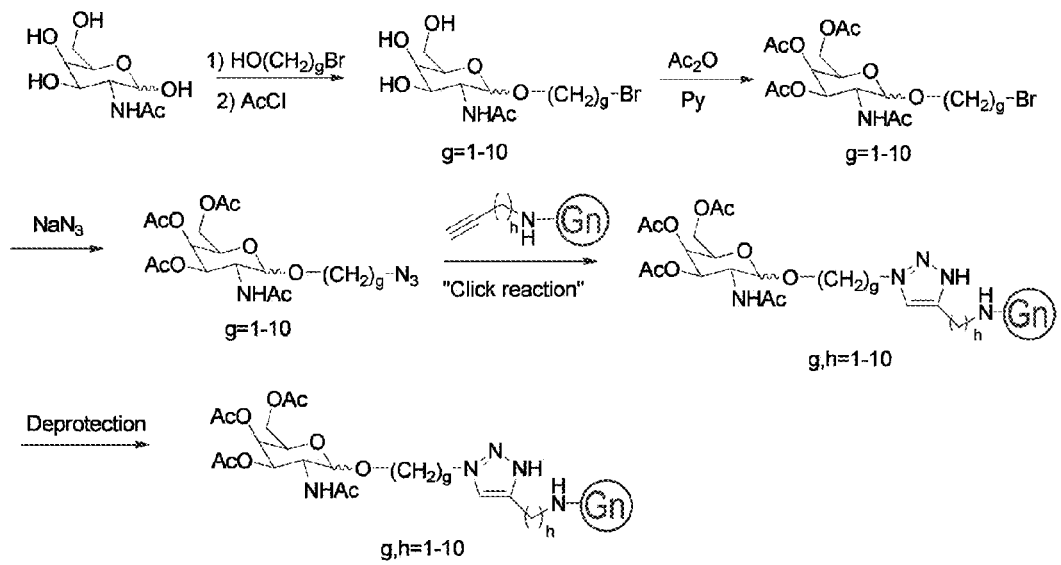
Figure 6E: Attachment of targeting NAcGal-ligand through the formation of a Shiff base and its reduction.
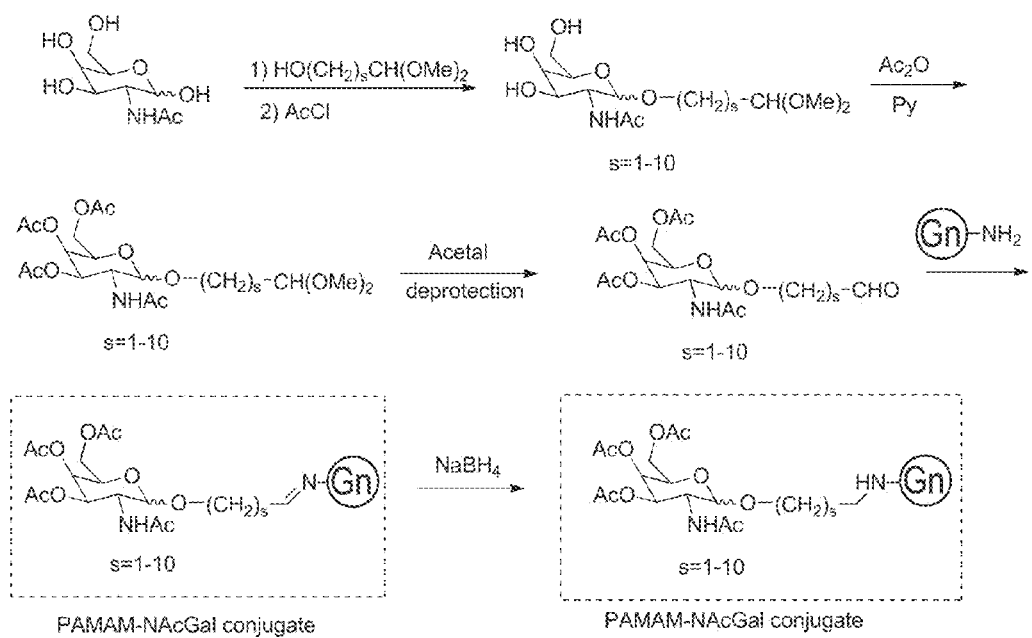

Figure 7A: Synthesis of fluorescein-labeled N-acetyl-galactosamine.
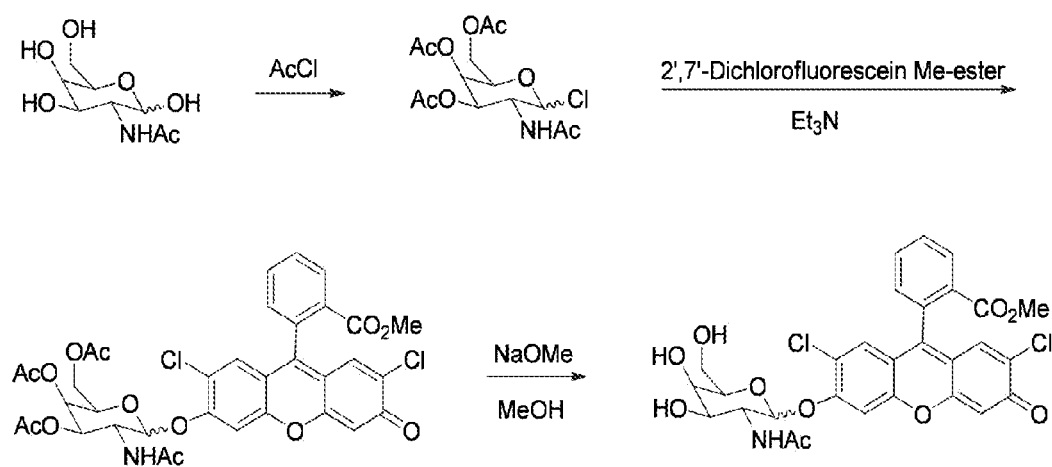
Figure 7B: Synthesis of [$^{14}$C]-labeled acetylated dendrimers ([$^{14}$C]-Gn-(Ac)$_y$).
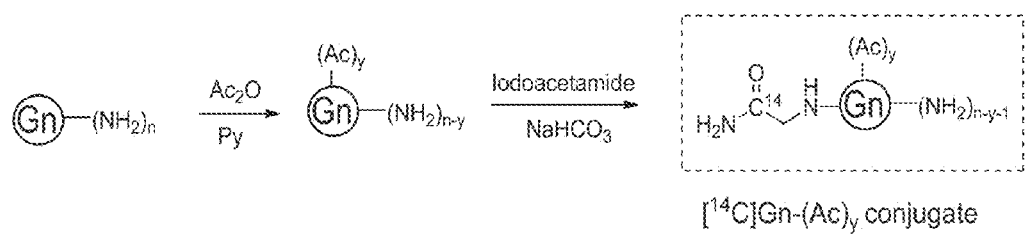
Figure 7C: Synthesis of [$^{14}$C]-labeled, acetylated, and PEGylated dendrimers ([$^{14}$C]-Gn-(Ac)$_y$-(PEG)$_p$).
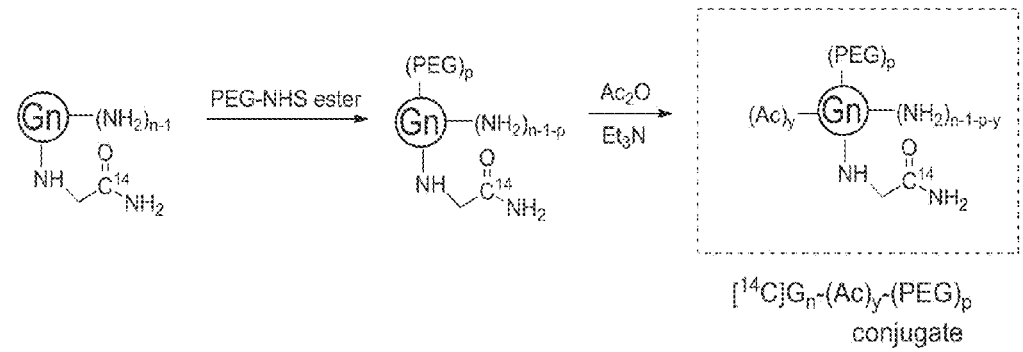

Figure 7D: Synthesis of [$^{14}$C]-labeled, acetylated, and galactosylated dendrimers ([$^{14}$C]-Gn-(Ac)$_y$-(NAcGal)$_x$).
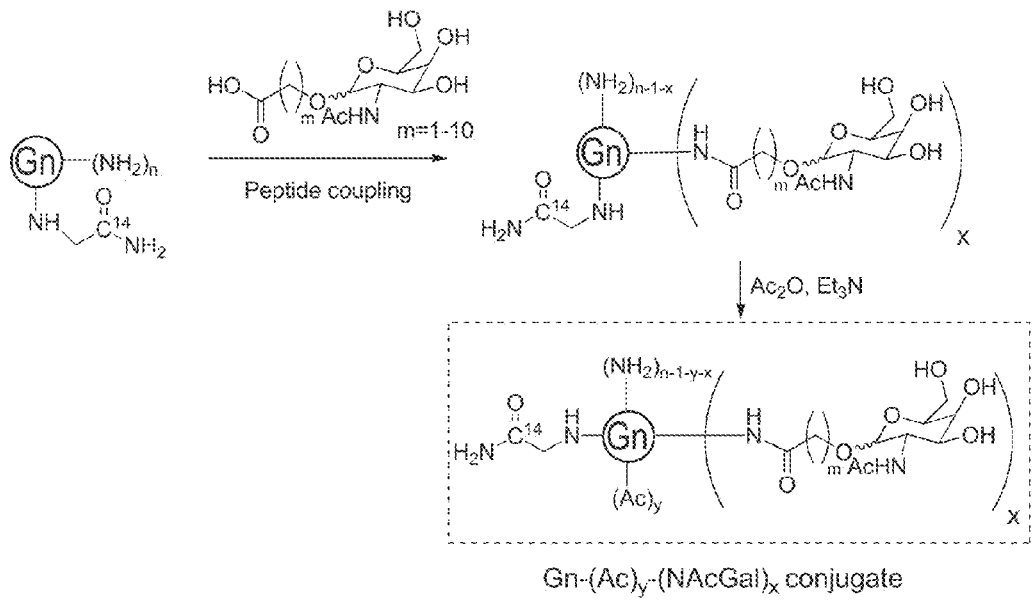
Figure 7E: Synthesis of [$^{14}$C]-labeled, acetylated, galactosylated, and PEGylated dendrimers ([$^{14}$C]-Gn-(Ac)$_y$-(NAcGal)$_x$-(PEG)$_p$).
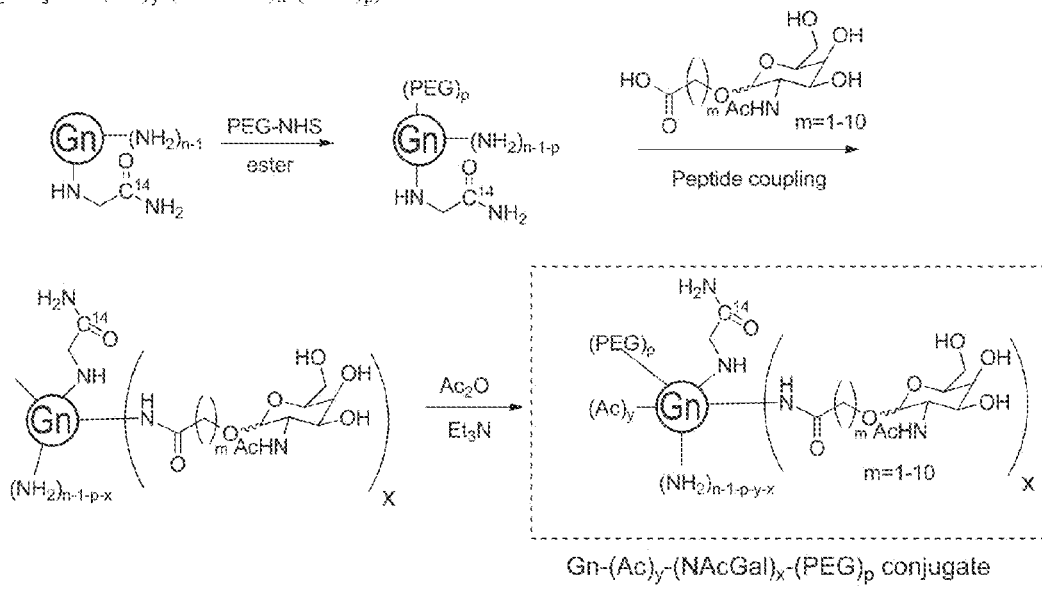

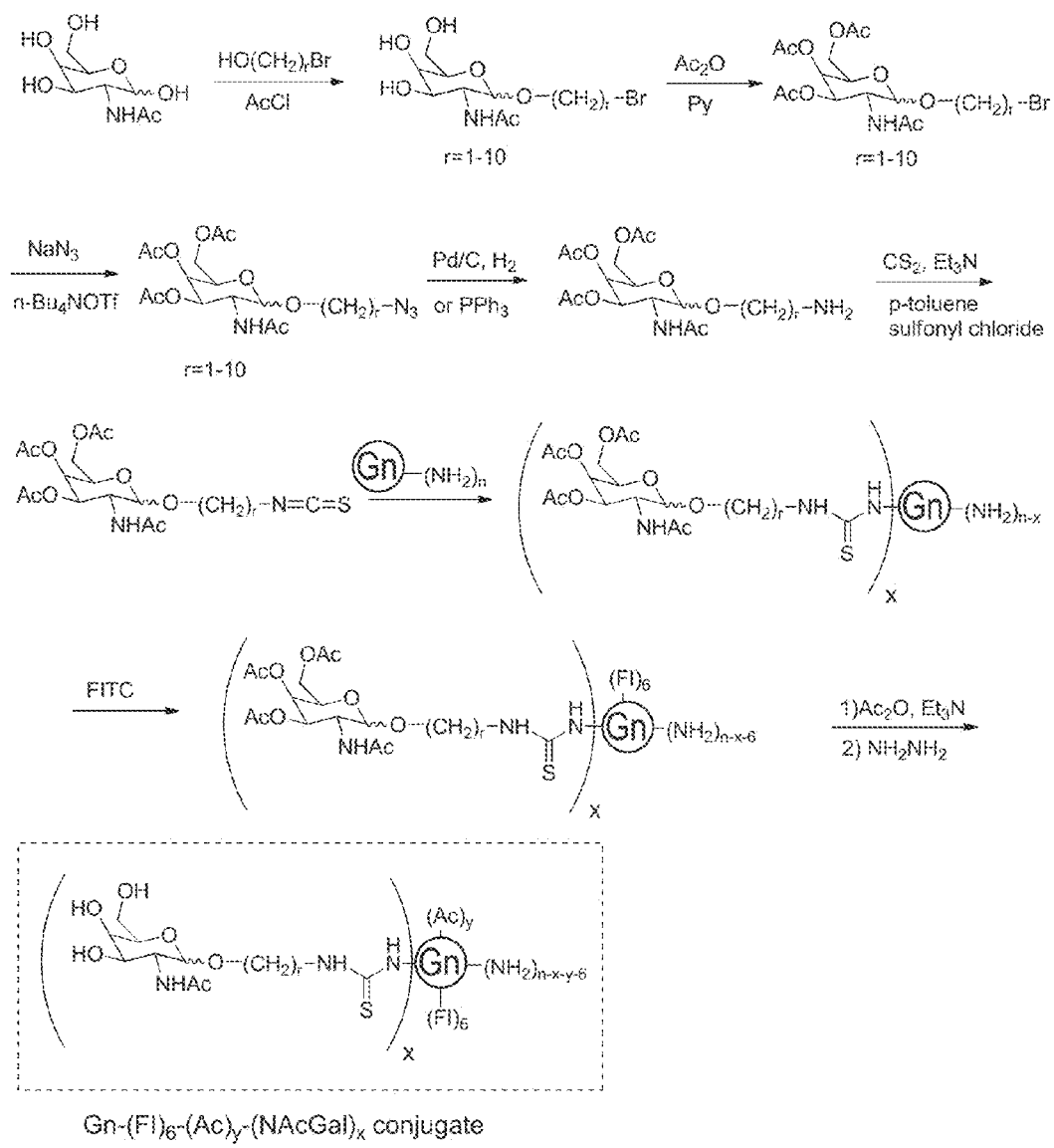
Figure 7F: Synthesis of fluorescently-labeled, acetylated, and galactosylated dendrimers $(Gn\text{-}(Fl)_6\text{-}(Ac)_y\text{-}(NAcGal)_x)$.

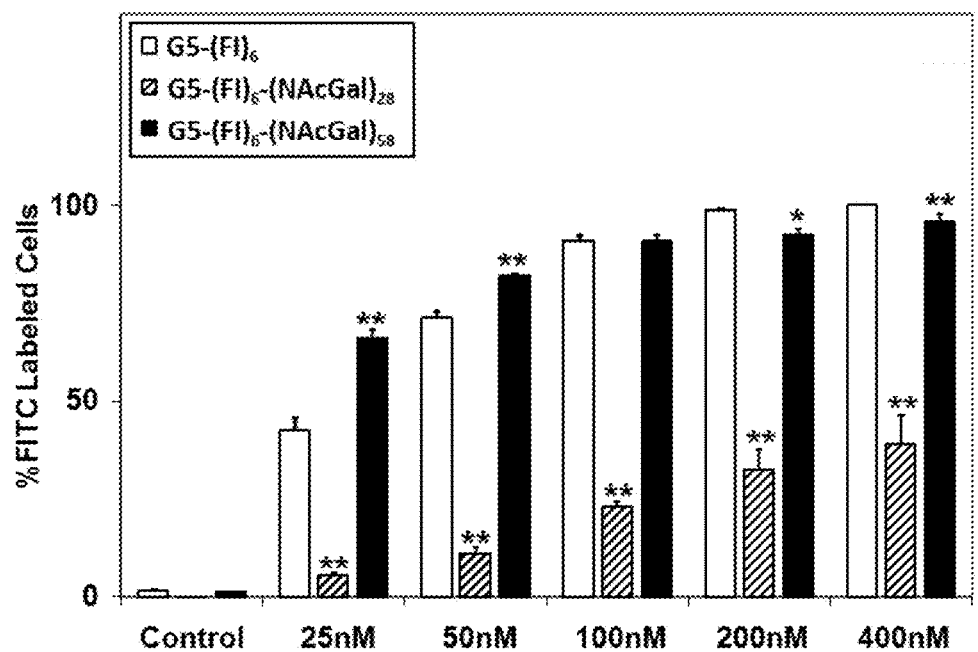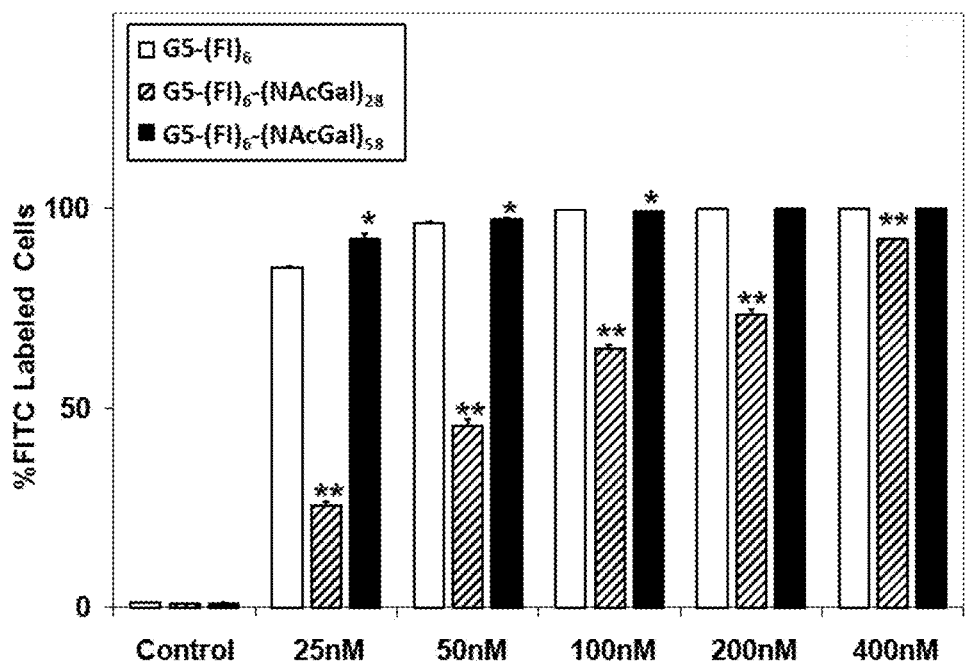

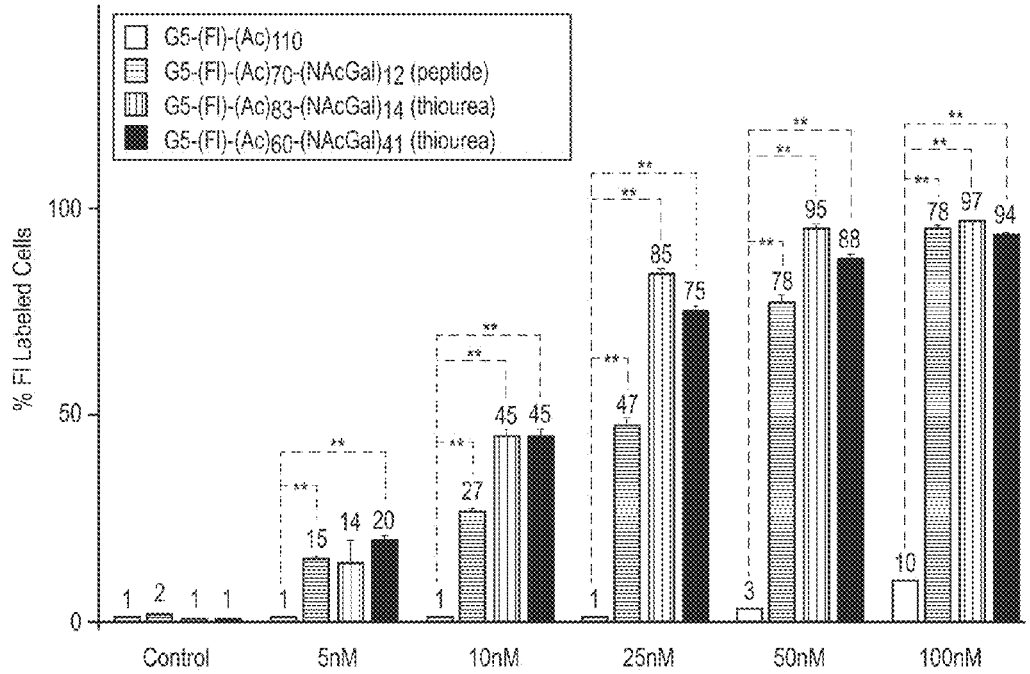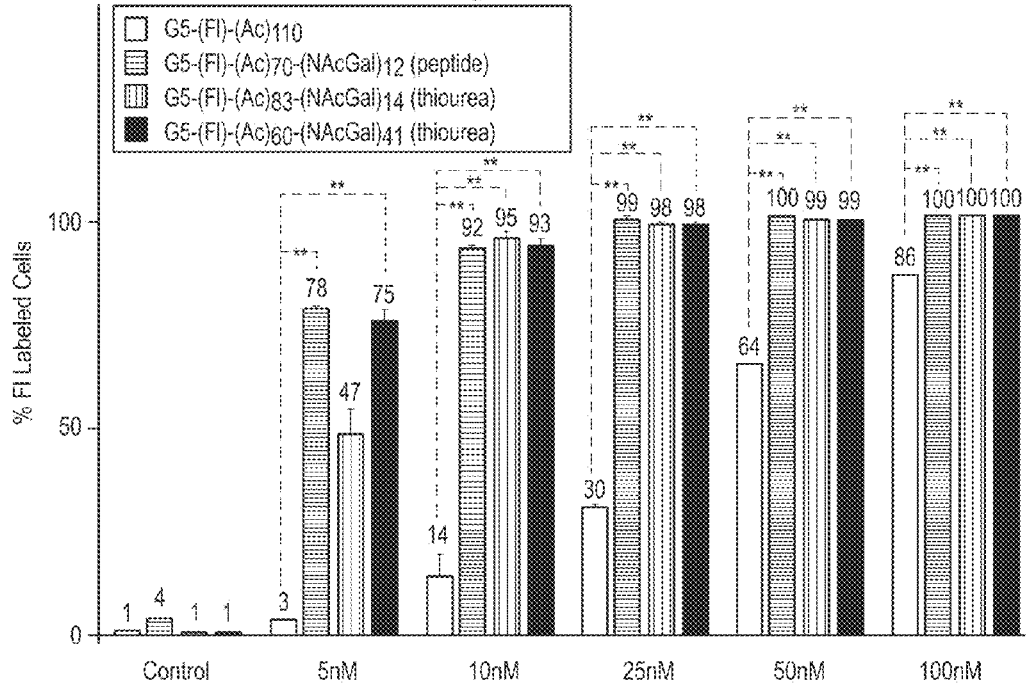

Preparation of G5-Alkyne Carrier for Click Chemistry Reaction

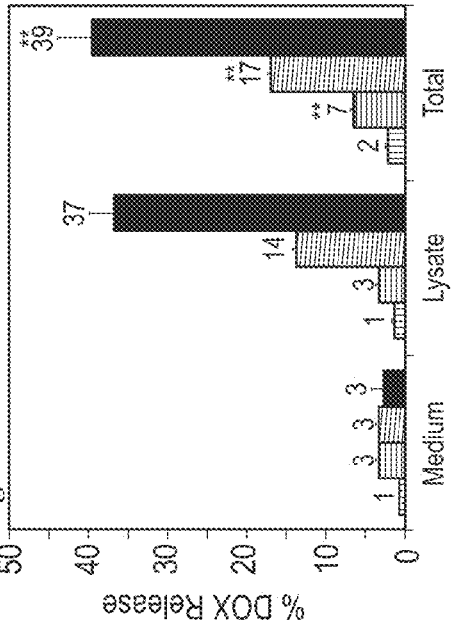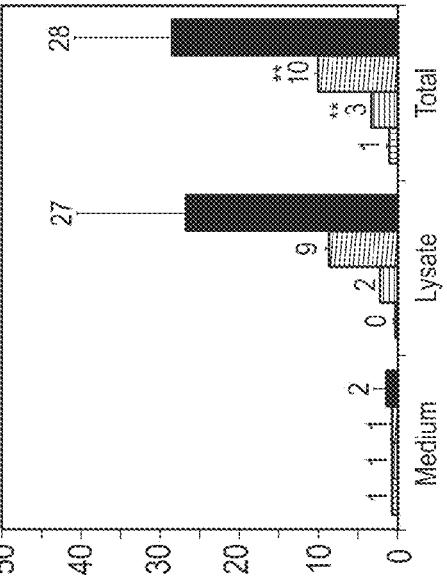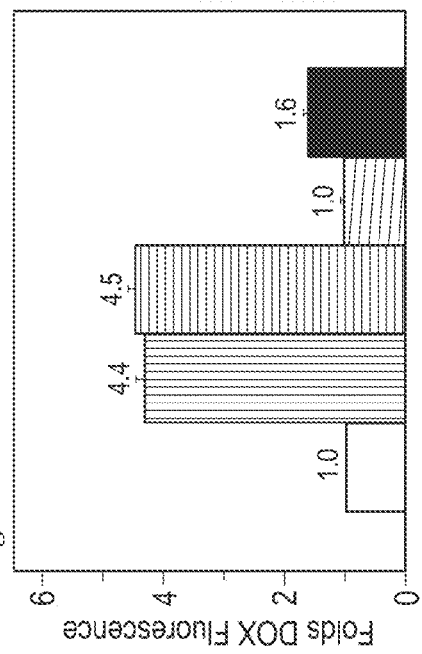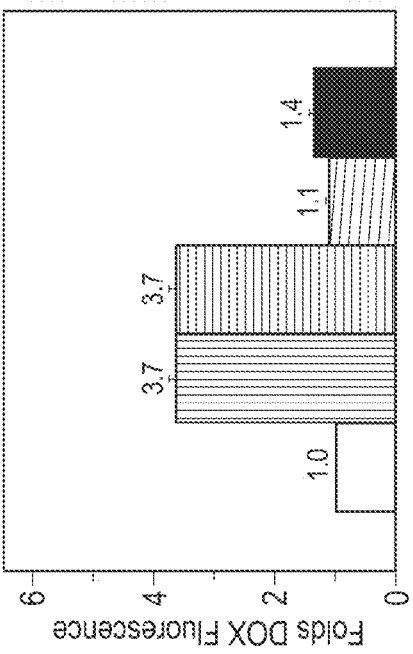

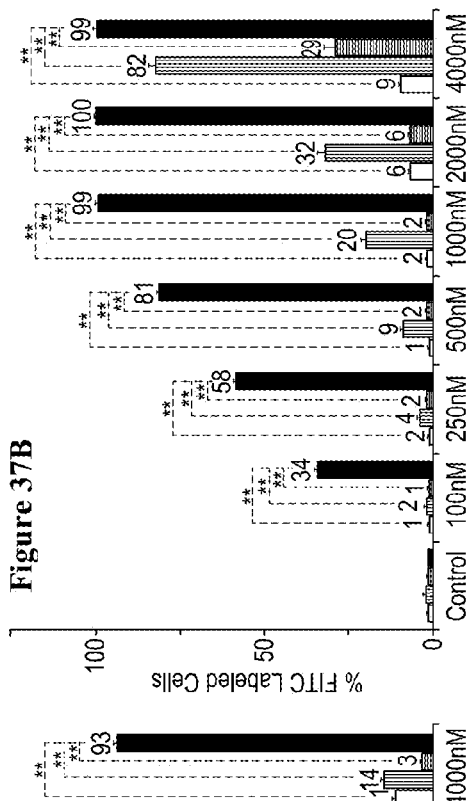
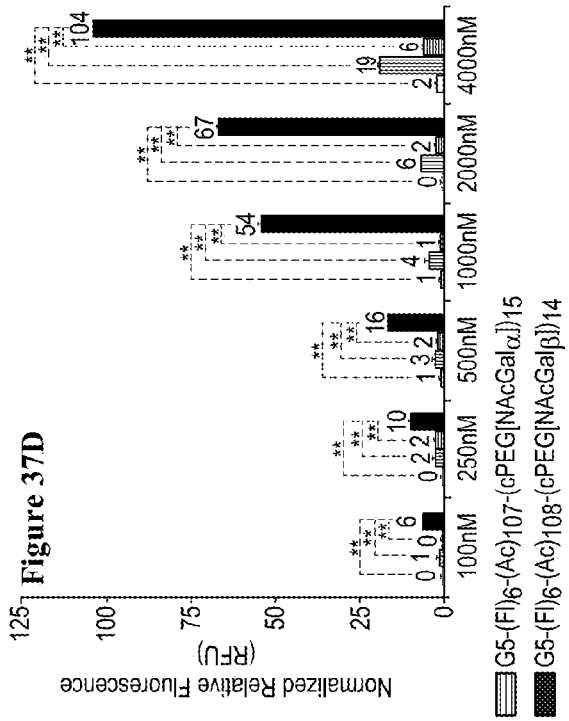
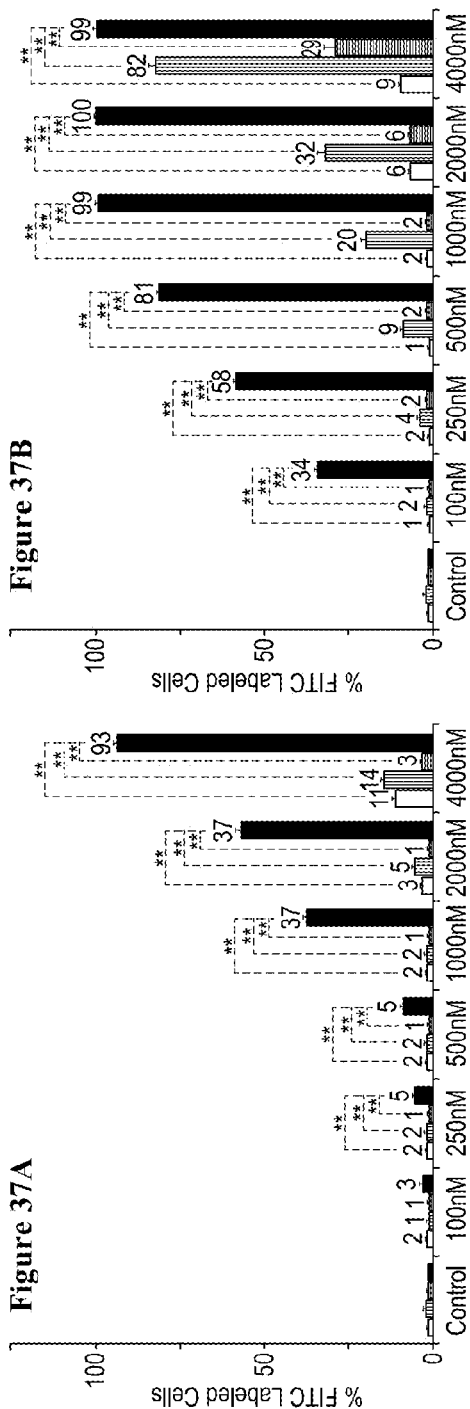
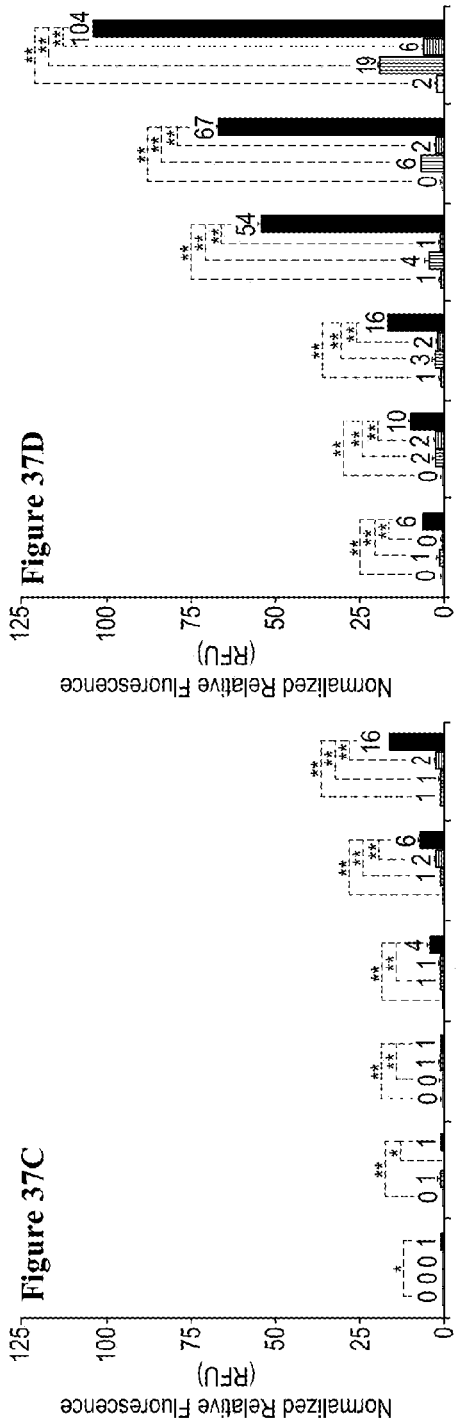
Figure 37A
Figure 37B
Figure 37C
Figure 37D

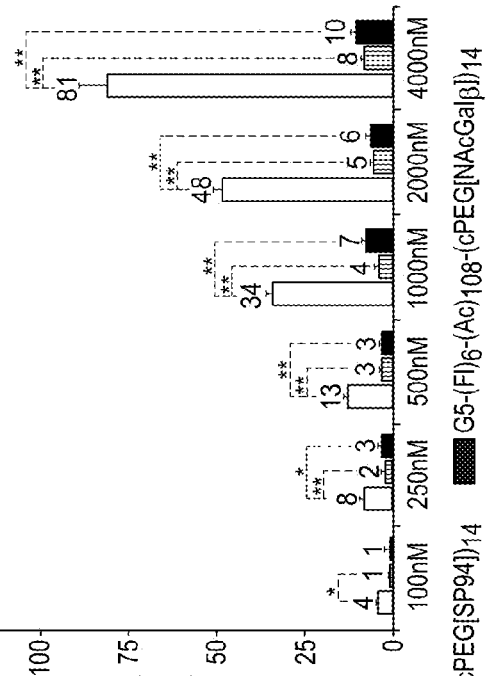
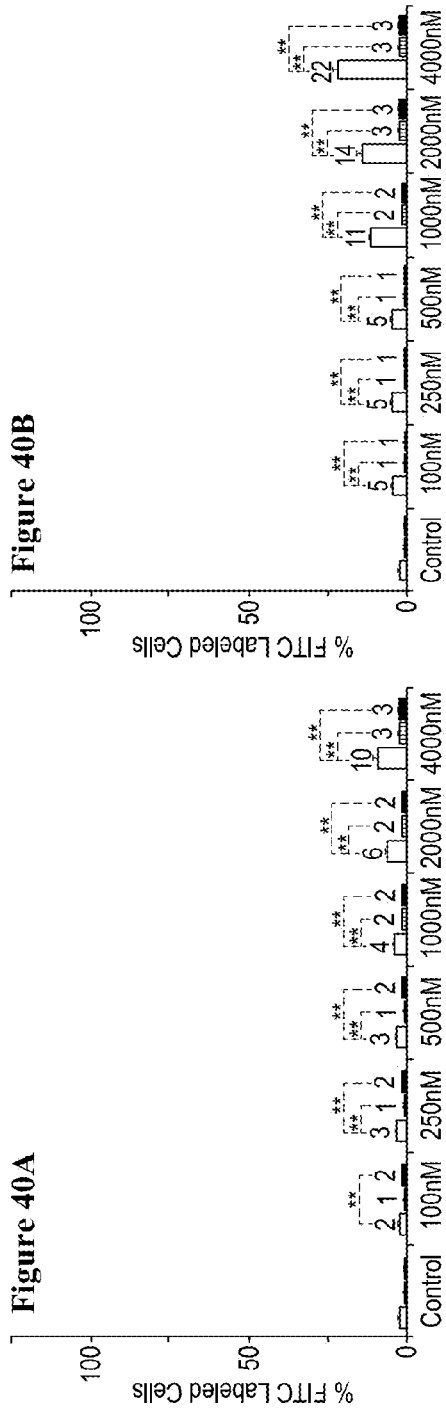
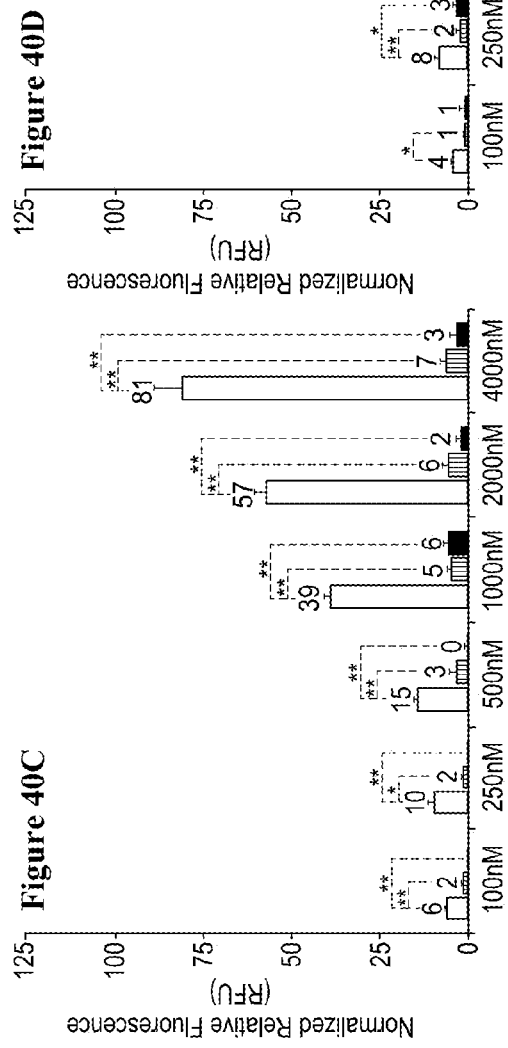
Figure 40A
Figure 40B
Figure 40C
Figure 40D

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: SP94 peptide

<400> SEQUENCE: 1

Ser Phe Ser Ile Ile His Thr Pro Ile Leu Pro Leu Gly Gly Cys
1               5                   10                  15

TARGETED DENDRIMER-DRUG CONJUGATES

CROSS-REFERENCE TO RELATED APPLICATIONS

This application claims priority to International Patent Application No. PCT/US2010/60093, filed on Dec. 13, 2010, which claims priority to U.S. Provisional Patent Application No. 61/285,811, filed Dec. 11, 2009; the contents of each are incorporated herein by reference in their entirety.

GRANT FUNDING

This invention was made with government support under CBET0747762 awarded by the National Science Foundation. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 4 kilobytes ACII (Text) file named "44652B_SeqListing.txt," created on Jun. 6, 2012.

FIELD OF INVENTION

The invention provides dendrimer conjugates useful for liver-specific delivery of therapeutic and imaging agents.

BACKGROUND

Advances in drug design, combinatorial synthetic chemistry, and high throughput screening methods have led to the discovery of thousands of drug candidates that can be used for treatment of life-threatening diseases such as inflammation, cancer, and AIDS. However, the majority (>95%) of these new molecules do not progress beyond the initial discovery phase to become clinically active therapies. The main hurdle facing their development into potent therapies with defined dosing regimen is the lack of effective formulation strategies that improve drug's aqueous solubility and stability, enhance its transport across epithelial and endothelial barriers encountered within the body, and allow selective drug accumulation and retention in diseased tissue and more specifically in the cytoplasm of targeted cells. One viable approach to overcome this challenge is to use biocompatible polymers as vehicles for targeted delivery of therapeutic molecules.

The use of polymers as carriers for pharmacologically active molecules started several decades ago, which eventually led to the development of different classes of polymeric drug delivery systems such as polymer-protein and polymer-drug conjugates, polymeric micelles, polyplexes, and supramolecular assemblies that are collectively known as "polymer therapeutics". Several polymer-protein conjugates have matured beyond the exploration phase to reach routine clinical use for treatment of life-threatening diseases. These clinically-approved polymer-protein conjugates utilize a water-soluble polymer, polyethylene glycol (PEG), to shield protein drugs from the degrading enzymes present in the systemic circulation, reduce drug's renal clearance and increase its circulation residence time, and improve its overall biocompatibility.

Despite the merits of these systems, there is a critical need for more sophisticated polymer-drug conjugates that can actively recognize and selectively accumulate in diseased tissue, trigger specialized transport mechanisms to enter target cells, and produce a spatially- and temporally-controlled drug release in specific sub-cellular compartments. To address this need, the present invention provides for the development of novel enzyme-activated, nano-sized, polymer-drug conjugates (dendrimers) for targeted drug delivery.

Liver cancer is the fifth most common cancer in the world accounting for approximately one million new cases per year. The American Cancer Society estimated that 19,160 new cases would be diagnosed with primary liver cancer with approximately 16,780 deaths in 2007. Surgical resection of tumor tissue is considered a good treatment option, however, only 15%-30% of hepatic cancer patients are operative candidates and they typically exhibit a 30%-60% recurrence rate. Other treatment options include thermal and chemical ablation, chemoembolization, and regional and systemic chemotherapy. Unfortunately, these treatment strategies are highly invasive with limited specificity towards cancer cells and have failed to improve the survival of hepatic cancer patients, which remains less than 12 months. This clearly indicates the urgent clinical need for innovative drug delivery systems, which can selectively shuttle a high dose of anticancer drug molecules into hepatic cancer cells and achieve the desired cancer cell death. To address this unmet clinical need, the present invention provides polymer-drug conjugates for treatment of primary liver cancer particularly hepatocellular carcinoma (HCC).

SUMMARY OF INVENTION

The present invention provides for methods of engineering nano-sized, water-soluble polymer-drug conjugates, such as dendrimer conjugates, which enhance the solubility of hydrophobic drug molecules, selectively extravasate from the systemic blood circulation into the diseased tissue, efficiently permeate into targeted cells and deliver the therapeutic cargo to the desired subcellular compartment. The dendrimer conjugates of the invention are designed to achieve tissue- and cell-specific drug release through a covalent linkage connecting therapeutic drug molecules to a dendrimer carrier, which will be specifically recognized and cleaved by cellular enzymes present solely in the diseased tissue. This design of dendrimer conjugates produces a high local concentration of drug molecules in the diseased tissue and diminished levels in healthy ones, which in turn results in a significantly enhanced therapeutic activity with minimal side effects.

Accordingly, the present invention provides a dendrimer conjugate comprising a dendrimer associated with an agent through an aromatic azo linkage, wherein the aromatic azo linkage is cleavable with a tissue specific enzyme. In some aspects, the aromatic azo linkage comprises an azobenzene. In certain aspects, the aromatic azo linkage comprises the structure of Formula I:

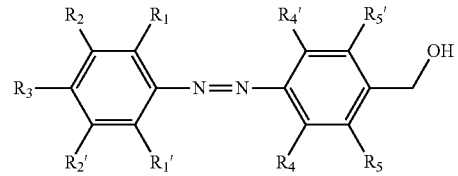

[Formula I]

wherein:
each of $R_1$ and $R_1'$ is independently H, $R_6$, or OR6,
each of $R_2$ and $R_2'$ is independently H or a halogen atom,
$R_3$ is $OR_6$ or $NHR_6$ or $NR_6R_7$,
each of $R_4$ and $R_4'$ is independently a straight chained or branched C1-C6 alkyl or —$CH_2OH$,
each of $R_5$, $R_5'$ and $R_6$ is independently a straight chained or branched C1-C6 alkyl, and $R_7$ is a straight chained or branched C1-C6 alkyl, or a C3-, C4-, C5-, or C6-carbon ring.

In some aspects, the aromatic azo linkage comprises the structure of Formula I, wherein either or both of $R_4$ and $R_4'$ is/are —$CH_2OH$ and the dendrimer is associated with one, two, or three agents through the aromatic azo linkage.

In additional aspects, the aromatic azo linkage, when in free form, has a Hammet constant that is less than or about −0.20 (e.g., less than or about −0.30, less than or about −0.35).

In some aspects, the dendrimer conjugate comprises a tissue-specific targeting molecule. In particular aspects, the tissue-specific targeting molecule is a liver-specific targeting molecule and the tissue-specific enzyme is a liver-specific enzyme. In particular aspects, the liver-specific targeting molecule is a ligand of the asialoglycoprotein receptor (AS-GPR), e.g., N-acetyl-galactosamine or the SP94 15 amino acid peptide with composition: SFSIIHTPILPLGGC (SEQ ID NO: 1). In some aspects, the tissue-specific targeting molecule is attached to the dendrimer though a non-degradable linkage or through a PEG chain, as further described herein.

In alternative or additional aspects, the dendrimer conjugate comprises a PEG chain, which, optionally is associated with the dendrimer through an acid hydrolysable linkage. In other aspects, the PEG chain is associated with the dendrimer through a non-degradable linkage. In some aspects, the PEG chain comprises two ends (e.g., termini) and a first end is (directly or indirectly) attached to the dendrimer and a second end is (directly or indirectly) attached to one or more tissue-specific targeting molecules.

Without being bound to a particular theory, a dendrimer conjugate comprising a dendrimer associated with an agent through an aromatic azo linkage and associated with a PEG chain through an acid hydrolysable linkage, wherein a first end of the PEG chain is associated with the dendrimer through an acid hydrolysable linkage and a second end of the PEG chain is associated with one or more tissue-specific targeting molecules, enters a cell of the tissue through receptor-mediated endocytosis due to the tissue-specific targeting molecule(s) binding to a receptor on the cell. When the dendrimer conjugate enters the lysosome or endosome of the cell, the acid hydrolysable chain is cleaved due to the reduction in pH at these subcellular locations, and, consequently, the PEG chain and tissue specific targeting molecule(s) are released from the dendrimer conjugate. The resulting increased exposure of the aromatic azo linkage leads to cleavage of the aromatic azo linkage by the tissue specific enzyme, and the agent is thereby released from the dendrimer conjugate.

In some aspects, the invention provides for a dendrimer conjugate comprising a dendrimer associated with 1) a therapeutic agent or imaging agent and 2) an N-acetyl-galactosamine (NAcGal) and/or the SP94 peptide, wherein said dendrimer is associated with the therapeutic agent or imaging agent through a covalent linkage that is cleavable with a tissue-specific enzyme.

In an embodiment, the invention provides for dendrimer conjugates, wherein said covalent linkage is cleavable by a liver-specific enzyme. For example, the dendrimer conjugate comprise a covalent linkage that is cleavable by a CYP450 enzyme, such as an azo-reducible linkage.

An exemplary dendrimer conjugate of the invention is set out in FIG. 1 wherein the therapeutic agent, such as doxorubicin, is attached to the dendrimer by an azo-reducible linkage that is cleaved by a CYP450 enzyme.

In one embodiment, the NAcGal is associated with the dendrimer through a non-degradable linker such as amide linkage through peptide coupling, urea moieties, thiourea moieties or carbamate moieties, linkage from terminal epoxide opening, linkage by formation of the Shiff bases and their reduction, or a linkage generated by "click" chemistry. Exemplary non-degradable linkages are set out in FIG. 3. The invention provides for dendrimer conjugates wherein about 0 to about 50% of the free dendrimer surface groups will be conjugated to NAcGal molecules.

In another embodiment, the therapeutic agent is associated with the dendrimer through a covalent linkage that is cleaved by a liver-specific enzyme such as the family of cytochrome P450 enzymes (CYP450). For example, the covalent linkage has the chemical structure of an aromatic azo bond that is connected to the therapeutic agent via a 1,6-self eliminating electronic cascade. This aromatic azo linkage and the associated therapeutic agent are coupled to the dendrimer carrier through a peptide linkage, triazole linkage, Shiff base, or other possible linkages. Exemplary linkages are set out in FIG. 2.

The invention provides for dendrimer conjugates wherein the dendrimer is a G4 dendrimer, a G5 dendrimer, a G6 dendrimer or a G7 dendrimer. In one embodiment, the dendrimer is a poly(amidoamine) (PAMAM) polymer. In addition, the invention provides for dendrimer conjugates wherein the dendrimer is optionally acetylated, such as dendrimer conjugates wherein about 0% to about 90% of the surface $NH_2$ groups of the dendrimer are acetylated. The invention also provides for dendrimer conjugates wherein the dendrimer is PEGylated, such as dendrimer conjugates wherein 0% to 25% of the surface $HN_2$ groups of the dendrimer are optionally PEGylated. The PEG chains have a molecular weight about 0.5 kDa to about 10 kDa.

In a further embodiment, the invention provides for a dendrimer conjugate wherein the dendrimer further comprises a label. Exemplary labels include radioactive labels including, but not limited to, $^3H$, $^{14}C$, $^{36}Cl$, $^{57}Co$, $^{58}Co$, $^{51}Cr$, $^{125}I$, $^{131}I$, $^{111}In$, $^{152}Eu$, $^{59}Fe$, $^{67}Ga$, $^{32}P$, $^{186}Re$, $^{35}S$, $^{75}Se$, Tc-99m, and $^{169}Yb$, as well as fluorescent dyes including, but not limited to, fluorescein (Fl), pyrene, Cy3, and Cy5. Additional exemplary labels include a radioisotope (e.g., $^{133}$Barium, $^{109}$Cadmium, $^{57}Co$, $^{60}Co$, $^{152}$Europium, $^{54}Mn$, $^{22}Na$, $^{65}Zn$, $^{99m}$Technetium, $^{90}$Strontium, $^{204}$Thallium, $^{14}C$, $^{32}P$, $^{125}I$) a fluorophore (e.g., hydroxycoumarin, methoxycoumarin, aminocoumarin, FAM, 6-carboxyfluorescein, Alexa fluor 430, Alexa fluor 488, Alexa fluor 532, Alexa fluor 546, Alexa fluor 555, Alexa fluor 568, Alexa fluor 594, Alexa fluor 633, Alexa fluor 660, Alexa fluor 680, fluorescein, HEX, Cy3, TRITC, R-phycoerythrin, rhodamine red-X, tamara, Rox, texas red, allophycocyanin, TruRed, Cy2, Cy3, Cy3.5 581, Cy5, Cy5.5, Cy7) and an elemental particle (e.g., gold, copper, silver), and the like.

The invention provides for compositions comprising any of the dendrimer conjugates of the invention. In one embodiment, the invention provides for pharmaceutical compositions comprising a dendrimer conjugate of the invention and a pharmaceutically acceptable carrier.

In another embodiment, the invention provides for a method of delivering a therapeutic agent to liver cells of a subject comprising contacting liver cells with a dendrimer conjugate of the invention under conditions sufficient to deliver the therapeutic agent to the liver cells.

In a further embodiment, the invention provides for a method of treating a liver disorder in a subject comprising administering a dendrimer conjugate of the invention in an amount effective to treat the disorder. Exemplary liver disorders include, but not limited to, hepatic cancer, liver cirrhosis, hemophilia, and hepatitis. For example, the therapeutic agent may be an anti-neoplastic agent such as doxorubicin.

BRIEF DESCRIPTION OF DRAWING

FIG. 2 provides a summary of different exemplary linkages that conjugate Azo-DOX to a PAMAM dendrimer (Gn).

FIG. 2(1) depicts a PAMAM-Azo-Dox conjugate wherein the Azo-DOX conjugate is connected to the PAMAM dendrimer through a peptide coupling.

FIG. 2(2) depicts a PAMAM-Azo-Dox conjugate wherein the Azo-DOX conjugate is connected to the PAMAM dendrimer through a terminal epoxide opening.

FIG. 2(3) depicts a PAMAM-Azo-Dox conjugate wherein the Azo-DOX conjugate is connected to the PAMAM dendrimer through a linker created by "click" chemistry.

FIG. 2(4) depicts a PAMAM-Azo-Dox conjugate wherein the Azo-DOX conjugate is connected to the PAMAM dendrimer through a urea, thiourea or carbamate linkage.

FIG. 2(5) depicts several DOX molecules connected to a dendrimer.

FIG. 3 provides a summary of different exemplary linkages that conjugate a NAcGal conjugates to a dendrimer (Gn).

FIG. 3(1) depicts a PAMAM-NAcGal conjugate wherein the NAcGal is attached to the PAMAM dendrimer through a peptide linker.

FIG. 3(2) depicts a PAMAM-NAcGal conjugate wherein the NAcGal is attached to the PAMAM dendrimer though a urea, thiourea or carbamate linker.

FIG. 3(3) depicts a PAMAM-NAcGal conjugate wherein the NAcGal is attached to the PAMAM dendrimer though a linker created by "click" chemistry.

FIG. 3(4) depicts a PAMAM-NAcGal conjugate wherein the NAcGal is attached to the PAMAM dendrimer though a Schiff-base formation.

FIG. 3(5) depicts a PAMAM-NAcGal conjugate wherein the NAcGal is attached to the PAMAM dendrimer though a Schiff-base reduction.

FIG. 4 provides a summary of different exemplary linkages the conjugate fluorescein isothiocyanate and PEG to the dendrimer (Gn).

FIG. 4C provides a scheme for the radio-labeling of PAMAM dendrimers with 14C-Iodoacetamide (IAC).

FIG. 4D provides a scheme for the conjugation of PEG chains to PAMAM dendrimers.

FIG. 4E depicts the composition of Gn-(Fl)z-(NHAc)y-(NAcGal)x-(PEG)p-(DOX)D conjugates.

FIG. 5 provides a summary of exemplary synthetic strategies for coupling of DOX, to PAMAM dendrimers (Gn).

FIG. 5A provides the scheme for synthesis of PAMAM-Azo-DOX conjugate through peptide coupling.

FIG. 5B provides the scheme for synthesis of PAMAM-Azo-DOX conjugate through opening of a terminal epoxide group.

FIG. 5C provides the scheme for synthesis of PAMAM-Azo-DOX conjugate through a linker created by "click" chemistry.

FIG. 5D provides the scheme for synthesis of PAMAM-Azo-DOX conjugate through a thiourea linkage.

FIG. 5E provides the scheme for synthesis of PAMAM-Azo-DOX conjugate bearing several DOX molecules in a single conjugate.

FIG. 6 provides a summary of exemplary synthetic strategies for coupling of NAcGal to the PAMAM dendrimer (Gn).

FIG. 6A provides a scheme for attachment of NAcGal through a short peptide linker.

FIG. 6B provides a scheme for attachment of NAcGal through a long peptide linker.

FIG. 6C provides a scheme for the attachment of NAcGal through a thiourea linkage.

FIG. 6D provides a scheme for the attachment of NAcGal through a linkage created using "click" chemistry.

FIG. 6E provides a scheme for the attachment of NAcGal through the formation of a Shiff base and its reduction.

FIG. 7 provides a summary of exemplary synthetic strategies for coupling of fluorescein isothiocyanate, PEG, and $^{14}$C-Iodoacetamide (IAC) to dendrimers (Gn).

FIG. 7A provides a scheme for synthesis of fluorescein-labeled N-acetyl-galactosamine.

FIG. 7B provides a scheme for synthesis of $[^{14}C]$-labeled acetylated dendrimers ($[^{14}C]$-Gn-(NHAc)y).

FIG. 7C provide a scheme for synthesis of $[^{14}C]$-labeled, acetylated, and PEGylated dendrimers ([14C]-Gn-(NHAc)y-(PEG)p).

FIG. 7D provides a scheme for synthesis of $[^{14}C]$-labeled, acetylated, and galactosylated dendrimers ($[^{14}C]$-Gn-(NHAc)y-(NAcGal)x).

FIG. 7E provides the scheme for synthesis of $[^{14}C]$-labeled, acetylated, galactosylated, and PEGylated dendrimers ($[^{14}C]$-Gn-(NHAc)y-(NAcGal)x-(PEG)p).

FIG. 7F provide a scheme for synthesis of fluorescently-labeled, acetylated, and galactosylated dendrimers (Gn-(Fl)6-(NHAc)y-(NAcGal)x).

FIG. 26 represents a collection of graphs that demonstrate the uptake of G5-L(x)-DOX conjugates and intracellular DOX release. Internalization of G5-L(x)-DOX conjugates into (A) HepG2 or (C) Hep3B human hepatic cancer cells after a 1 hour incubation. Intracellular DOX release from G5-L(x)-DOX conjugates upon a 24 hour incubation with (B) HepG2 or (D) Hep3B cells. Data are expressed as mean (n=3)±SEM.

FIG. 37 represents a series of graphs that demonstrate the uptake of $G5-(Fl)_6-(Ac)_{107}-(cPEG)_{15}$, $G5-(Fl)_6-(Ac)_{107}-(cPEG[NAcGal_\alpha])_{15}$, $G5-(Fl)_6-(Ac)_{108}-(cPEG[NAcGal_\beta])_{14}$ and $G5-(Fl)_6-(Ac)_{108}-(cPEG[SP94])_{14}$ incubated with HepG2 cells at 100-4000 nM targeting ligand concentrations for 2 (A,C) and 24 hours (B,D). Data presented as mean (n=4)+S.E.M. of the % labeled cells (A,B) and relative fluorescence per cell (C,D) after treatment.

FIG. 40 represents a series of graphs demonstrating uptake of $G5-(Fl)_6-(NH_2)_{122}$, $G5-(Fl)_6-(Ac)_{108}-(NAcGal)_{14}$, $G5-(Fl)_6-(Ac)_{107}-(cPEG)_{15}$, $G5-(Fl)_6-(Ac)_{108}-(cPEG[NAcGal_\beta])_{14}$ and $G5-(Fl)_6-(Ac)_{108}-(cPEG[SP94])_{14}$ conjugates incubated with primary rat hepatocytes at 100-4000 nM targeting ligand concentrations for 2 (A,C) and 24 hours (B,D). Data presented as mean (n=4)+S.E.M. of the % labeled cells (A,B) and relative fluorescence per cell (C,D) after treatment.

DETAILED DESCRIPTION

Figure 1:
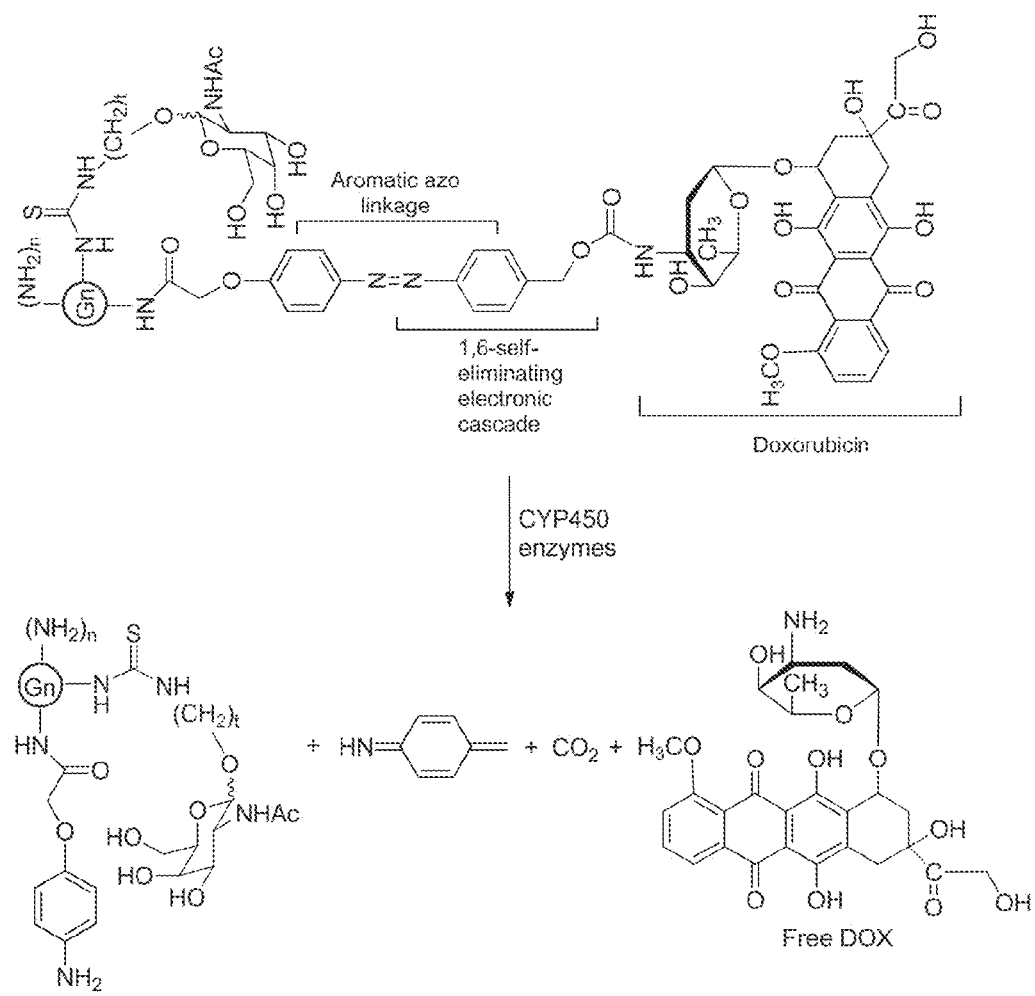
FIG. 1. Composition of NAcGal-targeted PAMAM-DOX conjugates with CYP450 enzyme-cleavable azo linkage. Cleavage of the azo linkage results in production of free DOX that causes cancer cell death.

In one aspect, the invention provides for a dendrimer-agent conjugate where dendrimers are covalently conjugated to an agent. In various aspects, the agent is a therapeutic agent, a prophylactic agent, or an imaging agent. Without being bound to a particular theory, for tissue specific delivery, the dendrimer conjugates bind to a tissue specific marker expressed on the surface of target cells, which triggers cellular uptake via receptor-mediated endocytosis: this shift in agent internalization mechanism from passive diffusion to endocytosis "masks" the agent from the membrane-bound efflux pumps of the cells and consequently reduce its secretion outside the cells. In some embodiments, internalized conjugates exploit the established buffering capacity of the tertiary amine groups present within the dendrimer backbone to escape the endosomal membrane using the proton sponge mechanism and reach the cytoplasm of cells. Once in the cytoplasm, tissue specific enzymes in some aspects reduce the linkage connecting the agent to the dendrimer thus producing a high concentration of free agent in the target cells. This strategy achieves cell-specific delivery of an agent resulting in a localized activity with lower side effects.

Exemplary dendrimer conjugates of the invention include those set out in Table 1. The percentages in the second column refer to the percent surface positions of the dendrimer occupied by a label (Fl or $^{14}C$-Acetamide), acetylation (referred to herein as NHAc or Ac) or PEGylation (PEG), or the percent free dendrimer surface that is galactoylated (NAcGal).

| General Formula | Composition |
| --- | --- |
| Fl-labeled | $Gn-(Fl)_{1-5\%}$ |
| $Gn-(Fl)_z$ | $G5-(Fl)_6$ |
| Radio-labeled | $Gn-(^{14}C\text{-Acetamide})_{1-5\%}$ |
| $Gn-(^{14}C\text{-Acetamide})_w$ | |
| Acetylated and Fl-labeled | $Gn-(Fl)_{1-5\%}-(NHAc)_{1-90\%}$ |
| $Gn-(Fl)_z-(NHAc)_y$ | $G5-(Fl)_6-(NHAc)_{110}$ |
| Acetylated and radio-labeled | $Gn-(^{14}C\text{-Acetamide})_{1-5\%}-(NHAc)_{1-90\%}$ |
| $Gn-(^{14}C\text{-Acetamide})_w-(NHAc)_y$ | |
| Galactosylated | $Gn-(NAcGal)_{1-50\%}$ |
| $Gn-(NAcGal)_x$ | |
| Fl-labeled and galactosylated | $Gn-(Fl)_{1-5\%}-(NAcGal)_{1-50\%}$ |
| $Gn-(Fl)_z-(NAcGal)_x$ | $G5-(Fl)_6-(NAcGal)_{28}$ |
| | $G5-(Fl)_6-(NAcGal)_{58}$ |
| Radio-labeled and galactosylated | $Gn-(^{14}C\text{-Acetamide})_{1-5\%}-(NAcGal)_{1-50\%}$ |
| $Gn-(^{14}C\text{-Acetamide})_w-(NAcGal)_x$ | |
| Acetylated and galactosylated | $Gn-(NHAc)_{1-90\%}-(NAcGal)_{1-50\%}$ |
| $Gn-(NHAc)_y-(NAcGal)_x$ | $G_5-(NHAc)_{85}-(NAcGal)_{14}$ |
| Acetylated, Fl-labeled and galactosylated | $Gn-(Fl)_{1-5\%}-(NHAc)_{1-90\%}-(NAcGal)_{1-50\%}$ |

-continued

| General Formula | Composition |
| --- | --- |
| Gn-(Fl)$_z$-(NHAc)$_y$-(NAcGal)$_x$ | G5-(Fl)$_6$-(NHAc)$_{60}$-(NAcGal)$_{41}$ |
|  | G$_5$-(Fl)$_6$-(NHAc)$_{83}$-(NAcGal)$_{18}$ |
|  | G5-(Fl)$_6$-(NHAC)$_{83}$-(NAcGal)$_{14}$ |
|  | G$_5$-(Fl)$_6$-(NHAc)$_{60}$-(NAcGal)$_{56}$ |
| Acetylated, radio-labeled and galactosylated Gn-($^{14}$C-Acetamide)$_w$-(NHAc)$_y$-(NAcGal)$_x$ | Gn-($^{14}$C-Acetamide)$_{1-5\%}$-(NHAc)$_{1-90\%}$-(NAcGal)$_{1-50\%}$ |
| PEGylated Gn-(PEG)$_P$ | Gn-(PEG)$_{1-25\%}$ |
| Acetylated and PEGylated Gn-(NHAc)$_y$-(PEG)$_P$ | Gn-(NHAc)$_{1-90\%}$-(PEG)$_{1-25\%}$ |
|  | G$_5$-(NHAc)$_{93}$-(PEG)$_{10}$ |
| Acetylated, PEGylated and Fl-labeled Gn-(Fl)$_z$-(NHAc)$_y$-(PEG)$_P$ | Gn-(Fl)$_{1-5\%}$-(NHAc)$_{1-90\%}$-(PEG)$_{1-25\%}$ |
|  | G$_5$-(Fl)$_6$-(NHAc)$_{90}$-(PEG)$_{13}$ |
| Acetylated, PEGylated and radio-labeled Gn-($^{14}$C-Acetamide)$_w$-(NHAc)$_y$-(PEG)p | Gn-($^{14}$C-Acetamide)$_{1-5\%}$-(NHAc)$_{1-90\%}$-(PEG)$_{1-25\%}$ |
| Acetylated, PEGylated and galactosylated Gn-(NHAc)$_y$-(NAcGal)$_x$-(PEG)$_P$ | Gn-(NHAc)$_{1-90\%}$-(NAcGal)$_{1-50\%}$-(PEG)$_{1-25\%}$ |
| Acetylated, PEGylated, Fl-labeled and galactosylated Gn-(Fl)$_z$-(NHAc)$_y$-(NAcGal)$_x$-(PEG)p | Gn-(Fl)$_{1-5\%}$-(NHAc)$_{1-90\%}$-(NAcGal)$_{1-50\%}$-(PEG)$_{1-25\%}$ |
| Acetylated, PEGylated, radio-labeled and galactosylated Gn-($^{14}$C-Acetamide)$_w$-(NHAc)$_y$-(NAcGal)$_x$-(PEG)p | Gn-($^{14}$C-Acetamide)$_{1-5\%}$-(NHAc)$_{1-90\%}$-(NAcGal)$_{1-50\%}$-(PEG)$_{1-25\%}$ |
| PAMAM-DOX Gn-(DOX)$_D$ | Gn-(DOX)$_{1-50\%}$ |
| Fl-labeled PAMAM-DOX Gn-(Fl)$_z$-(DOX)$_D$ | Gn-(Fl)$_{1-5\%}$-(DOX)$_{1-50\%}$ |
| Radio-labeled PAMAM-DOX Gn-($^{14}$C-Acetamide)$_w$-(DOX)$_x$ | Gn-($^{14}$C-Acetamide)$_{1-5\%}$-(DOX)$_{1-50\%}$ |
| Acetylated PAMAM-DOX Gn-(NHAc)$_y$-(DOX)$_D$ | Gn-(NHAc)$_{1-90\%}$-(DOX)$_{1-50\%}$ |
| Acetylated and Fl-labeled PAMAM-DOX Gn-(Fl)$_z$-(NHAc)$_y$-(DOX)$_D$ | Gn-(Fl)$_{1-5\%}$-(NHAc)$_{1-90\%}$-(DOX)$_{1-50\%}$ |
| Acetylated and radio-labeled PAMAM-DOX Gn-($^{14}$C-Acetamide)$_w$-(NHAc)$_y$-(DOX)$_D$ | Gn-($^{14}$C-Acetamide)$_{1-5\%}$-(NHAc)$_{1-90\%}$-(DOX)$_{1-50\%}$ |
| Acetylated and galactosylated PAMAM-DOX Gn-(NHAc)$_y$-(NAcGal)$_x$-(DOX)$_D$ | Gn-(NHAc)$_{1-90\%}$-(NAcGal)$_{1-50\%}$-(DOX)$_{1-50\%}$ |
| Acetylated, Fl-labeled and galactosylated PAMAM-DOX Gn-(Fl)$_z$-(NHAc)$_y$-(NAcGal)$_x$-(DOX)$_D$ | Gn-(Fl)$_{1-5\%}$-(NHAc)$_{1-90\%}$-(NAcGal)$_{1-50\%}$-(DOX)$_{1-50\%}$ |
| Acetylated, radio-labeled and galactosylated PAMAM-DOX Gn-($^{14}$C-Acetamide)$_w$-(NHAc)$_y$-(NAcGal)$_x$-(DOX)$_D$ | Gn-($^{14}$C-Acetamide)$_{1-5\%}$-(NHAc)$_{1-90\%}$-(NAcGal)$_{1-50\%}$-(DOX)$_{1-50\%}$ |
| Acetylated, PEGylated and galactosylated PAMAM-DOX Gn-(NHAc)$_y$-(NAcGal)$_x$-(PEG)$_P$-(DOX)$_D$ | Gn-(NHAc)$_{1-90\%}$-(NAcGal)$_{1-50\%}$-(PEG)$_{1-20\%}$-(DOX)$_{1-50\%}$ |
| Acetylated, PEGylated, Fl-labeled and galactosylated PAMAM-DOX Gn-(Fl)$_z$-(NHAc)$_y$-(NAcGal)$_x$-PEG)$_P$-(DOX)$_D$ | Gn-(Fl)$_{1-5\%}$-(NHAc)$_{1-90\%}$-(NAcGal)$_{1-50\%}$-(PEG)$_{1-20\%}$-(DOX)$_{1-50\%}$ |
| Acetylated, PEGylated, radio-labeled and galactosylated PAMAM-DOX Gn-($^{14}$C-Acetamide)$_w$-(NHAc)$_y$-(NAcGal)$_x$-(PEG)$_P$-(DOX)$_D$ | Gn-($^{14}$C-Acetamide)$_{1-5\%}$-(NHAc)$_{1-90\%}$-(NAcGal)$_{1-50\%}$-(PEG)$_{1-25\%}$-(DOX)$_{1-50\%}$ |
| Mono Galactose-functionalized PEG brush Gn-(PEG-NAcGal)$_K$ | Gn-(PEG-NAcGal)$_{1-50\%}$ |
| Acetylated, Mono Galactose-functionalized PEG brush Gn-(NHAc)$_y$-(PEG-NAcGal)$_K$ | Gn-(NHAc)$_{1-90\%}$-(PEG-NAcGal)$_{1-50\%}$ |
| Acetylated, Mono Galactose-functionalized PEG brush and radio-labeled Gn-($^{14}$C-Acetamide)$_w$-(NHAc)$_y$-(PEG-NAcGal)$_K$ | Gn-($^{14}$C-Acetamide)$_{1-5\%}$-(NHAc)$_{1-90\%}$-(PEG-NAcGal)$_{1-50\%}$ |
| Acetylated, Fl-labeled and Mono Galactose-functionalized PEG brush Gn-(Fl)$_z$-(NHAc)$_y$-(PEG-NAcGal)$_K$ | Gn-(Fl)$_{1-5\%}$-(NHAc)$_{1-90\%}$-(PEG-NAcGal)$_{1-50\%}$ |
| Tri Galactose-functionalized PEG brush Gn-(PEG-triNAcGal)$_M$ | Gn-(PEG-triNAcGal)$_{1-50\%}$ |
| Acetylated, Tri Galactose-functionalized PEG brush Gn-(NHAc)$_y$-(PEG-triNAcGal)$_M$ | Gn-(NHAc)$_{1-90\%}$-(PEG-triNAcGal)$_{1-50\%}$ |
| Acetylated, Tri Galactose-functionalized PEG brush and radio-labeled Gn-($^{14}$C-Acetamide)$_w$-(NHAc)$_y$-(PEG-triNAcGal)$_M$ | Gn-($^{14}$C-Acetamide)$_{1-5\%}$-(NHAc)$_{1-90\%}$-(PEG-triNAcGal)$_{1-50\%}$ |
| Acetylated, Fl-labeled, and Tri Galactose-functionalized PEG brush Gn-(Fl)$_z$-(NHAc)$_y$-(PEG-triNAcGal)$_M$ | Gn-(Fl)$_{1-5\%}$-(NHAc)$_{1-90\%}$-(PEG-triNAcGal)$_{1-50\%}$ |

-continued

| General Formula | Composition |
| --- | --- |
| Mono Galactose-functionalized PEG brush<br>Gn-(PEG-NAcGal)$_K$-(DOX)$_D$ | Gn-(PEG-NAcGal)$_{1-50\%}$-(DOX)$_{1-50\%}$ |
| Acetylated, Mono Galactose-functionalized PEG brush<br>Gn-(NHAc)$_y$-(PEG-NAcGal)$_K$-(DOX)$_D$ | Gn-(NHAc)$_{1-90\%}$-(PEG- NAcGal)$_{1-50\%}$-(DOX)$_{1-50\%}$ |
| Acetylated, Mono Galactose-functionalized PEG brush and radio-labeled<br>Gn-($^{14}$C-Acetamide)$_w$-(NHAc)$_y$-(PEG-NAcGal)$_K$-(DOX)$_D$ | Gn-($^{14}$C-Acetamide)$_{1-5\%}$-(NHAc)$_{1-90\%}$-(PEG-NAcGal)$_{1-50\%}$-(DOX)$_{1-50\%}$ |
| Acetylated, Fl-labeled and Mono Galactose-functionalized PEG brush<br>Gn-(Fl)$_z$-(NHAc)$_y$-(PEG-NAcGal)$_K$-(DOX)$_D$ | Gn-(Fl)$_{1-5\%}$-(NHAc)$_{1-90\%}$-(PEG-NAcGal)$_{1-50\%}$-(DOX)$_{1-50\%}$ |
| Tri Galactose-functionalized PEG brush<br>Gn-(PEG-triNAcGal)$_M$-(DOX)$_D$ | Gn-(PEG-triNAcGal)$_{1-50\%}$-(DOX)$_{1-50\%}$ |
| Acetylated, Tri Galactose-functionalized PEG brush<br>Gn-(NHAc)$_y$-(PEG-triNAcGal)$_M$-(DOX)$_D$ | Gn-(NHAc)$_{1-90\%}$-(PEG-triNAcGal)$_{1-50\%}$-(DOX)$_{1-50\%}$ |
| Acetylated, Tri Galactose-functionalized PEG brush and radio-labeled<br>Gn-($^{14}$C-Acetamide)$_w$-(NHAc)$_y$-(PEG-triNAcGal)$_M$-(DOX)$_D$ | Gn-($^{14}$C-Acetamide)$_{1-5\%}$-(NHAc)$_{1-90\%}$-(PEG-triNAcGal)$_{1-50\%}$-(DOX)$_{1-50\%}$ |
| Acetylated, Fl-labeled, and Tri Galactose-functionalized PEG brush<br>Gn-(Fl)$_z$-(NHAc)$_y$-(PEG-triNAcGal)M-(DOX)$_D$ | Gn-(Fl)$_{1-5\%}$-(NHAc)$_{1-90\%}$-(PEG-triNAcGal)$_{1-50\%}$-(DOX)$_{1-50\%}$ |

Dendrimers

The term "dendrimer" or "dendrimeric polymer" refers to repeatedly branched nano-sized macromolecules characterized by a symmetrical, well-defined three-dimensional shape. Dendrimers grow three-dimensionally by the addition of shells of branched molecules to a central core. The cores are spacious and various chemical units can be attached to points on the exterior of the central core. Dendrimeric polymers have been described extensively (Tomalia. (1994). *Advanced Materials* 6:529-539; Donald A. Tomalia, Adel M. Naylor, William A. Goddard III (1990). Angew, *Chem. Int. Ed. Engl.*, 29:138-175; incorporated herein by reference in their entireties). Dendrimeric polymers are synthesized as defined spherical structures typically ranging from 1 to 20 nanometers in diameter. Accordingly, in some aspects, the dendrimers of the dendrimer conjugates provided herein are about 1, about 2, about 3, about 4, about 5, about 6, about 7, about 8, about 9, about 10, about 11, about 12, about 13, about 14, about 15, about 16, about 17, about 18, about 19, or about 20 nm in diameter.

Dendrimers are identified by a generation number (Gn) and each complete synthesis reaction results in a new dendrimer generation. Molecular weight and the number of terminal groups increase exponentially as a function of generation number (the number of layers) of the dendrimer. Different types of dendrimers can be synthesized based on the core structure that initiates the polymerization process. Dendrimers of any generation are used for the invention. For example, the present invention provides for G4, G5, G6 and G7 dendrimers.

The dendrimer core structures in some aspects dictate several characteristics of the molecule such as the overall shape, density and surface functionality (Tomalia et al. (1990). *Angew. Chem. Int. Ed. Engl.*, 29:138). Spherical dendrimers have ammonia as a trivalent initiator core or ethylenediamine (EDA) as a tetravalent initiator core. Recently described rod-shaped dendrimers (Yin et al (1998). *J. Am. Chem. Soc.*, 120:2678) use polyethyleneimine linear cores of varying lengths; with longer cores leading to increased rod length. Dendritic macromolecules are available commercially in kilogram quantities and are produced under current good manufacturing processes (GMP) for biotechnology applications.

With respect to the present invention, the dendrimers in some aspects comprise a core structure which is less than or about 10 nm (e.g., less than or about 10 nm, less than about 9 nm, less than or about 8 nm, less than or about 7 nm, less than or about 6 nm, less than or about 5 nm, less than or about 4 nm, less than or about 3 nm, less than or about 2 nm, less than or about 1 nm) in diameter. In some aspects, the dendrimer comprises a core structure with a diameter within the range of about 3 nm to about 8 nm, e.g., about 5 to about 7 nm. In some aspects, the dendrimer comprises a 1,4-diamino butane core.

As used herein, the term "dendrimer" or "dendrimeric polymer" also refers to unsymmetrical or asymmetrical dendrimers having more than one radius due to asymmetry of the dendrimer. In some aspects, the asymmetrical dendrimer has two different radii. Such dendrimers and the synthesis thereof are further described in Lee et al., *Bioconjugate Chem.* 18: 579-584 (2007).

Dendrimers may be characterized by a number of techniques including, but not limited to, electrospray-ionization mass spectroscopy, matrix-assisted laser desorption/ionization-time of flight spectroscopy, $^{13}$C nuclear magnetic resonance spectroscopy, high pressure liquid chromatography, size exclusion chromatography with multi-angle laser light scattering, capillary electrophoresis and gel electrophoresis. These tests assure the uniformity of the polymer population and are important for monitoring quality control of dendrimer manufacture for GMP applications and in vivo usage. Extensive studies have been completed with neutralized dendrimers and show no evidence of toxicity when administered intravenously in vivo.

The invention contemplates the use of any type of dendrimer including but not limited to poly(amidoamine) (PAMAM) dendrimers such as dense star polymers and Starburst polymers, poly(amidoamine-organosilicon) (PAMAMOS) dendrimers, (Poly(Propylene Imine)) (PPI) dendrimers, tecto dendrimers, multilingual dendrimers, chiral dendrimers, hybrid dendrimers/linear polymers, amphiphilic dendrimers, micellar dendrimers and Fréchet-type dendrimers.

In one embodiment, the dendrimer conjugate comprises a PAMAM dendrimer. PAMAM dendrimers are a family of water-soluble polymers characterized by a unique tree-like branching architecture and a compact spherical shape in solution. Several classes of PAMAM dendrimers have been synthesized using different cores such as ethylene diamine (EDA) and 1,4-diamino butane (DAB) with different surface groups (e.g. amine, hydroxyl, or carboxyl). PAMAM dendrimers are identified by a generation number (Gn) in the range 0-10 where an increase in Gn denotes a controlled incremental increase in size, molecular weight, and number of surface groups. PAMAM dendrimers are efficient drug carriers due to the high degree of branching and the large number of surface groups, which can be utilized to immobilize drugs, imaging agents, or targeting ligands to achieve a high density of therapeutic molecules in a compact system.

Earlier studies have shown that PAMAM dendrimers can encapsulate small hydrophobic drug molecules in the voids of their branching architecture forming inclusion complexes with enhanced aqueous solubility. The encapsulated drug molecules, however, were quickly released under physiological conditions rendering these inclusion complexes ineffective as drug carriers. Recent reports described the conjugation of different classes of drug molecules including anticancer methotrexate, penicillin antibiotic, and antidepressant venlafaxine molecules to amine- and carboxyl-terminated PAMAM dendrimers through hydrolysable ester or hydrazone linkages. Although these PAMAM dendrimer-drug conjugates achieved sustained release of the incorporated drug in buffer solutions, they displayed a variable spectrum of activity compared to the free drug when evaluated in vitro using different cell lines, which can be a result of slow or incomplete linkage hydrolysis within the cells. Additionally, the use of ester and hydrazone linkages to prepare PAMAM dendrimer-drug conjugates is expected to produce a rapid and non-specific release of the attached drug in vivo. This apparent lack of cleavage specificity limits the ability of current PAMAM dendrimer-drug conjugates to achieve tissue- and cell-specific drug release and diminish their potential use for targeted drug delivery.

PAMAMOS dendrimers are composed of radially layered poly(amidoamine-organosilicon) units. These dendrimers are inverted unimolecular micelles that consist of hydrophilic, nucleophilic PAMAM interiors and hydrophobic organosilicon (OS) exteriors. These dendrimers may serve as precursors for the preparation of honeycomb-like networks with nanoscopic PAMAM and OS domains.

PPI dendrimers are generally poly-alkyl amines having primary amines as terminal groups. The PPI dendrimer interior consists of numerous tertiary tris-propylene amines. PPI dendrimers are also known as POPAM (Poly(Propylene Amine) with DAB cores.

Tecto dendrimers are composed of a core dendrimer, surrounded by dendrimers of differing type in order to impart specific regional functionality in the smart therapeutic nanodevice. Different compounds perform varied functions ranging from diseased cell recognition, diagnosis of disease state drug delivery, reporting location to reporting outcomes of therapy. Multilingual dendrimers are dendrimers in which the surface contains multiple copies of a particular functional group. Chiral dendrimers are based upon the construction of constitutionally different but chemically similar branches to chiral core. Hybrid dendrimers/linear polymers are hybrids (block or graft polymers) of dendritic and linear polymers. Amphiphilic dendrimers are dendrimers that have two segregated sites of chain end, one half is electron donating and the other half is electron withdrawing. Micellar dendrimers are unimolecular micelles of water soluble hyper branched polyphenylenes.

Fréchet-Type dendrimers are based on a poly-benzyl ether hyper-branched skeleton. These dendrimers usually have carboxylic acid groups as surface groups, serving as a good anchoring point for further surface fictionalization, and as polar surface groups to increase the solubility of this hydrophobic dendrimer type in polar solvents or aqueous media.

Liver Cell-Specific Targeting Molecules

The invention provides dendrimer conjugates comprising a liver-specific targeting molecule to direct delivery of the therapeutic agent to hepatic cells such as hepatic cancer cells. Any molecule that specifically targets hepatic cells may be used in the invention.

In some embodiments, the liver-specific targeting molecule is a ligand of the asialoglycoprotein receptor (ASGPR), including, but not limited to, any desialylated glycoprotein, N-acetyl-galactosamine, asialofetuin, and asialoorosomucoid.

In one embodiment, the invention provides for dendrimer conjugates comprising a NAcGal ligand for binding to the asialoglycoprotein receptor (ASGPR) expressed on the surface of hepatic cells. Binding of the conjugates of the invention to ASGPR through the NAcGal moieties triggers cellular uptake via receptor-mediated endocytosis. In one embodiment, the invention provides for dendrimer conjugates comprising NAcGal molecules associated via non-degradable linkages to serve as hepatic cell-targeting ligands. Other ASGPR ligands that serve as hepatic cell-targeting molecules include asialofetuin, lactosaminated human albumin, galactosylsphingosine, and anti-glypican-3 (GPC3) antibodies.

In another embodiment, the invention provides dendrimer conjugates comprising ligands for the transferrin receptor. Transferrin receptors are over-expressed in HCC, and therefore a ligand for this receptor may serve as a hepatic cell-targeting molecule. In addition, apolipoprotein A-1 (apo A-1) targets dendrimers to the LDL receptors on hepatic cells.

In a further embodiment, the invention provides dendrimers conjugates comprising peptides that target the dendrimer to hepatic cells. For example, the tetra peptide Gly-Phe-Leu-Gly (GFLG) targets dendrimers to hepatic stellate cells (HSC) Cyclic 8 amino acid peptides comprising the amino acid sequence Arg-Gly-Asp (RGD) targets dendrimers to collagen type VI receptors, which are up-regulated in activated HSCs of fibrotic livers.

In another embodiment, the invention provides dendrimers comprising mannose-6-phosphate moieties for targeting to hepatic stellate cells. Mannose-6-phosphate/insulin-like growth factor II receptors are expressed on the hepatic stellate cells and are over-expressed in activated HSCs during liver fibrosis.

The invention provides dendrimer conjugates wherein the tissue-specific targeting molecule (e.g., liver-specific targeting molecule) is associated with the dendrimer through a non-degradable linkage. Exemplary non-degradable linkages include urea, thiourea, peptide, and triazole linkages, linkages from terminal epoxide opening, amide linkage through peptide coupling, linkage by formation of the Shiff base, linkage formed by reduction of Shiff base and a linkage generated by "click" chemistry.

Exemplary compositions comprising various linkages that conjugate a tissue-specific targeting molecule, such as NAcGal, to a dendrimer (Gn) are provided in FIG. 3, while exemplary synthetic strategies to couple a targeting molecule, such as NAcGal, to a dendrimer are shown in FIG. 6.

In alternative aspects, the tissue-specific targeting molecule (e.g., liver-specific targeting molecule) is associated with the dendrimer through a non-degradable linkage comprising a polyalkylene glycol chain (e.g., polyethylene glycol (PEG) chain). The polyalkylene glycol chain may be any polyalkylene glycol chain known in the art, including, but not limited to, the polyalkylene glycol chains described herein under the section "Functionalized Dendrimers to Increase Biodistribution." In exemplary aspects, the polyalkylene glycol chain has a molecular weight of about 0.5 to about 10 kDa. In some aspects, the polyalkylene glycol chain is associated with the dendrimer through a non-degradable linkage and, in other aspects, the polyalkylene glycol chain is associated with the dendrimer through an acid hydrolysable linkage, as further described herein.

While it is contemplated that the non-degradable linkage bridges the dendrimer to one tissue-specific targeting molecule (e.g., liver-specific targeting molecule), it is furthermore contemplated that the non-degradable linkage bridges the dendrimer to more than one (e.g., two, three, four, five, six, seven, eight, or more) tissue-specific targeting molecules (e.g., liver-specific targeting molecules). In exemplary aspects, the non-degradable linkage comprises a branched structure of which each branch is attached to a tissue-specific targeting molecule (e.g., liver-specific targeting molecule). The branched structure in some aspects comprises —C(CH$_2$OH)$_3$, such as, —NHC(CH$_2$OH)$_3$.

Figure 12:
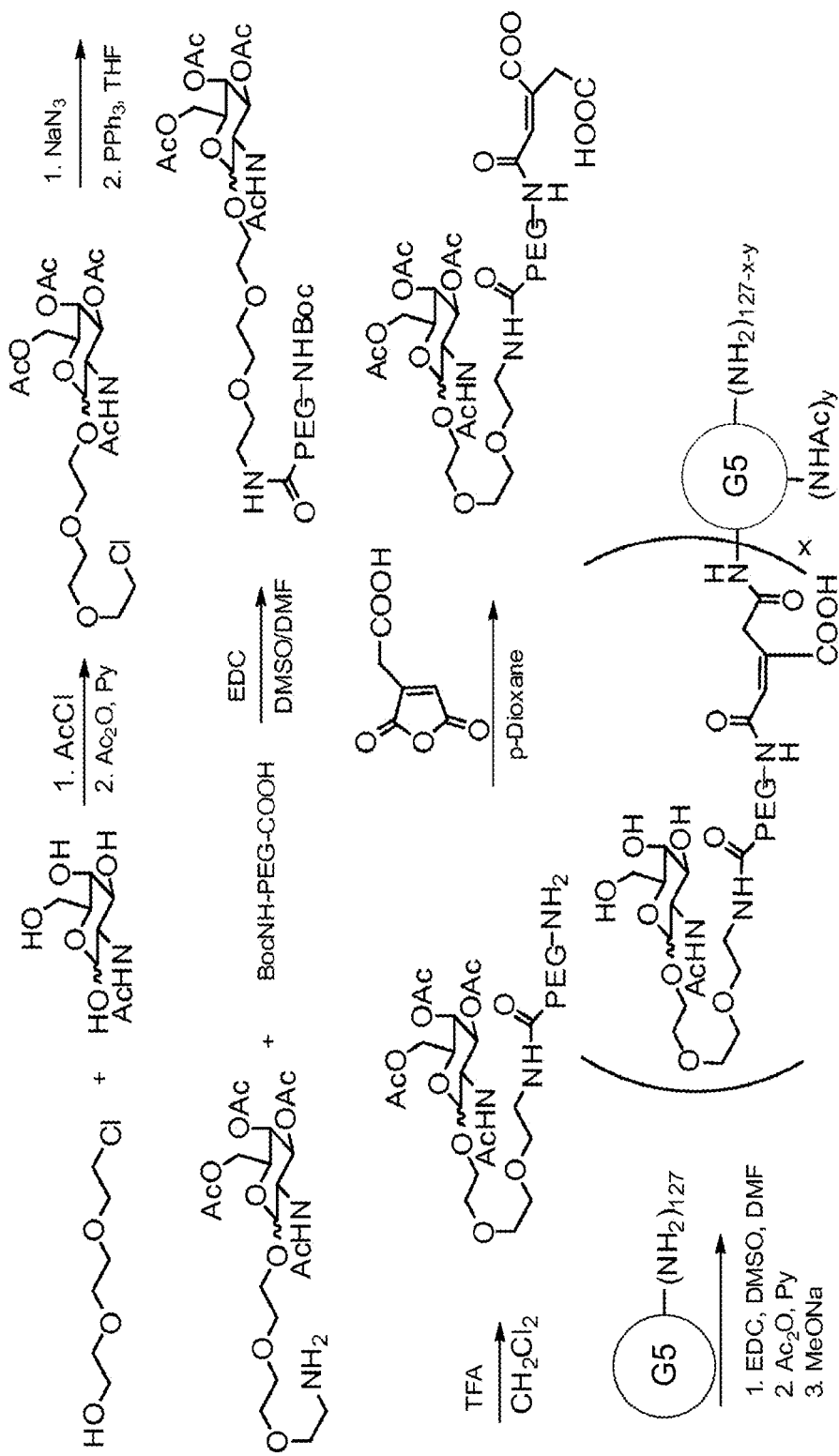
FIG. 12 represents a synthesis scheme for single Gal-PEG and attachment to G5 for hepatic cell targeting.
Figure 13:
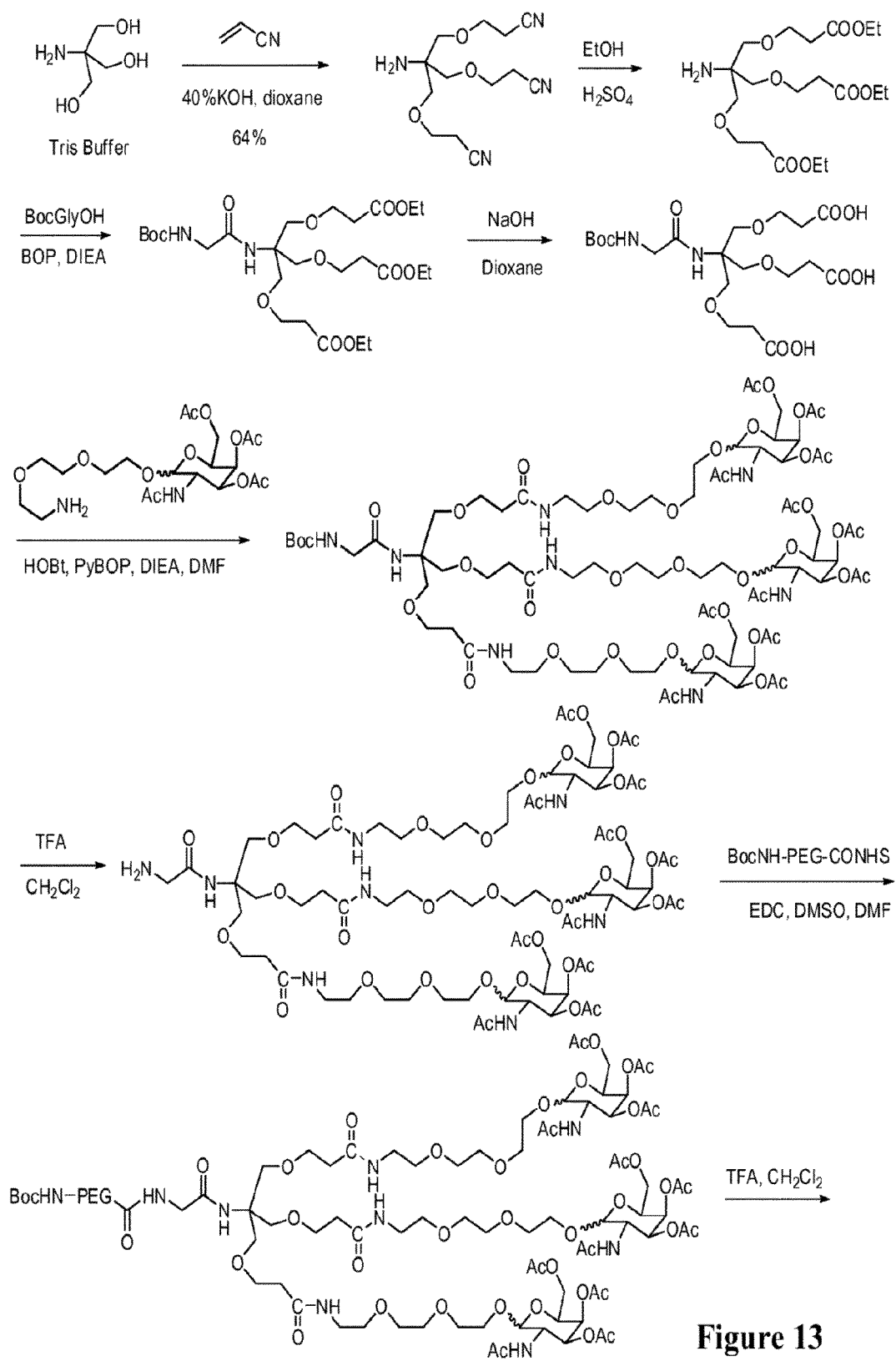
FIG. 13 represents a synthesis scheme for TriGal-PEG chains.
Figure 14:
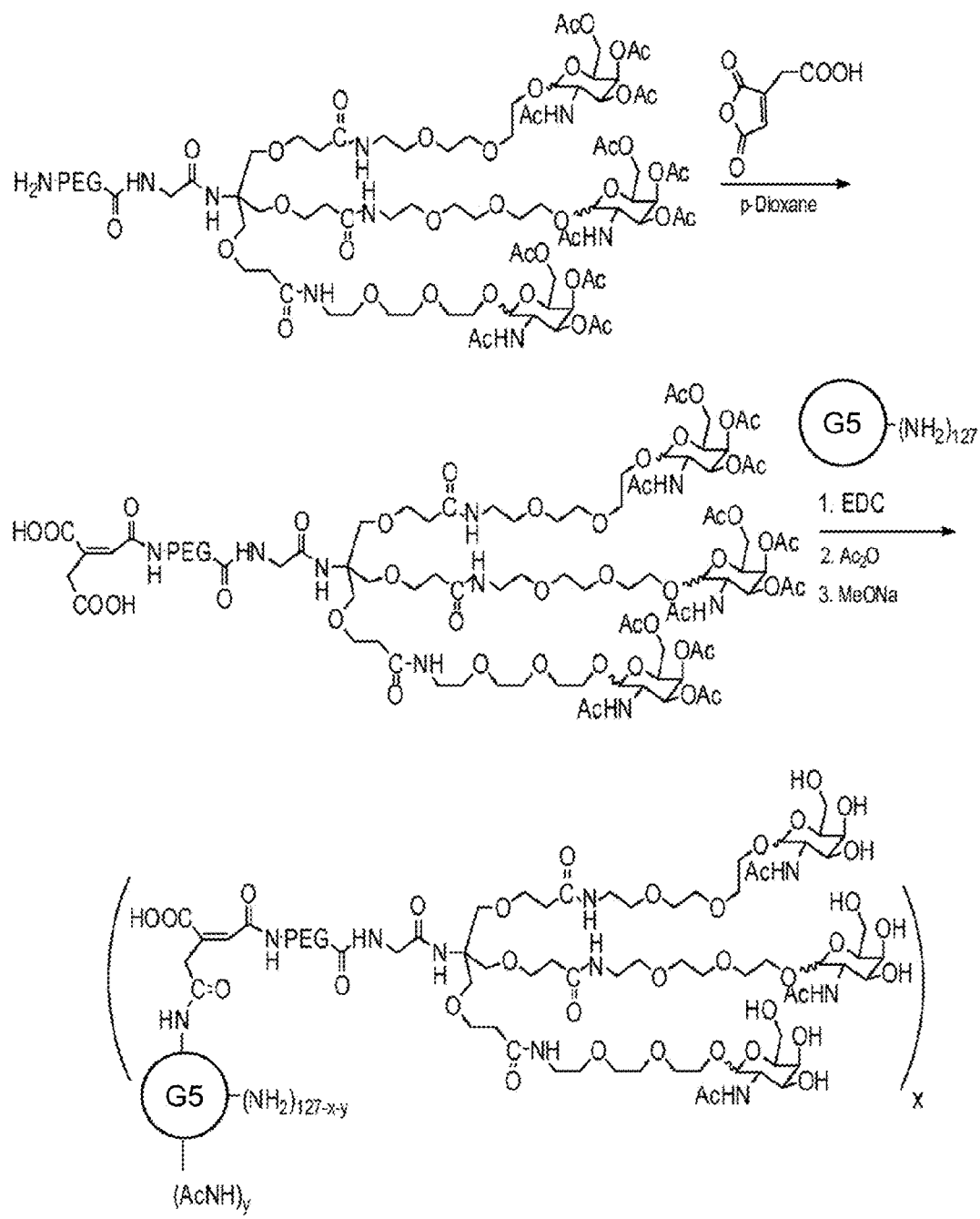
FIG. 14 represents a synthesis scheme for coupling TriGal-PEG chains to G5 for hepatic cell targeting.

For purposes of exemplifying this aspect, the non-degradable linkage in some instances comprises a PEG chain which binds to only one NAcGal. In other exemplary aspects, the non-degradable linkage comprises a PEG chain which binds to two or three NAcGal molecules. The synthesis schemes of such exemplary dendrimer conjugates comprising a PEG bridged to one NAcGal (monoGal-PEG) or three NAcGal molecules (TriGal-PEG) are provided in FIGS. 12 and 13. An exemplary synthesis scheme for coupling TriGal-PEG to a dendrimer is provided in FIG. 14.

In additional aspects, the tissue-specific targeting molecule (e.g., liver-specific targeting molecule) is attached through an acid hydrolysable linkage. Acid hydrolysable linkages are known in the art and are further described below under the section entitled "Functionalized Dendrimers to Increase Biodistribution."

In exemplary embodiments, about 0% to about 50% (e.g., about 0% to about 5%, about 0% to about 10%, about 5% to about 10%, about 10% to about 15%, about 10% to about 25%, about 15% to about 20%, about 20% to about 25%, about 25% to about 30%, about 25% to about 50%, about 30% to about 35%, about 35% to about 40%, about 40% to about 45% or about 45% to about 50%) of free dendrimer surface is conjugated to a liver-specific targeting molecule, wherein the liver specific targeting molecule is any of those described herein. In an embodiment, the invention provides for dendrimer conjugates wherein about 0% to about 50% of free dendrimer surface is conjugated to NAcGal. For example, the dendrimer conjugates have about 0% to about 5%, about 0% to about 10%, about 5% to about 10%, about 10% to about 15%, about 10% to about 25%, about 15% to about 20%, about 20% to about 25%, about 25% to about 30%, about 25% to about 50%, about 30% to about 35%, about 35% to about 40%, about 40% to about 45% or about 45% to about 50% of free dendrimer surface conjugated to NAcGal.

Tissue-Specific Cleavage

The dendrimer conjugates of the invention comprise a therapeutic agent that is associated through a covalent linkage that is cleavable with a tissue-specific enzyme such as the liver-specific CYP450 enzymes. An exemplary CYP450 enzyme is hepatic azoreductase.

The family of hepatic CYP450 enzymes is solely present in the liver, and therefore dendrimers which have a therapeutic agent associated via a CYP450 enzyme-reducible linker allow for liver-specific release of the therapeutic agent. The liver-targeting molecule facilitates endocytosis of the dendrimer into a hepatic cell. In the cytoplasm of the hepatic cell, the CYP450 enzymes reduce the linkage connecting the therapeutic molecule to the dendrimer thus producing a high concentration of free therapeutic agent in the hepatic cell. This strategy achieves liver tissue- and hepatic cancer cell-specific delivery of therapeutic molecules resulting in a higher therapeutic activity with lower side effects.

Azo Linkages

In some embodiments, the dendrimer conjugate is associated with (e.g., attached to) the agent (e.g., therapeutic agent or imaging agent) via an azo linkage which is cleavable by the tissue-specific enzyme (e.g., liver-specific enzyme). In particular aspects, the tissue-specific enzyme is a liver-specific enzyme, including, any of the hepatic CYP450 enzymes that are expressed only by liver cells.

In some aspects, the azo linkage of the dendrimer conjugates provided herein is an aromatic azo linkage. In particular aspects, the aromatic azo linkage comprises an azobenzene linkage, e.g., the aromatic azo linkage comprises a base structure:

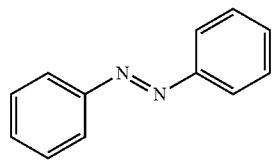

wherein, optionally, one or more carbon atoms of one or both benzene rings are substituted.

The Hammet equation describes a linear free-energy relationship relating reaction rates and equilibrium constants for many reactions of compounds containing phenyl groups with meta or para substituents. The linear correlation indicates that the change in free energy of activation of the reaction on introduction of a series of substituent groups is directly proportional to the change in free energy of ionization that is caused by the same series of substituents on benzoic acid. See, e.g., Carey and Sundberg, *Advanced Organic Chemistry*, 3$^{rd}$ ed., Plenum Press, New York, 1990; and Lowry and Richardson, *Mechanism and Theory in Organic Chemistry*, 3$^{rd}$ ed., Harper Collins, 1987.

In some aspects of the present invention, the azo linkage (e.g., in free form) is a meta- or para-substituted azobenzene linkage having a Hammet constant which is less than or about −0.20, e.g., less than or about −0.21, less than or about −0.22, less than or about −0.23, less than or about −0.24, less than or about −0.25, less than or about −0.26, less than or about −0.27, less than or about −0.28, less than or about −0.29, less than or about −0.30, less than or about −0.31, less than or about −0.32, less than or about −0.33, less than or about −0.34, less than or about −0.35, less than or about, −0.36, less than or about −0.37, less than or about −0.38, less than or about −0.39, less than or about −0.40, less than or about −0.41, less than or about −0.42, less than or about −0.43, less than or about −0.44, less than or about −0.45, less than or about −0.46, less than or about −0.47, less than or about −0.48, less than or about −0.49, less than or about −0.50. In some aspects, the Hammet constant is within the range of about −0.20 to about −0.50 or about −0.40 or about −0.30. In some aspects, the Hammet constant is within the range of −0.25 to about −1.5, e.g., −0.25 to about −1.4 or about −1.3 or about −1.2 or about −1.1 or about −1.0.

In some aspects, the azo linkage is an azobenzene linkage, or a substituted derivative thereof, comprising the structure of Formula I:

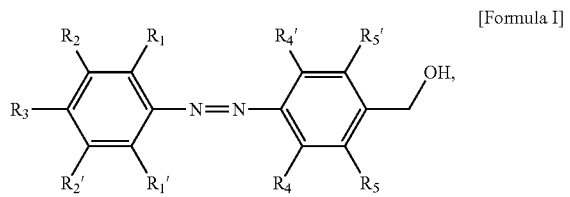

[Formula I]

wherein:
each of $R_1$ and $R_1'$ is independently H, $R_6$, or $OR_6$,
each of $R_2$ and $R_2'$ is independently H or a halogen atom,
$R_3$ is $OR_6$ or $NHR_6$ or $NR_6R_7$,
each of $R_4$ and $R_4'$ is independently H, a straight chained or branched C1-C6 alkyl or —CHOH,
each of $R_5$ and $R_5'$ is independently H or a straight chained or branched C1-C6 alkyl,
$R_6$ is a straight chained or branched C1-C6 alkyl, and
$R_7$ is a straight chained or branched C1-C6 alkyl, or a C3-, C4-, C5-, or C6-carbon ring.

As used herein, "C1-C6 alkyl" refers to a straight chained or branched chain of 1, 2, 3, 4, 5, or 6 carbon atoms. In some aspects, the C1-C6 alkyl is a straight chain of 1, 2, 3, 4, 5, or 6 carbon atoms, and in other aspects, the C1-C6 alkyl is a branched chain of three, four, five, or six carbon atoms.

As used herein, the halogen atom may be any of the atoms of Group 17 (according to the IUPAC classification system) of the Chemical Periodic Table. In some aspects, R2 is a halogen atom selected from the group consisting of Cl, Fl, and Br.

In certain exemplary aspects, $R_3$ is $OR_6$, and, optionally, $R_1$ or $R_1'$ is H, methyl, ethyl, or methoxy. In some aspects, wherein $R_3$ is $OR_6$, one of $R_4$, $R_4'$, $R_5$, and $R_5'$ is a C1-C6 alkyl, optionally, methyl.

In alternative aspects, $R_3$ is $NR_6R_7$, and, in particular alternative aspects, $R_7$ is phenyl or methyl. In some aspects, when $R_7$ is methyl, either $R_4$, $R_4'$, $R_5$, and $R_5'$ is a C1-C6 alkyl, optionally, methyl.

In other aspects, either or both of $R_4$ and $R_4'$ is/are —CH$_2$OH and the dendrimer is associated with one, two or three agents (e.g., therapeutic agents, imaging agents) through the aromatic azo linkage.

In exemplary aspects, each of $R_3$ and $R_1$ of Formula I is an electron donating group. In exemplary aspects, each of $R_3$ and $R_1$ modulate the Hammet constant. In exemplary aspects, $R_4$ of Formula I is an electron donating group (e.g., Cl or NO$_2$).

In particular aspects, the dendrimer conjugate is attached to the agent (e.g., therapeutic agent or imaging agent) via one of the azo linkages of Formula I shown in Table 2.

TABLE 2

| Oxygen Insensitive Linkage Structures | Expected Hammet Constant |
|---|---|
| Cl-substituted | 0.37 |
| unsubstituted | −0.22 |
| Me-substituted | −0.37 |
| Et-substituted | −0.51 |
| OMe-substituted | −0.53 |
| Ph,R-N- | <−0.60 |
| Me,R-N- | −0.80 |
| Me,R-N- with OMe | −1.13 |
| Me-substituted (other position) | −0.44 |
| Me, Me di-substituted | −0.44 |

TABLE 2-continued

| Oxygen Insensitive Linkage Structures | Expected Hammet Constant |
|---|---|
| 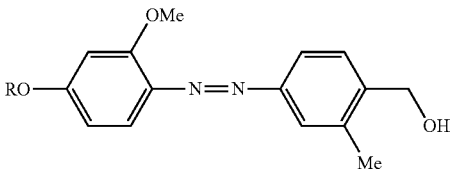 | −0.60 |
| 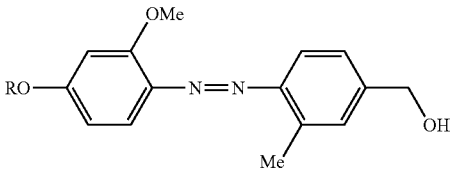 | −0.60 |
| 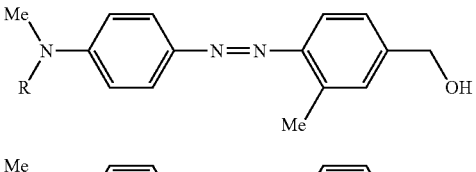 | −0.87 |
| 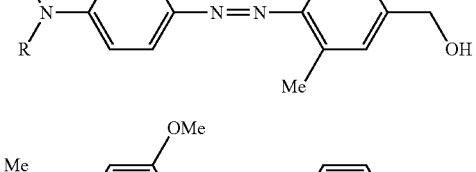 | −0.97 |
| 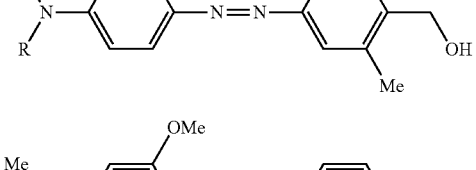 | −1.20 |
| 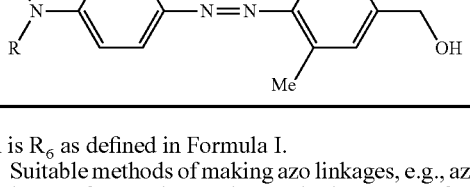 | −1.30 |

R is $R_6$ as defined in Formula I.

Figure 15:
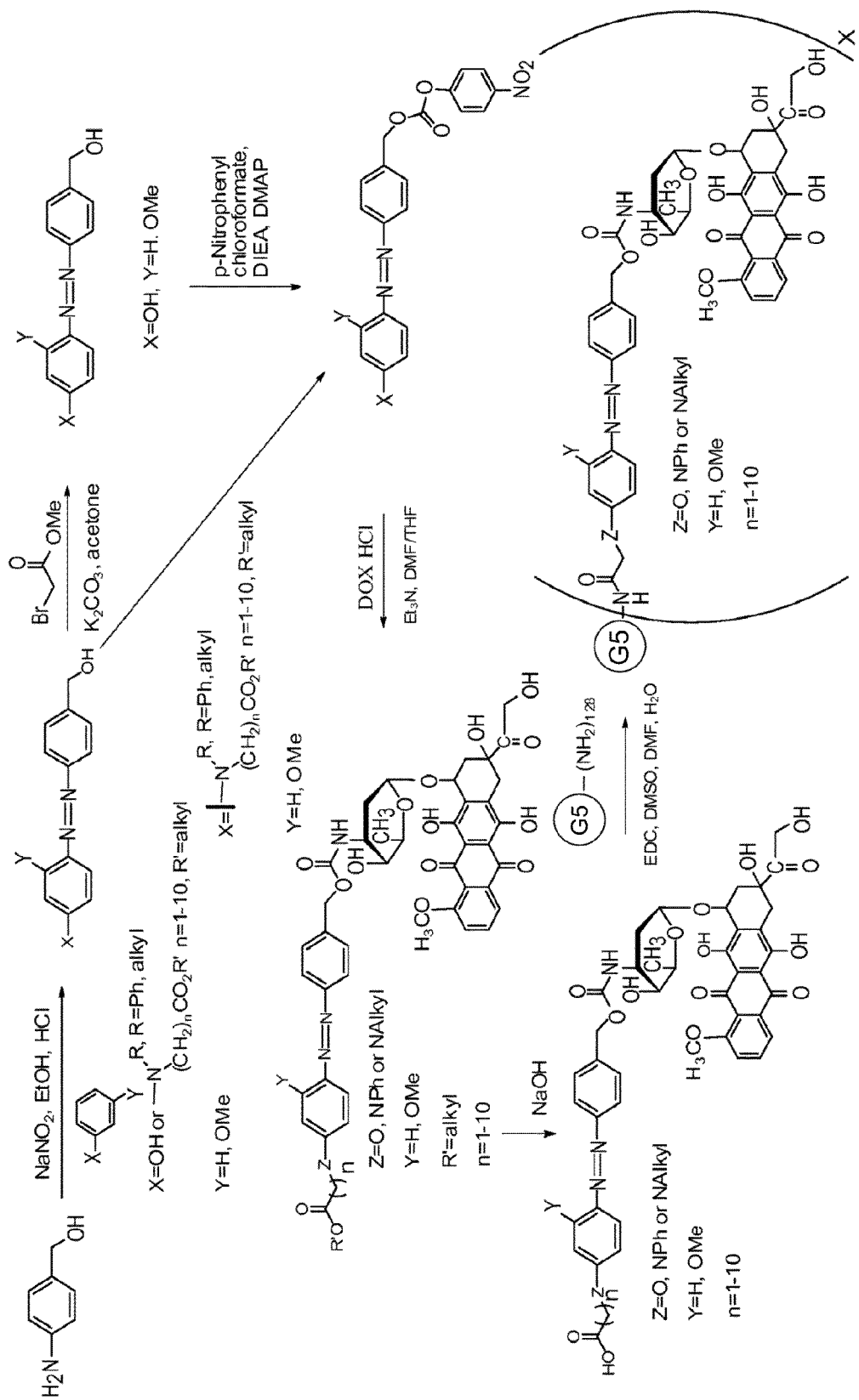
FIG. 15 represents a scheme for synthesis of G$_n$-DOX conjugates incorporating oxygen-insensitive azo linkers proposed in Table 2.

Suitable methods of making azo linkages, e.g., azobenzene linkages of Formula I are known in the art. See, for example, Krikova and Pisichenko, *Chem of Heterocyclic Compounds* 3(4): 244-248 (1967); U.S. Pat. No. 4,315,857, Grirrane et al., *Science* 322(5908) 1661-1664 (2008); and Priewisch and Ruck-Braun, *J. Org. Chem.* 70(6): 2350-2352 (2005). An exemplary synthesis scheme of making an azobenzene linkage is provided in FIG. 15.

In certain aspects, the dendrimer conjugate comprises a G5 PAMAM dendrimer attached to a therapeutic agent (e.g., an anti-cancer therapeutic agent (e.g., doxorubicin)) via one of the azo linkages in Table 2. In some aspects, the dendrimer conjugate further comprises a tissue-specific targeting molecule (e.g., a liver-specific targeting molecule) attached via a non-degradable linkage. In particular aspects, the liver-specific targeting molecule is NAcGal. In exemplary aspects, anys of the dendrimer conjugates shown in Table 1 comprise one of the azo linkages of Table 2.

Design of PAMAM-DOX Azo-Linkage:

Mammalian CYP450 enzymes are a family of flavoprotein enzymes localized in the liver and utilize NADH and NADPH as electron donors for reducing specific azo bonds. In one embodiment of the invention, a therapeutic agent such as DOX is conjugated to the $NH_2$ surface groups of a PAMAM dendrimer through an aromatic azo-linker coupled to a 1,6-self-eliminating spacer that will be selectively recognized and cleaved by CYP450 enzymes. Reduction of this aromatic azo linker will trigger an electronic cascade through the 1,6-self-eliminating spacer, which will result in a rapid release of the conjugated DOX molecules once the azo bond is reduced (FIG. 1).

Previous research has shown that self-eliminating spacers increase the efficacy of anticancer prodrugs due to faster hydrolysis kinetics. Additionally, this 1,6-self-eliminating spacer releases "clean" DOX molecules without any residual functional groups that may inhibit DOX activity in vitro or in vivo. The invention also provides for NAcGal moieties conjugated to the $NH_2$ surface groups in PAMAM-DOX conjugates for active binding to the ASGPR expressed on the surface of hepatic cancer cells. As shown in FIG. 1, the design for PAMAM-DOX conjugates allows us to optimize the number of free surface groups $(NH_2)_n$, the therapeutic load $(DOX)_D$, and number of targeting ligands $(NAcGal)_x$ to achieve the highest therapeutic activity in vitro and in vivo. This design also allows the attachment of fluorescent labels or radioisotopes to free $NH_2$ surface groups so one can visualize, track, and quantify conjugate concentration in biological samples.

In one embodiment of the invention, the PAMAM-DOX conjugates are administered by intravenous injection into the systemic circulation and access the liver through the hepatic artery. Similar to other polymer therapeutics, PAMAM-DOX conjugates utilize the pathology of hepatic cancer to effectively permeate across tumor's leaky vasculature and accumulate in cancerous tissue through the enhanced permeation and retention effect evident in solid tumors. NAcGal-targeted PAMAM-DOX conjugates will bind to ASGPR expressed on the surface of hepatic cancer cells through the attached NAcGal moieties, which triggers cellular uptake via receptor-mediated endocytosis and internalization of the PAMAM-DOX conjugates into the cytoplasm of hepatic cancer cells. In the hepatic cell cytoplasm, the CYP450 enzymes will reduce the linkage thus producing a high concentration of free anticancer drug in hepatic cancer cells.

Functionalized Dendrimers to Increase Biodistribution

In some embodiments of the present invention, the dendrimer conjugate comprises a polyalkylene glycol chain, e.g., a polyethylene glycol (PEG) chain. The polyalkylene glycol chain, e.g., PEG chain, in some aspects is associated with the dendrimer through an acid hydrolysable linkage. As used herein, the term "acid hydrolysable linkage" refers to a linkage of which one or more bonds of the linkage is/are broken when placed into an acidic environment. The pH of the acidic environment in some aspects is a pH less than or about 6.5, less than or about 6.0, less than or about 5.5, less than or about 5.0, or less than or about 4.0. Acid hydrolysable linkages are known in the art. See, e.g., Shen and Ryser, *Biochem and Biophys Res Comm* 102(3): 1048-1054 (1981); Bailey and Zhou, *Polymeric Drugs and Drug Delivery Systems*, Chapter 25, American Chemical Society, 1991, pages 285-300; Singh and Erickson, *Therapeutic Antibodies: Methods and Protocols* Vol 525, pages 1-23, 2009. In some aspects, the acid hydrolysable linkage is a cis-aconityl linkage, an acetal linkage, or a hydrazone linkage.

In alternative embodiments, the polyalkylene glycol chain, e.g., PEG chain, is associated with the dendrimer through a non-degradable chain. The non-degradable linkage in some aspects is selected from the group consisting of: a thiourea moiety, a urea moiety, a carbamate moiety, a linkage from terminal epoxide opening, an amide linkage through peptide coupling, a linkage by formation of the Shiff base, a linkage formed by reduction of Shiff base and a linkage generated by "click" chemistry.

In addition to the association of tissue-specific targeting molecules to the dendrimer conjugates of the invention, the dendrimers are functionalized to shift the biodistribution profile to achieve tissue-specific accumulation and retention. The dendrimer conjugates may comprise one or more functional groups in order to shift biodistribution.

In an exemplary embodiment the dendrimer conjugates comprise a hepatic-tumor targeting molecule. To functionalize these dendrimer conjugates to increase hepatic tumor accumulation and retention, the surface $NH_2$ groups of the dendrimer are in various aspects, acetylated and/or pegylated. The addition of these moieties to the dendrimer conjugates increases the net volume and thereby increases extravasation of the dendrimer conjugate into tumor tissue. For example, multiple PEG chains are conjugated to the surface of the dendrimer to increase its net hydrodynamic volume. The dendrimer conjugates of the invention are, in other aspects, functionalized with one type of moiety or more than one type of moiety or the dendrimer conjugates optionally do not contain any functionalization moieties.

In one embodiment, the invention provides for functionalized dendrimer conjugates wherein about 0% to about 25% of the polymer surface $NH_2$ groups contain PEG chains. For example, the functionalized dendrimer conjugates have PEG chains on about 0% to about 5%, about 0% to about 10%, about 0% to about 20%, about 5% to about 10%, about 5% to about 20%, about 5% to about 25%, about 10% to about 15%, about 10% to about 20% or about 20% to about 25% of the polymer surface $NH_2$ groups. An exemplary scheme for conjugation of PEG chains to the dendrimer is set out in FIG. 4D.

The molecular weight of the PEG chains ranges from about 0.5 kD to about 10 kD. For example, the molecular weight of the PEG chain is about 0.5 kD to about 1.0 kD, about 1 kD to about 2.5 kD, about 2.5 kD to about 5 kD, about 5 kD to about 7.5 kD, about 5 kD to 10 kD, about 7.5 kD to about 10 kD, about 8 kD to about 10 kD or about 9 kD to about 10 kD.

In another embodiment, the invention provides for functionalized dendrimer conjugates, which are acetylated to cover about 0% to about 90% of the polymer surface $HN_2$ groups. For example, the functionalized dendrimer conjugates are acetylated on about 0% to about 5%, about 0% to about 10%, about 0% to about 20%, about 0% to about 30%, about 0% to about 40%, about 0% to about 50%, about 0% to about 60%, about 0% to about 70%, about 0% to about 80%, about 5% to about 10%, about 5% to about 20%, about 10% to about 25%, about 20% to about 40%, about 25% to about 50%, about 30% to about 60%, about 40% to about 70%, about 50% to about 75%, about 80% to about 90% of the polymer surface $NH_2$ groups. An exemplary scheme for acetylation of the dendrimers is set out in FIG. 4B.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. In general, the term "about" is given its ordinary meaning of approximately.

For example, the invention provides for the following functionalized dendrimers for drug delivery to the hepatic tumors: acetylated Gn [Gn-$(NHAc)_{1-90\%}$], acetylated Gn with surface-anchored PEG chains [Gn-$(NHAc)_{1-90\%}$-$(PEG)_{1-25\%}$], acetylated and NAcGal-targeted Gn [Gn-$(NHAc)_{1-90\%}$-$(NAcGal)_{1-50\%}$], as well as acetylated, PEGylated and NAc-Gal-targeted Gn [Gn-$(NHAc)_{1-90\%}$-$(NAcGal)_{1-50\%}$-$(PEG)_{1-25\%}$] dendrimers. The percentages referred to the percent surface positions of the dendrimer occupied by the label (Fl or $^{14}C$-Acetamide), galactosylation (NAcGal), acetylation (NHAc or Ac) or PEGylation (PEG). Particular exemplary dendrimer conjugates of the invention include G5-$(Fl)_6$, G5-$(Fl)_6$-$(NHAc)_{110}$, G5-$(Fl)_6$-$(NAcGal)_{28}$, G5-$(Fl)_6$-$(NAcGal)_{58}$, $G_5$-$(NHAc)_{93}$-$(PEG)_{10}$, $G_5$-$(Fl)_6$-$(NHAc)_{90}$-$(PEG)_{13}$, $G_5$-$(NHAc)_{103}$, $G_5$-$(NHAc)_{85}$-$(NAcGal)_{14}$, G5-$(Fl)_6$-$(NHAc)_{60}$-$(NAcGal)_{41}$, $G_5$-$(Fl)_6$-$(NHAc)_{83}$-$(NAcGal)_{18}$, G5-$(Fl)_6$-$(NHAc)_{83}$-$(NAcGal)_{14}$, and $G_5$-$(Fl)_5$-$(NHAc)_{60}$-$(NAcGal)_{56}$.

In some aspects of the present invention, the polyalkylene glycol chain, e.g., the PEG chain, comprises two ends of which a first end is (directly or indirectly) attached to the dendrimer and a second end is (directly or indirectly) attached to one or more (e.g., one, two, three, four, five, six, seven, eight, or more) tissue-specific targeting molecules. For example, the dendrimer conjugate in some aspects comprises a mono-Gal-PEG or a TriGal-PEG. In alternative aspects, a first end of the polyalkylene glycol chain, e.g., the PEG chain, is (directly or indirectly) attached to the dendrimer and a second end is free of attachment to another molecule. In some aspects, the polyalkylene glycol chain, e.g., the PEG chain, is (directly or indirectly) attached to the dendrimer through an acid hydrolysable linkage, such as any of those known in the art or described herein. Further description of these aspects are found herein under the section entitled "Liver-Specific Targeting Molecules."

Therapeutic Agents

A wide range of therapeutic agents find use with the present invention. Any therapeutic agent that can be associated with a dendrimer conjugate of the invention may be delivered using the methods, systems, and compositions of the present invention. To illustrate delivery of therapeutic agents, the following discussion focuses mainly on the delivery of DOX for the treatment of HCC. Also discussed are various photodynamic therapy compounds, and various antimicrobial and antiviral compounds.

Doxorubicin (DOX) is a cytotoxic anthracycline antibiotic isolated from cultures of *Streptomyces peucetius* var. *caesius* that has anti-neoplastic activity. DOX consists of a naphthacenequinone unit linked through a glycosidic bond at position 7 to an amino sugar, daunosamine. Chemically, DOX hydrochloride is: 5,12-Naphthacenedione, 10-[(3-amino-2,3, 6-trideoxy-α-L-lyxo-hexopyranosyl)oxy]-7,8,9,10-tetrahydro-6,8,11-trihydroxy-8-(hydroxylacetyl)-1-methoxy-, hydrochloride (8S-cis). DOX binds to nucleic acids, presumably by specific intercalation of the planar anthracycline unit with the DNA double helix. The anthracycline group is lipophilic but the saturated end of the multi-cyclic system contains abundant hydroxyl groups from the amino sugar producing a hydrophilic center. The molecule is amphoteric, containing phenolic hydroxyl-groups as an acidic function and a basic function as the sugar amino group. It binds to cell membranes as well as plasma proteins.

Any pharmaceutical that is routinely used in a cancer therapy may be used in the present invention. In treating cancer according to the invention, the therapeutic component of the dendrimer conjugate may comprise compounds including, but not limited to, cisplatin, taxol, adriamycin (doxorubicin), 5-fluorouracil, etoposide, camptothecin, actinomycin-D, and mitomycin C. The agent may be prepared and used as a combined therapeutic composition, or kit, by combining it with the immunotherapeutic agent.

In some embodiments of the present invention, the dendrimer may comprise one or more agents that directly cross-link nucleic acids to facilitate DNA damage leading to a synergistic, anti-neoplastic agent. Agents that damage DNA also include compounds that interfere with DNA replication, mitosis and chromosomal segregation. Such chemotherapeutic compounds include adriamycin, also known as doxorubicin, etoposide, verapamil, podophyllotoxin and the like.

Agents that disrupt the synthesis and fidelity of nucleic acid precursors and subunits also lead to DNA damage and find use as chemotherapeutic agents in the present invention. A number of nucleic acid precursors have been developed such as 5-fluorouracil (5-FU).

The anti-cancer therapeutic agents that find use in the present invention are those that are amenable to incorporation into dendrimeric structures or are otherwise associated with dendrimer structures such that they can be delivered into a subject, tissue, or cell without loss of fidelity of its anti-cancer effect. For a more detailed description of cancer therapeutic agents such as a platinum complex, verapamil, podophyllotoxin, carboplatin, procarbazine, mechlorethamine, cyclophosphamide, camptothecin, ifosfamide, melphalan, chlorambucil, busulfan, nitrosourea, adriamycin, dactinomycin, daunorubicin, doxorubicin, bleomycin, plicamycin, mitomycin, etoposide (VP16), tamoxifen, taxol, transplatinum, 5-fluorouracil, vincristine, vinblastine, methotrexate, gemcitabine and other similar anti-cancer agents, those of skill in the art are referred to any number of instructive manuals including, but not limited to, the Physician's Desk reference and to Goodman and Gilman's "Pharmaceutical Basis of Therapeutics" ninth edition, Eds. Hardman et al., 1996.

Additional therapeutic agents include without limitation analgesics and analgesic combinations, anesthetics, anorexics, anti-allergics, antiarthritics, antiasthmatic agents, antibiotics, anticholinergics, anticonvulsants, antidepressants, antihemophilics, antidiabetic agents, antidiarrheals, antifungals, antigens, antihistamines, antihypertensives, anti-inflammatories, antimigraine preparations, antinauseants, antineoplastics, antiparkinsonism drugs, antiprotozoans, antipruritics, antipsychotics, antipyretics, antispasmodics, antivirals, calcium channel blockers, cardiovascular preparations, central nervous system stimulants, contraceptives, cough and cold preparations including decongestants, diuretics, enzyme inhibitors, enzymes, genetic material including DNA and RNA, growth factors, growth hormones, hormone inhibitors, hypnotics, immunoactive agents, immunosuppressive agents, microbicides, muscle relaxants, parasympatholytics, peptides, peripheral and cerebral vasodilators, proteins, psychostimulants, receptor agonists, sedatives, spermicides and other contraceptives, steroids, sympathomimetics, tranquilizers, vaccines, vasodilating agents including general coronary, viral vectors, small organic molecules, and combinations thereof.

Antiviral agents include nucleoside phosphonates and other nucleoside analogs, 5-amino-4-imidazolecarboxamide ribonucleotide (AICAR) analogs, glycolytic pathway inhibitors, anionic polymers, and the like, more specifically: anti-herpes agents such as acyclovir, famciclovir, foscarnet, ganciclovir, idoxuridine, sorivudine, trifluridine, valacyclovir, and vidarabine; and other antiviral agents such as abacavir, adefovir, amantadine, amprenavir, cidofovir, delviridine, 2-deoxyglucose, dextran sulfate, didanosine, efavirenz, entecavir, indinavir, interferon alpha and PEGylated interferon, interferon alfacon-1, lamivudine, nelfinavir, nevirapine, ribavirin, rimantadine, ritonavir, saquinavir, squalamine, stavudine, telbivudine, tenofovir, tipranavir, valganciclovir, zalcitabine, zidovudine, zintevir, and mixtures thereof. Still other antiviral agents are glycerides, particularly monoglycerides, which have antiviral activity. One such agent is monolaurin, the monoglyceride of lauric acid.

Anti-inflammatory agents include corticosteroids, e.g., lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, or methylprednisolone, or higher potency corticosteroids such as clobetasol propionate, betamethasone benzoate, betamethasone diproprionate, diflorasone diacetate, fluocinonide, mometasone furoate, triamcinolone acetonide, and mixtures thereof.

Antibiotic agents include those of the lincomycin family, such as lincomycin per se, clindamycin, and the 7-deoxy,7-chloro derivative of lincomycin (i.e., 7-chloro-6,7,8-trideoxy-6-[[(1-methyl-4-propyl-2-pyrrolidinyl)carbonyl] amino]-1-thio-L-threo-alpha-D-galacto-octopyranoside); other macrolide, aminoglycoside, and glycopeptide antibiotics such as erythromycin, clarithromycin, azithromycin, streptomycin, gentamicin, tobramycin, amikacin, neomycin, vancomycin, and teicoplanin; antibiotics of the tetracycline family, including tetracycline per se, chlortetracycline, oxytetracycline, demeclocycline, rolitetracycline, methacycline and doxycycline; and sulfur-based antibiotics, such as the sulfonamides sulfacetamide, sulfabenzamide, sulfadiazine, sulfadoxine, sulfamerazine, sulfamethazine, sulfamethizole, and sulfamethoxazole; streptogramin antibiotics such as quinupristin and dalfopristin; and quinolone antibiotics such as ciprofloxacin, nalidixic acid, ofloxacin, and mixtures thereof.

Antifungal agents include miconazole, terconazole, isoconazole, itraconazole, fenticonazole, fluconazole, ketoconazole, clotrimazole, butoconazole, econazole, metronidazole, 5-fluorouracil, amphotericin B, and mixtures thereof.

Antihemophilic agents include antifibrinolytic amino acids, aprotinin, 1-deamino-8-d-arginine vasopressin, aminocaproic acid, tranexamic acid and conjugated estrogens, and mixtures thereof (Mannucci et al. (1998). *New. Eng. J. Med.* 339:245)

Other anti-infective agents include miscellaneous antibacterial agents such as chloramphenicol, spectinomycin, polymyxin B (colistin), and bacitracin, anti-mycobacterials such as such as isoniazid, rifampin, rifabutin, ethambutol, pyrazinamide, ethionamide, aminosalicylic acid, and cycloserine, and antihelminthic agents such as albendazole, oxfendazole, thiabendazole, and mixtures thereof.

Any of the therapeutic agents may be administered in the form of a salt, ester, amide, prodrug, conjugate, active metabolite, isomer, fragment, analog, or the like, provided that the salt, ester, amide, prodrug, conjugate, active metabolite, isomer, fragment, or analog is pharmaceutically acceptable and pharmacologically active in the present context. Salts, esters, amides, prodrugs, conjugates, active metabolites, isomers, fragments, and analogs of the agents may be prepared using standard procedures known to those skilled in the art of synthetic organic chemistry and described, for example, by J. March, Advanced Organic Chemistry: Reactions, Mechanisms and Structure, 5th Edition (New York: Wiley-InterScience, 2001).

Pharmaceutically acceptable salts include the acid addition salts (formed with the free amino groups of the peptide) and which are formed with inorganic acids such as, e.g., hydrochloric or phosphoric acids, or such organic acids as acetic, oxalic, tartaric, mandelic. Salts formed with the free carboxyl groups may also be derived from inorganic bases such as, e.g., sodium, potassium, ammonium, calcium, or ferric hydroxides, and such organic bases as isopropylamine, trimethylamine, 2-ethylamino ethanol, histidine, and procaine.

Administration

The dendrimer conjugates of the invention are used in conjunction with appropriate salts and buffers to render delivery of the compositions in a stable manner to allow for uptake by target cells. Buffers also are employed when the dendrimer conjugates are introduced into a patient. Aqueous compositions comprise an effective amount of the dendrimer conjugates dispersed in a pharmaceutically acceptable carrier or aqueous medium. The phrases "pharmaceutically" or "pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. Except insofar as any conventional media or agent is incompatible with the vectors or cells of the present invention, its use in therapeutic compositions is contemplated. Supplementary active ingredients may also be incorporated into the compositions.

Generally, this entails preparing compositions that are essentially free of pyrogens, as well as other impurities that could be harmful to humans or animals. However, in some embodiments of the present invention, a straight dendrimer formulation may be administered using one or more of the routes described herein. The compositions comprising the dendrimer conjugates of the invention may be delivered via any suitable method, including, but not limited to intramuscular, subcutaneous, intravenous, intraperitoneal, intratracheal, intrathecal, transdermal, oral, rectal, vaginal, sublingual, intranasal, orthotopic, transmucosal (including buccal), transarterial infusion or transarterial chemoembolization modes of administration.

Compositions of the invention may be administered as injectables, either as liquid solutions or suspensions; solid forms suitable for solution in, or suspension in, liquid prior to injection may also be prepared. Compositions of the invention also may be administered intravenously. The preparation may also be emulsified. The active immunogenic ingredient is often mixed with excipients, which are pharmaceutically acceptable and compatible with the active ingredient. Suitable excipients are, e.g., water, saline, dextrose, glycerol, ethanol, or the like and combinations thereof.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Compositions may also be administered parenterally, intraperitoneally or intratumorally. Solutions of the active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The compositions in some embodiments are administered to a subject through hepatic arterial infusion (HAI). In some aspects, a catheter is placed into an artery in the groin that leads directly to the liver, and the dendrimer conjugates are administered via the catheter. In some aspects, the compositions are administered via transarterial chemoembolization (TACE, a.k.a., hepatic artery chemoembolization (HACE)) in which hepatic artery embolization is combined with hepatic artery chemoinfusion. In some aspects, HAI is combined with TACE to achieve administration of the compositions provided herein. Formulations may be presented in unit-dose or multi-dose containers, for example, sealed ampules and vials and may be stored in a freeze-dried condition requiring only the addition of the sterile liquid carrier immediately prior to use.

Upon formulation, the dendrimer compositions are administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered, if necessary, and the liquid diluent first rendered isotonic with sufficient saline or glucose. These particular aqueous solutions are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). In some embodiments of the present invention, the active particles or agents are formulated within a therapeutic mixture to comprise about 0.0001 to 1.0 milligrams, or about 0.001 to 0.1 milligrams, or about 0.1 to 1.0 or even about 10 milligrams per dose or so. Multiple doses may be administered.

Liver Disorders

The dendrimer conjugates of the present invention may be used for treatment in any liver disorder, liver cancer or liver tumor. For example, the dendrimer conjugates may be used to treat liver cancers such as HCC, fibrolamellar carcinoma, secondary liver cancer and cholangiocarcinoma (bile duct tumor).

The dendrimer conjugates of the invention may be used to treat cirrhosis including primary biliary cirrhosis, primary sclerosing cholangitis, autoimmune hepatitis, non-alcoholic fatty liver disease (non-alcoholic steatohepatitis), hemochromatosis, cryptogenic chirrhosis, secondary biliary cirrhosis, liver fibrosis and biliary fibrosis. In addition, the dendrimer conjugates of the invention may be used to treat genetic liver diseases including Wilson disease, Alpha-1 antitrypsin deficiency, Crigler-Naijer syndrome and Gilbert syndrome. The dendrimer conjugates of the invention may also be used to treat hepatitis A, hepatitis B, hepatitis C, hepatitis D, hepatitis E, hepatitis G and alcoholic hepatitis.

Assays to Evaluate Anti-Cancer Activity

The invention provides for a dendrimer conjugate that is associated with a therapeutic agent, wherein the therapeutic agent has anti-cancer or anti-neoplastic activity, such as DOX. The anticancer activity of the dendrimer conjugates of the invention may be evaluated using any method known in the art. The following description is described in terms of the effect of the PAMAM-DOX conjugates of the invention, but any dendrimer conjugate associated with any anti-cancer or anti-neoplastic agent may be substituted.

The anti-cancer activity may be evaluated using a method which compares the PAMAM-DOX conjugates with free DOX using tumor models such as HepG2 and Hep3B human cancer cells cultured following published protocols (Darlington et al. (1987). *In Vitro Cellular and Developmental Biology: Journal of the Tissue Culture Association.* 23:349). The anti-cancer activity may also be evaluated using an animal tumor model such as those reviewed in Heindryckx et al. (2009). *Intl. J. Exp. Path.* 90:367.

Animal models of HCC include chemically-induced HCC in mice by administration of an agent such as administration of N-nitrodiethylamine (DEN), a peroxidome proliferators, aflatoxin $B_1$, thioacetamide or carbon tetrachloride. HCC may also be induced in mice that are subjected to a long-term choline deficient diet. Xenograft models of HCC are created by injecting human cancer cells in immune-deficient mice via ectopic implantation, orthopic implantation or using the hollow fibre model. Transgenic mouse models of HCC include transfection of a viral gene such as HBx or HCV, overexpression of an oncogene such as c-myc, E2F1, β-catenin, H-ras, overexpression of a growth factor gene such as TGF-α, EGF, FGF19 or SV40 T-antigen or knock-out of the ELF gene which is involved in TGF-β signaling. HCC animal models are also generated by creating a tumor environment and mimicking the injury-fibrosis of HCC such as transgenic mice expressing a transport-impaired alpha-1 antitrypsin (ATT) gene which leads to decreased ATT activity, transgenic mice that are deficient in the phosphatase and tensine homolog (PTEN) tumor suppressor gene, transgenic mice overexpressing platelet-derived growth factor (PDGF), transgenic mice overexpressing TGF-β and glycine N-methyltransferase (GMNT) knock-out mice which have unregulated DNA methylation.

Anti-cancer activity of the dendrimer conjugates of the invention will be based on their ability to inhibit cell proliferation, reduce long-term cell survival and induce apoptotic cell death. In addition, cellular uptake, intracellular concentration, and sub-cellular distribution profile between free DOX and different PAMAM-DOX conjugates are also investigated.

1. Cell Proliferation & Long-Term Survival Assays:

Cell proliferation may be measured using any known assay, such as manual/visual cell counting or using flow cytometry, measuring metabolic activity, e.g. MTT, XTT, or WST-1 assays, and measuring DNA synthesis using 5'-Bromo-2-deoxy-uridine (BrdU) labeling or [$^3$H] thymidine incorporation. For example, HepG2/Hep3B cells cultured in 24-well plates are treated with increasing doses (0.01, 0.1, 1.0, 5.0, or 10 nM) of free DOX or the corresponding amount of PAMAM-DOX conjugates of the invention for variable exposure times (6, 12, 24, or 48 hours) under normal culture conditions. The cells are harvested and the viable cells are counted to calculate % inhibition in cell proliferation compared to untreated cells using a procedure such as staining with trypan blue (Cook et al. (1989) *Anal. Biochem.* 179:1). The viable cells will be cultured for 14 days before staining and visually counting the number of formed colonies, which will reflect cell's ability to recover and grow after each DOX treatment. The initial number of viable cells and the final number of colonies will reflect immediate and long-term effects of different DOX treatments, respectively. The $IC_{50}$ (the concentration that results in 50% cancer cell death compared to the control group) for free DOX and PAMAM-DOX conjugates also is calculated.

Apoptosis Assays:

Induction of apoptosis by the dendrimer conjugates of the invention may be evaluated using any method known in the art. For example, cellular changes associated with the multiple phases of cancer cell death are quantitatively monitored to compare the anticancer activity of different PAMAM-DOX conjugates to that of free DOX. The following exemplary cellular characteristics are measured: i) the appearance of phosphatidylserine (death marker) on cell surface using flow cytometry (Engeland et al. (1996). *Cytometry.* 24:131), ii) mitochondrial leakage of caspase-3 and/or caspase-7 enzymes (Karvinen et al. (2002). *J. Biomol. Screening.* 7:223), iii) the collapse in mitochondrial membrane potential (Reers et al. (1991). *Biochem.* 30:4480; Reers et al. (1995). *Methods in Enzymology.* 260:406), iv) chromatin condensation (nuclear death) using Hoechst staining (Mocharla et al. (1987). *Nucleic Acids Research.* 15:10589; Sterzel et al. (1985). *Analytical Biochem.* 147:462), DNA laddering, cell membrane degradation by staining with annexin-V and v) the increase in pro-apoptotic (Bax, Bak, Bok/Mtd) and the suppression in anti-apoptotic (Bcl-2, Bcl-xL, Mcl-1, Bcl-w, A1/Bfl-1) gene expression using RT-PCR analysis (Mullis et al. (1987). *Methods in Enzymology.* 155:335; Saiki et al. (1988). *Science.* 239:487). In addition, the cells can be evaluated using TUNEL staining to visualize and count the number of apoptotic nuclei in tumor sections (Negoescu et al. (1996). *J. Histochemistry Cytochemistry.* 44:959).

Cellular Uptake Studies:

Cellular uptake studies allow for: i) measure the total concentration of DOX molecules accumulated within cancer cells based on its inherent fluorescence ($\lambda_{ex}$=470 nm, $\lambda_{em}$=585 nm) using flow cytometry, and ii) "map" the differences in intracellular DOX distribution profiles between different treatments using laser scanning confocal microscopy. It is expected that the PAMAM-DOX conjugates of the invention will produce a higher cytoplasmic and nuclear concentration of DOX molecules compared to equal doses of free DOX.

Evaluation of In Vivo Anticancer Activity:

Evaluation of in vivo anti-cancer activity of the PAMAM-DOX conjugates of the inventions should display a statistically higher activity compared to free DOX in vitro. In addition, tumor-specific accumulation and retention of different PAMAM-DOX conjugates are measured and compared to accumulation and retention in other organs. The activity of different PAMAM-DOX conjugates is also evaluated based on their ability to induce apoptotic cancer cell death and reduce tumor size. Biocompatibility of PAMAM-DOX conjugates is determined through histological examination of different body organs and measuring blood levels of cardiac toxicity markers typically associated with DOX treatment. For example, in vivo studies will utilize a hepatic cancer animal model as described in above. For example, $10^7$ cells of human hepatic cancer cells are injected directly into the liver of male nude mice and allow them to grow for 10-12 days into a 100 $mm^3$ mass (Symon et al. (2001). *Intl. J. Radiation Oncology, Biology, Physics.* 50:473).

After intravenous injection of a daily dose of 12 mg/kg of free DOX or PAMAM-DOX conjugates into the animal model, the animals are sacrificed and the tumor tissue is harvested. The change in tumor size/volume in response to each treatment [tumor volume ($mm^3$)=length×width/2] is measured. The extent of cancer cell death in excised tumor tissue will be evaluated using TUNEL staining to visualize and count the number of apoptotic nuclei in tumor sections. The amount of pro-apoptotic (Bax, Bak, Bok/Mtd) and anti-apoptotic (Bcl-2, Bcl-xL, Mcl-1, Bcl-w, A1/Bfl-1) proteins present in tumor tissues are quantitated using immunohistochemical staining and western blotting techniques (Kovar et al. (2004). *J. Cont. Rel.* 90:301). Free PAMAM carriers and saline treatments may be used as control groups in all tests. PAMAM-DOX conjugates of the invention that caused a reduction in tumor size compared to an equal dose of free DOX are considered to be therapeutically effective.

Biocompatibility of PAMAM-DOX Conjugates:

To analyze the biocompatibility of the PAMAM-DOX conjugates of the invention, these conjugates are injected into healthy male balb-C mice and the animals are monitored for any signs of toxicity for 24 hours. The animals are sacrificed and their major organs (brain, heart, lungs, kidneys, liver, spleen, bone, and bone marrow) are collected. These tissues are fixed, stained, and examined for signs of toxicity. In addition, changes in leukocyte count and blood levels of LDH and CK enzymes (cardiac toxicity markers) are measured as quantitative indicators of toxicity (Bishop et al. (1971). *Clinical Chemistry* 17:548). The toxicity of PAMAM-DOX conjugates is also compared to equal doses of free DOX, free PAMAM carriers and saline treatments as controls. It is expected that that PAMAM-DOX conjugates will be significantly less toxic compared to free DOX due to selective accumulation in tumor tissue instead of non-specific distribution to the heart and other body organs.

Diagnostics

In some embodiments of the present invention, the dendrimer conjugate comprises a label or an imaging agent. Without being bound to a particular theory, it is contemplated that such dendrimer conjugates comprising a label or imaging agent is useful for imaging a tissue, e.g., a liver tissue, or cells thereof. Accordingly, the present invention additionally provides a method of imaging a liver cell of a liver tissue. In certain aspects, the method comprises administering to a subject a dendrimer conjugate comprising a label or imaging agent, a composition comprising the same, or a pharmaceutical composition comprising the same, of the present invention in an amount effective to image the liver cell. A method of diagnosing a disease, e.g., a liver disorder, is further provided herein. The diagnostic method comprises imaging a liver cell of a liver tissue, as described herein.

In some embodiments of the present invention, the dendrimer conjugates comprise a label or a module that can be readily imaged for use in diagnostic methods. The present invention is not limited by the nature of the imaging component used.

In some embodiments of the present invention, imaging labels comprise Positron Emission Tomography (PET) scanning isotopes such as $^{18}F$, $^{66}Ga$, $^{68}Ga$, $^{64}Cu$, $^{86}Y$ and $^{124}I$ (Erdi (2007). *Current Medical Imaging Reviews,* 3:3).

In some embodiments of the present invention, imaging modules comprise surface modifications of quantum dots (See e.g., Chan and Nie (1998). *Science* 281:2016) such as zinc sulfide-capped cadmium selenide or other colloidal compounds comprised of cadmium sulfide, zinc selenide, cadmium telluride or lead selenide coupled to biomolecules (Sooklal et al. (1998). *Adv. Mater.* 10:1083; Medintz et al. (2005). *Nature Materials.* 4:435).

In one embodiment, dendrimer-conjugates comprise dendrimers produced according to the "nanocomposite" concept (Balogh et al. (1997). *Proc. of ACS PMSE.* 77:118; Balogh and Tomalia (1998). *J. Am. Che. Soc.* 120:7355). In these embodiments, dendrimers are produced by reactive encapsulation where a reactant is preorganized by the dendrimer template and is then subsequently immobilized in/on the polymer molecule by a second reactant. Size, shape, size distribution and surface functionality of these nanoparticles are determined and controlled by the dendritic macromolecules. These materials have the solubility and compatibility of the host and have the optical or physiological properties of the guest molecule (i.e., the molecule that permits imaging). While the dendrimer host may vary according to the medium, it is possible to load the dendrimer hosts with different compounds and at various guest concentration levels. Complexes and composites may involve the use of a variety of metals or other inorganic materials. The high electron density of these materials considerably simplifies the imaging by electron microscopy and related scattering techniques. In addition, properties of inorganic atoms introduce new and measurable properties for imaging in either the presence or absence of interfering biological materials. In some embodiments of the present invention, encapsulation of gold, silver, cobalt, iron atoms/molecules and/or organic dye molecules such as fluorescein are encapsulated into dendrimers for use as nanocomposite labels/tracers, although any material that facilitates imaging or detection may be employed.

In some embodiments of the present invention, imaging is based on the passive or active observation of local differences in density of selected physical properties of the investigated complex matter. These differences may be due to a different shape (e.g., mass density detected by atomic force microscopy), altered composition (e.g. radiopaques detected by X-ray), distinct light emission (e.g., fluorochromes detected by spectrophotometry), different diffraction (e.g., electron-beam detected by TEM), contrasted absorption (e.g., light detected by optical methods), or special radiation emission (e.g., isotope methods), etc. Thus, quality and sensitivity of imaging depend on the property observed and on the technique used. The imaging techniques for cancerous cells have to provide sufficient levels of sensitivity to observe small, local concentrations of selected cells. The earliest identification of cancer signatures requires high selectivity (i.e., highly specific recognition provided by appropriate targeting) and the highest possible sensitivity.

Magnetic Resonance Imaging

For example, once the targeted dendrimer conjugates has attached to (or been internalized into) the target tissue such as hepatic tumor cells, one or more modules on the device serve to image its location. Dendrimers have already been employed as biomedical imaging agents, perhaps most notably for magnetic resonance imaging (MRI) contrast enhancement agents (See e.g., Wiener et al. (1994). *Mag. Reson. Med.* 31:1, an example using PAMAM dendrimers). These agents are typically constructed by conjugating chelated paramagnetic ions, such as Gd(III)-diethylenetriaminepentaacetic acid (Gd(III)-DTPA), to water-soluble dendrimers. Other paramagnetic ions that may be useful in this context of the include, but are not limited to, gadolinium, manganese, copper, chromium, iron, cobalt, erbium, nickel, europium, technetium, indium, samarium, dysprosium, ruthenium, ytterbium, yttrium, and holmium ions and combinations thereof. In an embodiment of the present invention, DTPA is attached to dendrimers via the isothiocyanate of DTPA as described by Wiener et al. (1994). *Mag. Reson. Med.* 31:1.

Dendrimeric MRI agents are particularly effective due to the polyvalency, size and architecture of dendrimers, which results in molecules with large proton relaxation enhancements, high molecular relaxivity, and a high effective concentration of paramagnetic ions at the target site. Dendrimeric gadolinium contrast agents have even been used to differentiate between benign and malignant breast tumors using dynamic MRI, based on how the vasculature for the latter type of tumor images more densely (Adam et al. (1996). *Ivest. Rad.* 31:26). In some aspects, dendrimer conjugates of the present invention comprises an imaging agent which is a magnetic resonance imaging (MRI) constrast agent, e.g., gadolinium. Exemplary MRI contrast agents include, for example, gadodiamide (Omniscan), gadobenic acid (Multihance), gadopentetic acid (Magnevist), gadoteridol (Prohance), gadofosveset (Ablavar), gadoversetamide (OptiMARK), gadoxetic acid (Eovist in the USA, Primovist in other parts of the world), gadobutrol (approved in Canada), gadocoletic acid, gadodenterate, gadomelitol, gadopenamide, gadoteric acid (Dotarem). Thus, MRI provides a particularly useful imaging system of the present invention.

Microscopic Imaging

The dendrimer conjugates of the present invention allow functional microscopic imaging of tumors and provide improved methods for imaging. The methods find use in vivo, in vitro, and ex vivo. For example, in one embodiment of the present invention, dendrimers of the present invention are designed to emit light or other detectable signals upon exposure to light. Although the labeled dendrimers may be physically smaller than the optical resolution limit of the microscopy technique, they become self-luminous objects when excited and are readily observable and measurable using optical techniques. In some embodiments of the present invention, sensing fluorescent biosensors in a microscope involves the use of tunable excitation and emission filters and multi-wavelength sources (Farkas et al. (1997). *SPEI*. 2678:200). In embodiments where the imaging agents are present in deeper tissue, longer wavelengths in the Near-infrared (NMR) are used (See e.g., Lester et al. (1998). *Cell Mol. Biol.* 44:29). Dendrimeric biosensing in the Near-IR has been demonstrated with dendrimeric biosensing antenna-like architectures (Shortreed et al. (1997). *J. Phys. Chem.*, 101:6318). Biosensors that find use with the present invention include, but are not limited to, fluorescent dyes and molecular beacons.

In some embodiments of the present invention, in vivo imaging is accomplished using functional imaging technique. Functional imaging is a complementary and potentially more powerful technique as compared to static structural imaging. Functional imaging is best known for its application at the macroscopic scale, with examples including functional Magnetic Resonance Imaging (fMRI) and PET. However, functional microscopic imaging may also be conducted and find use in in vivo and ex vivo analysis of living tissue. For example, in some embodiments of the present invention, biosensor-comprising dendrimers of the present invention are used to image upregulated receptor families such as the folate or EGF classes. In such embodiments, functional biosensing therefore involves the detection of physiological abnormalities relevant to carcinogenesis or malignancy, even at early stages. A number of physiological conditions may be imaged using the compositions and methods of the present invention including, but not limited to, detection of nanoscopic dendrimeric biosensors for pH, oxygen concentration, $Ca^{2+}$ concentration and other physiologically relevant analytes.

EXAMPLES

Example 1

Selection of the PAMAM-NH$_2$ Carrier

Based on our earlier results, small PAMAM-NH$_2$ dendrimers with an ethylene diamine (EDA) core (1-5 nm diameter) distribute quickly to normal tissues (El-Sayed et al. (2001) *Pharmaceutical Research*. 18:23). Consequently, larger PAMAM-NH$_2$ dendrimers with a 1,4-diamino butane (DAB) core (5-7 nm diameter) are used in the present invention as these have proved to preferentially extravasate into tumors (D'Emanuele et al. (2005). *Adv. Drug Deliv. Rev.* 57:2147). In order to select an effective PAMAM-NH$_2$ carrier, the effect of size, molecular weight and generation number on biodistribution of cationic PAMAM-NH$_2$ dendrimers in a tumor-bearing nude mouse model was investigated.

G5 and G6 PAMAM dendrimers were labeled using [$^{14}$C] Iodoacetamide followed by purification of [$^{14}$C]G5 and [$^{14}$C] G6 PAMAM dendrimers by dialysis and characterization using gel permeation chromatography. These dendrimers were analyzed in an in vivo tumor model, in which $1\times10^6$ HepG2 (human liver cancer cells; ATCC No. HB-8065) were injected into the right hepatic lobe of athymic nude mice. Tumors were allowed to grow for approximately 3-4 weeks with a target volume of 100 mm$^3$.

For administration, [$^{14}$C] labeled dendrimers were dissolved in sterile saline and administered to the mice by tail vein injection. At 1, 2, 8, 24 and 48 hour time points the mice were euthanized, followed by harvesting of tumor tissue and vital organs for processing by physical homogenization and chemical digestion. The amount of [$^{14}$C] labeled dendrimers was analyzed using a scintillation counter.

Over all time points, 2-4% of the injected [$^{14}$C]G5 PAMAM dendrimers accumulated in the tumor tissue. Whereas, [$^{14}$C]G6 PAMAM dendrimers were readily recognized and taken up by the reticular endothelium system at similar time points. These results demonstrate that [$^{14}$C]G5 PAMAM dendrimers preferentially accumulated in tumor tissue compared to free anticancer drugs, polymer-drug conjugates, and similar PAMAM carriers. Therefore, G5 PAMAM dendrimers were selected for the synthesis of fluorescein-labeled PAMAM-NAcGal conjugates for targeting to liver tissue.

Example 2

Synthesis of Fluorescently-Labeled NAcGal-PAMAM Conjugates

Figure 4A:
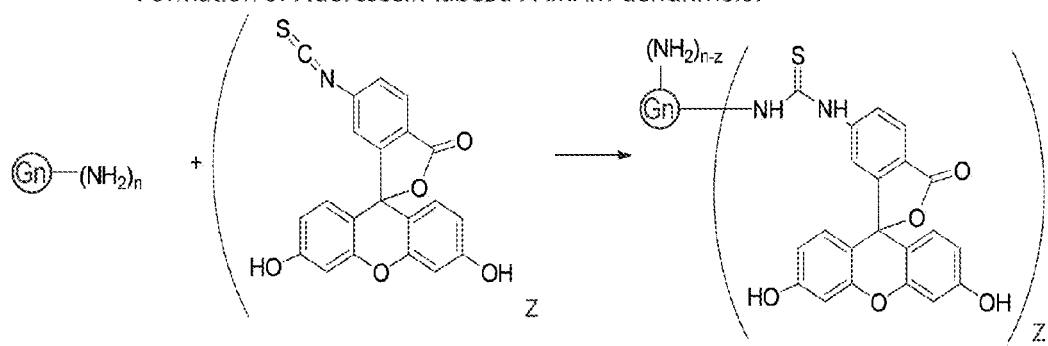
FIG. 4A provides a scheme for the formation of Fluorescein-labeled PAMAM-dendrimers.
Figure 4B:
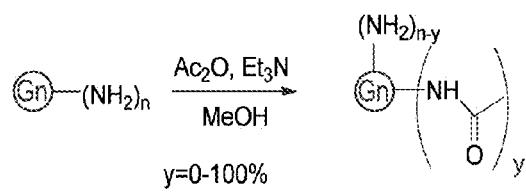
FIG. 4B provides a scheme for the acetylation of PAMAM dendrimers.

Fl-labeled N-acetyl galactosamine (NAcGal)-PAMAM dendrimer conjugates, such as the composition shown in FIG. 4A, were synthesized via non-degradable linkages with an average of 6 fluorescein molecules per dendrimer according to the scheme set out as FIG. 7F. NAcGal ligands can be attached to G5 PAMAM dendrimers by a number of different protocols (FIGS. 6A and 6B) employing a number of conjugation techniques including peptide coupling (e.g. short and long peptide linkers) (FIGS. 6A and 6B), thiourea linkage (FIG. 6C), "click" chemistry (FIG. 6D) or Shiff base formation (FIG. 6E).

In order to synthesize this conjugate with a thiourea linkage, NAcGal was reacted with a hydroxyalkyl bromide, followed by acetylation and conversion of the bromine moiety to an azide. Reduction of the azide to an amine furnished the NH$_2$ terminated NAcGal ligands for reaction with carbondisulfide to produce the isothiocyanate derivatized ligands (FIG. 7F). The functionalized NAcGal ligands were reacted with G5 PAMAM dendrimer carriers to achieve about 22% and about 44% coverage of dendrimer surface groups. Finally, acetylated derivatives of G5 PAMAM dendrimer and NAcGal-PAMAM dendrimer conjugates were prepared by reaction with acetic anhydride in molar ratios to cover approximately 90% of the remaining free surface amine groups followed by Fluorescein-labeling (FIG. 7F).

After deprotection of the NAcGal protective acetyl groups (NHAc), and purification by dialysis non-acetylated G5-(Fl)$_6$ and G5-(Fl)$_6$-(NAcGal)$_X$, as well as acetylated G5-(Fl)$_6$-(NHAc)$_Y$ and G5-(Fl)$_6$-(NHAc)$_Y$-(NAcGal)$_X$ conjugates were collected; where 'Y' represents number of acetylated surface groups, and 'X' the number of NAcGal ligands attached per dendrimer (FIG. 7F).

This synthesis resulted in production of non-acetylated G5 PAMAM-Fl and G5 PAMAM-Fl-NAcGal conjugates with an average of 6 fluorescein molecules, and 28 or 58 NAcGal ligands per dendrimer to produce i) G5-(Fl)$_6$, (ii) G5-(Fl)$_6$-(NAcGal)$_{28}$ and G5-(Fl)$_6$-(NAcGal)$_{58}$ conjugates with NAcGal capping ratios of 0%, 21% and 45% of surface NH$_2$ groups, respectively. Acetylated G5 PAMAM-Fl and G5 PAMAM-Fl-NAcGal conjugates carried 6 fluorescein and 18 or 56 NAcGal ligands per dendrimer (capping ratios 14% and 43% of surface NH$_2$ groups, respectively). After acetylation, the three acetylated conjugates (i) G5-(Fl)$_6$-(NHAc)$_{110}$, (ii) G$_5$-(Fl)$_6$-(NHAc)$_{83}$-(NAcGal)$_{18}$ and (iii) G$_5$-(Fl)$_6$-(NHAc)$_{60}$-(NAcGal)$_{56}$ with an achieved total surface group capping of 90%, 79% and 91%, respectively. Characterization of the G5 PAMAM-NAcGal conjugates was performed by MALDI-TOF analyses. Both the acetylated and non-acetylated conjugates were evaluated for their uptake by hepatic and breast cancer cells.

Figure 8A:
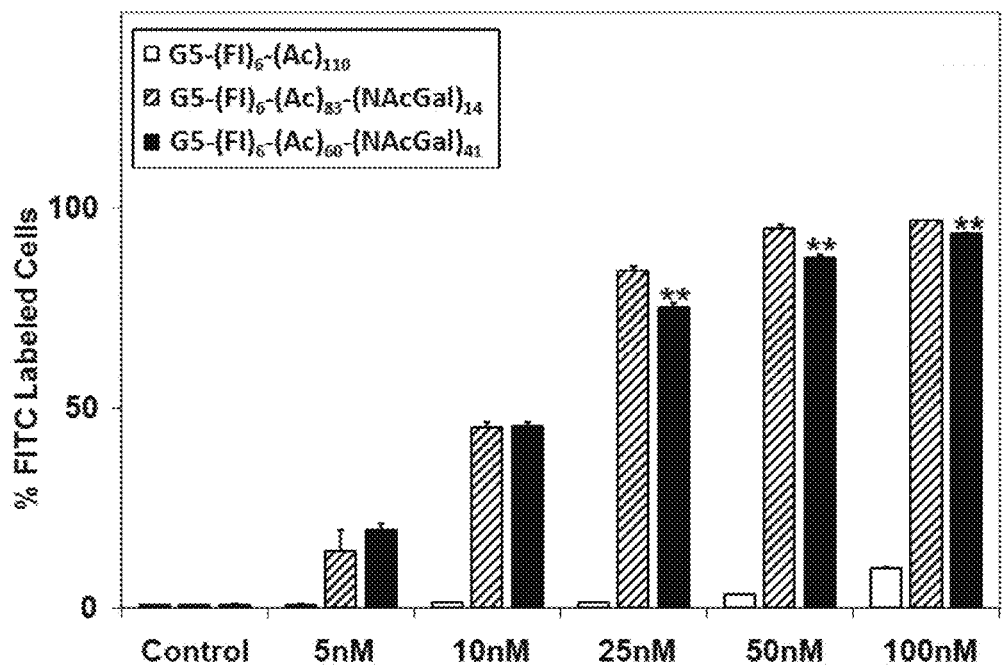
FIG. 8 depicts uptake of acetylated [A & b] and non-acetylated [C & D] fluorescently-labeled and galactosylated conjugates upon incubation with HepG2 cells for 2 [A & C] and 24 [B & D] hours. Results are the average of four independent experiments +SEM. * denotes p<0.05 and ** denotes p<0.01 compared to G5-(Fl)$_6$-(NHAc)$_{83}$-(NAcGal)$_{14}$[A,B] or G5-(Fl)$_6$[C,D].
Figure 8B:
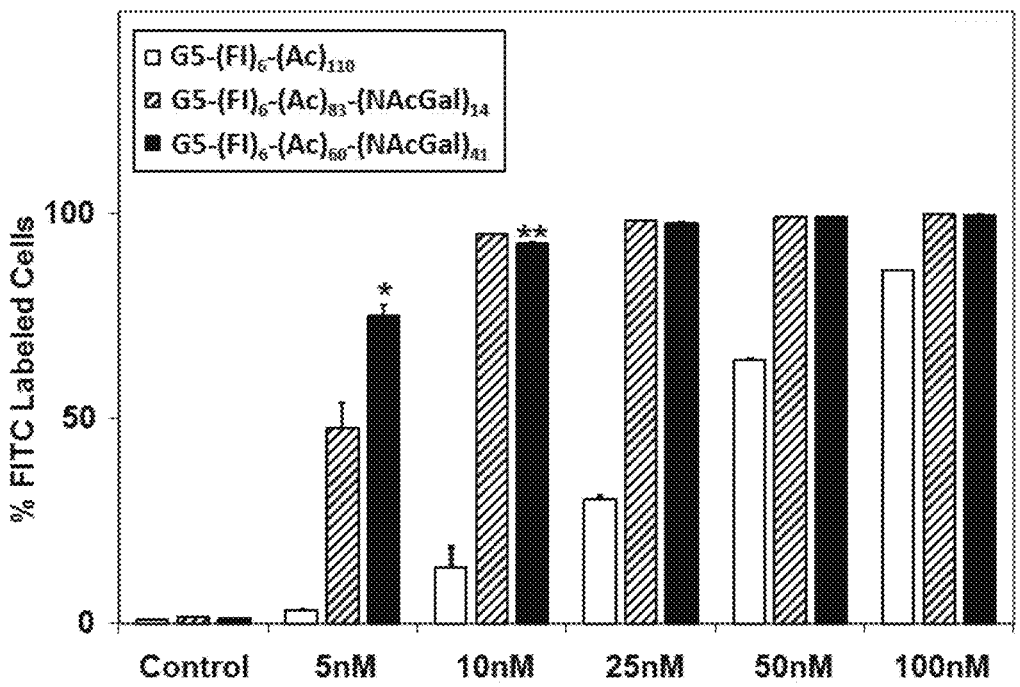

Uptake of Fluorescein-labeled acetylated G5 PAMAM-NAcGal conjugates (described above) was investigated in vitro using the human hepatic cancer cell line HepG2. 5×10$^5$ HepG2 cells/well were seeded in 24 well plates, and these cells were incubated with neutralized G5-(Fl)$_6$-(NHAc)$_{110}$ and G5-(Fl)$_6$-(NHAc)$_Y$-(NAcGal)$_X$ conjugates. Acetylated G5-(Fl)$_6$-(NHAc)$_{110}$, G5-(Fl)$_6$-(NHAc)$_{83}$-(NAcGal)$_{14}$ or G5-(Fl)$_6$-(NHAc)$_{60}$-(NAcGal)$_{41}$ conjugates were incubated at varying concentrations (5, 10, 25, 50 and 100 nM) for 2 and 24 hours. After incubation the cells were washed, trypsinized and suspended in cold PBS for analysis by flow cytometry. Flow cytometry was performed by gating on average fluorescence of untreated controls. As shown in FIG. 8 (panels [A] and [B]), incubation of HepG2 cells with G5-(Fl)$_6$-(NHAc)$_{83}$-(NAcGal)$_{14}$ and G5-(Fl)$_6$-(NHAc)$_{60}$-(NAcGal)$_{41}$ conjugates for 2 [A] and 24 hours [B] showed a significantly higher uptake into cancer cells when compared to uptake of G5-(Fl)$_6$-(NHAc)$_{110}$ at each concentration. Uptake of the G5-(Fl)$_6$-(NHAc)$_{83}$-(NAcGal)$_{14}$ and G5-(Fl)$_6$-(NHAc)$_{60}$-(NAcGal)$_{41}$ conjugates at 2 hours were statistically different at 25-100 nM concentrations, while at 24 hours the difference in uptake occurred for the lowest two concentrations 5 and 10 nM. Nevertheless, uptake profiles for both of the acetylated PAMAM-NAcGal conjugates were very similar for all time points and concentrations tested and in particular show saturation of the cancer cells receptors at similar concentrations.

To study the effect of adsorptive endocytic mechanisms on accumulation of cationic G5 PAMAM-NAcGal conjugates into hepatic cancer cells, the uptake of non-acetylated G5-(Fl)$_6$, G5-(Fl)$_6$-(NAcGal)$_{28}$ and G5-(Fl)$_6$-(NAcGal)$_{58}$ was studied. HepG2 cells were incubated for 2 and 24 hours at varying concentrations (25, 50, 100, 200 and 400 nM). As shown in FIG. 8 (panels [C] and [D]), at low concentrations (25 nM and 50 nM), G5-(Fl)$_6$ showed lower uptake into HepG2 cells compared to G5-(Fl)$_6$-(NAcGal)$_{58}$ at 2 [C] and 24 hour [D] incubation times, with G5-(Fl)$_6$-(NAcGal)$_{28}$ displaying the lowest accumulation at each time point and concentration. This profile for the non-acetylated conjugates can be attributed to different internalization mechanism, given that G5-(Fl)$_6$ has approximately 122 free NH$_2$ surface groups that are positively charged at physiologic pH, leading to electrostatic interaction with the HepG2 cell surface triggering non-specific adsorptive endocytosis. Conversely, G5-(Fl)$_6$-(NAcGal)$_{28}$ and G5-(Fl)$_6$-(NAcGal)$_{58}$ conjugates have fewer NH$_2$ surface groups due to capping by NAcGal ligands, which limits non-specific absorptive interactions and instead rely on the ASGPR to be internalized by receptor-mediated endocytosis.

Figure 9:
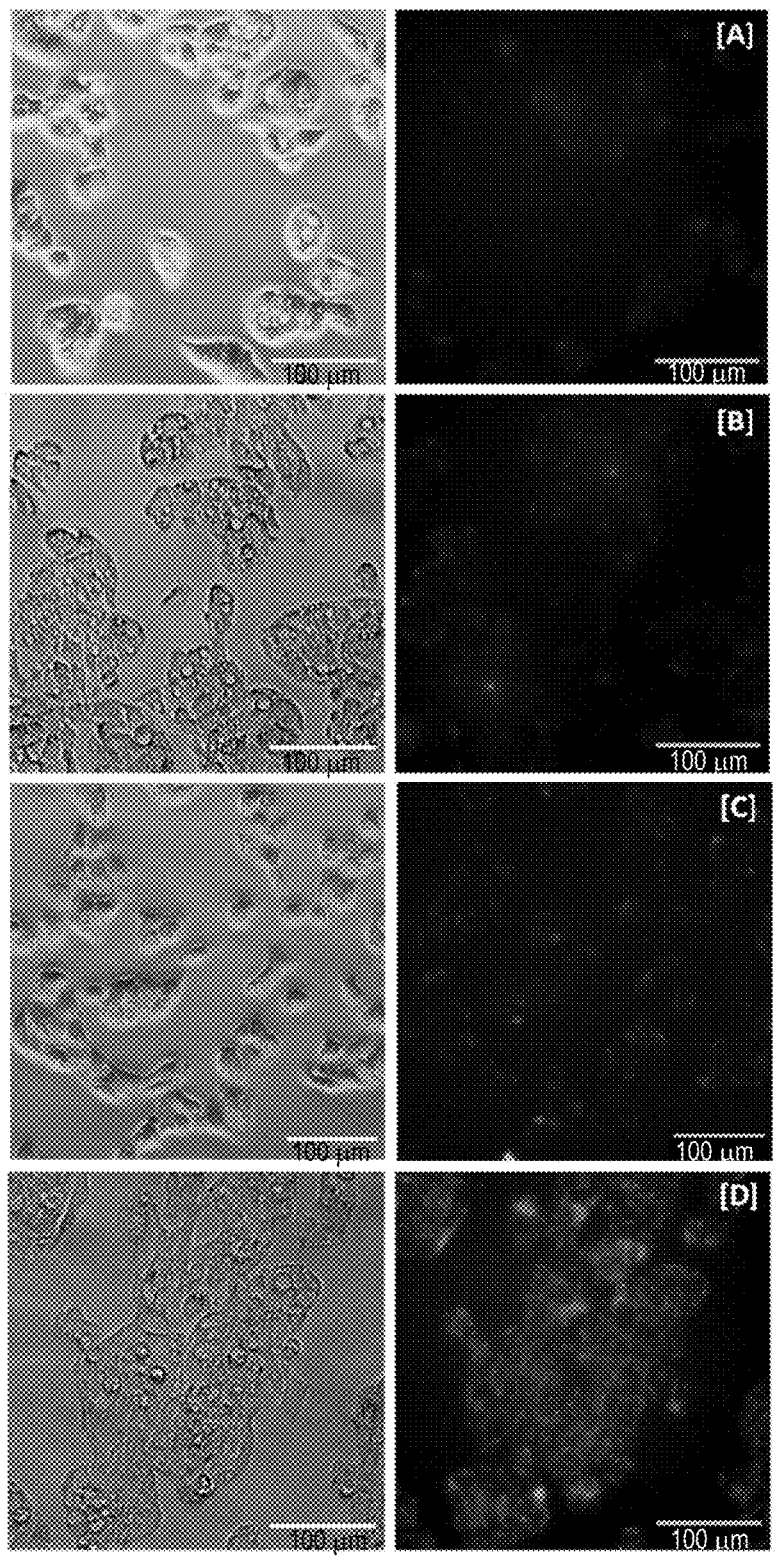
FIG. 9 provides fluorescent microscopy images of [A] untreated HepG2 cells compared to HepG2 cells treated with [B] G5-(Fl)$_6$-(NHAc)$_{110}$, [C] G5-(Fl)$_6$-(NHAc)$_{90}$-(PEG)$_{13}$, or [D] G5-(Fl)$_6$-(NHAc)$_{83}$-(NAcGal)$_{14}$.

Internalization of Fluorescein-labeled PAMAM-NAcGal conjugates into hepatic cancer cells was visualized using fluorescent confocal microscopy. 1×10$^5$ HepG2 cells/well were seeded on 24 well plates and incubated for 4 hours with 200 nM of non-targeted G5-(Fl)$_6$-(NHAc)$_{110}$, non-targeted PEGylated G5-(Fl)$_6$-(NHAc)$_{90}$-(PEG)$_{13}$, or ligand-targeted G5-(Fl)$_6$-(NHAc)$_{83}$-(NAcGal)$_{14}$ conjugates. As shown in FIG. 9 only the PAMAM-NAcGal conjugates were readily taken up into HepG2 cells, which displayed high intracellular fluorescein signal compared to untreated controls and cells incubated with non-targeted or PEGylated PAMAM conjugates.

In order to evaluate the selectivity of the uptake of Fluorescein-labeled PAMAM-NAcGal conjugates into HepG2 cells internalization was inhibited by competition of free NAcGal in solution. 5×10$^5$ HepG2 cells/well were seeded on 24 well plates and incubated for 2 and 24 hours with G5-(Fl)$_6$-(NHAc)$_{83}$-(NAcGal)$_{14}$ (5, 10, 25, 50 and 100 nM) alone or co-incubated with 100 mM free NAcGal. Flow cytometry was performed by gating on average florescence of untreated controls (NAcGal pre-incubation). The uptake of G5-(Fl)$_6$-(NHAc)$_{83}$-(NAcGal)$_{14}$ in HepG2 cells was completely inhibited in the presence of free NAcGal ligands at 5-25 nM concentrations at 2 hours. This inhibition in conjugate uptake due to competitive binding of free NAcGal ligands confirmed the selectivity of the targeted conjugates to the ASGPR present on the surface of hepatic cancer cells.

Furthermore, selective recognition of Fluorescein-labeled acetylated PAMAM-NAcGal conjugates by the ASGPR was confirmed in vitro using the human breast cancer cell line MCF-7, which does not express the ASGPR. 5×10$^5$ MCF-7 cells/well were seeded in 24 well plates and incubated them with G5-(Fl)$_6$-(NHAc)$_{110}$, G5-(Fl)$_6$-(NHAc)$_{83}$-(NAcGal)$_{14}$ or G5-(Fl)$_6$-(NHAc)$_{60}$-(NAcGal)$_{41}$ conjugates, at varying concentrations (5, 10, 25, 50 and 100 nM) for 2 and 24 hours. After incubation, the cells were washed, trypsinized and suspended in cold PBS for analysis by flow cytometry. Flow cytometry was performed by gating on average fluorescence of untreated controls. Incubation of MCF-7 cells with G5-(Fl)$_6$-(NHAc)$_{110}$, G5-(Fl)$_6$-(NHAc)$_{83}$-(NAcGal)$_{14}$ and G5-(Fl)$_6$-(NHAc)$_{60}$-(NAcGal)$_{41}$ conjugates for 2 hours [A] showed negligible uptake of conjugates at every time point and concentration. After 24 hours [B] of incubation minor uptake of the conjugate was observed for the two highest concentrations (50 nM and 100 nM), likely due to a non-specific pinocytosis mechanism. Even at the highest concentration and long exposure times (24 hours), conjugate is internalized in fewer than 20% of treated cells. This experiment clearly showed that uptake of NAcGal-PAMAM conjugates is selective for the ASGPR expressed on hepatic cancer cells.

Example 3

Synthesis of Radioactively Labeled Acetylated Conjugates

The dendrimer conjugates were radiolabeled to study their biodistribution and accurately measure their concentration in different tissues. Briefly, $^{14}$C-iodoacetamide was mixed with different generations of dendrimers in sodium bicarbonate buffer (pH 10) for 12 hours. The reaction mixtures were then fractionated using size exclusion chromatography (SEC) to collect pure $^{14}$C-labeled dendrimers. The specific activity and number of $^{14}$C-radionuclides per Gn were calculated using liquid scintillation counting (Bubnis & Ofner, Analytical Biochemistry 297 (1992) 129-133).

Synthesis of [$^{14}$C]G5-(NHAc)$_{103}$ Conjugates

To generate [$^{14}$C]G5-(NHAc)$_{103}$ conjugates, 20 mg of G5-NH$_2$ dendrimer was dissolved in dry methanol and reacted with a 103 fold molar concentration of acetic anhydride in the presence of triethylamine (TEA) and stirred for 16 hours at room temperature to yield 18.1 mg of G5-(NHAc)$_{103}$ after purification (90.5% yield) (FIG. 5D. Purified G5-(NHAc)$_{103}$ was mixed with [$^{14}$C]-IAc (see FIG. 4C) at a 1:1.25 molar ratio while monitoring the progress of the radiolabeling reaction using GPC and liquid scintillation counting. This scheme resulted in 50% labeling efficiency after 5 days of mixing. The reaction was scheduled to go for 3 additional days to achieve >90% labeling efficiency before purification and characterization of [$^{14}$C]G5-(NHAc)$_{103}$ conjugates (FIG. 7B).

Synthesis of [$^{14}$C]G5-(NHAc)$_{93}$-(PEG)$_{10}$ Conjugates:

To generate [$^{14}$C]G5-(NHAc)$_{93}$-(PEG)$_{10}$ conjugates, 46.3 mg of G5-NH$_2$ dendrimer in dry methanol were reacted with 60.3 mg (18 fold molar excess) of activated PEG-NHS (2 kDa) for 24 hours at room temperature. The product was purified by dialysis to yield 65 mg of G5-PEG conjugates, which was characterized by MALDI-TOF and showed that approximately 13 PEG chains are attached per G5 molecule. G5-PEG conjugates were reacted with acetic anhydride at a molar concentration of 1:93 in the presence of TEA to acetylate the G5-PEG conjugates. Acetylated G5-PEG conjugates were purified by dialysis followed by reaction with [$^{14}$C]-IAC to get the radio-labeled conjugates. (FIG. 7C).

Synthesis of [$^{14}$C]G5-(NHAc)$_{85}$-(NAcGal)$_{14}$ Conjugates:

Synthesis of acetylated and NAcGal-targeted G5 dendrimers to develop radiolabeled G5-(NHAc)$_{85}$-(NAcGal)$_{18}$ conjugates was carried out according to the scheme set out in FIG. 7D. This scheme involves a modified multi-step synthesis of the NAcGal targeting ligand to achieve stronger bonding with G5 through an amide bond.

Synthesis of [$^{14}$C]G5-(NHAc)$_{75}$-(NAcGal)$_{18}$-(PEG)$_{10}$ Conjugates

Synthesis of radiolabeled acetylated, PEGylated, and NAcGal-targeted G5 dendrimers to develop G5-(NHAc)$_{75}$-(NAcGal)$_{14}$-(PEG)$_{10}$ conjugates, which will be radio-labeled for biodistribution experiments is carried out according to the scheme set out in FIG. 7E.

Example 4

Biodistribution of Dendrimer Conjugates

To generate the hepatic carcinoma tumor model 1×10$^6$ HepG2 cells were suspended in a matrigel matrix into the liver of nude athymic mice. Expected tumor growth after 4 weeks were between 100-150 mm$^3$ in size. After the tumors were well-established (>100 mm$^3$), the conjugates were injected into the systemic circulation of the mice via a single intravenous (iv) bolus dose of [$^{14}$C]G5 or [$^{14}$C]G6. For analysis, each group was sacrificed at a specific time point (1, 2, 8, 24 or 48 hours) after administration. The amount of $^{14}$C-labeled dendrimers present in plasma, tumor tissue, brain, heart, lungs, kidneys, liver, spleen, pancreas, intestine, lymph nodes, bone marrow, urine and feces was measured.

Figure 10A:
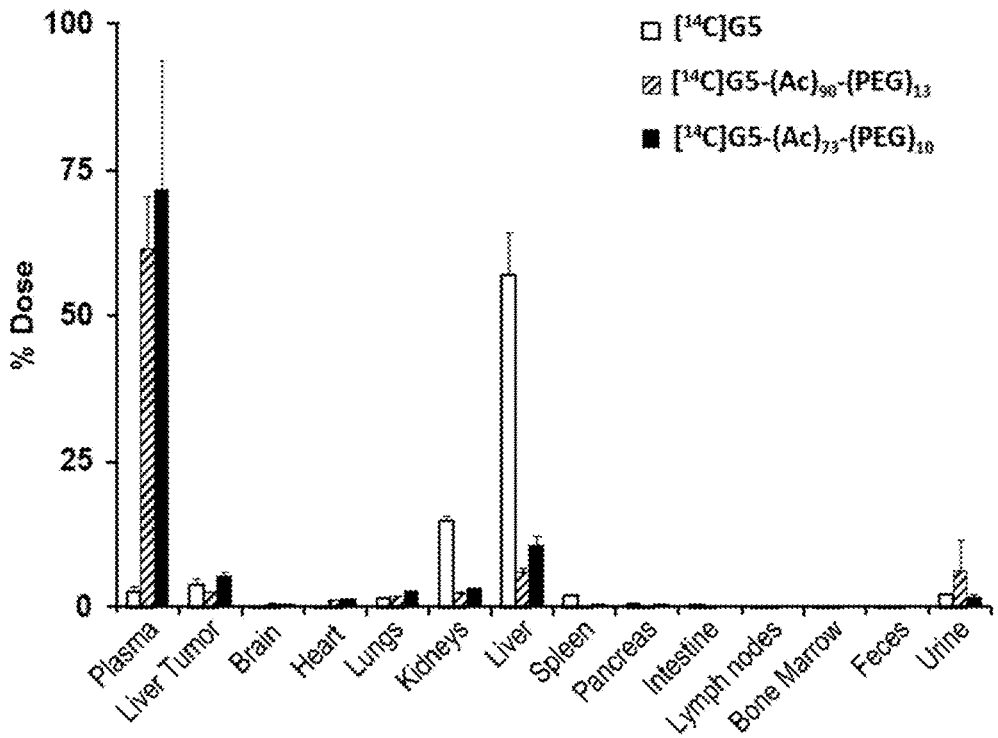
FIG. 10 provides results showing % of $[^{14}C]$-G5 and $[^{14}C]$-G5-(NHAc)y-(PEG)$_p$ conjugates dose present in the plasma, hepatic tumor tissue, brain, heart, lungs, liver, kidneys, spleen, pancreas, intestine, lymph nodes, bone marrow, urine, and feces upon injection into nude tumor-bearing mice after [A] 2 and [B] 24 hours. Results are the average +SEM of experiments using 3-4 mice per treatment group.
Figure 10B:
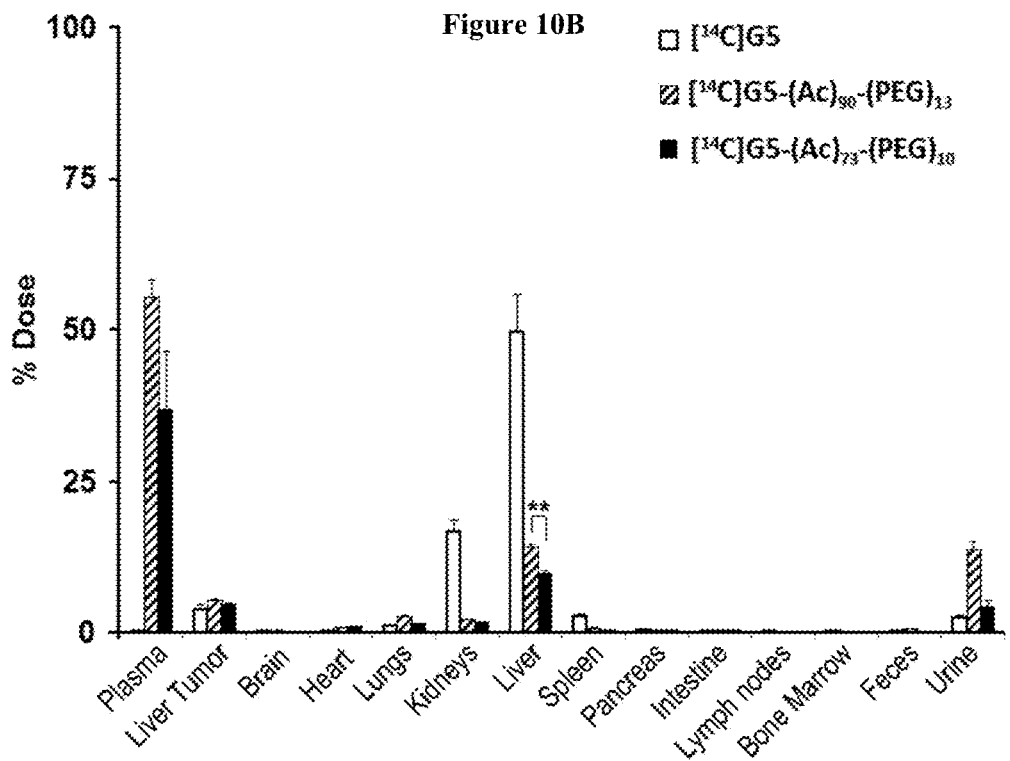
Figure 11A:
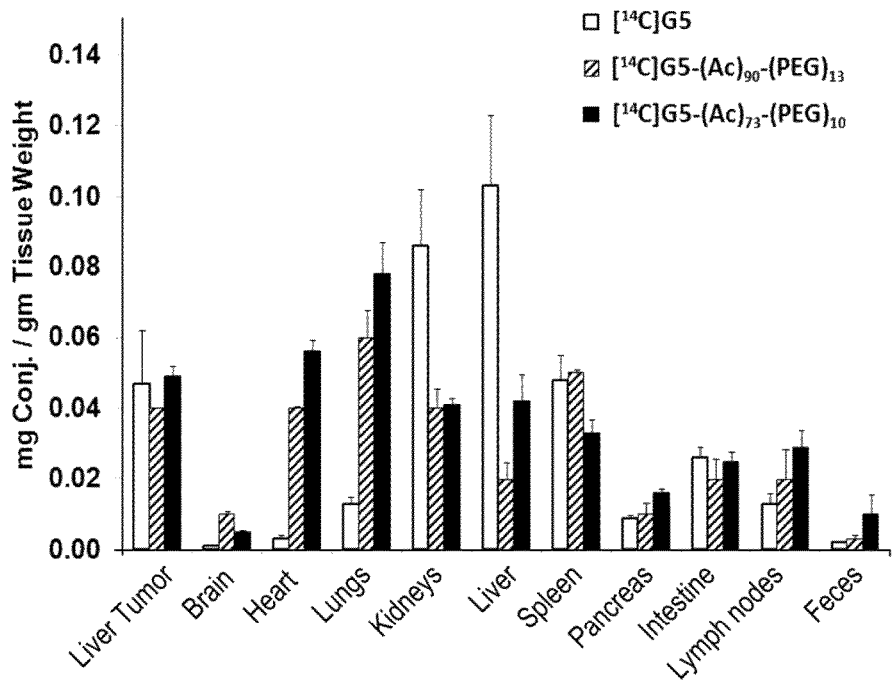
FIG. 11 provides results showing the mg of $[^{14}C]$-G5 and $[^{14}C]$-G5-(NHAc)$_y$-(PEG)$_p$ conjugates accumulated per gram of tissue weight upon injection into nude tumor-bearing mice after [A] 2 and [B] 24 hours. Results are average +SEM of experiments using 3-4 mice per treatment group.
Figure 11B:
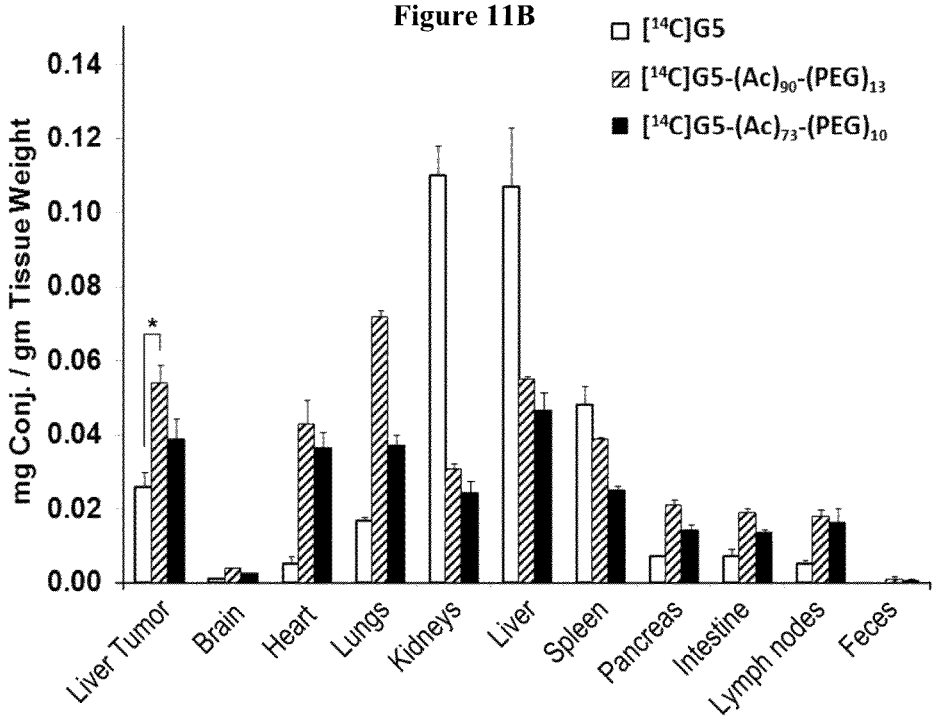

The following $^{14}$C-labeled dendrimer conjugates were injected into the tumor bearing mice as described above: [14C]-G5, [$^{14}$C]-G5-(NHAc)$_{90}$-(PEG)$_{13}$ and [$^{14}$C]-G5-(NHAc)$_{73}$-(PEG)$_{10}$. FIG. 10 provides results showing % of the $^{14}$C-labeled dendrimer conjugates dose present in the plasma, hepatic tumor tissue, brain, heart, lungs, liver, kidneys, spleen, pancreas, intestine, lymph nodes, bone marrow, urine, and feces upon injection into nude tumor-bearing mice after 2 and 24 hours. FIG. 11 provides results showing the mg of $^{14}$C-labeled dendrimer conjugates accumulated per gram of tissue weight upon injection into nude tumor-bearing mice after 2 and 24 hours.

This analysis allowed for determination of which of these conjugates exhibit highest tumor-specific accumulation and retention. In addition, this analysis identified which Gn has the optimum balance of size, molecular weight, and surface charge to preferentially accumulate in hepatic tumor tissue.

Example 5

Determination of the Selectivity of G5-NAcGal Dendrimer Conjugates Toward ASGPR

To determine selectivity of G5-NAcGal conjugates towards the asialoglycoprotein receptor (ASGPR), the effect of co-incubation of 100 nM solution of free NAcGal molecules with G5-(Fl)$_6$-(NHAc)$_{83}$-(NAcGal)$_{14}$ conjugates on their internalization of dendrimer conjugates into HepG2 cells was examined after exposure for 2 and 24 hours. The uptake of G5-(Fl)$_6$-(NHAc)$_{83}$-(NAcGal)$_{14}$ in HepG2 cells is completely inhibited in the presence of free NAcGal ligands at 5-25 nM concentrations at 2 hours. (See FIGS. 16G and 16H). This inhibition in conjugate uptake due to competitive binding of free NAcGal ligands confirmed the selectivity of the targeted conjugates to the ASGPR present on the surface of hepatic cancer cells.

Example 6

Synthesis and Purification of G5-DOX Conjugates with Enzyme-Reducible Aromatic Azo Linkages Formation of the G5-Azo-DOX conjugates with enzyme-reducible azo-linkages was performed with a multi-step synthesis via several intermediates (FIGS. 5A-5E). After the synthesis, the effect of chemical reduction of the azo-linkage on the release of free and clean DOX was tested.

In the protocol with peptide linkage (FIG. 5A) reaction of phenol with p-amino benzyl alcohol (PABA) yielded compound 2 with the desired aromatic azo linkage. The second step was selective alkylation of phenolic hydroxy-group with methyl bromoacetate to produce compound 3. To incorporate the 1,6-self-eliminating electronic cascade in the linkage design, compound 3 was reacted with p-nitrophenyl chloroformate yielding compound 4. The next step involves the reaction between compound 4 and free DOX molecules, which will replace the terminal p-nitrophenyloxy group present in the linkage to the DOX yielding Azo-DOX conjugate 5 with the desired azo bond and 1,6-self-eliminating electronic cascade linkage (Gao et al. *Journal of Controlled Release* 2006, 110, 323-331). Me-ester in conjugate 5 was hydrolyzed by the reaction with 1N NaOH producing the free acid 6 which was conjugated to the G5-PAMAM-dendrimer using published protocol (Baker et all *J. Med. Chem.*, 2005, 48, 5892).

Alternatively, PAMAM-Azo-DOX conjugate are synthesized using the strategy outlined in FIG. 5B. The final step involves the terminal epoxide opening by the amino-group of the dendrimer. The aromatic azo-linker 2 synthesized according to FIG. 5A is reacted with alkenyl bromide providing benzyl alcohol 8 which benzylic alcohol moiety is activated by reacting with 4-nitrophenylchloroformate or DSC to provide carbonates 9. The reaction of carbonates 9 with free DOX in the presence of Et₃N leads to the Azo-DOX conjugate 10 which terminal double bond is transformed into the epoxide 11. Reaction of epoxide 11 with PAMAM-dendrimer produces final PAMAM-Azo-DOX conjugate 12. The strategy which involves using the "click" chemistry also can be applied to the synthesis of PAMAM-Azo-DOX conjugate (FIG. 5C). Again, aromatic azo-linker 2 was transformed to the bromide 13 by reacting with alkyldibromide in the presence of base. Bromide 13 was reacted with NaN₃ providing the azide 14 which benzylic alcohol moiety was activated by reacting with 4-nitrophenylchloroformate or DSC to provide carbonates 15. The reaction of carbonates 15 with free DOX in the presence of Et₃N leads to the azide 16 which reacts with modified PAMAM-dendrimer under "click" chemistry conditions providing the final PAMAM-Azo-DOX conjugate 17. Finally, Azo-DOX is conjugated to the PAMAM-dendrimer using urea, thiourea or carbamate linkages (FIG. 5D). For this purpose azide 16 synthesized as described FIG. 5C is reduced to the amine 18 using PPh₃ which upon the reaction with carbon disulfide provides the isothiocyanite 19. Reaction of PAMAM-dendrimer with compound 19 leads to the final PAMAM-Azo-DOX conjugate 20. Also, several DOX molecules can be attached to the conjugate (FIG. 5E). Compound 21 is synthesized using the same protocol which was used for preparation of 2. Then it can be used instead of 2 in all protocols described in FIG. 5.

The number of DOX molecules attached per dendrimer molecules is varied by controlling the number of azo-DOX linkages displayed on Gn-NH₂ surface. Azo-DOX conjugate are attached to the G5-dendrimer via peptide, urea, thiourea and carbamate linkages, also by opening the terminal epoxy-group and "click" chemistry. Purity and chemical composition of all intermediates and the final PAMAM-DOX conjugate are verified using a library of analytical techniques such as $^1$H-NMR and mass spectroscopy. DOX molecules are conjugated following schemes in FIG. 6 starting with either Gn-NAcGal conjugates synthesized following the schemes set out in FIGS. 6A-6E or free Gn-NH₂ PAMAM-dendrimers to synthesize NAcGal-targeted or un-targeted PAMAM-DOX conjugates, respectively.

Synthesis of Compound 2:

As shown in FIG. 5A, 360 mg of phenol and 212 mg of NaNO₂ were dissolved in a mixture of 2 ml of EtOH and 1 ml of water. The solution was added dropwise to 4.4 ml of 2 N HCl with stirring at 0° C. within 5 minutes. After 5 minutes stirring at 0° C. the resulting solution was added dropwise to a solution of 275 mg of phenol dissolved in 2.75 ml of 2 N NaOH at 0° C. At the end of introduction the pH of the solution was adjusted from 5 to 7-8 using sodium bicarbonate solution. After 10 minutes of stirring at 0° C., the red precipitate was collected on the bottom of the flask using centrifugation, and the solution was removed by the pipet. Precipitate was then dissolved in acetone (100 ml), dried with MgSO₄ and concentrated under reduced pressure. The residue was dissolved in ethyl acetate (EtOAc; 100 ml) and the solution was dried again with MgSO₄. After concentration, the residue was purified by column chromatography using acetone/hexanes 1:2 as an eluting system to produce 470 mg (71%) of product as a red-brown solid.

Synthesis of Compound 3:

400 mg of compound 2 and 280 mg of methyl bromoacetate were dissolved in 40 ml of acetone and 726 mg of K₂CO₃ was added as a solid. After stirring overnight at room temperature, the reaction was diluted with 100 ml of EtOAc, washed with water (2×50 ml), dried with MgSO₄ and concentrated to produce 450 mg (71%) of product as a yellow solid. This solid was used in the next step without further purification.

Synthesis of Compound 4:

200 mg of compound 3 was dissolved in 10 ml of CH₂Cl₂, the solution was cooled to 0° C., and 471 mg of p-nitrophenyl chloroformate dissolved in 4 ml of CH₂Cl₂ was added dropwise at 0° C., subsequently 0.35 ml of N,N-Diisopropylethylamine (DIEA) was added dropwise. After addition was complete the cooling bath was removed and the reaction mixture was stirred at room temperature for 3 hours. The reaction was diluted with 100 ml of EtOAc, washed with water (2×50 ml), dried with MgSO₄ and concentrated. The residue was purified by column chromatography using gradient EtOAc/hexanes (from 1:4 to 1:1) as an eluting system to produce 170 mg (55%) of product as a yellow solid.

Synthesis of Compound 5:

20 mg of compound 4 was dissolved in 2 ml of tetrahydrofuran (THF) and 35 mg of free DOX (dissolved in 2 ml of dimethylformamide (DMF)) was added via syringe at room temperature. The reaction was stirred at room temperature overnight and solvents were removed under reduced pressure. The residue was purified by column chromatography using gradient CH₂Cl₂/MeOH (from 100:0 to 97:3) as an eluting system to produce 30 mg (80%) of product as a red solid. The azo linkage-Dox conjugate (5) was characterized by $^1$H-NMR and mass spectroscopy, where $^1$H-NMR showed the presence of definitive compound peaks and mass spectroscopy displayed a peak corresponding to the expected molecular weight 869 Da+sodium ion (Na) 23=892.3 Da, confirming the presence of the compound 5.

Synthesis of Compound 6:

8 mg of compound 5 was dissolved in 1.1 ml of a mixture of THF/H₂O (1.75:1), the solution was cooled to 0° C., and 0.036 ml of 1.0 N NaOH was added via syringe. After 10 minutes stirring at 0° C. the reaction was neutralized by the addition of 0.5 N HCl pH 2-3, diluted with EtOAc (15 ml) and water (5 ml). The aqueous layer was extracted with EtOAc (2×15 ml) after separation of the layers. Combined EtOAc layers were dried over MgSO₄ and concentrated producing 3.5 mg (45%) of crude acid 6 which was used in the next step without further purification.

Synthesis of Compound 7:

3.5 mg of compound 6 was dissolved in 1.3 ml of a mixture DMF/DMSO (3:1) and 7.85 mg of ethylene dicholoride (EDC) was added as a solid at room temperature. After stirring for 1 h at room temperature, the solution was added to the 0.020 ml of G5-Dendrimer (10% solution in methyl alcohol (MeOH)), and dissolved in 0.5 ml of water. After stirring for 2 days at room temperature, solvents were removed under reduced pressure. The residue was then dissolved in water and purified by dialysis to produce 3.3 mg (60%) of PAMAM-Azo-DOX conjugate 7. The structure was supported by the results of $^1$H-NMR and MALDI-TOF analysis.

Example 7

Characterization of the PAMAM-DOX Conjugates

Figure 16A:
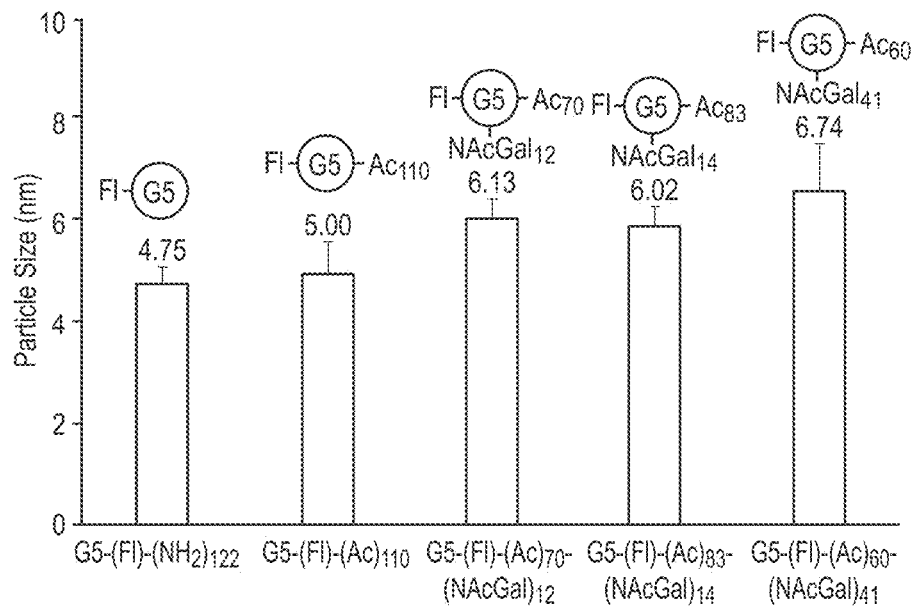
FIG. 16 represents a series of graphs that demonstrate the characterization and uptake of G5-NAcGal conjugates into hepatic and breast cancer cells and confirm the tissue specificity of the conjugates. The particle size (FIG. 16A) and zeta potential (FIG. 16B) of G5-NAcGal conjugates. The uptake of cationic G5-Fl conjugates into HepG2 cells after incubation for 2 (FIG. 16C) and 24 hours (FIG. 16D). The uptake of G5-NAcGal conjugates prepared via thiourea and peptide linkages into HepG2 cells after incubation for 2 (FIG. 16E) and 24 hours (FIG. 16F). Inhibition of G5-NAcGal conjugate uptake into HepG2 cells after co-incubation with an excess of NAcGal ligand for 2 (FIG. 16G) and 24 hours (FIG. 16H). Uptake of G5-NAcGal conjugates non-ASGPR expressing MCF-7 cells after incubation for 2 (FIG. 16I) and 24 hours (FIG. 16J). Cytotoxicity of G5-NAcGal conjugates towards HepG2 cells after incubation for 2 (FIG. 16K) and 24 hours (FIG. 16L).
Figure 16B:
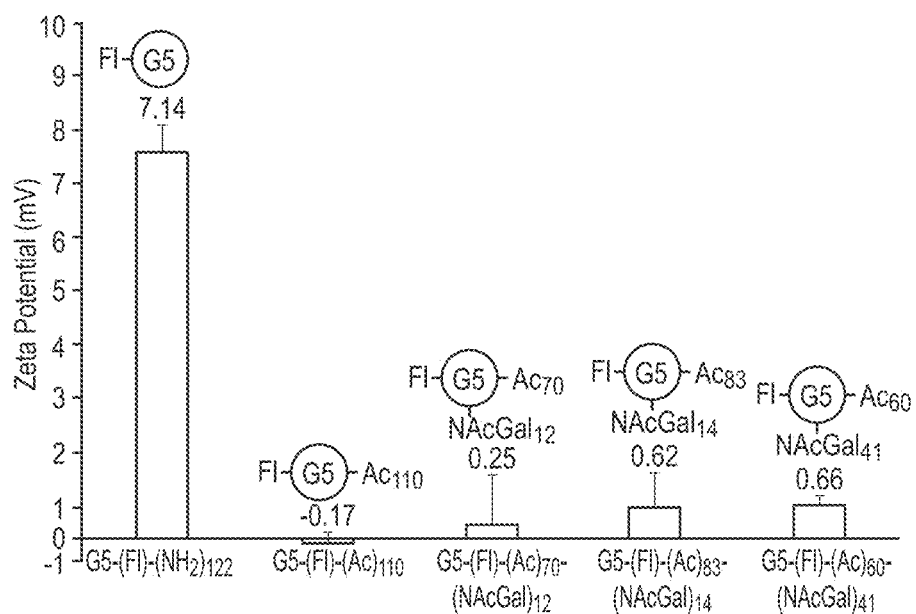

Physicochemical Characterization of PAMAM-DOX Conjugates:

The hydrodynamic diameter and zeta potential of PAMAM-DOX conjugates are measured by dynamic light scattering using our ZetaPALS system (Brookhaven Instruments, Corp., Holtsville, N.Y.). The molecular weight of PAMAM-DOX conjugates is determined by MALDI-TOF analysis. G5-NAcGal conjugates characterized in this manner are shown in FIGS. 16A and B.

Estimation of DOX Content in PAMAM-DOX Conjugates:

The number of DOX molecules attached per dendrimer will be determined by examining the $^1$H-NMR spectra of PAMAM-DOX conjugates. In addition, 0.1 µmoles of different conjugates are incubated with a known amount of dithionite solution (reducing agent) to reduce the azo linkages and release the attached DOX molecules. Reduction of the azo linkage will produce PAMAM-AA conjugate ($\lambda_{ex}$=340) and free DOX ($\lambda_{ex}$=470), which are quantified by measuring their fluorescence intensity at 410 nm and 585 nm, respectively. The ratio between PAMAM-AA and DOX molar concentrations in solution is calculated as a measure of the % of hydrolyzed azo bonds. A ratio of 1 indicates that 100% of the synthesized azo bonds are reduced resulting in an immediate hydrolysis of the 1,6-self eliminating cascade with a quantitative release of DOX molecules.

In Vitro Stability of PAMAM-DOX Conjugates:

Non-specific cleavage of PAMAM-DOX azo linkages are determined by monitoring DOX release upon shaking 0.1 µmoles of the conjugate with blank phosphate buffer (pH 7.4), whole blood, or homogenates of different organs (brain, heart, lungs, kidney, spleen) at 37° C. for 24 hours. Samples from each solution are collected every hour, separate free DOX molecules by solid phase are extraction, and the DOX concentration is measured using HPLC methods as described in Seymour et al. (1990). *Biochemical Pharmacology.* 39:1125, Minko et al. (1998). *Journal of Chromatography B.* 712:129. The results are then used to calculate the rate and extent of non-specific DOX release in healthy tissues, which should not exceed 5% of conjugated DOX molecules.

Measurement of DOX Release Kinetics in Hepatic Tumor Tissue:

0.1 µmoles of different PAMAM-DOX conjugates are incubated with: i) commercial CYP450 enzyme preparations, ii) CYP450 enzymes separated from liver microsomal preparations of normal mice and iii) homogenized hepatic tumors raised in nude mice at 37° C. for 24 hours. Samples from each solution are collected hourly to separate and quantify free DOX molecules as described earlier. The rate of DOX release (amount of free DOX produced per minute per 100 mg of pure enzyme or homogenized tumor tissue) is calculated for each condition. Results of this assay confirm the specificity of DOX release in response to liver CYP450 enzymes.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

Example 8

Figure 16C:
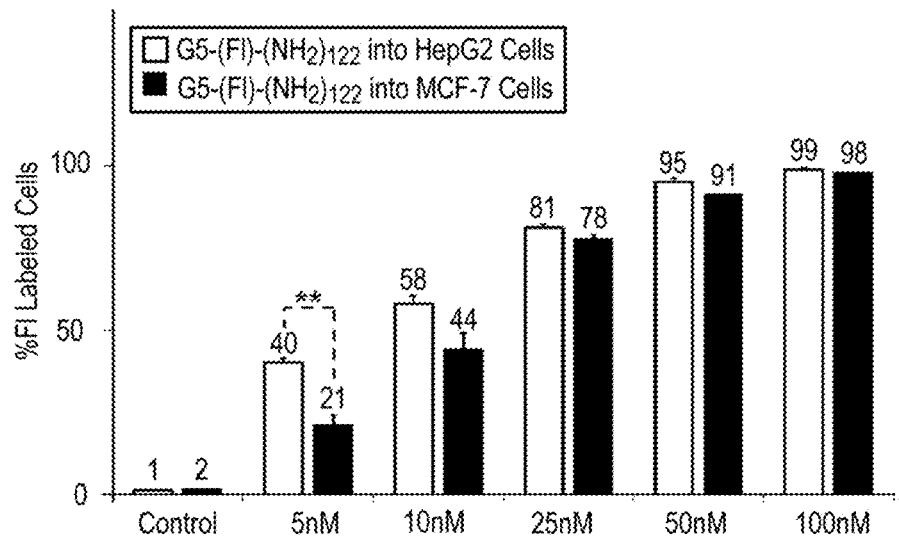
Figure 16D:
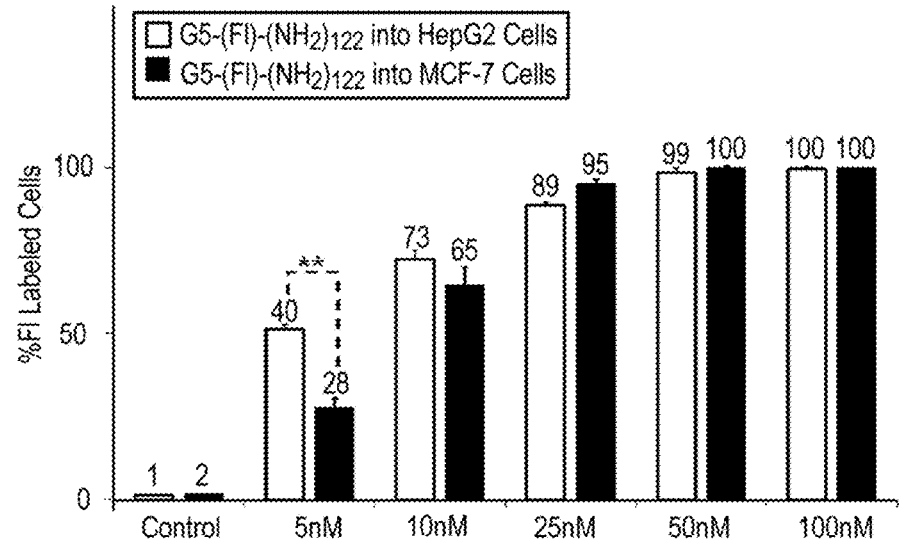
Figure 16G:
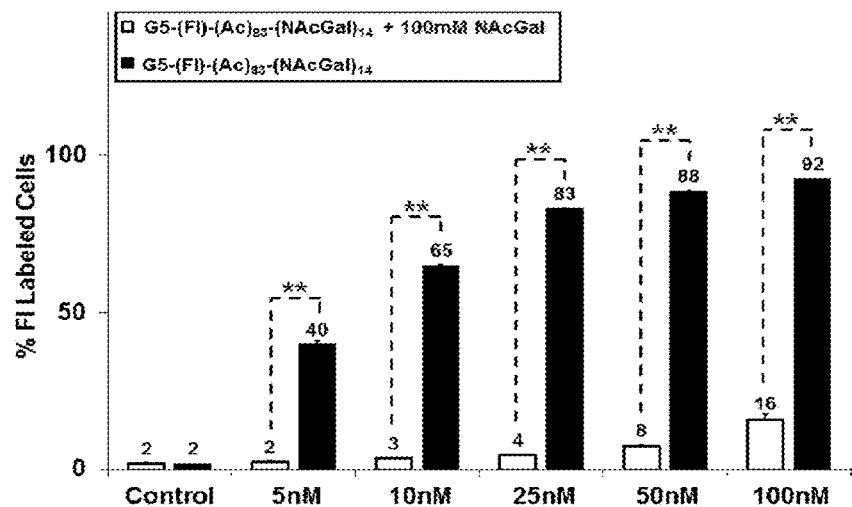
Figure 16H:
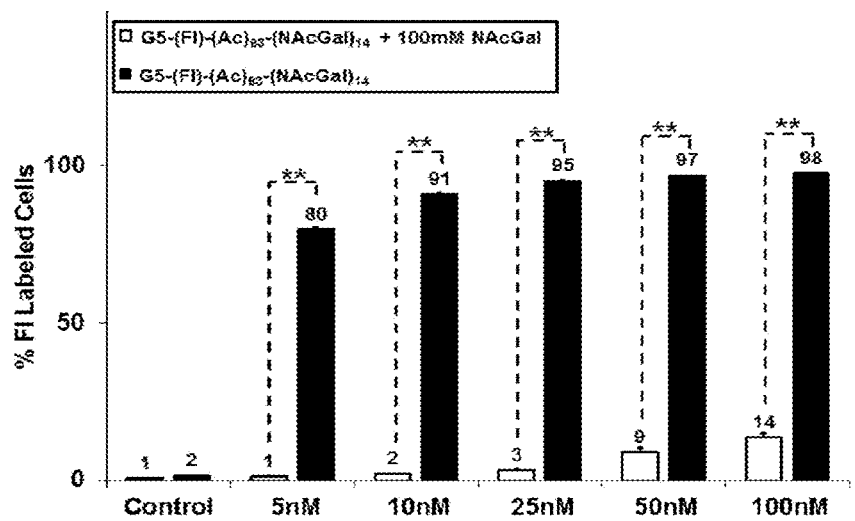

The ability of dendrimer conjugates to be internalized by HepG2 cells or breast MCF-7 cells was demonstrated by incubating these cells with 5, 10, 25, 50, or 100 nM of G5-(Fl)-(NH$_2$)$_{122}$ for 2 or 24 hours in vitro. The % fluorescently labeled cells were determined after incubation. A control set of cells were incubated without a dendrimer conjugate and the % fluorescently labeled cells of this control set established the baseline fluorescence. As shown in FIGS. 16C and 16D, the conjugates were internalized by each type of cells at each concentration. In contrast, the control lacking a tissue-specific targeting molecule (G5(Fl)-(Ac)$_{110}$) was not internalized by either type of cells even after 24 hours.

The ability of exemplary acetylated dendrimer conjugates comprising a liver-specific targeting molecule (NAcGal) to be internalized by HepG2 cells was demonstrated by incubating these cells with 5, 10, 25, 50, or 100 nM of G5-(Fl)-(NH$_2$)$_{122}$ for 2 or 24 hours in vitro. The NAcGal molecules were attached to the dendrimer via a non-degradable peptide linkage or a non-degradable thiourea linkage. The % fluorescently labeled cells were determined after incubation and was compared to that of cells incubated with an acetylated dendrimer conjugate lacking NAcGal. As shown in FIGS. 16E and 16F, at all tested doses, little to no dendrimer conjugates lacking NAcGal were internalized by HepG2 cells after 2 hours of incubation, whereas greater than or about 50% of cells demonstrated an uptake of dendrimer conjugates comprising NAcGal molecules when incubated with 25 nM or more. After the 24 hour incubation, greater than or about 50% of cells demonstrated uptake of dendrimer conjugates comprising NAcGal molecules when incubated with as little as 5 nM of conjugate.

Figure 16I:
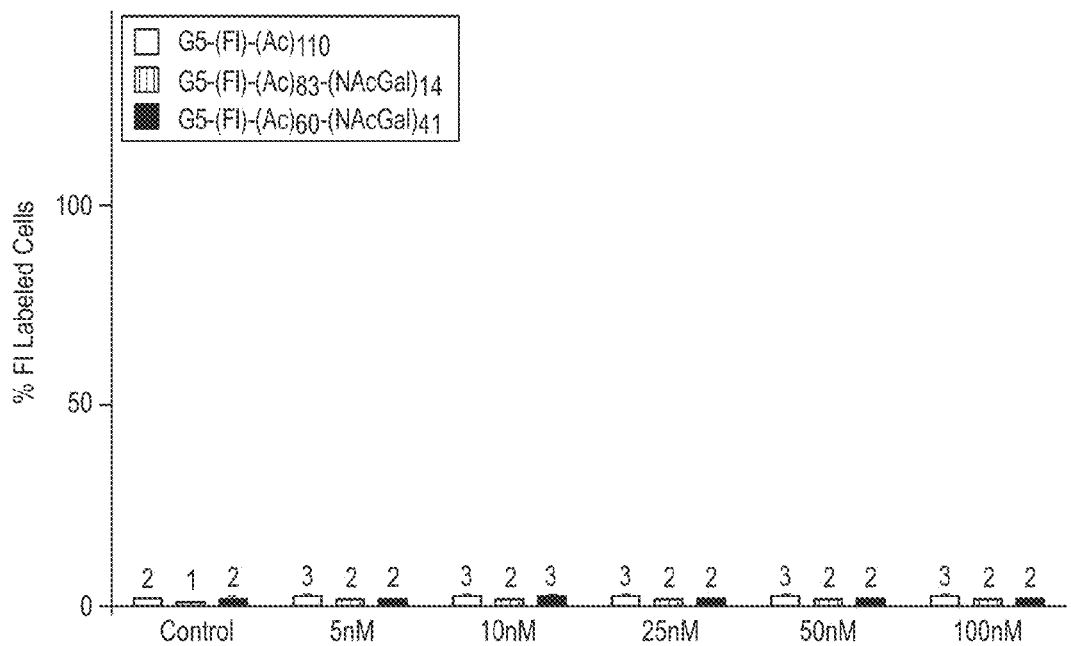
Figure 16J:
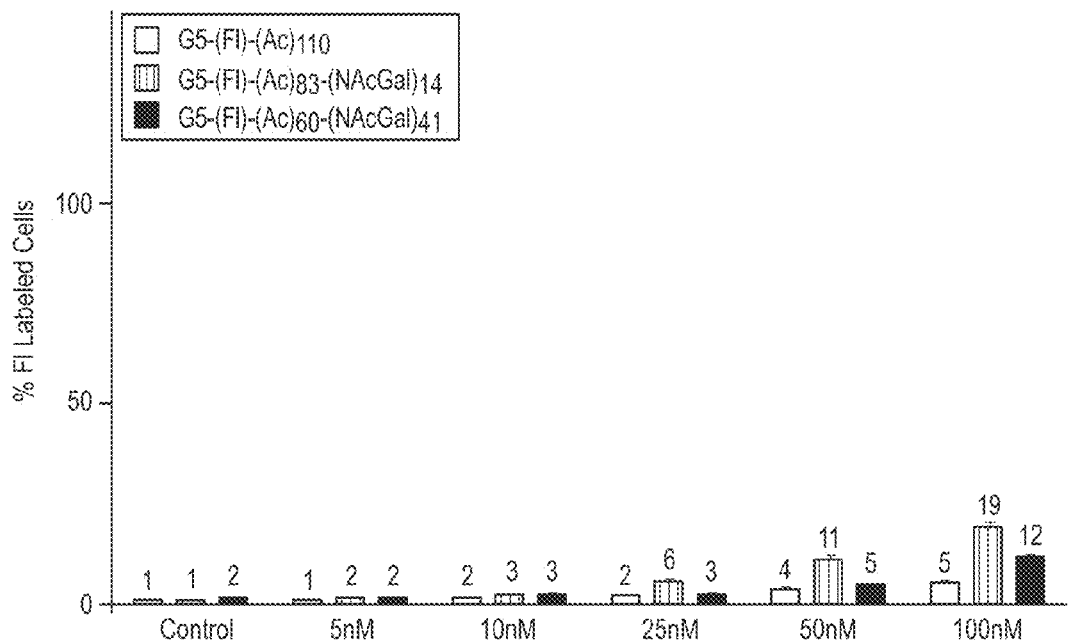

The tissue specificity of acetylated dendrimer conjugates comprising NAcGal molecules was demonstrated by incubating for 2 or 24 hours G5-(Fl)-(Ac)$_{110}$, G5-(Fl)-(Ac)$_{83}$-(NAcGal)$_{14}$, or G5-(Fl)-(Ac)$_{60}$-(NAcGal)$_{41}$ at 5, 10, 25, 50, or 100 nM with breast MCF-7 cells which do not express ASGPR. The % fluorescently labeled cells were determined after incubation. As shown in FIGS. 16I and 16J, none of the conjugates were internalized by the breast cells after 2 hours and little to no conjugates were internalized after 24 hours.

Example 9

Figure 16K:
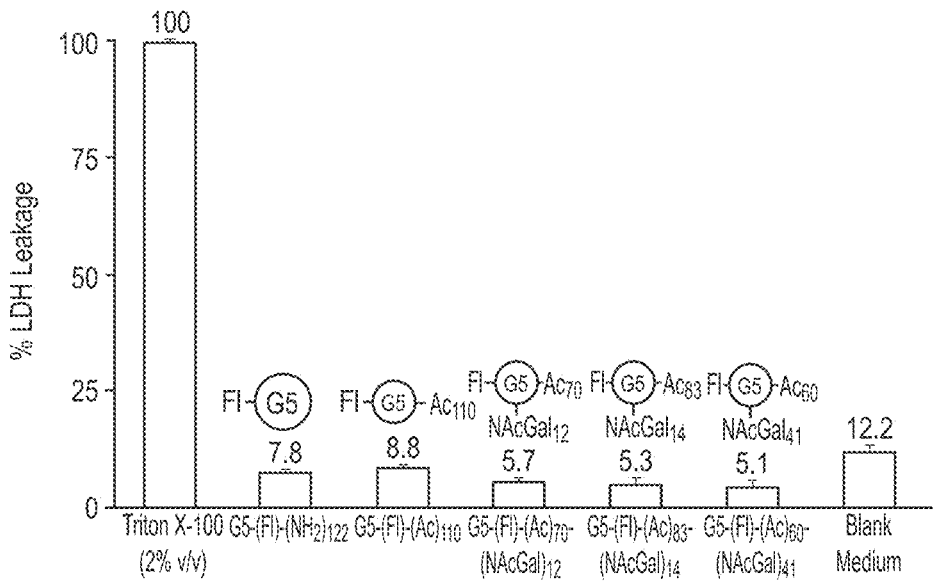
Figure 16L:
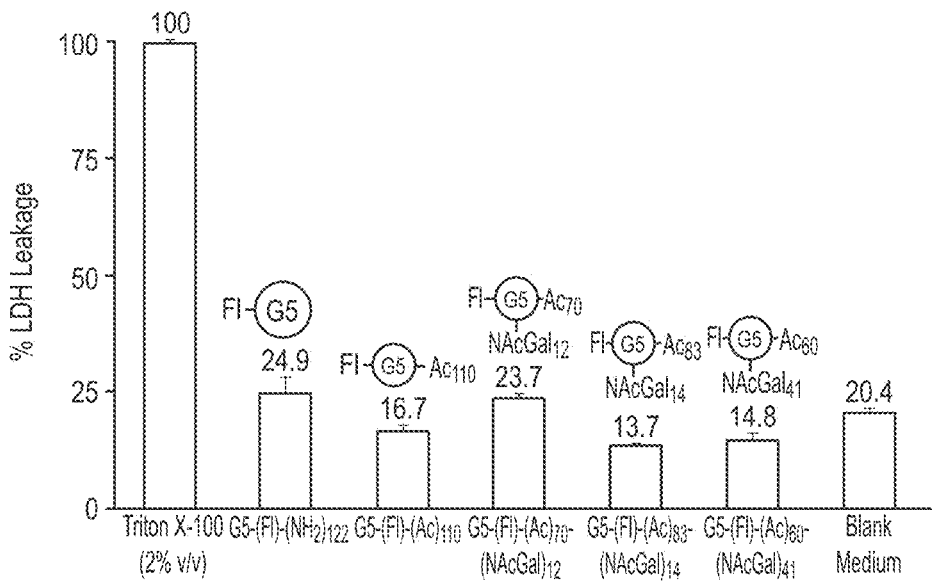

To analyze the cytotoxicity (or biocompatibility) of the dendrimer conjugates of the invention, exemplary dendrimer conjugates (some of which comprised NAcGal molecules) were incubated with HepG2 cells for 2 or 24 hours. The % cells that leaked lactate dehydrogenase (LDH) was measured after incubation. As shown in FIGS. 16K and 16L, less than 10% cells leaked LDH from the liver cells after 2 hours of incubation with the conjugates. For conjugates comprising NAcGal molecules, less than 6% cells leaked LDH after 2 hours incubation. After 24 hours of incubation, less than 25% cells leaked LDH from the liver cells. This example demonstrates the biocompatibility of the dendrimer conjugates with liver cells.

Example 10

Nude tumor bearing mice were administered by intravenous injection a single dose of 6, 8, 10, or 12 mg/kg of free DOX (one dose/week for 3 weeks). The mice were sacrificed two weeks after the last administration and the tumors were harvested for analysis. Tumor size was measured and compared to the size of tumors harvested from mice administered a saline control. From this experiment, it was observed that 6 mg/kg did not cause any substantial reduction in tumor size, but that the 12 mg/kg dose was too toxic to mice. Both 8 and 10 mg/kg doses inhibited tumor growth compared to control mice, although the 10 mg/kg dose was associated with a slight increase in toxicity without an observable increase in activity. The results achieved with these doses were very similar demonstrating their potential for therapeutic doses.

The above experiment was repeated with an 8 mg/kg dose of free DOX and two additional test groups of mice: one group of mice were administered a dendrimer conjugate com prising a G5 dendrimer conjugated to DOX (G5-OXY-DOX) comprising an azo linkage comprising the structure of

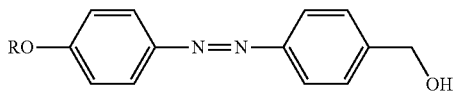

and a second group of mice were administered a dendrimer conjugate comprising a G5 dendrimer conjugated to DOX (G5-DIOXY-DOX) comprising an azo linkage comprising the structure of

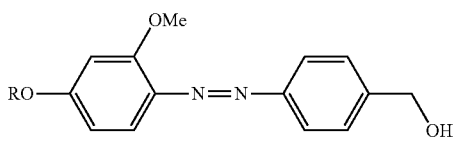

Figure 17:
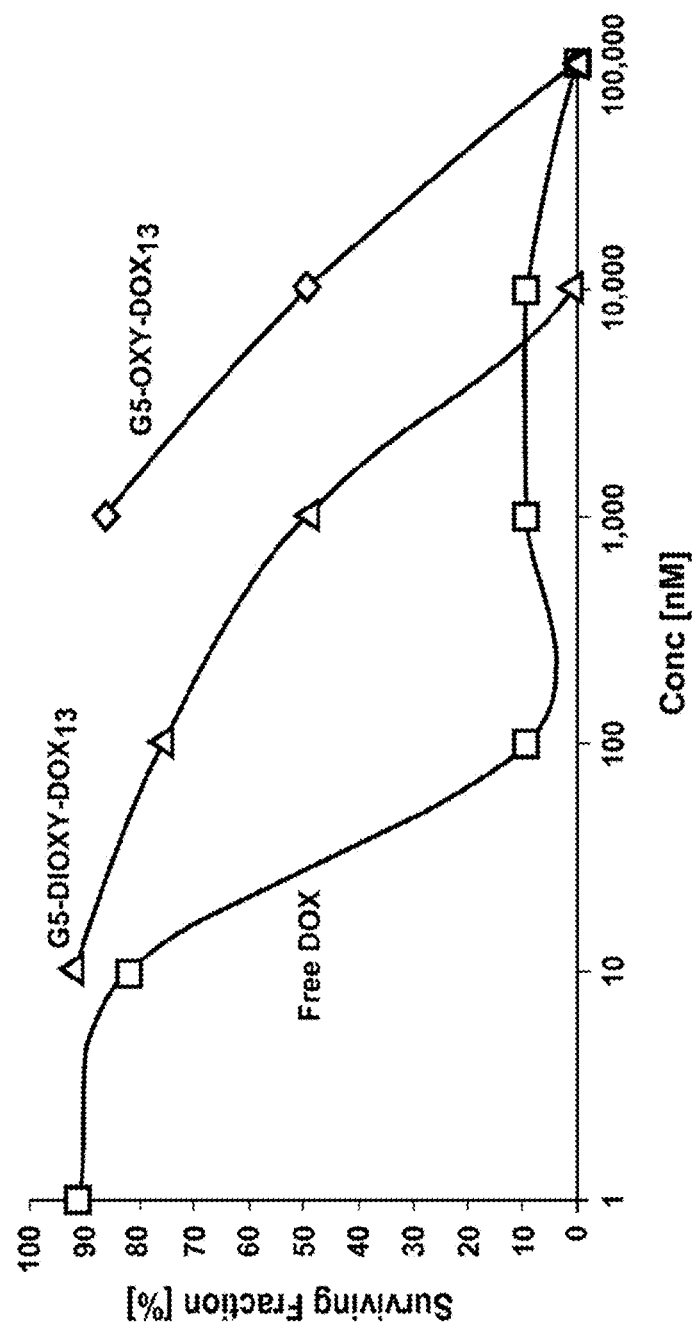
FIG. 17 represents a graph of the dose-response curves for three compounds: Free doxorubicin (Free DOX), and two dendrimer conjugates comprising a G5 dendrimer (G5-DI-OXY-DOX13 and G5-OXY-DOX13). Cytotoxicity as represented by the % surviving fraction of HepG2 cells in a clonogenicity assay was measured upon incubation of one of the three compounds at various concentrations (nM) with HepG2 cells for 72 hours.
Figure 18A:
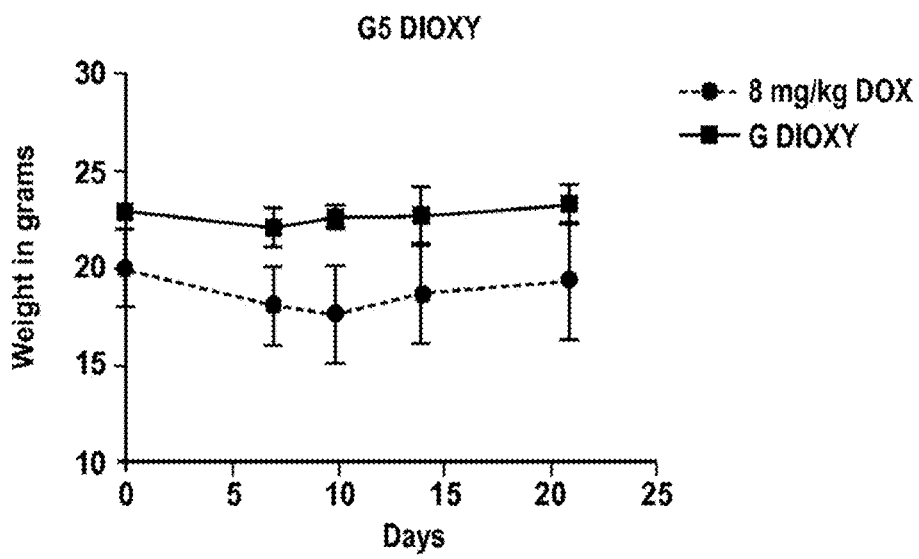
FIG. 18 represents two graphs demonstrating the biocompatibility of dendrimer conjugates when administered to mice. Top graph: free doxorubicin (8 mg/kg DOX) or an exemplary dendrimer conjugate comprising doxorubicin of the present invention (G DIOXY) was administered to mice and the weight (g) of mice was periodically measured up to 20 days post-administration. Bottom graph: free doxorubicin (8 mg/kg DOX) or an exemplary dendrimer conjugate comprising doxorubicin of the present invention (G5 OXY) was administered to mice and the weight (g) of mice was periodically measured up to 20 days post-administration. As shown in both graphs, mice that received the G DIOXY dendrimer conjugate or G5 OXY dendrimer conjugate did not lose any more weight than mice that received free doxorubicin, demonstrating that the dendrimer conjugates are no more toxic to the mice than free doxorubicin.
Figure 18B:
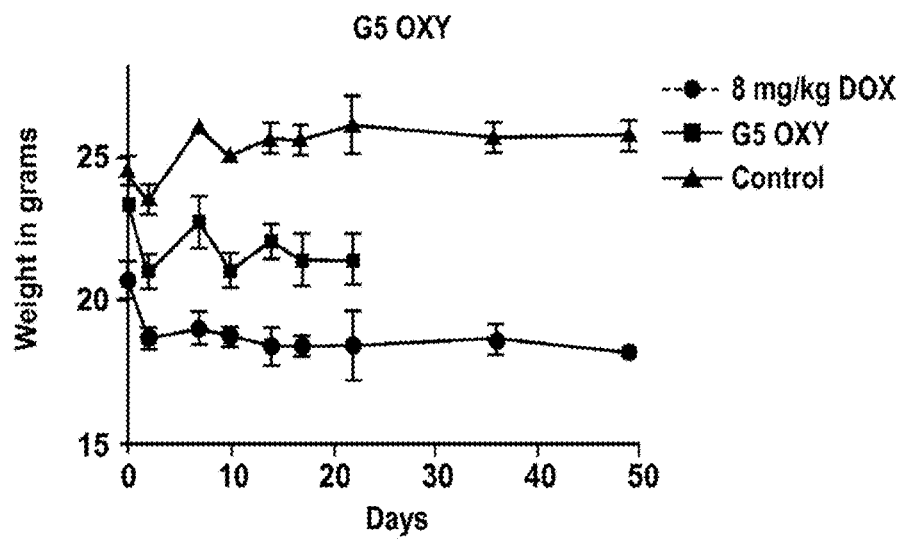

Also, in this experiment, instead of being sacrificed two weeks after the last administration, the tumor volumes of the mice were measured one week after the last administration and then measured again four weeks later. As shown in FIG. 17, the dendrimer conjugates did not achieve an inhibition in tumor growth. As shown in FIG. 18, the weight of the mice stayed essentially the same to demonstrate that the dendrimer conjugates were no more toxic to the mice than the free form of doxorubicin. These data demonstrate that the dendrimer conjugates themselves are not toxic to cells and therefore demonstrates the biocompatibility of the dendrimer conjugates of the present invention.

Another experiment is run with a dendrimer conjugate comprising a liver-specific targeting molecule (NAcGal) attached to the dendrimer via a non-degradable linkage and DOX attached to the dendrimer via an azo linkage. About 0-50% of the surface NH2 groups of the dendrimer is attached to the liver-specific molecule and about 0-25% of the surface NH2 groups of the dendrimer is attached to DOX. In vitro results of this dendrimer conjugate is assayed via a clonogenicity assay, and in vivo activity is determined by measuring tumor size and tumor volume of the mice. The conjugate is expected to release 20% free DOX in hepatic tumor cells.

Example 11

The following materials and methods were utilized in the study described in Example 12.

Materials

G5-(NH$_2$)$_{128}$ PAMAM dendrimers with a dimethylaminobutane core were purchased from Dendritic Nanotechnologies Inc. (Midland, Mich.) and purified by dialysis against deionized water using Slide-A-Lyzer dialysis cassettes (MWCO 10 kDa, Thermo Fisher Scientific, Rockford, Ill.) to remove imperfect dendrimers and polymer debris. Doxorubicin-HCl was purchased from AvaChem Scientific (San Antonio, Tex.). All solvents, chemicals and reagents were purchased from Sigma-Aldrich Inc. (St. Louis, Mo.) as American Chemical Society purity grade unless otherwise specified. BD Gentest™ human liver microsomes (HLM) (50 donor pool, protein concentration of 20 mg/mL), insect control protein and NADPH generating system were purchased from Becton-Dickinson (Franklin Lakes, N.J.). BCA total protein assay kit and cytotoxicity detection kit (Lactate Dehydrogenase leakage detection assay) were purchased from Thermo Fisher Scientific (Rockford, Ill.) and Roche Diagnostics (Indianapolis, Ind.), respectively. Dulbecco's modified eagle medium (DMEM), Minimum essential medium (MEM), OPTI-MEM reduced serum medium, Hanks balanced salt solution (HBSS), fetal bovine serum (FBS), 0.25% trypsin/0.20% EDTA solution, phosphate buffered saline (PBS), penicillin/streptomycin/amphotericin solution, sodium pyruvate and non-essential amino acid solutions were purchased from Invitrogen Corporation (Carlsbad, Calif.). HepG2 and Hep3B human hepatic cancer cell lines were a generous gift from Dr. Donna Shewach (University of Michigan, Department of Pharmacology, Ann Arbor, Mich. 48109) and adult rat cardiomyocytes were isolated and provided as a suspension or seeded in 24-well plates as a generous gift from Dr. Margaret V. Westfall and Dr. Daniel E. Michele (University of Michigan, Department of Molecular and Integrative Physiology, Ann Arbor, Mich. 48109), respectively.

General Experimental Procedures.

All reactions were carried out with anhydrous solvents in flame-dried glassware and under nitrogen unless otherwise noted. Chemicals used were reagent grade as supplied except where noted. Analytical thin-layer chromatography was performed using silica gel 60 F254 glass plates. Compound spots were visualized by UV light (254 nm) and by staining with a yellow solution containing Ce(NH$_4$)$_2$(NO$_3$)$_6$ (0.5 g) and (NH$_4$)$_6$Mo$_7$O$_{24}$.4H$_2$O (24.0 g) in 6% H$_2$SO$_4$ (500 mL). Flash column chromatography was performed on silica gel 60 (230-400 Mesh). NMR spectra were referenced using Me$_4$Si (0 ppm), residual CDCl$_3$ ($\delta$ $^1$H-NMR 7.26 ppm, $^{13}$C-NMR 77.0 ppm), CD$_3$SOCD$_3$ ($\delta$ $^1$H-NMR 2.49 ppm, $^{13}$C-NMR 39.5 ppm), CD$_3$OD ($\delta$ $^1$H-NMR 3.30 ppm, $^{13}$C-NMR 49.00 ppm), D$_2$O ($\delta$ $^1$H-NMR 4.56 ppm). Peak and coupling constant assignments are based on $^1$H-NMR, $^1$H-$^1$H gCOSY and (or) $^1$H-$^{13}$C gHMQC experiments. ESI-MS measurements were performed according to the published procedures 2 on a Q-TOF Ultima API LC-MS instrument with Waters 2795 Separation Module (Waters Corporation, Milford, Mass.). All samples passed through an EagleEye HPLC C18 column, 3 mm×150 mm, 5 µm at a flow rate of 0.5 mL/min with a linear gradient from 10% eluent B to 26% eluent B over eight minutes with the column temperature maintained at 45° C. All injections were performed in the full-loop injection mode using a 10 µL sample loop. Eluent A consisted of a pure aqueous solution and eluent B contained 75% acetonitrile/25% aqueous solution (v/v). The following instrument settings were common for analyses S16 performed in both positive and negative ion modes: source temperature 120° C., desolvation temperature 400° C., collision energy 10 eV. When operated in negative ion mode, the mass spectrometer used the following instrument settings: capillary voltage 2.0 kV, cone voltage 35 V, extraction cone 4 V. The following instrumental parameters were used for data acquisition in positive ion mode: capillary voltage 3.5 kV, cone voltage 35 V. Sample concentrations were 1 mg/mL. MALDI-TOF analysis of G5-DOX conjugates, as well as the parent G5 dendrimer, was performed at the University of Michigan Mass Spectrometry Core or the Michigan State University Mass Spectrometry Facility. Briefly, 1 mg of sample was diluted in 50:50 water:methanol before mixing with the 2,5-dihydroxybenzoic acid matrix solution prepared at 10 mg/mL in an acetonitrile:water (1:1) mixture containing 0.1% TFA. Sample solutions were evaporated to dryness on the target plate and analyzed by either a Waters Tofspec-2E or Shimadzu Biotech Axima CFR MALDI-TOF instrument; both calibrated using BSA in sinapinic acid

Synthesis of G5-L(x)-DOX Conjugates

Figure 19:
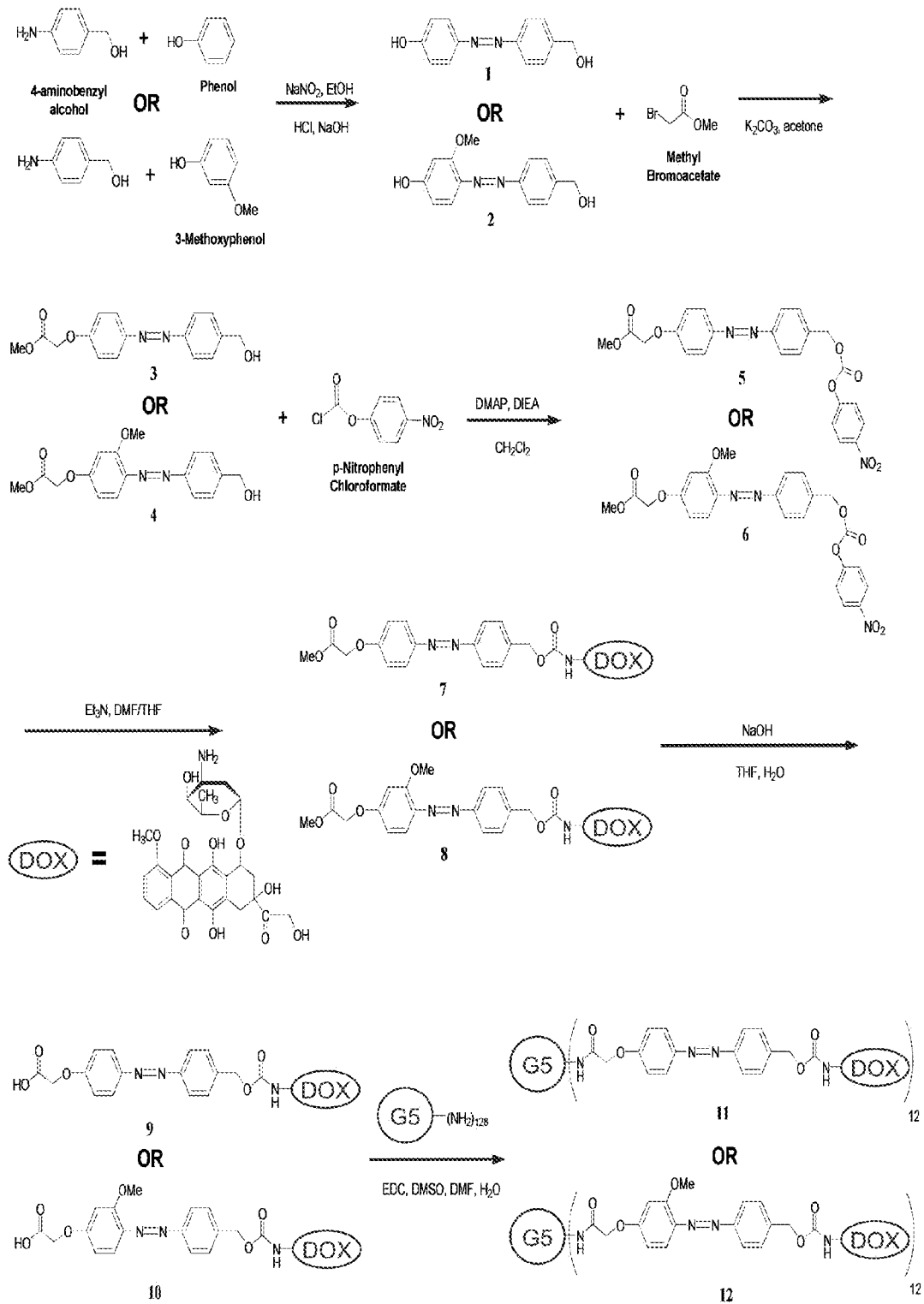
FIG. 19 represents a scheme illustrating a synthetic strategy for G5-L1-DOX and G5-L2-DOX conjugates prepared by coupling azo-bond containing enzyme-activated linkages to G5 dendrimers through a stable peptide bond.
Figure 21:
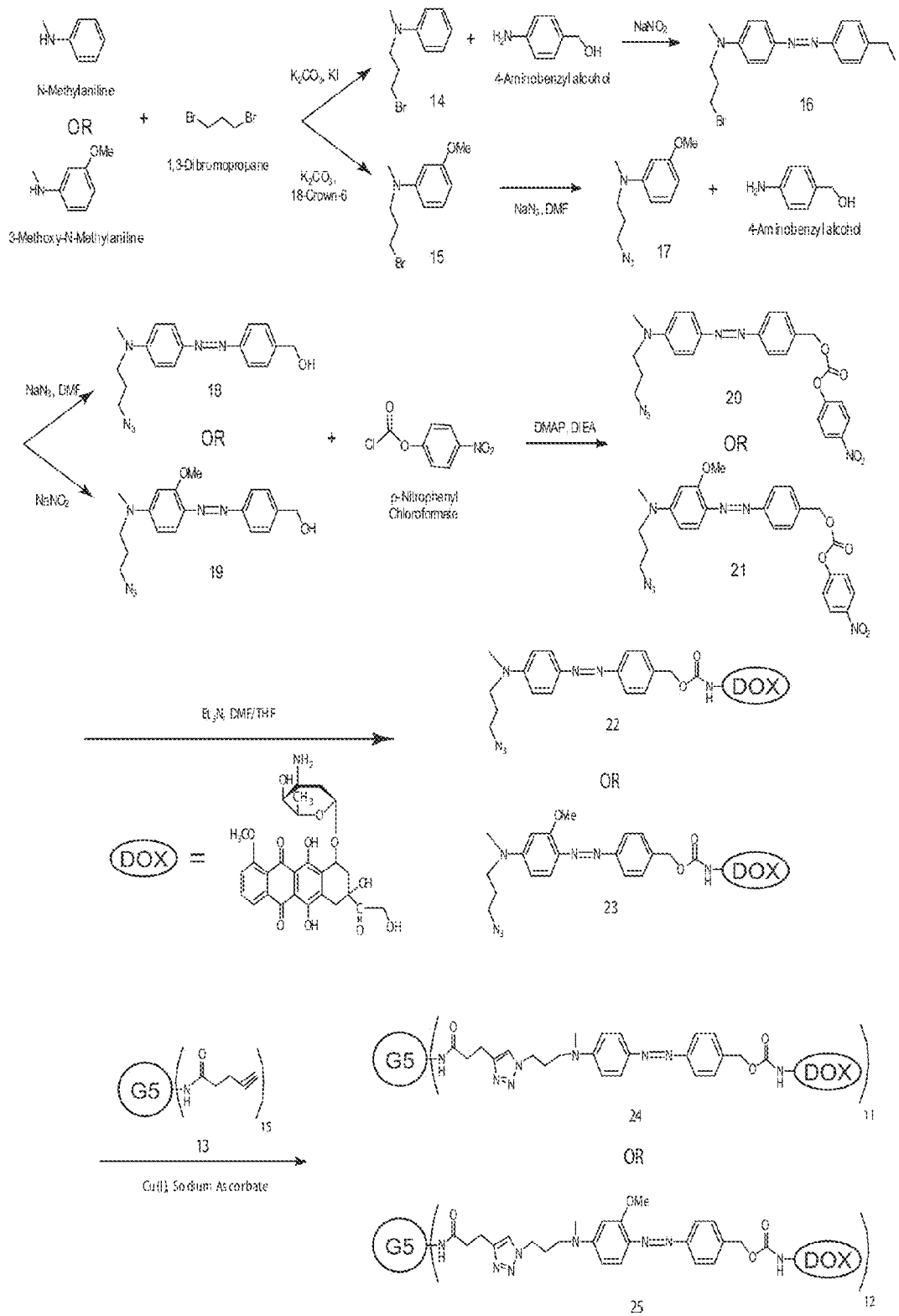
FIG. 21 represents a synthesis scheme of G5-L3-DOX and G5-L4-DOX conjugates prepared by coupling azo-bond containing enzyme-activated linkages to G5 dendrimers through a 'clicked' triazole spacer
Figure 22:
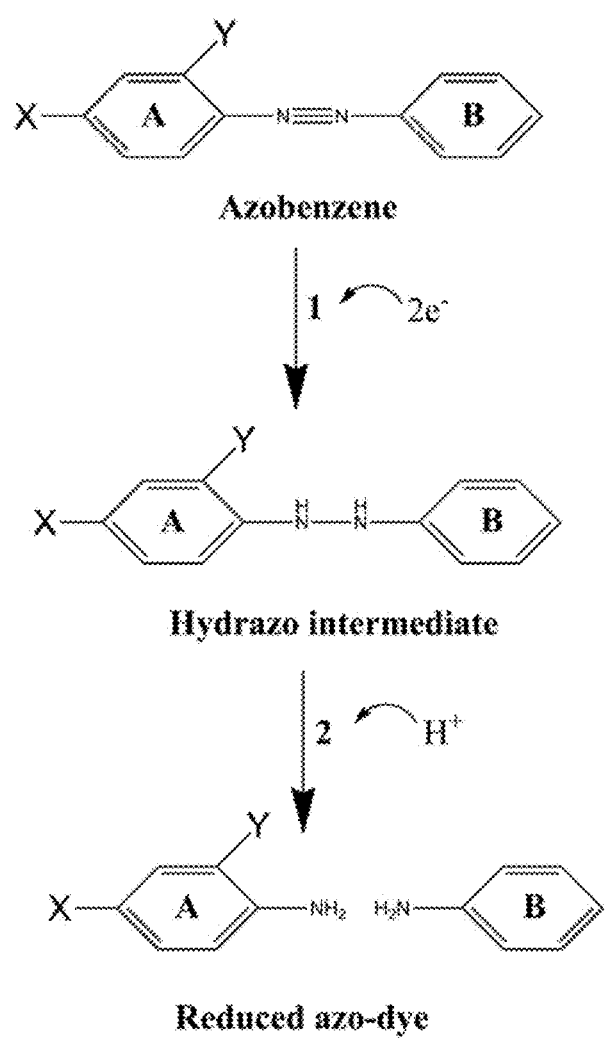
FIG. 22 is an illustration of azobenzene being converted to reduced azo-dye: Azo dyes with electron-donating groups in the para (X) or ortho (Y) positions relative to the azo-bond, and have Hammett constant $\sigma \leq -0.37$, are substrates for the azoreductase enzymes present exclusively in the cytoplasm of hepatic cells. (1) Azoreductase enzymes catalyze the addition of an electron pair from NADPH to the azo-bond, followed by the addition of a second pair of electrons from the non-bonding polar substituents (X & Y). Dissociable protons from water add to the azo-bond forming an unstable hydrazo intermediate, (2) that is quickly reduced to the respective amines.
Figure 23:
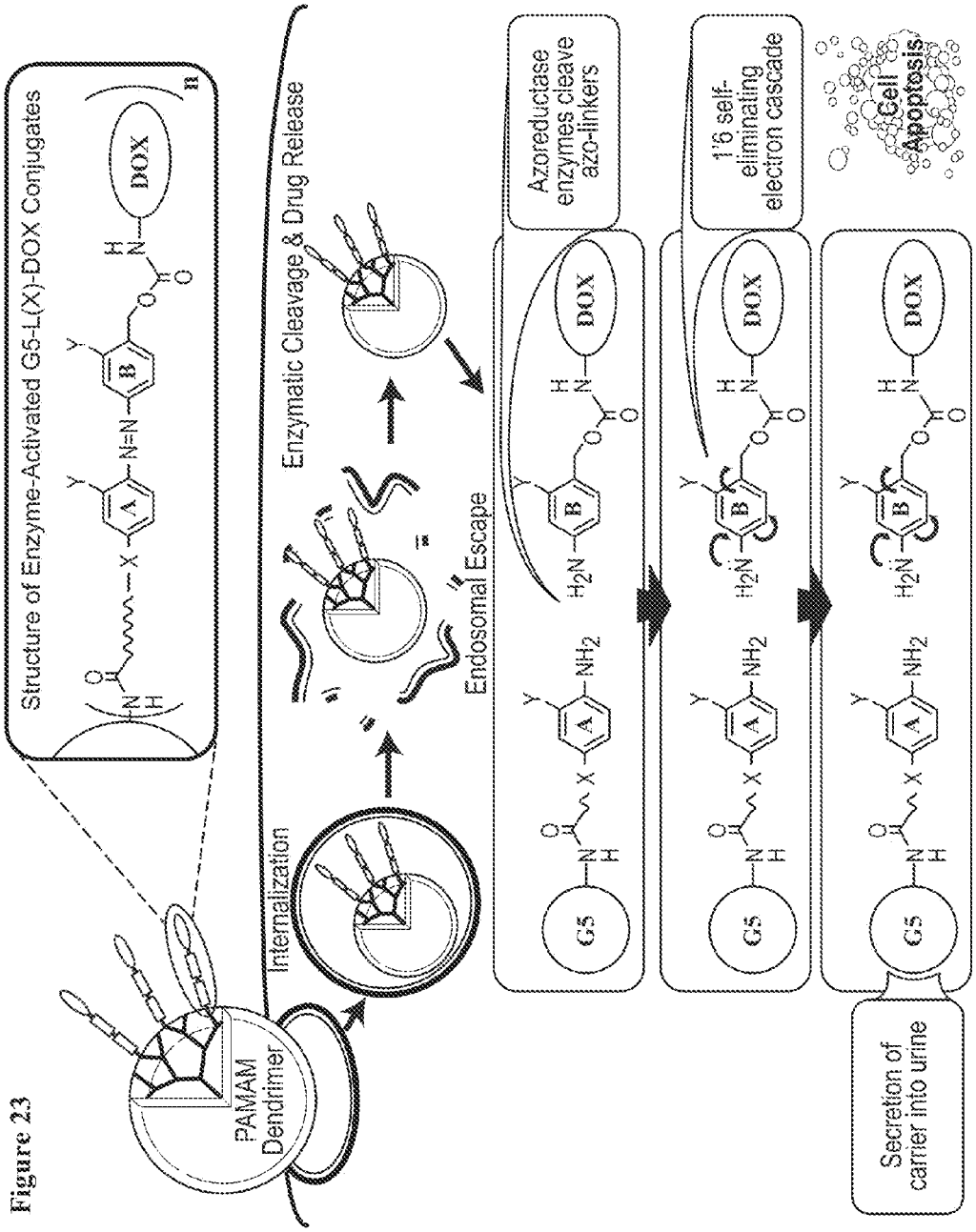
FIG. 23 is a diagram depicting G5-L(x)-DOX conjugate activation by the liver-specific azoreductase enzymes. After internalization into hepatic cancer cells via endocytosis G5-L(x)-DOX conjugates escape the endosomal compartment by the proton sponge mechanism and are delivered to the cytoplasm. After internalization of G5-DOX conjugates the liver-specific azoreductase enzyme binds to the azo-linker resulting in selective reduction of the azo-bond. After cleavage a 1'6 self-eliminating electronic cascade releases free DOX to the cytoplasm of hepatic cancer cells resulting in apoptosis, while the carrier is secreted into the urine.
Figure 24A:
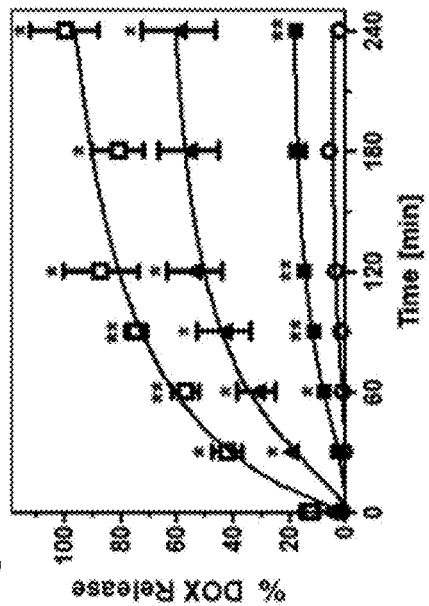
FIG. 24 represents a collection of graphs that demonstrate enzymatic cleavage and DOX release from G5-L(x)-DOX Conjugates. (A) % intact G5-L(x)-DOX conjugates and corresponding (B) % DOX released upon incubation with HLM or (C,D) HepG2 S9 enzyme solutions. Data are expressed as mean (n=3)±SEM., *P<0.05, **P<0.01. P values were determined for L2, L3 and L4 G5-DOX conjugates as compared to G5-L1-DOX results following a two-tailed Student's t-test. Curves were fit by a Michaelis-Menten model using Graphpad Prism software.
Figure 24C:
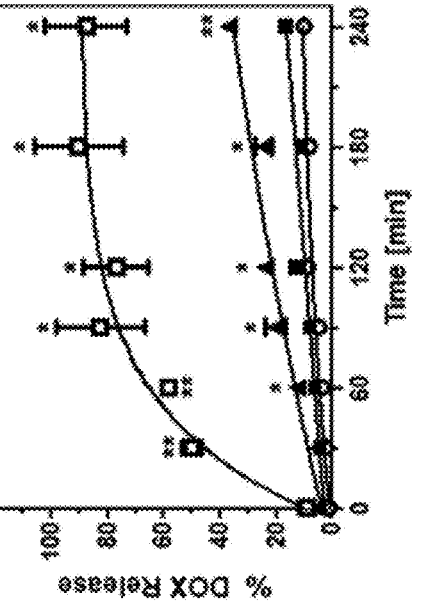
Figure 24B:
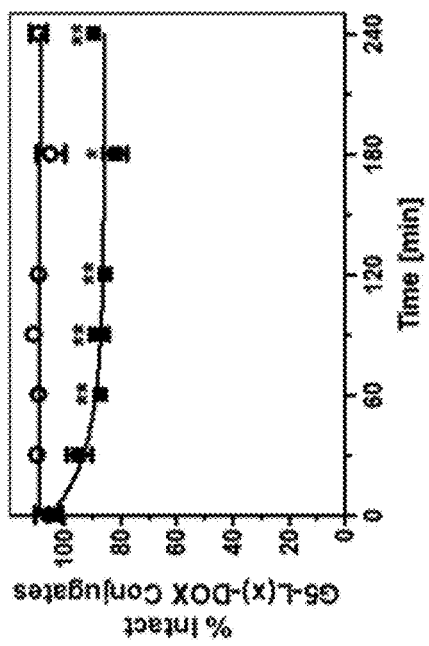
Figure 24D:
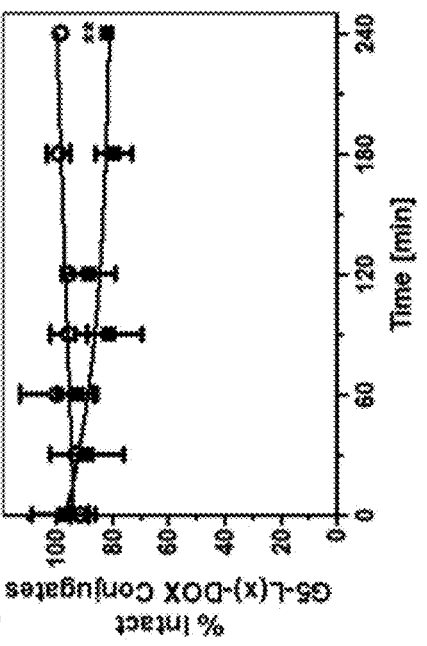

In the following paragraphs directed to syntheses, compounds (1) to (12) are illustrated in FIG. 19, while compounds (13) to (25) are illustrated in FIG. 21.

Synthesis of 4-((4-(hydroxymethyl)phenyl)diazenyl)phenol (1)

4-Aminobenzyl alcohol (0.36 g, 2.92 mmol) and $NaNO_2$ (0.22 g, 3.21 mmol) were dissolved in 7.5 mL EtOH:water (1.5:1), added to 2 N HCl solution (4.5 mL) and stirred at 0° C. for 1 hour. Phenol (0.275 g, 2.92 mmol) in EtOH was added followed by NaOAc (0.15 g) at 0° C. and stirred for 6 hours at room temperature. Reaction mixture was quenched with saturated sodium bicarbonate solution (150 mL) and extracted with DCM. The organic layer was washed with water (200 mL), brine (950 mL), and dried over $Na_2SO_4$. Solvents were evaporated under reduced pressure and the residue was purified by silica gel column chromatography (EtOAc:n-hexane 4:6) to obtain compound 1. Yield: 0.473 g (71%). $^1$H NMR and mass-spectrum data are in good agreement with previously published results.[27]

Synthesis of 4-((4-(hydroxymethyl)phenyl)diazenyl)-3-methoxyphenol (2)

4-Aminobenzyl alcohol (0.275 g, 2.24 mmol) and $NaNO_2$ (0.16 g, 2.35 mmol) were dissolved in 7.5 mL EtOH:water (1.5:1) and added to 2 N HCl solution (4.5 mL) and reaction mixture stirred at 0° C. for 1 hour. 3-methoxyphenol (0.25 g, 2.01 mmol) in EtOH was added, followed by addition of NaOAc (0.15 g) at 0° C. and remaining procedure followed as described for compound 1 to obtain compound 2. Yield: 0.435 g (84%). $^1$H NMR (500 MHz, $CD_3SOCD_3$) δ 3.34 (bs, 4H, OMe, —OH), 4.55 (bs, 2H, $H_f$), 5.31 (s, 1H, phenol-OH), 6.43-6.46 (m, 1H, $H_b$), 6.57-6.60 (m, 1H, $H_e$), 7.44-7.48 (m, 2H, $H_e$), 7.53-7.57 (m, 1H, $H_a$), 7.69-7.74 (m, 2H, $H_d$). $^{13}$C NMR (125 MHz, $CD_3SOCD_3$) δ 55.7 (OMe), 62.5 ($C_f$), 99.9 ($C_c$), 107.9 ($C_b$), 117.4 ($C_i$), 121.9 ($C_d$), 127.0 ($C_e$), 134.8 ($C_a$), 144.7 ($C_k$), 151.5 ($C_j$), 158.9 ($C_h$), 162.6 ($C_g$). ESI-MS: [M+H]$^+$ $C_{14}H_{15}N_2O_3$ calcd 259.1083, obsd 259.10.

Synthesis of 4-(4-(Carbomethoxy)methoxyphenylazo)benzyl alcohol (3)

Compound 1 (0.4 g, 1.75 mmol) and methyl bromoacetate (0.28 g, 1.83 mmol) were dissolved in 40 mL of acetone, and $K_2CO_3$ (0.726 mg, 5.26 mmol) was added at room temperature followed by stirring overnight. The reaction mixture was diluted with 100 mL of EtOAc and washed with water (2×50 ml), brine (50 ml), and dried over $Mg_2SO_4$. After evaporation of solvents under reduced pressure the residue was purified by silica gel column chromatography (EtOAc:n-hexane 4:6) affording compound 3. Yield: 0.395 g (75%). $^1$H NMR (400 MHz, DMSO-$d_6$) δ 3.71 (s, 3H, $H_g$), 4.58 (s, 2H, $H_e$), 4.92 (s, 2H, $H_f$), 5.33 (s, 1H, —OH), 7.10-7.14 (m, 2H, $H_a$), 7.47-7.49 (m, 2H, $H_d$), 7.80-7.86 (m, 4H, $H_b$, $H_c$). $^{13}$C NMR (100 MH, DMSO-$d_6$) δ 52.4 ($C_g$), 62.9 ($C_f$), 65.3 ($C_e$), 115.7, 122.6, 124.8, 127.6, 146.3, 147.1, 151.4, 160.6 169.4. HRMS (ESI$^+$) m/z: [M+H]$^+$ calcd for $C_{16}H_{17}N_2O_4$ 301.1188. Found 301.1176.

Synthesis of methyl 2-(4-((4-(hydroxymethyl)phenyl)diazenyl)-3-methoxyphenoxy)acetate (4)

Compound 2 (0.375 g, 1.45 mmol) was dissolved in 20 mL anhydrous acetone to which $K_2CO_3$ (0.6 g, 4.35 mmol) was added, followed by methyl-bromoacetate (0.15 mL, 1.59 mmol) at room temperature and reaction mixture stirred for 12 hours. The remaining procedure was followed as described for compound 3 to obtain compound 4. Yield: 0.41 g (86%). $^1$H NMR (500 MHz, $CD_3SOCD_3$) δ 3.71 (s, 3H, H, (OMe)), 3.94 (s, 3H, aromatic-$OCH_3$), 4.56 (d, 2H, J=6.0 Hz, $H_f$), 4.93 (s, 2H, $H_l$), 5.34 (t, 1H, J=6.0 Hz, —OH), 6.54-6.64 (m, 1H, $H_b$), 6.78-6.82 (m, 1H, $H_c$), 7.45-7.49 (m, 2H, $H_e$), 7.57-7.61 (m, 1H, $H_a$), 7.73-7.78 (m, 2H, $H_d$). $^{13}$C NMR (125 MHz, $CD_3SOCD_3$) δ 51.96 ($C_m$), 52.2 (aromatic-OMe), 62.5 ($C_f$), 64.8 ($C_l$), 100.0 ($C_c$), 106.4 ($C_b$), 117.2 ($C_i$), 122.1 ($C_d$), 127.0 ($C_e$), 136.2 ($C_a$), 145.3 ($C_k$), 151.4 ($C_j$), 158.4 ($C_h$), 161.7 ($C_g$), 168.8 (CO). ESI-MS: [M+H]$^+$ $C_{17}H_{19}N_2O_5$ calcd 331.1294, obsd 331.11.

Synthesis of 4-(4-(carbomethoxy)methoxyphenylazo)benzyl-4'-nitrophenyl carbonate (5)

Compound 3 (0.2 g, 0.67 mmol) was dissolved in DCM (15 mL) to which freshly activated 4° A M.S (0.1 g) was added and reaction mixture stirred for 10 minutes. DIPEA (0.35 mL, 2.01 mmol) and DMAP (0.01 g) were then added at 0° C. p-Nitrophenyl chloroformate (0.471 g, 2.35 mmol) in DCM (3 mL) was added slowly and mixture stirred at 0° C. for 1 hour, followed by an additional 4 hours at room temperature. The solvents were evaporated under reduced pressure and the residue was purified by silica gel column chromatography (EtOAc:n-hexane 3.5:6.5) affording compound 5. Yield: 0.28 g (86%). $^1$H NMR (400 MHz, $CDCl_3$) δ 3.82 (s, 3H, $H_g$), 4.72 (s, 2H, $H_f$), 5.35 (s, 2H, $H_e$), 6.96-7.02 (m, 2H, $H_a$), 7.34-7.38 (m, 2H, $H_d$), 7.53-7.57 (m, 2H, $H_h$), 7.86-7.90 (m, 4H, $H_b$, $H_c$), 8.24-8.28 (m, 2H, $H_i$); $^{13}$C NMR (100 MHz Varian, $CDCl_3$) δ 52.5 ($C_g$), 65.3 ($C_f$), 70.4 ($C_e$), 114.9, 115.6, 121.8, 123.0, 124.9, 125.3, 126.2, 129.3, 136.3, 145.4, 147.5, 152.4, 152.9, 155.5, 160.2, 161.7, 169.1. HRMS (ESI$^+$) m/z: [M+H]$^+$ calcd for $C_{23}H_{20}N_3O_8$ 466.1250. Found 466.1246.

Synthesis of methyl 2-(3-methoxy-4-((4-((((4-nitrophenoxy)carbonyl)oxy)methyl)phenyl)diazenyl)phenoxy)acetate (6)

Compound 4 (0.1 g, 0.0302 mmol) was dissolved in DCM (15 mL) and freshly activated 4° A M.S (0.15 g) was added and reaction mixture stirred for 10 minutes. DIPEA (0.215 mL, 1.2 mmol) and DMAP (0.05 g) were added and reaction mixture cooled to 0° C. p-Nitrophenyl chloroformate (0.15 g, 0.0757 mmol) in DCM was added slowly and reaction mixture stirred at 0° C. for 1 hour, followed by an additional 4 hours at room temperature. The remaining procedure was followed as described for compound 5 to obtain compound 6 (E:Z isomers). Yield: 0.11 g (76%). $^1$H NMR (500 MHz, $CDCl_3$) δ 3.79 (s, 3H, $H_n$ (OMe), for Z), 3.82 (s, 3H, $H_n$ (OMe), for E), 3.99 (s, 3H, aromatic-OMe for Z), 4.00 (s, 3H, aromatic-OMe for E), 4.58 (s, 2H, $H_f$ for Z), 4.71 (s, 2H, $H_f$ for E), 5.21 (s, 2H, $H_l$ for Z), 5.34 (s, 2H, $H_l$ for E), 6.22-6.28 (m, 1H, $H_b$ for Z), 6.44-6.50 (m, 2H, $H_b$ for E), 6.52-6.60 (m, 1H, $H_e$ for Z), 6.64-6.70 (m, 1H, $H_e$ for E), 6.84-6.95 (m, 2H, $H_e$ for Z), 7.30-7.40 (m, 2H, $H_e$ for E), 7.42-7.50 (m, 1H, $H_a$ for Z), 7.50-7.54 (m, 1H, $H_a$ for E), 7.54-7.58 (m, 2H, $H_n$ for Z), 7.68-7.75 (m, 2H, $H_n$ for E), 7.80-7.90 (m, 4H, $H_d$ for Z and E), 8.08-8.14 (m, 2H, $H_o$ for Z), 8.22-8.30 (m, 2H, $H_o$ for E). $^{13}$C NMR (125 MHz, $CD_3SOCD_3$) δ 52.3, 52.44 ($C_n$), 55.4, 56.34 (aromatic-OMe), 65.2, 65.2 ($C_f$), 67.3, 67.4 ($C_l$), 70.1, 70.4, 100.2 ($C_c$), 104.2, 105.3 ($C_b$), 115.62, 116.9 ($C_i$), 118.0, 120.04, 121.5, 121.7, 121.75, 122.8, 122.9, 125.3, 126.0, 128.7, 128.9, 129.2, 135.9, 137.3, 145.3, 152.3, 154.4, 155.4, 158.7, 161.7, 168.7 (CO). ESI-MS: [M+H]$^+$ C$_{24}$H$_{22}$N$_3$O$_9$ calcd 496.1356, obsd 496.12.

Synthesis of N-(4-(4-(carbomethoxy)methoxyphenylazo)benzyloxycarbonyl)doxorubicin (7)

Compound 5 (0.02 g, 0.043 mmol) was dissolved in anhydrous DMF (1.5 mL) and freshly activated 4° A M.S (0.15 g) was added, followed by stirring of the reaction mixture for 10 minutes. Neutralized Doxorubicin-HCl (0.035 g, 0.060 mmol, 1.4 eq.) was added in 3 mL of DMF via syringe at room temperature, followed by the addition of Et$_3$N (0.015 mL, 0.11 mmol, 2.8 eq.) and reaction mixture stirred at 32° C. for 24 hours. After completion of the reaction (monitored by TLC) water (25 mL) and EtOAc (50 mL) was added and product extracted twice. The organic layer was washed with water (2×50 ml), brine (50 ml), and dried over Na$_2$SO$_4$. After evaporation of solvents under reduced pressure the product was purified by silica gel column chromatography (DCM: MeOH 9.5:0.5) affording compound 7. Yield: 0.03 g (80%). $^1$H NMR (400 MHz, CDCl$_3$) δ1.27 (d, J=6.7 Hz, 3H, H$_g$), 1.76-1.79 (m, 1H, H$_i$), 1.86-1.90 (m, 1H, H$_j$), 2.03 (bd, J=6.7 Hz, 1H, H$_p$), 2.14 (dd, J=14.4 and 4.0 Hz, 1H, H$_p$), 2.32 (d, J=14.4 Hz, 1H, H$_p$), 3.04-2.92 (m, 2H, H$_q$, H$_n$), 3.23 (d, J=18.8 Hz, 1H, H$_q$), 3.67 (bd, 1H, H$_k$), 3.81 (s, 3H, H$_g$), 3.86 (m, 1H, H$_l$), 4.04 (s, 3H, H$_w$), 4.13 (m, 1H, H$_o$), 4.51 (bs, 1H, —OH), 4.69 (s, 2H, H$_f$), 4.74 (d, J=4.0 Hz, 2H, H$_r$), 5.07 (s, 2H, H$_e$), 5.24 (m, 2H, H$_i$), 5.48 (d, J=3.8 Hz, 1H, —OH), 6.94-6.98 (m, 2H, H$_a$), 7.32-7.38 (m, 3H, H$_d$, H$_v$), 7.88-7.69 (m, 5H, H$_b$, H$_c$, H$_l$), 7.99 (d, J=7.4 Hz, 1H, NH), 13.19 (s, 1H, H$_s$), 13.97 (s, 1H, H$_s$). ESI/MS m/z 892.3 (M+Na)$^+$; HRMS (ESI$^+$) m/z: [M+Na]$^+$ calcd for C$_{44}$H$_{43}$N$_3$O$_{16}$Na 892.2541. Found 892.2555.

Synthesis of methyl 2-(3-methoxy-4-((4-(((carbonyl) oxy)methyl)phenyl)diazenyl)phenoxy)acetate doxorubicin (8)

Compound 6 (0.052 g, 0.0105 mmol) was dissolved in anhydrous DMF (2 mL) and freshly activated 4° A M.S (0.15 g) was added and reaction mixture stirred for 10 minutes. Neutralized Doxorubicin-HCl (0.091 g, 0.01575 mmol) in DIPEA (0.075 mL) in DMF (2 mL) was added and reaction mixture stirred at 30° C. for 24 hours. The remaining procedure was followed as described for compound 7 to obtain compound 8 (E:Z isomers). Yield: 0.07 g (76%). $^1$H NMR (500 MHz, CDCl$_3$): δ 1.28 (d, 3H, J=7.5 Hz, H$_m$), 1.78 (dt, 2H, J=3.0, 7.5 Hz, H$_h$, H$_i$), 1.87 (dt, 2H, J=3.0, 7.5 Hz, H$_h$, H$_i$), 2.02-2.08 (m, 1H, H$_l$), 2.13-2.20 (m, 2H, H$_p$), 2.28-2.36 (m, 1H, H$_n$), 2.94-3.08 (m, 2H, H$_q$), 3.23 (bs, 1H, —OH), 3.27 (bs, 1H, —OH), 3.60-3.70 (m, 2H, H$_{j,k}$), 3.80-3.92 (m, 4H, OMe & OH), 3.97 (s, 3H, OMe), 4.06 (s, 3H, OMe), 4.10-4.18 (m, 1H, H$_o$), 4.54 (d, 1H, J=2.5 Hz, —OH), 4.69 (s, 2H, H$_r$), 4.75 (s, 2H, H$_g$), 5.07 (s, 2H, H$_f$), 5.22 (d, 1H, J=4.0 Hz, —OH), 5.26 (bs, 1H, phenolic-OH), 5.50 (d, 1H, J=4.0 Hz, —OH), 6.42-6.52 (m, 1H, H$_b$), 6.64-6.68 (m, 1H, H$_c$), 7.34-7.44 (m, 3H, H$_e$, H$_v$), 7.62-7.84 (m, 5H, H$_a$, H$_d$, H$_u$, H$_w$), 8.00 (d, 1H, J=7.5 Hz, —NH), 13.21 (bs, 1H, OH, H$_s$), 13.96 (bs, 1H, OH, H$_t$). ESI-MS: [M+H]$^+$ C$_{46}$H$_{48}$N$_3$O$_{16}$ calcd 898.3035, obsd 898.32.

Synthesis of N-(4-(4-carboxymethoxyphenylazo) benzyloxycarbonyl)doxorubicin (9)

Compound 7 (0.1 g, 0.011 mmol) was dissolved in THF: water mixture (1.5:1=3 mL) and added to a 1 N NaOH solution (0.1 mL) at −4° C., followed by stirring of the reaction mixture for 20 minutes. After completion of the reaction (monitored by TLC) the mixture was neutralized by addition of 1 N HCl solution at 0° C. to until it reached pH 2-3. After neutralization, water (20 mL) was added and product extracted with EtOAc (2×30 mL). The organic layer was washed with water (2×50 ml), brine (50 ml), and dried over Na$_2$SO$_4$. Solvents were evaporated under reduced pressure and the residue was purified by silica gel column chromatography (DCM:MeOH 9.5:0.5) to get compound 5 (E:Z isomers). Yield: 0.08 g (82%). ESI-MS m/z 878.2 (M+Na)$^+$; HRMS (ESI$^+$) m/z: [M+Na]$^+$ calcd for C$_{43}$H$_{41}$N$_3$O$_{16}$Na 878.2385. Found 878.2396.

Synthesis of 2-(3-methoxy-4-((4-(((benzyloxycarbonyl)doxorubicinmethyl)phenyl)diazenyl)phenoxy) acetic acid (10)

Compound 8 (0.040 g, 0.004 mmol) was dissolved in THF: water (1.5:1=3 mL) and 1 N NaOH solution (0.1 mL) added at −4° C. and reaction mixture stirred for 20 minutes. The remaining procedure was followed as described for compound 9 to obtain compound 10. Yield: 0.034 g (86%). $^1$H NMR (500 MHz, CDCl$_3$): δ 1.26 (d, 3H, J=7.5 Hz, H$_m$), 1.76 (dt, 2H, J=3.0, 7.0 Hz, H$_{h,i}$), 1.88 (dt, 2H, J=3.0, 7.0 Hz, H$_{h,i}$), 2.01-2.07 (m, 1H, H$_l$), 2.13-2.20 (m, 2H, H$_p$), 2.26-2.34 (m, 1H, H$_n$), 2.92-3.06 (m, 2H, H$_q$), 3.23 (bs, 1H, —OH), 3.26 (bs, 1H, —OH), 3.60-3.72 (m, 2H, H$_{j,k}$), 3.79-3.90 (m, 4H, OMe & OH), 3.97 (s, 3H, OMe), 4.10-4.18 (m, 1H, H$_o$), 4.54 (d, 1H, J=2.5 Hz, —OH), 4.68 (s, 2H, H$_r$), 4.75 (s, 2H, H$_g$), 5.06 (s, 2H, H$_f$), 5.22 (d, 1H, J=4.0 Hz, —OH), 5.26 (bs, 1H, phenolic-OH), 5.52 (d, 1H, J=4.0 Hz, —OH), 6.42-6.52 (m, 1H, H$_b$), 6.64-6.68 (m, 1H, H$_c$), 7.34-7.44 (m, 3H, H$_e$, H$_v$), 7.60-7.82 (m, 5H, H$_a$, H$_d$, H$_u$, H$_w$), 8.01 (d, 1H, J=7.5 Hz, —NH), 13.21 (bs, 1H, OH), 13.96 (bs, 1H, OH). ESI-MS: [M+H]$^+$ C$_{45}$H$_{46}$N$_3$O$_{16}$ calcd 884.2878, obsd 884.26.

Coupling of Compound 9 to G5-(NH$_2$)$_{128}$ Dendrimers to Prepare G5-L1-DOX (11)

To a solution of compound 9 (86.5 mg, 0.101 mmol, 120 eq.) dissolved in 15 ml DMF:DMSO (3:1) was added EDC (0.195 g, 1.012 mmol, 1200 eq.) as a solid at room temperature, and the reaction mixture stirred for 1 hour. A solution of G5-(NH$_2$)$_{128}$ PAMAM dendrimers (24.3 mg, 0.0008 mmol) in 5 mL water was added and reaction mixture stirred for 2 days at room temperature. The mixture was then concentrated under reduced pressure and the residue was dissolved in water and purified by dialysis (10 kDa MWCO) for 2 days to produce G5-L1-DOX. Yield: 28 mg (0.0007 mmol, 84.3%). MALDI-TOF analysis of compound G5-L1-DOX showed a molecular weight of 38,260 Da.

Coupling of Compound 10 to G5-(NH$_2$)$_{128}$ Dendrimers to Prepare G5-L2-DOX (12)

To a solution of compound 10 (126 mg, 0.114 mmol, 100 eq.) dissolved in 16 mL DMF:DMSO (3:1) was added EDC (218 mg, 1.14 mmol, 1000 eq.) as a solid at room temperature and reaction mixture stirred for 1 hour at room temperature. A solution of G5-(NH$_2$)$_{128}$ PAMAM dendrimers (32.8 mg, 0.0011 mmol) in 5 mL of water was added and reaction mixture stirred for 2 days at room temperature. The mixture was then concentrated under reduced pressure and the residue was dissolved in water and purified by dialysis (10 kDa MWCO) for 2 days to produce G5-L2-DOX. Yield: 25.0 mg (0.0006 mmol, 84%). MALDI-TOF analysis of compound G5-L2-DOX showed a molecular weight of 38,010 Da.

Synthesis of G5-alkyne (13)

Figure 20:
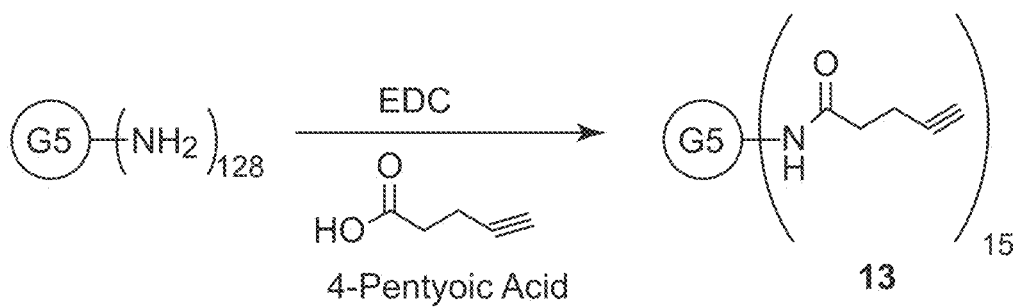
FIG. 20 represents a synthesis scheme of a G5-alkyne intermediate (Compound (13) utilized in the synthesis scheme of FIG. 21.

G5-(NH$_2$)$_{128}$ PAMAM dendrimers (0.060 g, 0.002 mmol) and 1-pentynoic acid (0.003 g, 0.03 mmol) were dissolved in anhydrous DMSO (6 mL), to which PyBOP (0.016 g, 0.032 mmol) and DIPEA (base, 0.020 mL) were added and reaction mixture stirred 36 hours at room temperature. Reaction mixture was purified by dialysis (10 kDa MWCO) for 2 days, followed by lyophilization to afford compound 13 (see FIG. 20). Yield: 0.06 g (96%). $^1$H NMR (500 MHz, D$_2$O): δ 2.18-2.34 (m, 48H, G5-H), 2.40-2.50 (m, 22H, G5-H), 2.56 (s, 2.5H, pentyne-H), 2.58-2.74 (m, 58H, G5-H), 2.97 (t, 2H, J=6.0 Hz, pentyne-H), 3.03-3.24 (m, 44H, G5-H), 3.24 (bs, 0.5H,).

Synthesis of N-(3-bromopropyl)-N-methylaniline (14)

N-methylaniline (300 mg, 2.80 mmol), 1,3-dibromopropane (0.568 mL, 5.6 mmol), K$_2$CO$_3$ (1.16 g, 8.40 mmol) and 18-crown-6 (49.8 mg, 0.30 mmol) were dissolved in 20 mL of anhydrous DMF and mixture stirred for 24 hours at 35° C. The reaction mixture was filtered and washed with DCM, and filtrate dissolved in DCM (100 mL) before extraction in water. The organic layer was washed with water (2×50 ml), brine (50 ml), and dried over Na$_2$SO$_4$, followed by evaporation of solvents under reduced pressure and the residue purified by silica gel column chromatography (EtOAc:n-hexane 1:20 to 1:10) to obtain compound 14. Yield: 0.260 g (74%). $^1$H NMR (500 MHz, CDCl$_3$): δ 2.16 (tt, 2H, J=6.5 and 13.5 Hz, H$_c$), 2.99 (s, 3H, NCH$_3$, H$_a$), 3.46-3.55 (m, 4H, H$_b$ and H$_d$), 6.71-6.79 (m, 2H, H$_e$ and H$_g$), 7.24-7.29 (m, 2H, H$_f$). EI-MS: [M+H]$^+$ C$_{10}$H$_{15}$BrN calcd 228.03, obsd 228.04.

Synthesis of N-(3-bromopropyl)-3-methoxy-N-methylaniline (15)

N-methyl-3-methoxyaniline (1.0 g, 7.294 mmol) was dissolved in anhydrous DMF (20 mL), to which 1,3-dibromopropane (1.48 mL, 14.589 mmol), K$_2$CO$_3$ (3.018 g, 21.884 mmol) and 18-crown-6 (0.24 g, 1.458 mmol) were added at room temperature, and reaction mixture stirred at 35° C. for 24 hours. The remaining procedure was followed as described for compound 14 to obtain compound 15. Yield: 0.760 g (75%). $^1$H NMR (500 MHz, CDCl$_3$): δ 2.16 (tt, 2H, J=6.5, 13.5 Hz, H$_c$), 2.98 (s, 3H, NCH$_3$, H$_a$), 3.46-3.54 (m, 4H, H$_b$ and H$_d$), 3.83 (s, 3H, OMe), 6.32-6.66 (m, 2H, H$_g$ and H$_i$), 6.38-6.42 (m, 1H, H$_a$), 7.16-7.21 (m, 1H, H$_f$); $^{13}$C NMR (125 MHz, CDCl$_3$): δ 29.90 (C$_c$), 31.34 (C$_d$), 38.65 (C$_a$), 50.79 (C$_b$), 55.02 (OCH$_3$), 98.77 (C$_i$), 101.26 (C$_e$), 105.31 (C$_g$), 129.81 (C$_f$), 150.32 (C$_j$), 160.72 (C$_h$). EI-MS: [M+H]$^+$ C$_{11}$H$_7$BrNO calcd 258.05, obsd 258.04.

Synthesis of 4-((4-((3-bromopropyl)(methyl)amino) phenyl)diazenyl)phenyl)methanol (16)

4-Aminobenzyl alcohol (80 mg, 0.65 mmol) and NaNO$_2$ (47 mg, 0.68 mmol) were dissolved in 2.5 mL of EtOH:water (1.5:1), and added to 3 mL of 2 N HCl solution at 0° C. The reaction mixture was then stirred at 0° C. for 1 hour followed by dropwise addition of compound 14 (0.152 g, 0.66 mmol) in EtOH and reaction mixture stirred overnight at 0° C. The remaining procedure was followed as described for compound 3 to obtain compound 16 which was used as a crude mixture for the next step. Yield: 0.126 g (99%). EI-MS: [M+H]$^+$ C$_{17}$H$_{21}$BrN$_3$O calcd 362.0868, obsd 362.10.

Synthesis of N-(3-azidopropyl)-3-methoxy-N-methylaniline (17)

Compound 15 (0.5 g, 1.94 mmol) was dissolved in anhydrous DMF (20 mL) and sodium azide (1.26 g, 19.43 mmol) was added, followed by stirring of the reaction mixture at 70° C. for 16 hours. The remaining procedure was followed as described for compound 16 to obtain compound 17. Yield: 0.340 g (80%). $^1$H NMR (500 MHz, CDCl$_3$): δ 1.86 (tt, 2H, J=6.5, 13.5 Hz, H$_c$), 2.93 (s, 3H, NCH$_3$, H$_a$), 3.36 (t, 2H, J=6.5 Hz, H$_d$), 3.40 (t, 2H, J=7.5 Hz, H$_b$), 3.79 (s, 3H, OMe), 6.20-6.25 (m, 1H, H$_i$), 6.26-6.30 (m, 1H, H$_g$), 6.33-6.38 (m, 1H, H$_e$), 7.10-7.18 (m, 1H, H$_f$); $^{13}$C NMR (125 MHz, CDCl$_3$): δ 26.32 (C$_c$), 38.56 (C$_a$), 49.14 (C$_d$), 49.77 (C$_b$), 55.10 (OCH$_3$), 98.90 (C$_i$), 101.16 (C$_e$), 105.39 (C$_g$), 129.91 (C$_f$), 150.47 (C$_j$), 160.81 (C$_h$). EI-MS: [M+H]$^+$ C$_{11}$H$_{17}$N$_4$O calcd 221.14, obsd 221.12.

Synthesis of 4-((4-((3-azidopropyl)(methyl)amino) phenyl)diazenyl)phenyl)methanol (18)

Compound 16 (0.060 g, 0.166 mmol) was dissolved in 4 mL of anhydrous DMF followed by addition of sodium azide (0.043 g, 0.665 mmol) and reaction mixture stirred at 80° C. for 48 hours. After completion of the reaction (monitored by TLC) the product was filtered and DMF removed under reduced pressure at 40° C., and residue dissolved in DCM (100 mL) and extracted with water. The organic layer was washed with water, brine and dried over Na$_2$SO$_4$, followed by evaporation of solvents the residue under reduced pressure and residue was purified by silica gel column chromatography (EtOAc:n-hexane 3:10 to 3:6) to obtain compound 18. Yield: 0.046 g (86%). $^1$H NMR (500 MHz, CDCl$_3$): δ 1.82 (m, 3H, H$_c$ and —OH), 3.05 (s, 3H, NCH$_3$, H$_a$), 3.42 (t, 2H, J=6.5 Hz, H$_d$), 3.54 (t, 2H, J=7.5 Hz, H$_b$), 4.78 (s, 2H, H$_j$), 6.72-6.79 (m, 2H, H$_e$), 7.42-7.50 (m, 2H, H$_h$), 7.82-7.92 (m, 4H, H$_f$, H$_g$); $^{13}$C NMR (125 MHz, CDCl$_3$): δ 26.41 (C$_c$), 38.8 (C$_a$), 48.9 (C$_d$), 49.5 (C$_b$), 65.0 (C$_j$), 1114 (C$_e$), 122.4 (C$_g$), 125.1 (C$_f$), 127.4 (C$_h$), 142.1 (C$_k$), 143.7 (C$_m$), 151.1 (C$_j$), 152.6 (C$_l$). EI-MS: [M+H]$^+$ C$_{17}$H$_{21}$N$_6$O calcd 325.1777, obsd 325.16.

Synthesis of (4-((4-((3-azidopropyl)(methyl)amino)-2-methoxyphenyl)diazenyl)phenyl)methanol (19)

4-aminobenzylalcohol (0.275 g, 2.24 mmol) and NaNO$_2$ (0.16 g, 2.35 mmol) were dissolved in EtOH/water (4.5+3.0 mL=7.5 mL), to which 2 N HCl solution (4.5 mL) was added at 0° C. and reaction mixture stirred at 0° C. for 1 hour. Compound 17 (0.45 g, 2.04 mmol) in EtOH was added followed by addition of NaOAc (0.15 g) at 0° C. and mixture stirred for 6 hours at room temperature. The remaining procedure was followed as described for compound 1 to obtain compound 19. Yield: 0.58 g (81%). $^1$H NMR (500 MHz, CDCl$_3$): δ 1.87 (tt, 2H, J=6.5, 13.0 Hz, H$_c$), 2.31 (bs, 1H, OH), 3.03 (s, 3H, NCH$_3$, H$_a$), 3.36 (tt, 2H, J=3.0 & 6.5 Hz, H$_d$), 3.49 (tt, 2H, J=3.0 & 7.5 Hz, H$_b$), 4.00 (s, 3H, OMe), 4.67 (s, 2H, H$_j$), 6.20-6.25 (m, 1H, H$_g$), 6.30-6.33 (m, 1H, H$_e$), 7.35-7.42 (m, 2H, H$_i$), 7.70-7.80 (m, 3H, H$_h$, H$_f$); $^{13}$C NMR (125 MHz, CDCl$_3$): δ 26.46 (C$_c$), 38.62 (C$_a$), 48.82 (C$_d$), 49.45 (C$_b$), 55.20 (OCH$_3$), 64.77 (C$_j$), 94.94 (C$_g$), 104.65 (C$_e$), 118.18 (C$_f$), 122.33 (C$_i$), 127.29 (C$_h$), 133.54 (C$_l$), 141.85 (C$_n$), 152.85 (C$_m$), 152.91 (C$_k$), 159.19 (C$_o$). EI-MS: [M+H]$^+$ C$_{18}$H$_{23}$N$_6$O$_2$ calcd 355.18, obsd 355.16.

Synthesis of 4-((4-((3-azidopropyl)(methyl)amino) phenyl)diazenyl)benzyl(4-nitrophenyl)carbonate (20)

Compound 18 (0.020 g, 0.0512 mmol) was dissolved in 3 mL of DCM and freshly activated 4° A M.S (0.1 g) was added and reaction mixture stirred for 10 minutes. DIPEA (0.038 ml, 0.220 mmol) and DMAP (cat) were then added at 0° C.

p-Nitrophenyl chloroformate (0.023 g, 0.116 mmol) in DCM was added dropwise and the reaction mixture stirred at 0° C. for 10 minutes, followed by stirring at room temperature for an additional 30 minutes. The remaining procedure was followed as described for compound 5 to obtain compound 20. Yield: 0.024 g (80%). $^1$H NMR (500 MHz, CDCl$_3$): δ 1.93 (tt, 2H, J=6.5, 13.0 Hz, H$_c$), 3.07 (s, 3H, NCH$_3$, H$_a$), 3.39 (t, 2H, J=6.5 Hz, H$_d$), 3.56 (t, 2H, J=7.0 Hz, H$_b$), 5.34 (s, 2H, H$_i$), 6.72-6.78 (m, 2H, H$_e$), 7.32-6.40 (m, 2H, H$_j$), 7.50-7.58 (m, 2H, H$_h$), 7.81-7.92 (m, 4H, H$_f$ and H$_k$), 8.22-8.28 (m, 2H, H$_g$); $^{13}$C NMR (125 MHz, CDCl$_3$): δ 25.46 (C$_c$), 38.2 (C$_a$), 49.1 (C$_d$), 49.6 (C$_b$), 70.2 (C$_i$), 111.4, 121.8, 131.2, 125.6, 129.2, 134.4, 143.4, 145.3, 151.2, 152.3, 153.6, 155.6. EI-MS: [M+H]$^+$ C$_{24}$H$_{24}$N$_7$O$_5$ calcd 490.1839, obsd 490.17.

Synthesis of 4-((4-((3-azidopropyl)(methyl)amino)-2-methoxyphenyl)diazenyl)benzyl(4-nitrophenyl) carbonate (21)

Compound 19 (0.470 g, 1.32 mmol) was dissolved in DCM (15 mL) and freshly activated 4° A M.S (0.1 g) was added and reaction mixture stirred for 10 minutes. DIPEA (0.925 mL, 5.30 mmol) and DMAP (0.05 g) were then added and reaction mixture cooled to 0° C. p-Nitrophenyl chloroformate (0.535 g, 2.65 mmol) in DCM (2 mL) was added slowly and mixture stirred at 0° C. for 1 hour, followed by an additional 2 hours at room temperature. The remaining procedure was followed as described for compound 6 to obtain compound 21. Yield: 0.48 g (75%).

$^1$H NMR (500 MHz, CDCl$_3$): δ 1.93 (tt, 2H, J=6.5, 13.0 Hz, H$_c$), 3.10 (s, 3H, NCH$_3$, H$_a$), 3.43 (t, 2H, J=3.5 Hz, H$_d$), 3.56 (t, 2H, J=7.0 Hz, H$_b$), 4.05 (s, 3H, OMe), 5.22 (s, 2H, H$_j$), 6.25-6.30 (m, 1H, H$_g$), 6.32-6.38 (m, 1H, H$_e$), 7.00-7.10 (m, 2H, H$_i$), 7.46-7.52 (m, 2H, H$_k$), 7.74-7.90 (m, 3H, H$_j$, H$_f$), 8.12-8.26 (m, 2H, H$_h$); $^{13}$C NMR (125 MHz, CDCl$_3$): δ 26.46 (C$_c$), 38.62 (C$_a$), 48.82 (C$_d$), 49.45 (C$_b$), 55.20 (OCH$_3$), 64.77 (C$_j$), 94.94 (C$_g$), 104.65 (C$_e$), 118.18 (C$_f$), 122.33 (C$_i$), 127.29 (C$_h$), 133.54 (C$_l$), 141.85 (C$_n$), 152.85 (C$_m$), 152.91 (C$_k$), 159.19 (C$_o$). [M+H]$^+$ C$_{25}$H$_{26}$N$_7$O$_6$ calcd 520.19, obsd 520.17.

Synthesis of 4-((4-((3-azidopropyl)(methyl)amino) phenyl)diazenyl)benzyl-Doxorubicin carbonate (22)

Compound 20 (0.020 g, 0.04 mmol) was dissolved in 2 mL of anhydrous DMF and freshly activated 4° A M.S (0.1 g) was added and reaction mixture for 10 minutes. Neutralized Doxorubicin-HCl (0.035 g, 0.061 mmol) in DIPEA (0.075 mL) was added and reaction mixture stirred at 32° C. for 24 hours. The reaction mixture was concentrated under reduced pressure and residue purified by silica gel column chromatography (DCM:MeOH 9.5:0.5) to produce compound 22. Yield: 0.03 g (82%). $^1$H NMR (500 MHz, CDCl$_3$) δ 1.26 (t, 3H, J=7.5 Hz, CH$_3$, H$_o$), 1.72-1.92 (m, 4H, H$_c$, H$_k$, H$_j$), 2.06-16 (m, 3H, H$_n$, H$_j$, H$_k$), 2.23-2.34 (m, 2H, H$_q$), 2.86 (bd, 1H, J=7.5 Hz, —OH), 3.00-3.04 (m, 4H, —OH, NCH$_3$, H$_a$), 3.18 (d, 1H, J=7.5 Hz, —OH), 3.35 (t, 2H, J=6.5 Hz, H$_d$), 3.49 (t, 2H, J=7.0 Hz, H$_b$), 3.65 (m, 1H, —OH), 3.80-3.90 (m, 1H, H$_l$), 4.02 (s, 3H, OMe), 4.10-4.20 (m, 2H, H$_m$, H$_r$), 4.52 (bs, 1H, OH), 4.73 (s, 2H, H$_s$), 5.02 (s, 2H, H$_t$), 5.18-5.29 (m, 3H, OH, H$_r$), 5.46 (bs, 1H, OH), 6.64-6.74 (m, 2H, H$_c$), 7.27-7.40 (m, 4H, H$_u$, H$_v$, H$_w$, H$_g$), 7.64-7.82 (m, 5H, H$_f$, H$_g$, H$_h$), 7.94 (m, 1H, NH), 13.14 (bs, 1H, OH, H$_t$), 13.98 (bs, 1H, OH, H$_t$). ESI-MS: [M+H]$^+$ C$_{46}$H$_{50}$N$_7$O$_{13}$ calcd 908.3467, obsd 908.27.

Synthesis of 4-((4-((3-azidopropyl)(methyl)amino)-2-methoxyphenyl)diazenyl)benzyl(4-Doxorubisine) carbonate (23)

Compound 21 (0.020 g, 0.038 mmol) was dissolved in anhydrous DMF (2 mL) and freshly activated 4° A M.S (0.1 g) was added and reaction mixture stirred for 10 minutes. Neutralized Doxorubicin-HCl (0.033 g, 0.057 mmol) in DIPEA (0.015 mL) was added and reaction mixture stirred at room temperature for 24 hours. After completion of the reaction (monitored by TLC) the solvents were evaporated under reduced pressure and residue purified by silica gel column chromatography (EtOAc:n-hexane 3.5:6.5) affording compound 23. Yield: 0.028 g (76%). $^1$H NMR (500 MHz, CDCl$_3$): δ 0.94 (t, 3H, J=7.5 Hz, H$_q$), 1.56 (dt, 2H, J=3.0, 7.5 Hz, H$_{k,l}$), 1.62 (dt, 2H, J=3.0, 7.5 Hz, H$_{k,l}$), 1.81 (m, 1H, H$_o$), 1.93 (tt, 2H, J=7.5 Hz, H$_c$), 2.18 (t, 2H, J=10.5 Hz, H$_s$), 2.36 (m, 2H, H$_p$), 3.00-3.12 (m, 5H, H$_t$, NCH$_3$, H$_a$), 2.28 (d, 1H, J=1.5 Hz, OH), 3.31 (d, 1H, J=1.5 Hz, OH), 3.41 (t, 2H, J=6.0 Hz, H$_d$), 3.54 (t, 2H, J=7.0 Hz, H$_b$), 3.62-3.72 (m, 2H, H$_m$, OH), 3.86-3.94 (m, 2H, H$_u$, OH), 4.02 (s, 3H, OMe, H$_w$), 4.08 (s, 3H, OMe), 4.10-4.20 (m, 2H, H$_r$, OH), 4.57 (bs, 1H, OH), 4.77 (d, 2H, J=2.5 Hz, H$_u$), 5.04-5.20 (m, 3H, H$_j$, OH), 5.30 (bs, 1H, OH), 5.52 (bs, 1H, OH), 6.22-6.29 (m, 1H, H$_g$), 6.32-6.37 (m, 1H, H$_e$), 7.35-7.44 (m, 3H, H$_y$, H$_i$), 7.74-7.84 (m, 4H, H$_f$, H$_h$, H$_x$, H$_z$), 8.03-8.06 (m, 1H, H$_h$), 13.26 (bs, 1H, OH, H$_v$), 13.99 (bs, 1H, OH, H$_v$). EI-MS: [M+H]$^+$ C$_{46}$H$_{51}$N$_7$O$_{14}$ calcd 925.34, obsd 925.16.

Coupling of Compound 22 to G5-alkyne (13) to Prepare G5-L3-DOX (24)

Sodium Ascorbate (0.002 g, 0.002 mmol), bathophenonthroline sulfonated sodium salt (SBP, 0.0055 g, 0.002 mmol) and Cu(I) (0.001 g, 0.001 mmol) were dissolved in THF:water (1:1=3 mL) and bubbled with nitrogen for 10 minutes. In a separate flask compound 22 (0.0043 g, 0.0003 mmol) and compound 13 (0.012 g, 0.0003 mmol) in THF were combined and solution bubbled with nitrogen for 10 minutes. The flask was then heated to 75° C. for 3-4 minutes, during which time the solution became red in color, followed by cooling to room temperature. The mixture of compounds 13 and 22 were then removed via syringe and added to the catalytic flask dropwise, after which the vessel was capped with a septum, flushed with nitrogen and stirred slowly (~300 rpm) in the dark for 48 hours at room temperature. The reaction mixture was then purified by dialysis (10 kDa MWCO) for 2 days to afford G5-L3-DOX. Yield: 0.014 g (82%). MALDI-TOF analysis of compound G5-L3-DOX showed a molecular weight of 37,900 Da.

Coupling of Compound 23 to G5-(NH$_2$)$_{128}$ Dendrimers to Prepare G5-L4-DOX (25)

Sodium Ascorbate (0.002 g, 0.002 mmol), bathophenonthroline sulfonated sodium salt (SBP, 0.0055 g, 0.002 mmol) and Cu(I) (0.001 g, 0.001 mmol) were dissolved in THF:water (1:1=3 mL) and bubbled with nitrogen for 10 minutes. In a separate flask compound 23 (0.0043 g, 0.0003 mmol) and compound 13 (0.012 g, 0.0003 mmol) in THF were combined and solution bubbled with nitrogen for 10 minutes. The flask was then heated to 75° C. for 3-4 minutes, during which time the solution became red in color, followed by cooling to room temperature. The mixture of compounds 13 and 23 were then removed by syringe added to the catalytic flask dropwise, after which the vessel was capped with a septum, flushed with nitrogen at stirred slowly (~300 rpm) in the dark for 48 hours at room temperature. The reaction mixture was then purified by dialysis (10 kDa MWCO) for 2 days to afford G5-L4-

DOX. Yield: 0.016 g (85%). MALDI-TOF analysis of compound G5-L4-DOX showed a molecular weight of 35,670 Da.

Characterization of G5-L(x)-DOX Conjugates

G5-L(x)-DOX conjugates were dissolved in deionized water at a concentration of 1 µM followed by measuring the size and zeta potential of each conjugate using a 90Plus particle size analyzer with ZetaPALS capability (Brookhaven Instruments Corporation, Holtsville, N.Y.). G5-L(x)-DOX conjugates were dissolved in anhydrous DMF containing 0.1M tetrabutylammonium perchlorate at a concentration of 3 mM of the incorporated azo-linker and the solution was bubbled with nitrogen for 10 minutes before starting cyclic voltammetry (CV) measurements. CV measurements were performed using an Ag—AgCl reference electrode and a platinum wire as both the counter and working electrode. Scans were performed from 0 to +2V at a 0.05 V/s scan rate and data was recorded using an electrochemical potentiostat/galvanostat (Autolab PGSTAT12, Eco Chemie, Urtecht, Netherlands). Analysis of 4-HAB and dimethylaminoazobenzene (DAB) azobenzenes standards using CV measurements was done to compare our results to published work,[28] validate our experimental setup, and determine whether the G5 carrier or attached DOX molecules mask the potential peaks characteristic of the azo-linkers.

Calculation of DOX Loading Per G5 Dendrimer (n):

Number of DOX molecules attached per G5 carriers (n) in each G5-L(x)-DOX conjugate was quantified by measuring the UV absorbance of an aqueous solution of different conjugates ($\lambda_{max}$=500 nm) in deionized water at a 1 mg/mL conjugate concentration. The peak absorbance for each G5-L(x)-DOX conjugate was compared against a DOX concentration versus absorbance calibration curve following Beers Lambert Law[29] to calculate n as described in Eq. 1:

$$DOX\ Conc = 1\frac{mg\ G5\text{-}L(x) - DOX}{ml} * [G5\ MW + n(MW\ of)]^{-1} \quad (1)$$

$$\frac{mmoles\ G5\text{-}L(x) - DOX}{mg\ G5\text{-}L(x) - DOX} * \frac{n}{1}\frac{mmoles\ DOX}{mmoles\ G5\text{-}L(x) - DOX}$$

which is simplified to calculate n as described in Eq. 2:

$$n = \frac{DOX\ Conc * G5MW}{1 - (MW\ of\ L(x) - DOX * DOX\ Conc)} \quad (2)$$

The number of L(x)-DOX attached per G5 dendrimer was also calculated by measuring the increase in molecular weight using MALDI-TOF analysis compared to free G5 analyzed at the same time as each G5-L(x)-DOX conjugates. Molecular weight of G5-L(x)-DOX conjugates from MADLI-TOF analysis was calculated as the geometric mean of the curve, and number of attached DOX per dendrimer (n) calculated as described in Eq. 3.

$$n = \frac{G5 - DOX_{(geo\ mean)} - G5Dendrimer_{(geo\ mean)}}{MW\ of\ L(x) - DOX} \quad (3)$$

Each analysis was performed in triplicate for each G5-L(x)-DOX conjugate and the calculated DOX loading per G5 dendrimer was averaged for the two methods to calculate n.

Cell Culture

HepG2 and Hep3B cells were cultured in T-75 flasks using MEM supplemented with 10% FBS, 1% penicillin/streptomycin/amphotericin (antibiotic-antimycotic), 1% sodium pyruvate and 1% non-essential amino acids. HepG2 and Hep3B cells were culture at 37° C., 5% $CO_2$ and 95% relative humidity with medium change every 48 hours. Cells were passaged at 80-90% confluency using a 0.25% trypsin-EDTA solution. Adult rat cardiomyocytes were isolated from Sprague-Dawley rats following establish protocols[30,31] and used immediately either as a cell suspension in DMEM ($1\times10^6$ cells/mL) or plated in laminin coated 24-well plates at a seeding density of $10\times10^3$-$20\times10^3$ cells/well.

Preparation of S9 Fractions

To prepare the S9 fraction, which are the cytosolic and/or microsomal subcellular fraction of lysed cells,[32] from HepG2 hepatic cancer cells or rat cardiomyocytes cells were pelleted by spinning at 1000 rpm for 5 minutes, followed by re-suspending the cell pellet in 500 λL fractionation buffer (250 mM sucrose, 20 mM HEPES, 10 mM KCl, 1.5 mM $MgCl_2$ and 1 mM EDTA in deionized water containing 0.1% 1 mM dithiothreitol and 0.5% v/v of protease inhibitor cocktail (Sigma Aldrich, St. Louis, Mo.)). Cell suspension was passed 20 times through a 27 G needle and kept on ice for 20 minutes to ensure complete cell lysis before centrifuging the lysate at 9,000×g for 20 minutes to separate the S9 fraction in the supernatant. All S9 fractions isolated from a particular cell type were pooled together and total protein content was determined using the BCA protein assay (Thermo Fisher Scientific, Rockford, Ill.). S9 fractions were divided into 100 µL aliquots and stored at −80° C. till used.

Enzymatic Cleavage of G5-L(x)-DOX Conjugates

Cleavage of G5-L(x)-DOX conjugates upon incubation with HLM, S9 fractions isolated from HepG2 cells or rat cardiomyocytes, or control insect protein solution was investigated by monitoring the cleavage of the azo-linker and the associated DOX release as a function of time. Briefly, G5-L(x)-DOX conjugates were dissolved in 0.1M $KH_2PO_4$ buffer (pH=7.4) at a concentration of 100 µM equivalent DOX, followed by mixing 300 µL of conjugate's solution with HLM, S9 fraction, or control insect protein solution to achieve 0.5 mg/mL in polypropylene tubes. This solution was treated with 5 µL NADPH regenerating solution A and 1 µL NADPH regenerating solution B following manufacturer's specifications (Becton-Dickinson, Franklin Lakes, N.J.), followed by incubation at 37° C. while shaking at 200 rpm to initiate the enzymatic cleavage of G5-L(x)-DOX conjugates. We collected 200 µL of the G5-L(x)-DOX solution at selected time points (0-240 minutes) and mixed it with 300 µL of 0.1M $KH_2PO_4$ buffer (pH=7.4) in a quartz cuvette, added 20 µL of 6N HCl to eliminate NADPH absorbance ($\lambda_{max}$=340 nm) which masks the characteristic absorbance of L1 and L2 azo-linkers, and measured solution's absorbance ($\lambda_{L1}$=346 nm; $\lambda_{L2}$=374 nm) on a DU 730 UV/Vis Spectrophotometer (Beckman Coulter, Indianapolis, Ind.). The % intact azo-linker was calculated for G5-L1-DOX and G5-L2-DOX by dividing the absorbance peak value of the azo-linker at each time point by the initial peak absorbance. We simultaneously mixed 100 µL of the G5-L(x)-DOX solution with 1 mL chloroform to extract free DOX released in solution in response to different treatments, followed by extensive vortexing of this mixture and discarding the aqueous layer. The chloroform fraction was dried under nitrogen and the collected residue dissolved in 100 µL acetonitrile for HPLC analysis. Concentration of free DOX was quantified by measuring its absorbance in the collected fractions at 500 nm using a Symmetry300 C4 5 µm (4.6×250 mm) column connected to a Waters HPLC system equipped with a Waters UV dual λ absorbance detector. A mixture of water:acetonitrile containing 0.14% v/v trifluoroacetic acid was used as a mobile phase to separate free DOX on the C4 column using a solvent gradient of 76:24 for 7 minutes, 48:52 for 7 minutes, and 5:95 for 16 minutes at a flow rate of 1 mL/min. Amount of free DOX present in each sample was quantified by integrating its absorbance intensity at 500 nm versus elution volume using the Waters Breeze software compared to a series of DOX standards with concentrations of 100, 50, 25 and 10 µM. We determined the extraction efficiency of free DOX from the enzyme solutions following the same extraction procedure and HPLC analytical method in parallel with every enzymatic cleavage assay, which was routinely >90%. Percentage of DOX release from G5-L(x)-DOX conjugates in response to different treatments was normalized to the corresponding DOX extraction efficiency. Reduction of G5-L(x)-DOX conjugates by different treatments was investigated in triplicate and results show the average ±standard error of the mean (SEM).

Uptake of G5-L(x)-DOX Conjugates and Intracellular DOX Release

HepG2 or Hep3B hepatic cancer cells were seeded in 24-well plates at a seeding density of 5×10$^5$ cells/well and allowed to adhere overnight before incubating with 0.5 mL of G5-L(x)-DOX conjugates dissolved in OPTI-MEM at a concentration of 100 µM equivalent DOX. Uptake of G5-L(x)-DOX conjugates into HepG2 and Hep3B cells was examined after incubation for 1 hour, whereas the intracellular concentration of released DOX was quantified after incubation for 24 hours. Similarly, uptake of free DOX and G5-L4-DOX conjugates dissolved in Hank's Balanced Salt Solution (HBSS) at a concentration of 100 µM equivalent DOX into plated rat cardiomyocytes was assayed after incubation for 4 and 8 hours. Briefly, cells were washed with cold PBS, trypsinized and centrifuged at 1,000 rpm for 5 minutes before re-suspending the cell pellet in 1 mL of PBS and measuring the number of cells that internalized free DOX or G5-L(x)-DOX conjugates using flow cytometry ($\lambda_{ex}$=488 nm, $\lambda_{em}$=617 nm) following published protocols.[15] Cleavage of G5-L(x)-DOX conjugates and release of the attached DOX molecules upon incubation with HepG2 and Hep3B cells was investigated by measuring the concentration of free DOX in the culture medium and in cell lysates. Free DOX present in the culture medium was extracted by mixing 250 µL of the medium with 2.5 mL of chloroform followed by vigorous vortexing, discarding the medium layer, drying the chloroform fraction under nitrogen, and dissolving the collected residue in 100 µL of acetonitrile to prepare for HPLC analysis. Treated HepG2 and Hep3B cell monolayers were washed with cold PBS, trypsinized, and centrifuged at 1,000 rpm for 5 minutes before re-suspending the cell pellet in 250 µL of the lysis buffer (10 mM borate buffer, pH 9.7, 0.5% v/v Triton X-100), tip-sonicating cell suspension for 10 seconds on ice, and incubating for 30 minutes at 37° C. Cell lysates were mixed with 10 folds its volume of chloroform followed by vigorous mixing and placing this mixture in a sonicating water bath at 37° C. for 30 minutes to separate the aqueous and organic layers. The aqueous layer was discarded while the chloroform layer was dried under nitrogen to obtain a dry residue that was dissolved in 250 µL acetonitrile before analysis by HPLC. Amount of free DOX present in culture medium and cell lysates was quantified by HPLC analysis using a Symmetry300 C4 5 µm (4.6×250 mm) column connected to a Hewlett Packard 1090 HPLC system equipped with an HP 1046 fluorescence detector set at $\lambda_{ex}$ of 486 nm, $\lambda_{em}$ of 560 nm, and photo multiplier gain of 16. A 60:40 water:acetonitrile mixture containing 0.14% v/v trifluoroacetic acid was used at a flow rate of 1 mL/min as a mobile phase to separate free DOX on the C4 column for 15 minutes. Amount of free DOX present in each sample was quantified by integrating its fluorescence intensity versus elution volume using the HP Chemstation software compared to a series of DOX standards with concentrations of 100, 10 and 1 µM. We determined the extraction efficiency of free DOX following the same extraction procedure and HPLC analytical method, which was routinely >85%. Percentage of free DOX present in the culture medium or cell lysate was normalized to the corresponding DOX extraction efficiency. Intracellular cleavage of G5-L(x)-DOX conjugates and the associated DOX release profile was investigated in triplicate for each conjugate in each cell line and results show the average ±SEM.

Clonogenic Survival of Hepatic Cancer Cells

We compared the anticancer activity of G5-L(x)-DOX conjugates to free DOX as a function of concentration by measuring their effect on clonogenic survival of HepG2 and Hep3B hepatic cancer cells. Briefly, HepG2 and Hep3B cells were seeded at a density of 2.5×10$^5$ cells/T-25 flask and allowed to adhere overnight before incubating with different concentrations (1 nM-100 µM equivalent concentration of DOX) of free DOX or G5-L(x)-DOX conjugates dissolved in OPTI-MEM solution. HepG2 and Hep3B cells were also incubated with acetylated G5-(Ac)$_{11}$ dendrimers (at equivalent polymer concentrations to G5-L(x)-DOX conjugates) prepared via partial acetylation of the dendrimer surface amine groups following published protocols,[33] and fresh culture medium as negative controls. After 72 hours HepG2 and Hep3B cells were washed with cold PBS, trypsinized using a 0.25% trypsin-EDTA solution and centrifuged at 1,000 rpm for 5 minutes. Cell pellets were suspended in fresh culture medium, counted, and plated in 6-well plates at a seeding density of 500-10,000 cells/well and allowed to grow undisturbed for 14 days under normal culture conditions. The formed colonies were gently washed with cold PBS, treated with 1 mL methanol/glacial acetic acid (75/25) and 0.04% w/v trypan blue for 5 minutes and counted. Plating efficiency (PE) for each cell line was calculated by dividing the number of colonies by the cell seeding density for cells incubated with fresh culture medium (negative control). The surviving fraction (SF) represents the number of hepatic cancer cells that can replicate after treatment with different concentration of free DOX and G5-L(x)-DOX conjugates and is calculated by normalizing the number of counted colonies to the product of the original seeding density and plating efficiency (PE). All samples were prepared in triplicate for each seeding density and treatment condition, and results expressed as the average % SF±SEM. Cytotoxicity curves were fit by a log(conc.) vs. response (% survival) model and IC$_{50}$ (dotted horizontal line) calculated using Graphpad Prism software.

Cardiac Toxicity of Free DOX and G5-L4-DOX Conjugates

Toxicity of G5-L4-DOX conjugates and free DOX in rat cardiomyocytes was evaluated using the lactate dehydrogenase (LDH) leakage cell viability assay. Briefly, each well was counted for total number of cardiomyocytes before an 8 hour treatment with free DOX or G5-L4-DOX (100 µM eq. DOX) conjugates dissolved in 0.5 mL HBSS. The amount of LDH released to the medium was assayed by mixing 1000 µL of the treatment solution in a 96-well plate with the enzyme substrate (1:1) included in the assay kit following the manufacturer's guidelines. The plate was then measured at λ=490 nm using a Multiskan microplate reader (Thermo Scientific, Waltham, Mass.), and results compared to cardiomyocytes incubated with blank HBSS and 10% v/v Triton X-100 solution as negative and positive controls, respectively. Amount of LDH leakage for treatment solution and controls were normalized to the number of seeded cells, and all values compared to the positive control (set as 100% LDH leakage reference) to obtain the percentage of LDH leakage as a function of treatment. Treatments resulting in statistically higher LDH leakage versus the negative control were considered cytotoxic.

Example 12

This example demonstrates the development of enzyme-activated nano-conjugates.

Synthesis of G5-L(x)-DOX Conjugates

Synthesis of the azo-linkers incorporated into G5-L(x)-DOX conjugates was performed via diazotization of different aromatic compounds, with yields of each intermediate matching similar reactions described in the literature,[18,27] to produce the desired azo-dyes with a characteristic red color distinguishable by UV (see $\lambda_{max}$ in Table 3).

substituent obtained from published constants.[22,23] To calculate the cumulative $\sigma$ value of the azo-linkers each substituents $\sigma$ value for was added to the contribution of the R—CH—R' group ($\sigma_C$=−0.17) in the para position of the opposite benzyl moiety, resulting in $\sigma$ values for G5-L(x)-DOX conjugates calculated as −0.44, −0.71, −1.00 and −1.27 for G5-L1-DOX, G5-L2-DOX, G5-L3-DOX and G5-L4-DOX, respectively (Table 3). CV analysis showed all conjugates had a single positive potential peak that fell between 1.00V-1.60V (Table 3; FIG. 30). Attachment of DOX molecules to the G5 carriers resulted in molecular weights of G5-L(x)-DOX conjugates between 36-38 kDa as determined by MALDI-TOF analysis, and particle sizes of 18.6 nm for G5-L1-DOX, 18.0 nm for G5-L2-DOX, 24.6 nm for G5-L3-DOX and 22.4 nm for G5-L4-DOX. All G5-L(x)-DOX conjugates had an approximately neutral charge (0.61-1.02 mV) determined by zeta potential analysis.

Enzymatic Activation of G5-L(x)-DOX Conjugates by Azoreductase Enzymes

In order to achieve therapeutic activity G5-L(x)-DOX conjugates must release free DOX molecules to the cytoplasm of

TABLE 3

Characterization of G5-L(x)-DOX conjugates

| Conjugate | X, Y Substitution | Substitution $\sigma$ Value | Hammett Sigma Value ($\sigma$) | Positive Potential Peak[a] [V] | Azo-linkage $\lambda_{max}$ [nm] | Molecular Weight[b] [Da] | n[c] | Size[d] [nm] | Zeta Potential [mV] |
|---|---|---|---|---|---|---|---|---|---|
| G5-L1-DOX | X = O<br>Y = H | $\sigma_X$ = −0.27<br>$\sigma_Y$ = 0.00<br>$\sigma_C$ = −0.17 | −0.44 | +1.18 | 346 | 38,260 | 12 ± 1 | 18.6 ± 2.9 | 0.97 ± 0.26 |
| G5-L2-DOX | X = O<br>Y = O—CH$_3$ | $\sigma_X$ = −0.27<br>$\sigma_Y$ = −0.27<br>$\sigma_C$ = −0.17 | −0.71 | +1.29 | 374 | 38,010 | 12 ± 2 | 18.0 ± 1.4 | 0.70 ± 0.27 |
| G5-L3-DOX | X = N—CH$_3$<br>Y = H | $\sigma_X$ = −0.8<br>$\sigma_Y$ = 0.00<br>$\sigma_C$ = −0.17 | −1.00 | +1.07 | 485 | 37,900 | 11 ± 1 | 24.6 ± 1.3 | 0.61 ± 0.28 |
| G5-L4-DOX | X = N—CH$_3$<br>Y = O—CH$_3$ | $\sigma_X$ = −0.83<br>$\sigma_Y$ = −0.27<br>$\sigma_C$ = −0.17 | −1.27 | +1.09 | 480 | 36,710 | 12 ± 3 | 22.4 ± 5.8 | 1.02 ± 0.20 |

[a]Determined by Cyclic Voltammetry (FIG. 30)
[b]Determined by MALDI-TOF analysis (FIG. 29, or not shown)
[c]Calculated as average from UV and MALDI-TOF results (Eq. 2 and Eq. 3)
[d]Determined by Dynamic Light Scattering.

A p-Nitrophenyl chloroformate group was installed on ring B of the azo-molecules to create the 1'6 self-eliminating spacer and allow for coupling of DOX based on published protocols,[34] with L(x)-DOX yields of 76%-82%. Covalent attachment of the L(x)-DOX carboxylic acid to G5-(NH$_2$)$_{128}$ dendrimers through a stable amide bond was accomplished via facile EDC coupling to produce G5-L1-DOX and G5-L2-DOX conjugates. This coupling strategy resulted in poor yields (<50%) during the synthesis of G5-L3-DOX and G5-L4-DOX conjugates due to intermolecular azo-DOX reactions of the aniline derivatives during EDC activation. To enhance the specificity for coupling of azo-DOX to the G5 carrier, and avoid side reactions, a triazole "click" spacer was employed to synthesize G5-L3-DOX and G5-L4-DOX conjugates resulting in improved yields (>80%). G5-L(x)-DOX conjugates were synthesized with an equal number of DOX molecules (11-12) per dendrimer as confirmed by UV and molecular weight analysis (Table 3).

Characterization of G5-L(x)-DOX Conjugates

G5-L(x)-DOX conjugates were synthesized with different O ($\sigma$=−0.27) and/or N ($\sigma$=−0.83) substitutions in the para and ortho position of the azo-linker, with the $\sigma$ value for each hepatic cancer cells after reduction of the azo-linkers by azoreductase enzymes. The selectivity of G5-L(x)-DOX cleavage and subsequent DOX release in the presence of azoreductase enzymes was quantified via UV and HPLC analysis, respectively, upon incubation of the conjugates with HLM enzymes, S9 cytoplasmic enzyme fractions from human hepatic cancer cells, and non-enzymatic control proteins for 4 hours. Results show G5-L1-DOX conjugates were not cleaved by HLM enzymes as ~100% of the azo-linkages were intact after the 4 hour incubation period as determined by UV monitoring (FIG. 24; Panel A). G5-L2-DOX showed a linear increase in cleavage by HLM enzymes resulting in 85% of the conjugate intact after 1.5 hours of incubation, which remained at this level for the remainder of the 4 hour incubation period. Cleavage of G5-L3-DOX and G5-L4-DOX conjugates could not be monitored by UV because of the $\lambda_{max}$ for these linkers (480-485 nm) falling within the UV absorbance peak of the attached DOX molecules (500 nm). The cleavage of G5-L(x)-DOX conjugates was correlated to DOX release upon reduction and self-elimination of the azo-linkers as determined by HPLC analysis. Results show 4% DOX was released from G5-L1-DOX conjugates after a 4 hour incubation with HLM enzymes (FIG. 24; Panel B). Incubation of G5-L2-DOX with HLM enzymes resulted in a linear increase in DOX release which plateaued at 17% after 2 hours of incubation. G5-L3-DOX and G5-L4-DOX conjugates incubated with HLM enzymes also showed a linear drug release profile achieving 60% and 100% total DOX release after 2 hours of incubation, respectively.

While HLM enzymes represent an in situ system containing the azoreductase enzymes to validate the enzymatic activation of G5-L(x)-DOX, they are isolated from healthy human hepatocytes and do not represent the enzymatic composition of hepatic cancer cells. To evaluate the cleavage of G5-L(x)-DOX in the cytoplasm of human hepatic cancer cells the S9 cytoplasmic enzyme fraction was isolated from HepG2 cells and incubated with each conjugate for 4 hours. UV monitoring of G5-L1-DOX conjugate cleavage by HepG2 S9 enzymes showed 96% of the azo-linkers intact after 4 hours of incubation (FIG. 24; Panel C), while 82% of G5-L2-DOX conjugates remained under the same conditions. These results closely matched the total DOX released from G5-L(x)-DOX conjugates in the presence of HepG2 S9 enzymes (FIG. 26; Panel D). G5-L1-DOX and G5-L2-DOX conjugates displayed a linear increase in DOX release over the 4 hour incubation period resulting in 8% and 17% total DOX released, respectively. Similarly, incubation of G5-L3-DOX conjugates with HepG2 S9 enzymes resulted in a linear release profile totaling 37% DOX release after 4 hours. G5-L4-DOX conjugates showed 89% total DOX release after 2 hours of incubation, and remained at this value for the remainder of the 4 hour incubation period.

Figure 25A:
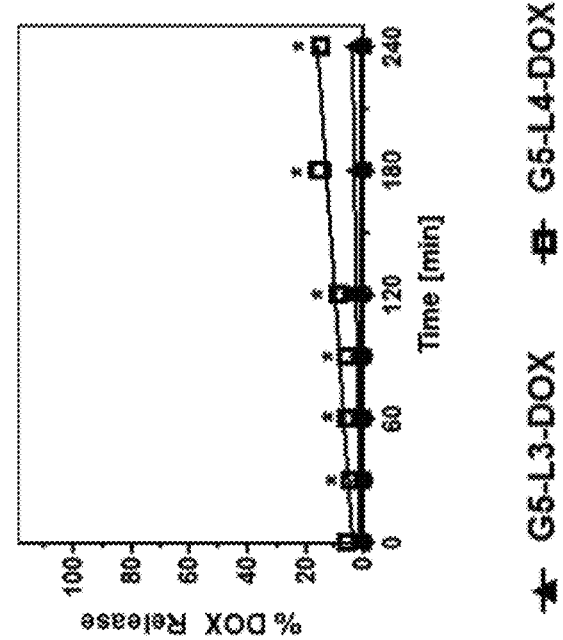
FIG. 25 represents a pair of graphs that demonstrate Control azo-linker reduction and DOX release from G5-L(x)-DOX Conjugates. (A) % intact G5-L(x)-DOX conjugates and corresponding (B) % DOX released upon incubation of conjugates with non-enzymatic control protein. Data are expressed as mean (n=3)±SEM, *P<0.05. P values were determined for L2, L3 and L4 G5-L(x)-DOX conjugates as compared to G5-L1-DOX results following a two-tailed Student's t-test. Curves were fit by a Michaelis-Menten model using Graphpad Prism software.
Figure 25B:
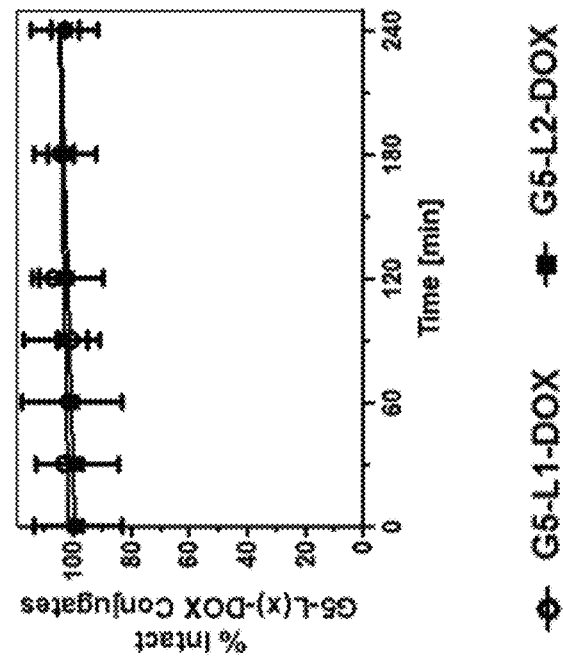
Figure 32:
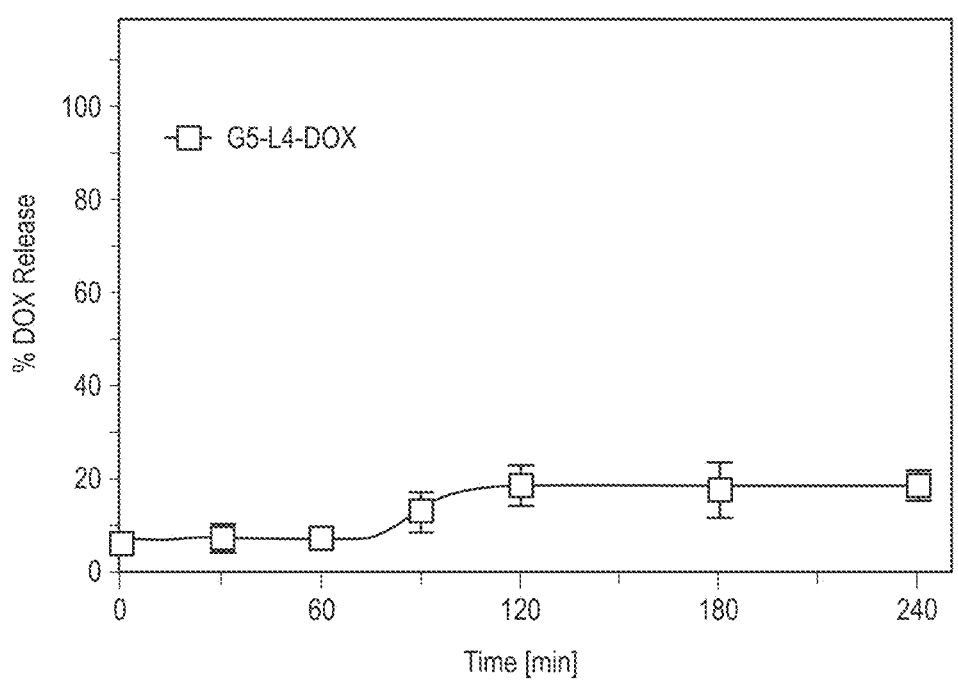
FIG. 32 represents a graph of the Percent of DOX released from G5-L4-DOX conjugates upon incubation with NADPH enzyme cofactor as a function of time. Data are expressed as mean (n=3)±SEM. Curve was fit by a Michaelis-Menten model using Graphpad Prism software.
Figure 33:
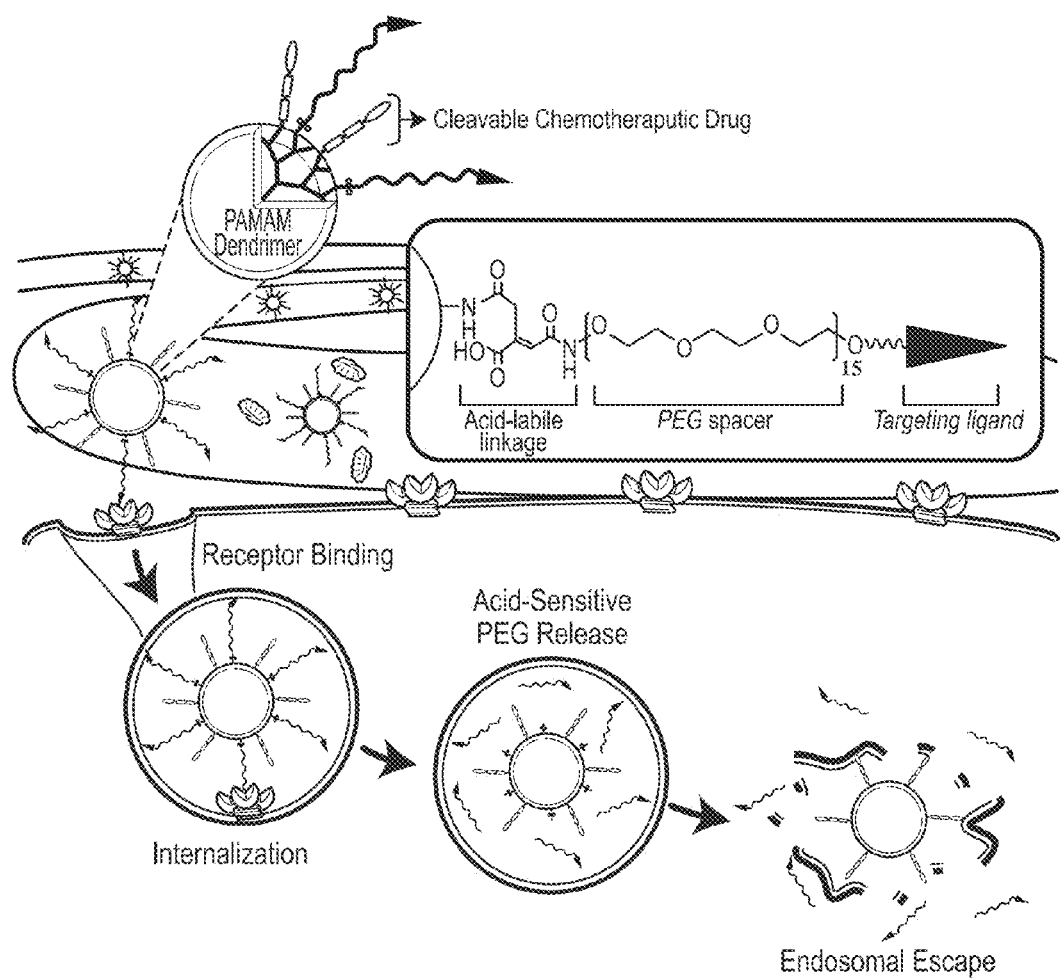
FIG. 33 represents a schematic drawing showing the composition of a drug-loaded targeted G5-(cPEG) conjugates recognized by the ASGPR expressed on the surface of hepatic cancer cells (e.g. HepG2) after preferential distribution to liver tumor tissue via the EPR effect while avoiding opsonization in the systemic circulation due to the PEG corona. The binding of the displayed targeting ligand to the ASGPR triggers receptor-mediated endocytosis of these conjugates, followed reduction of the cis-aconityl linkages by the acidic endosome and endosomal escape of the dendrimer carrier.

To confirm that cleavage of G5-L(x)-DOX and DOX release was selective for the azoreductase enzymes, each conjugate was incubated with non-enzymatic control proteins and the NADPH cofactors. Results show ~100% of G5-L1-DOX and G5-L2-DOX conjugates were intact after the 4 hour incubation period with control proteins (FIG. 25; Panel A). This correlated to <1% DOX release for both G5-L1-DOX and G5-L2-DOX conjugates over the same incubation time as determined by HPLC analysis (FIG. 25; Panel B). G5-L3-DOX conjugates showed 4% DOX release in the presence of control proteins, while G5-L4-DOX released 16% of the loaded DOX after 4 hours. To evaluate the influence of the NADPH cofactor on non-specific DOX release from G5-L4-DOX in the presence of the non-enzymatic control proteins the conjugate was incubated with the NADPH regenerating solution without the presence of protein for 4 hours, resulting in 18% total DOX release (FIG. 32).

Hepatic Cancer Cell Uptake and Intracellular Drug Release from G5-L(x)-DOX Conjugates To confirm that the enzymatic activation of G5-L(x)-DOX conjugates translated to cytoplasmic delivery of free DOX in whole hepatic cancer cells the uptake and intracellular DOX release of each conjugate in HepG2 and Hep3B human hepatic cancer cells was investigated. Uptake studies showed G5-L(x)-DOX conjugates were internalized by 100% of the treated HepG2 and Hep3B cells after only 1 hour of incubation. By normalizing the average fluorescence intensity of cells treated with G5-L(x)-DOX conjugates to the fluorescence of cells treated with free DOX we determined the folds DOX fluorescence as a function of treatment and cell type (FIG. 26; Panels A & C). Uptake results show nearly all G5-L(x)-DOX conjugates delivered higher concentrations of DOX to the cytoplasm of hepatic cancer cells compared to incubation with free DOX. Specifically, G5-L1-DOX and G5-L2-DOX conjugates achieved 4.4-4.5 folds the intracellular concentration of DOX in HepG2 cells compared to cells treated with free DOX after a 1 hour incubation period (FIG. 26; Panel A). Relative uptake of G5-L3-DOX and G5-L4-DOX conjugates into HepG2 cells showed 1.0 and 1.6 folds the intracellular concentration of DOX compared to cells treated with free DOX for 1 hour.

Despite this differential uptake profile between the G5-L(x)-DOX conjugates intracellular release of free DOX to hepatic cancer cells after 24 hours of incubation (FIG. 26, Panels B & D) matched the same rank order of DOX release as observed during azoreductase enzymatic reduction of each conjugate (FIG. 24, Panel B). Specifically, incubation of HepG2 cells with G5-L1-DOX resulted in 1% of the loaded DOX released to both the medium and intracellular lysate, totaling 2% release of the loaded DOX after 24 hours of incubation (FIG. 26; Panel B). Approximately 3% of the loaded DOX was released to the medium for L2-L4 G5-L(x)-DOX conjugates, while intracellularly released DOX assayed in the lysate increased from 3% for G5-L2-DOX, to 14% and 37% for G5-L3-DOX and G5-L4-DOX, respectively. This resulted in 7%, 17% and 39% total DOX release from G5-L2-DOX, G5-L3-DOX and G5-L4-DOX conjugates, respectively, after 24 hours of incubation with HepG2 cells.

Figure 27A:
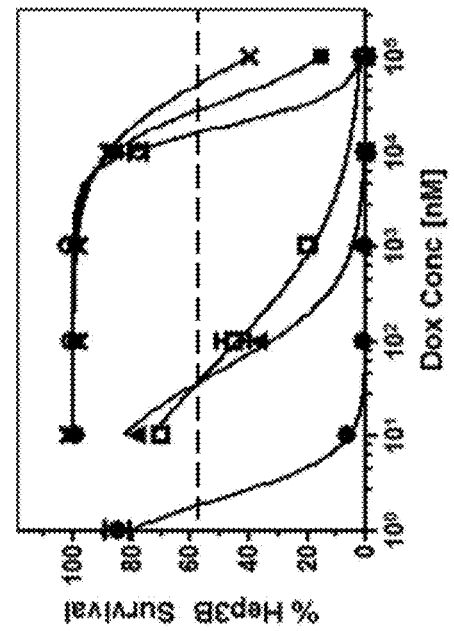
FIG. 27 represents a pair of graphs that demontrate Clonogenic survival of hepatic cancer cells treated with G5-L(x)-DOX conjugates. (A) HepG2 and (B) Hep3B cytotoxicity profiles upon treatment with 1 nM-100 µM concentrations of free DOX, G5-L(x)-DOX conjugates or an equivalent concentration of the G5-$(Ac)_{11}$ polymer control. Data are expressed as the mean for all seeding densities (n=3)±SEM. Curves were fit by a log(conc.) vs. response (% survival) model and $IC_{50}$ (dotted horizontal line) calculated using Graphpad Prism software.
Figure 27B:
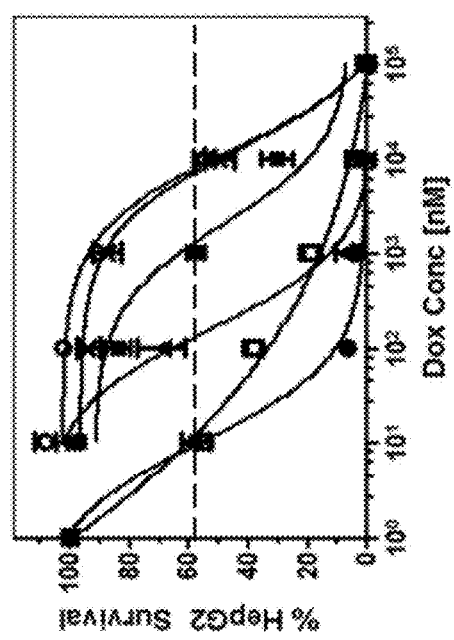

Uptake and intracellular DOX release from G5-L(x)-DOX conjugates in Hep3B cells matched results obtained for HepG2 cells under similar conditions. G5-L1-DOX and G5-L2-DOX conjugates showed a 3.7-fold increase in the intracellular DOX concentrations in Hep3B cells relative to cells treated with free DOX after a 1 hour incubation (FIG. 26; Panel C). Incubation of Hep3B cells with G5-L3-DOX conjugates for 1 hour resulted in equivalent intracellular DOX concentrations as compared to the free DOX, while G5-L4-DOX achieved 1.4 folds the intracellular drug concentration. Intracellular DOX release from G5-L(x)-DOX conjugates in Hep3B cells showed 1-2% DOX release to the medium for all the conjugates tested after a 24 hour incubation period (FIG. 26; Panel D). Similarly to HepG2, intracellularly released DOX from G5-L(x)-DOX conjugates assayed in the lysate of treated Hep3B cells followed a rank order of release which matched the affinity of the azo-linker to azoreductase reduction, achieving 0%, 2%, 9% and 27% DOX released to the cytoplasm of Hep3B cells after a 24 hour incubation with G5-L1-DOX, G5-L2-DOX, G5-L3-DOX and G5-L4-DOX conjugates, respectively. This resulted in 1%, 3%, 10% and 28% total DOX released from G5-L1-DOX, G5-L2-DOX, G5-L3-DOX and G5-L4-DOX conjugates, respectively, after 24 hours of incubation with Hep3B cells Anticancer Activity of G5-L(x)-DOX Conjugates Enzymatic activation of G5-L(x)-DOX conjugates and selective DOX release to the cytoplasm of hepatic cancer cells is expected to result in significant anticancer activity of these conjugates in vitro. We tested this by performing a clonogenic survival assay on HepG2 and Hep3B cells incubated with G5-L(x)-DOX conjugates or free DOX at different equivalent DOX concentrations, and compared the percentage of surviving colonies after treatment to cells incubated with G5-(Ac)$_{11}$ or blank medium as negative controls (FIG. 27). Results showed a concentration dependant decline in the % SF of HepG2 cells treated with free DOX for 72 hours (FIG. 27; Panel A), resulting in an IC$_{50}$ of 10 nM (Table 4).

TABLE 4

Clonogenic Survival of G5-L(x)-DOX Conjugates

| Treatment | HepG2 IC$_{50}$ [nM] | Hep3B IC$_{50}$ [nM] |
| --- | --- | --- |
| Free DOX | 10 ± 4 | 2 ± 1 |
| G5-L4-DOX | 13 ± 5 | 48 ± 1** |

TABLE 4-continued

Clonogenic Survival of G5-L(x)-DOX Conjugates

| Treatment | HepG2 IC$_{50}$ [nM] | Hep3B IC$_{50}$ [nM] |
| --- | --- | --- |
| G5-L3-DOX | 158 ± 3** | 63 ± 1** |
| G5-L2-DOX | 2,042 ± 5** | 17,782 ± 3** |
| G5-L1-DOX | 12,303 ± 3** | 33,113 ± 1** |
| G5-Ac (Control) | 12,882 ± 6** | 67,608 ± 1** |

**P < 0.01. P values were determined for the IC$_{50}$ value of each G5-L(x)-DOX conjugate, or G5-Ac polymer control, as compared to free DOX results following a paired two-tailed t-test.

To determine the contribution of the dendrimer carrier to G5-L(x)-DOX conjugate cytotoxicity HepG2 cells were treated with the G5-(Ac)$_{11}$ polymer control for 72 hours, resulting in an IC$_{50}$ of 12,882 nM which is a >1,000-fold reduction in toxicity compared to free DOX. Similarly, G5-L1-DOX conjugates were found to be non-toxic after a 72 hour incubation with HepG2 cells due to limited DOX release observed during the in vitro intracellular release studies (FIG. 26; Panel B), resulting in an IC$_{50}$ similar to the G5-(Ac)$_{11}$ polymer control of 12,303 nM. G5-L2-DOX, which released 7% of the loaded DOX molecules after a 24 hour incubation with HepG2 cells, showed an increase in cytotoxicity compared to G5-L1-DOX with an IC$_{50}$ of 2,042 nM after a 72 hour incubation with the cells. Similarly, a shift in HepG2 cytotoxicity was observed for G5-L3-DOX and G5-L4-DOX conjugates with IC$_{50}$ values of 158 nM and 13 nM, respectively. This led to IC$_{50}$ of the most labile G5-L4-DOX conjugates which was not statistically different from free DOX after a 72 hour incubation with HepG2 cells. The decreasing IC$_{50}$ values of L1-L4 G5-L(x)-DOX conjugates confirms their cytotoxicity profiles match the rank order of DOX release observed from enzymatic and intracellular release studies.

Incubation of Hep3B cells with G5-L(x)-DOX conjugates showed a similar cytotoxicity profile to that of HepG2 cells (FIG. 27; Panel B). Incubation of Hep3B cells with free DOX for 72 hours resulted in an IC$_{50}$ of 2 nM, which is a 5-fold reduction in IC$_{50}$ of the free drug compared to the HepG2 cells. Treatment of Hep3B cells with the G5-(Ac)$_{11}$ polymer control resulted in limited toxicity with IC$_{50}$ values of 67,608 nM, a >6,000-fold reduction in toxicity compared to free DOX. Both G5-L1-DOX and G5-L2-DOX conjugates showed limited cyototixicty towards Hep3B cells due to their limited intracellular release to these cells (FIG. 26; Panel D), resulting in IC$_{50}$ values of 17,782 nM and 33,113 nM, respectively. Similar HepG2 cells, a shift in cytotoxicity of G5-L3-DOX and G5-L4-DOX was observed in Hep3B cells after a 72 hour incubation, resulting in IC$_{50}$ values of 48 nM and 63 nM, respectively.

Cardiac Toxicity of G5-L(x)-DOX Conjugates

Figure 28A:
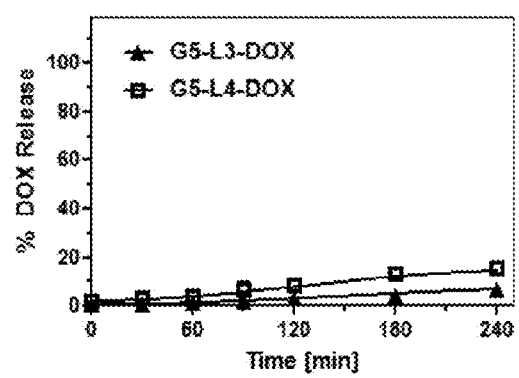
FIG. 28 represents a series of graphs that demonstrate cardiac toxicity of G5-L(x)-DOX conjugates. (A) DOX release from L3 and L4 G5-L(x)-DOX conjugates in the presence of adult rat cardiomyocyte S9 enzymes. (B) Uptake and (C) LDH toxicity of G5-L4-DOX conjugates in adult rat cardiomyocyte compared to an equivalent dose of free DOX. Data are expressed as mean (n=3)±SEM. **P<0.01. P values were determined for free DOX and G5-L4-DOX conjugates compared to negative control (blank medium) following a two-tailed Student's t-test.
Figure 28B:
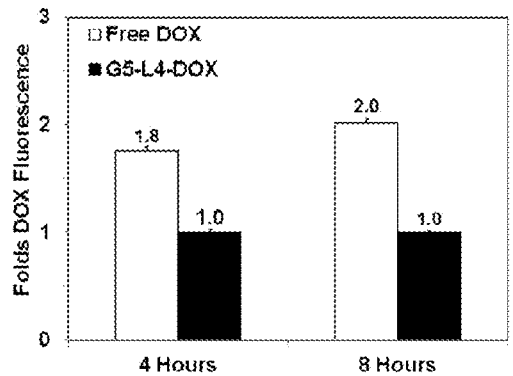
Figure 28C:
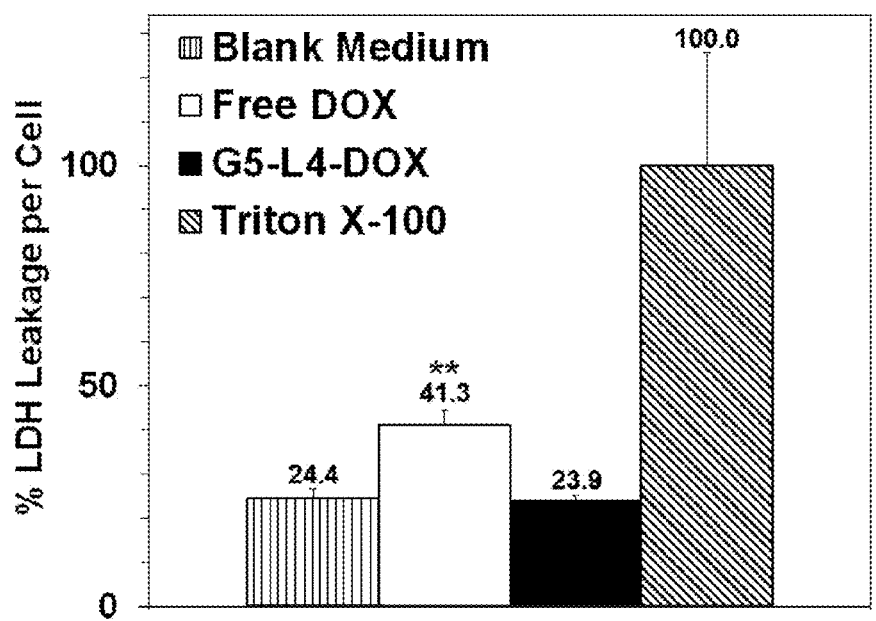
Figure 29A:
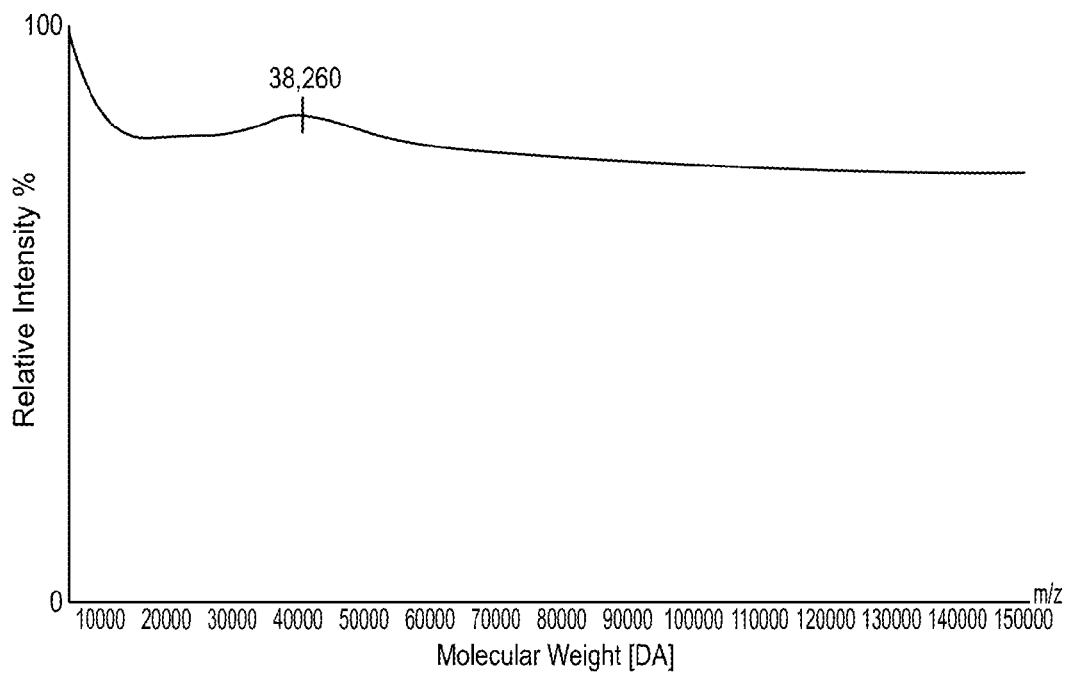
FIG. 29 represents a collection of MALDI-TOF results of (A) G5-L1-DOX, (B) G5-L2-DOX, (C) G5-L3-DOX and (D) G5-L4-DOX analyzed on a Shimadzu Biotech Axima CFR (Kyoto, Japan).
Figure 29B:
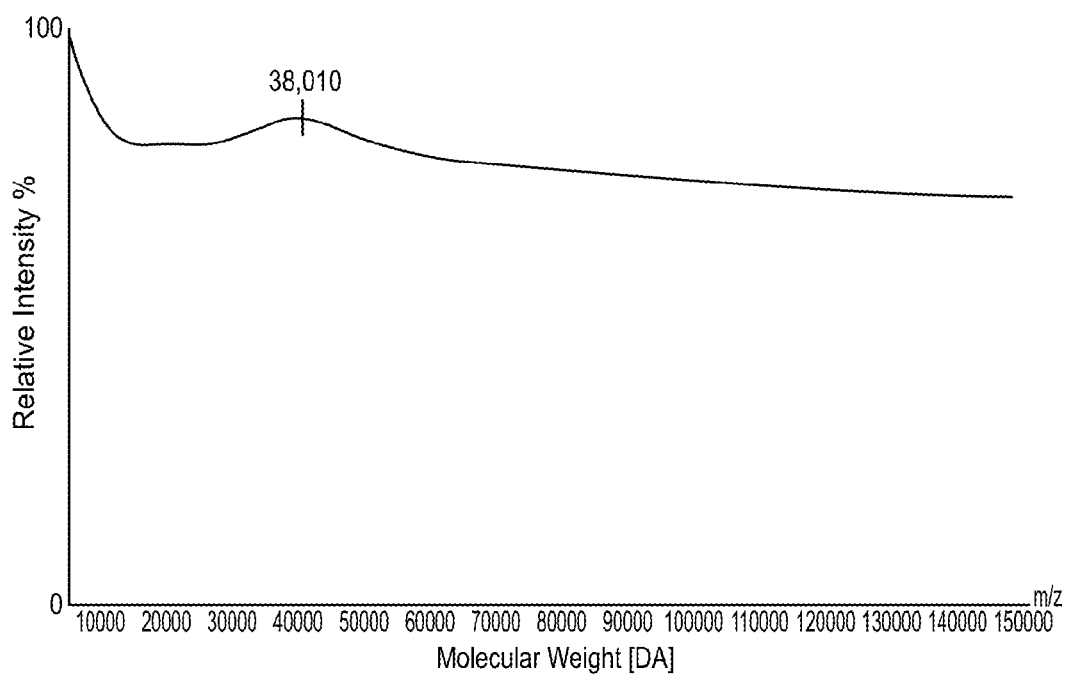
Figure 29C:
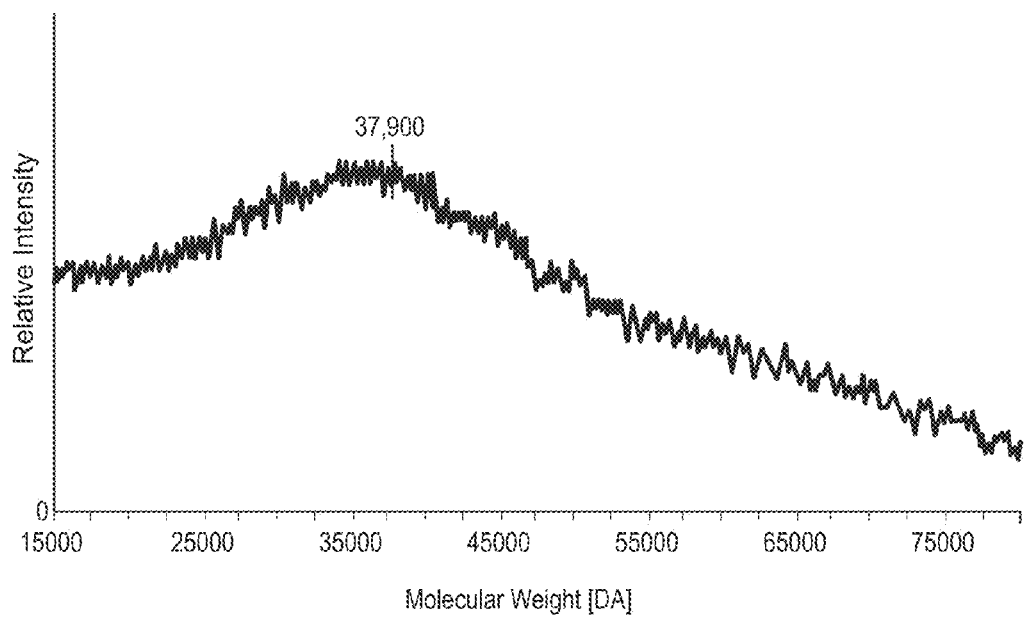
Figure 29D:
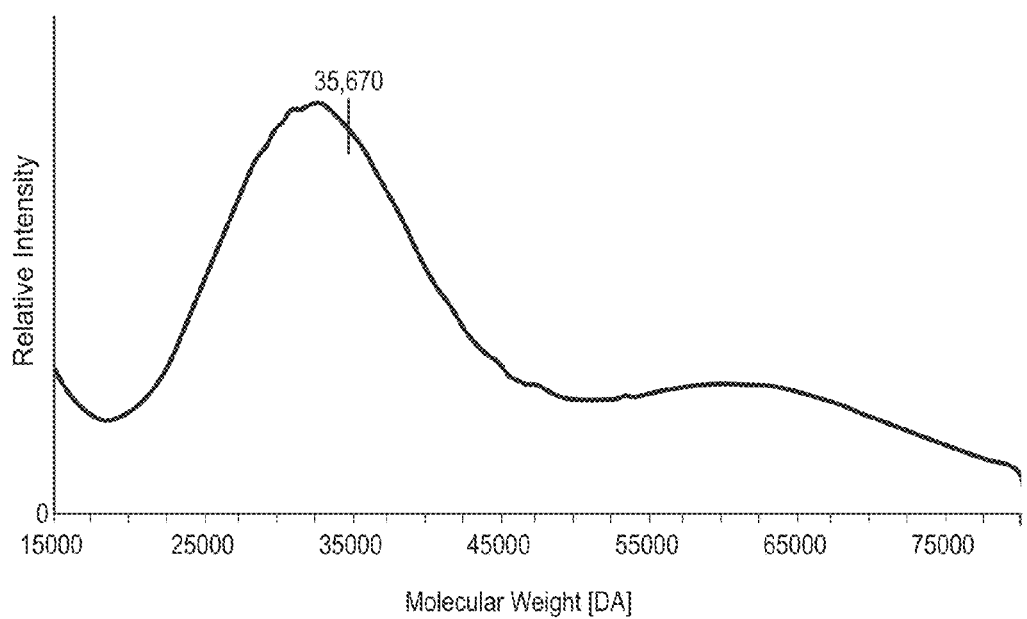
Figure 30A:
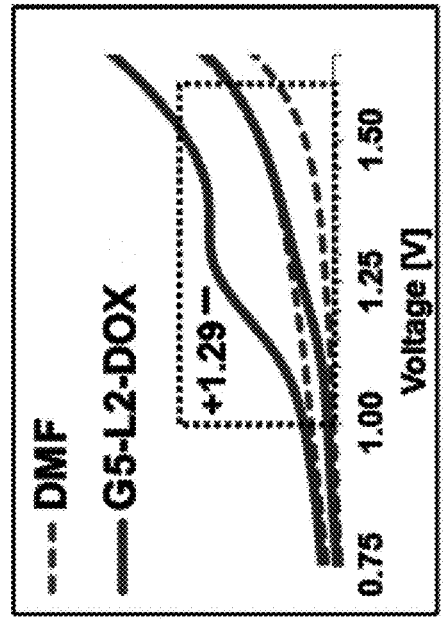
FIG. 30 represents a series of graphs that depict CV analysis of G5-DOX conjugates. (a) G5-L1-DOX, (b) G5-L2-DOX, (c) G5-L3-DOX and (d) G5-L4-DOX conjugates positive potential peaks. Relative current (y-axis) was plotted versus voltage (V).
Figure 30B:
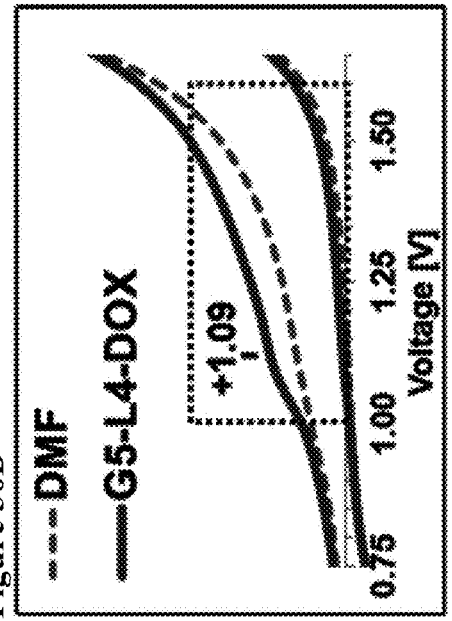
Figure 30C:
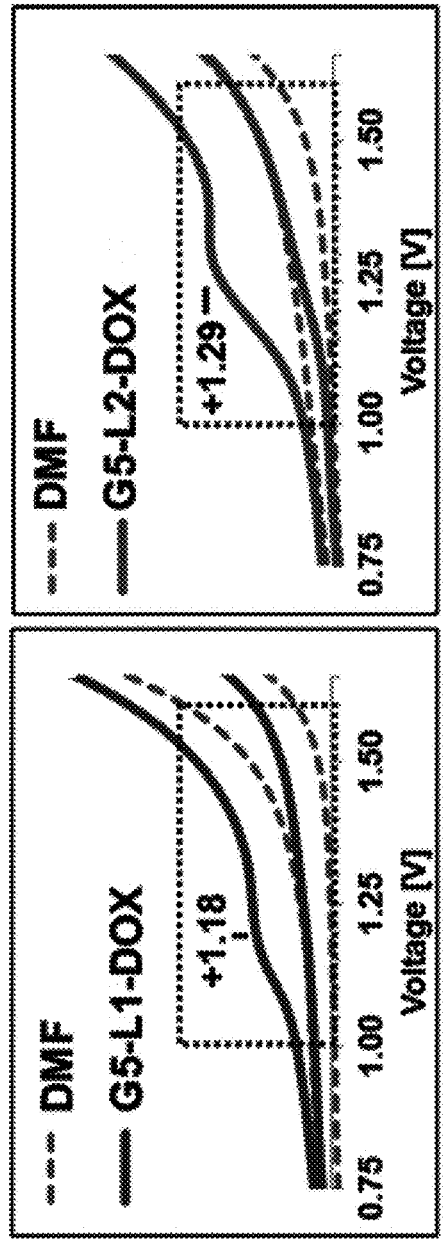
Figure 30D:
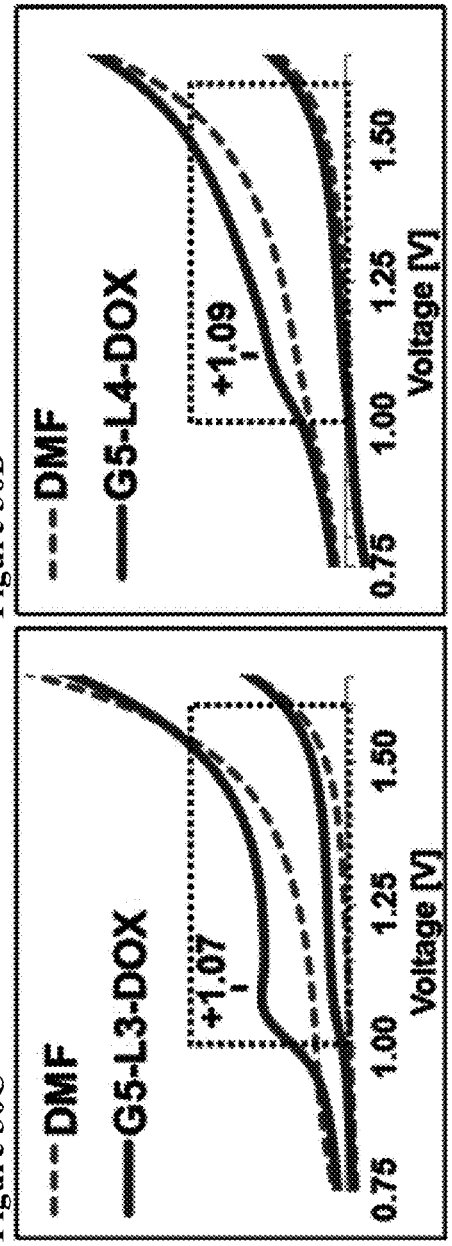
Figure 31A:
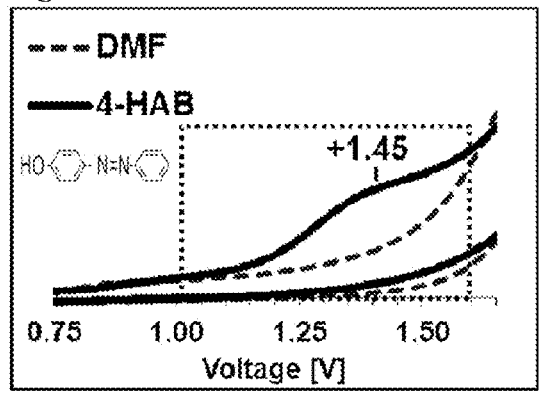
FIG. 31 represents a series of graphs that depict CV standards and controls. Positive potential peaks of (a) 4-hydroxyazobenzene and (b) dimethylaminoazobenzene standards correlated well with previous work indicating equivalency of experimental setup. (c) Free DOX and (d) G5 dendrimer controls showed no contribution to signal during CV analysis of conjugates. Relative current (y-axis) was plotted versus voltage (V).
Figure 31B:
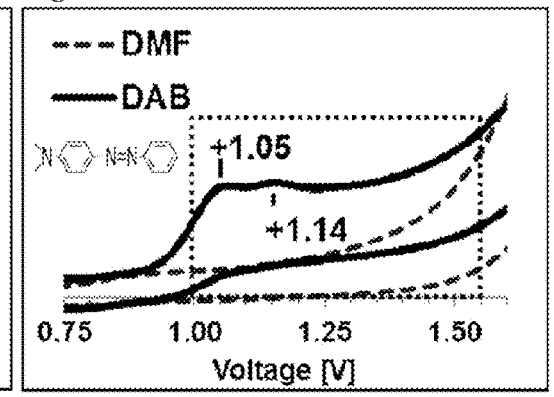
Figure 31C:
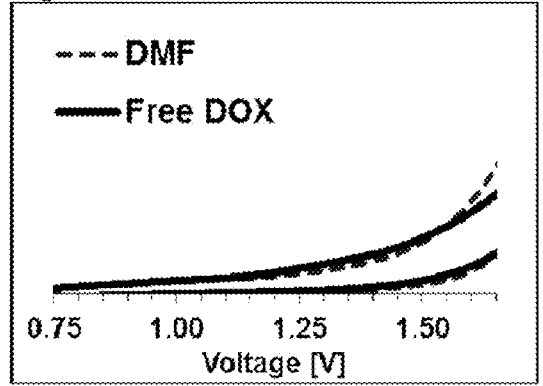
Figure 31D:
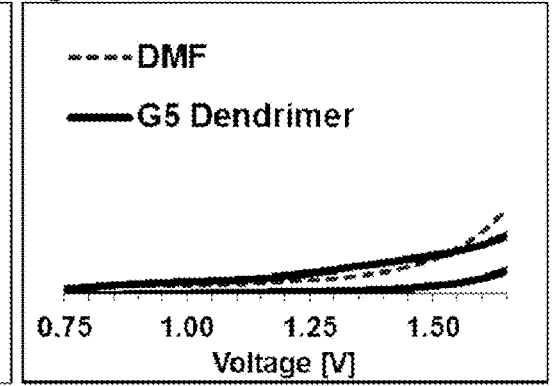

Due to the well-documented cardiomyopathy associated with the clinical use of free DOX[26] the intracellular DOX release, uptake and toxicity of G5-L(x)-DOX conjugates towards cardiac cells was studied using isolated primary adult rat cardiomyocytes. Intracellular DOX release from G5-L3-DOX and G5-L4-DOX conjugates in the presence of cardiomyocyte S9 cytoplasmic enzyme fractions and the NADPH enzyme cofactor was investigated resulting in 6% of the loaded DOX molecules released from G5-L3-DOX conjugates after 4 hours of incubation, while G5-L4-DOX conjugates released 16% under the same conditions (FIG. 28; Panel A). Based on this profile G5-L4-DOX conjugates were selected for to study the uptake of G5-L(x)-DOX conjugates in rat cardiomyocytes after 4 and 8 hours of incubation. Results showed a 1.8 fold reduction in the intracellular concentration of DOX upon incubation of cardiomyocytes with G5-L4-DOX conjugates for 4 hours, while a 2 fold reduction was observed at 8 hours, compared to cell treated with an equivalent concentration of free DOX (FIG. 28; Panel B). To determine whether the internalization and intracellular DOX release profiles of G5-L4-DOX conjugates in cardiomyocytes translated to cardiotoxicity an LDH leakage cell viability assay was performed (FIG. 28; Panel C). This assay method allows for the quantification of the LDH toxicity marker released to the medium from cardiomycoytes as a function of treatment, and results compared to cells lysed with Triton X-100 or incubated with blank medium as positve and negative controls, respectively, to determine toxicity. Results showed no statistical difference in the amount of the LDH toxicity marker released to the medium from rat cardiomyocytes after an 8 hour incubation with G5-L4-DOX conjugates and blank medium (negative control). Free DOX, however, was found to nearly double the % of LDH leakage compared to G5-L4-DOX treated cells at an equivalent DOX concentration and incubation time, and as a result showed a statistical increase in toxicity compared to cells incubated with blank medium (negative control).

Discussion

Synthesis and Characterization of G5-L(x)-DOX Conjugates

G5-(NH$_2$)$_{128}$ PAMAM dendrimers, a class of water soluble hyperbranched nano-polymers capable of high loading capacities of chemotherapeutic moleucles,[35-37] were utilized to prepare G5-L(x)-DOX conjugates. DOX was selected as the chemotherapeutic agent due to its established clinical use in systemic[38] and loco-regional[39] chemotherapy of HCC patients. G5-L1-DOX and G5-L2-DOX conjugates were successfully synthesized via amide coupling, while G5-L3-DOX and G5-L4-DOX incorporated triazole 'clicked' linkages connecting L(x)-DOX molecules to the G5 carrier. This difference in the linkage chemistry utilized to prepare G5-L(x)-DOX conjugates resulted in a small increase in the particle sizes for G5-L3-DOX and G5-L4-DOX conjugates (22-24 nm) compared to G5-L1-DOX and G5-L2-DOX (~18 nm). This is due to the increase in spacer length from a 2 atom bond coupling the dendrimer amine and azo-molecule for L1 and L2 G5-L(x)-DOX conjugates, to a 9 atom spacer of the triazole linked L3 and L4 G5-L(x)-DOX conjugates. However, it is expected this difference in the coupling strategy will not affect linkage accessibility of G5-L(x)-DOX conjugates to the azoreductase enzymes since an equivalent number of DOX molecules were attached per dendrimer. This ensures that each conjugate has equal water-solubility, as well as similar surface steric properties which is well known to affect the metabolic activity of hepatic enzymes.[40]

All G5-L(x)-DOX conjugates had an approximately neutral surface charge, which in combination with their small size, results in favorable biodistribution, toxicity and cellular uptake profiles.[41] Specifically, it has been shown that neutral polymeric nanoparticles ≤150 nm in diameter retain effective internalization into hepatic cancer cells, while showing decreased phagocytosis by macrohpages and lower non-specific accumulation to liver and lung tissue in vivo compared to both cationic and large diameter (>150 nm) nanoparticles.[41] In addition, neutralization of the cationic surface charge characteristic of PAMAM dendrimers has been shown to improve their biocompatability in vitro[42] and in vivo[43]. The molecular weight of all G5-L(x)-DOX conjugates was found to be below the renal excretion limit of ~50 kDa,[44] indicating these conjugates will be excreted into the urine after intravenous administration to avoid long-term residence in vivo known to cause systemic toxicity of non-biodegradable polymeric nanoparticles.[45] Finally, all G5-L(x)-DOX conjugates displayed a positive potential peak during cyclic voltammetry analysis within 1.00-1.60V (FIG. 30), a range previously shown to be characteristic for azo-dyes known to be substrates for the azoreductase enzymes.[28] These results confirm synthesized azo-linkers retain the electrochemical properties necessary for azoreductase reduction after covalent conjugation to DOX molecules and the G5 dendrimer carrier.

Cleavage and DOX Release from G5-L(x)-DOX Conjugates by Azoreductase Enzymes

Enzyme-activated G5-L(x)-DOX conjugates represent a novel drug release strategy able to achieve selective DOX delivery to hepatic cancer cells with tunable release based on linkage affinity to azoreductase enzymes. To determine the extent and rate of DOX release from these conjugates in the presence of azoreductase enzymes we incubated G5-L(x)-DOX with HLM. This led to an increase in the rate of cleavage and DOX release from G5-L(x)-DOX conjugates as a function of decreasing σ value beyond the −0.37 threshold, similar to the profile observed for azo-dyes studied during Zbaida's experiments.[19-21] Specifically, incubation of G5-L1-DOX conjugates with HLM enzymes resulted in limited cleavage of the azo-linker and DOX release due to the linkage σ value (−0.44) approaching the substrate σ threshold necessary for azoreductase binding (σ=−0.37). G5-L2-DOX, G5-L3-DOX and G5-L4-DOX conjugates followed an expected increase in DOX release rate due to azoreductase cleavage as a function of decreasing azo-linker σ value, resulting in 100% DOX release from G5-L4-DOX after a 4 hour incubation with HLM enzymes.

To determine the extent of DOX release from G5-L(x)-DOX conjugates in the cytoplasm of hepatic cancer cells conjugates were incubated with S9 cytoplasmic enzymes isolated from HepG2 cells. This resulted in a rank order of DOX release from G5-L(x)-DOX conjugates which matched HLM results. However, L3 and L4 G5-L(x)-DOX conjugates showed an ~10-20% reduction in the total DOX released after a 4 hour incubation with S9 enzymes prepared from hepatic cancer cells as compared to HLM isolated from normal human hepatocytes. This is likely due to the reduction in expression levels of common metabolic enzymes characteristic of malignant transformation of hepatocytes to hepatic cancer phenotypes.[46-48] This difference in enzymatic reduction between HepG2 S9 and HLM enzymes was not observed for G5-L1-DOX and G5-L2-DOX conjugates due to their low affinity to azoreductase enzymes resulting in saturation of the reduction rate despite a decrease in enzyme expression levels.

DOX release from G5-L(x)-DOX conjugates was confirmed to be selective for the azoreductase enzymes with limited reduction of the azo-linker for G5-L1-DOX and G5-L2-DOX conjugates after a 4 hour incubation period with non-enzymatic control proteins. This correlated to negligible DOX release from L1-L3 G5-L(x)-DOX conjugates in the presence of the control protein solution, while G5-L4-DOX conjugates released 16% of the loaded DOX molecules under the same conditions. Incubation of G5-L4-DOX conjugates in the NADPH generating system without protein confirmed that this non-specific DOX release was a result of azo-linker reduction by the NADPH enzyme cofactor (FIG. 32). The non-specific reduction of azo-dyes by NADPH has been previously reported,[20] and is expected to increase as a function of azo-linker electronegativity resulting in the greatest cleavage observed for the highly labile G5-L4-DOX conjugates.

Hepatic Cancer Cell Uptake and Intracellular Drug Release from G5-L(x)-DOX Conjugates To confirm G5-L(x)-DOX can achieve selective release of DOX to the cytoplasm of hepatic cancer cells in vitro uptake and intracellular drug release of each conjugate in HepG2 and Hep3B cells was studied. Results showed a substantial increase in intracellular DOX concentrations after a 1 hour of incubation with G5-L1-DOX and G5-L2-DOX conjugates compared to an equivalent concentration of free DOX. This is due to the ability of the loaded DOX molecules on G5-L(x)-DOX conjugates to avoid recognition and efflux by the P-glycoprotein (Pgp) multi-drug transport protein overexpressed in cancer cells[49] when bound to macromolecules like polymeric carriers.[50,51] In addition, L1 and L2 G5-L(x)-DOX conjugates showed a 2-4 fold increase in intracellular DOX concentrations after a 1 hour incubation with HepG2 and Hep3B cells compared to an equivalent concentration of G5-L3-DOX and G5-L4-DOX conjugates. This extensive internalization of G5-L1-DOX and G5-L2-DOX is likely caused by precipitation of the amphilic conjugates out of solution via particle aggregation as a result of the displayed hydrophobic DOX corona. This dissolution results in rapid contact of the particles with the cell surface increasing the potential for both fluid-phase pinocytosis as well as partitioning of drug-loaded nanoparticles through the cellular lipid membrande via fusion of the hydrophobic DOX corona.[52] This is supported by the observation that L1 and L2 G5-L(x)-DOX conjugates formed visible precipitations after a two week storage period at room temperature in deionized water, while L3 and L4 G5-L(x)-DOX conjugates were found to be stable for months at similar storage conditions. We believe this difference in aqeuous stability is due to the increased distance of DOX molecules from the G5 carriers for G5-L3-DOX and G5-L4-DOX conjugates which incoporate triazole 'clicked' linkages covalently coupling azo-DOX molecules to the dendrimer, while G5-L1-DOX and G5-L2-DOX are prepared through shorter peptide-bonds. This architecture may allow for improved solvency of the particles and therefore explain the reduced internalization profile of L3 and L4 G5-L(x)-DOX conjugates as compared to L1 and L2 G5-L(x)-DOX formulations into both HepG2 and Hep3B cells.

Despite this differential uptake profile for G5-L(x)-DOX conjugates intracellular drug release studies found the rank order for the amount of DOX released from the conjugates correlated to results from HLM and HepG2 S9 enzymatic reduction studies. This resulted in the greatest intracellular amount of DOX release observed from G5-L4-DOX conjugates with 37% and 27% total DOX released after a 24 hour incubation with HepG2 and Hep3B hepatic cancer cells, respectively. The difference in extent of DOX release from each G5-L(x)-DOX conjugates between HepG2 and Hep3B cell lines is due to the reported variance in their expression of drug-metabolizing enzymes.[53,54] Studies are currently underway to further investigate this difference in DOX release from G5-L(x)-DOX conjugates between the tested hepatic cancer cell lines by identifying the key hepatic enzymes responsible for conjugate cleavage.

A small fraction of DOX was assayed in the medium of treated HepG2 (1-3%) and Hep3B cells (1-2%) due to recognition and efflux of the intracellularly released DOX from G5-L(x)-DOX conjugates by the Pgp. In addition, the total percentage of DOX effluxed by Pgp to the medium for both cell lines was similar for all the tested G5-L(x)-DOX conjugates despite a large increase in intracellular DOX released, indicating the rate of DOX effluxed by Pgp after liberation from G5-L(x)-DOX conjugates was saturated at a relatively low intracellular drug concentration. This minimal amount of DOX efflux highlights the advantage of cell-specific drug delivery using polymeric carriers to achieve high intracellular drug concetrations in hepatic cancer cells.[49,50]

Anticancer Activity of G5-L(x)-DOX Conjugates

Cytotoxicity of G5-L(x)-DOX conjugates towards hepatic cancer cells was assessed via the clonogenic survival assay,[25] which measures both the viability of treated cancer cells similar to standard cytoxicity assays (e.g. MTT and trypan blue exlusion) as well as the inability of living cells to proliferate after DNA damage triggered by the chemotherapeutic agent. Results of the clonogenic survival study showed the rank order of anticancer activity for G5-L(x)-DOX matches the corresponding decrease in azo-linker σ value, and confirms that intracellular activation and release of free DOX from G5-L(x)-DOX corresponds to effective apoptosis in vitro. Specifically, G5-L(x)-DOX conjugates were found to be non-toxic in their parent form towards HepG2 and Hep3B cells (G5-L1-DOX), until activated by the azoreductase enzymes resulting in a shift in cytotoxicity of G5-L(x)-DOX conjugates based on azo-linker σ value and subsequently their relative affinity to azoreductase cleavage. This resulted in a cytotoxicity profile for G5-L4-DOX conjugates which matched the free drug in HepG2 cells.

Treatment of Hep3B cells with free DOX resulted in a 5-fold reduction in $IC_{50}$ values compared to HepG2 cells which is a due to the increased sensitivity of Hep3B cells to DOX-meadiated DNA damage due to a p53 deletion while HepG2 has retained wild-type p53.[55] Though G5-L2-DOX conjugates were toxic in HepG2 cells, both G5-L1-DOX and G5-L2-DOX were found to be relatively non-toxic in Hep3B cells due to the lack of intracellular DOX release. This difference is attributed to the differential expression of metabolic enzymes between the HepG2 and Hep3B hepatic cancer cell lines.[53,54] Interestingly, G5-L3-DOX and G5-L4-DOX conjugates had similar $IC_{50}$ values in Hep3B cells (48 nM and 63 nM, respectively) after a 72 hour incubation period, indicating a threshold toxicity in these cells was achieved by the activated G5-L(x)-DOX conjugates. This is likely due to the reported p53-independent modulation of p27, a potent cell-cycle arrest protein, after exposure of Hep3B cells to DOX resulting in a potential dose-dependant DOX apoptotic threshold.[55]

While these G5-L(x)-DOX conjugates show effective anticancer activity in vitro, the most signifcant advantage of polymer-based nanoparticles is their ability to enhance the water solubility of the loaded chemotherapeutic agents in vivo,[14,50,56] leading to preferential tumor tissue distribution,[57,58] and the ability to achieve cancer cell-specific drug delivery leading to high anticancer activity while avoiding non-specific toxicity.[50,61,62]

Biocompatability of G5-L(x)-DOX Conjugates

The major dose-limiting toxicity of DOX administration in the clinic is acute and chronic cardiomyopathy at high cumulative doses.[26] In order for G5-L(x)-DOX conjugates to be cardiotoxic the conjugates must be internalized and release free DOX to the cytoplasm of cardiac cells. To study the relative intracellular DOX release from G5-L(x)-DOX conjugates in cardiac cells G5-L3-DOX and G5-L4-DOX were incubated with S9 cytoplasmic enzyme fractions isolated from primary rat cardiomyocytes. Results showed G5-L3-DOX conjugates released a negligible amount of DOX over the 4 hour incubation period, while G5-L4-DOX conjugates had a similar DOX release profile in the presence of cardiomyocyte S9 enzymes to incubation with only the NADPH cofactor (FIG. 32). This confirms that G5-L(x)-DOX conjugates show limited DOX release to normal cardiomyocytes due to low expression of metabolic enzymes in cardiac tissue.[59]

Coupling of DOX to G5 dendrimers to prepare G5-L4-DOX conjugates resulted in a 1.8-2 fold reduction of the intracellular DOX concentration in rat cardiomyocytes compared to an equivalent dose of free DOX up to 8 hours of incubation. This is due to the requirement of macromolecular G5-L4-DOX conjugates to be internalized into cardiac cells by endocytosis, while free DOX can passively diffuse through the cellular lipid membrane and into the cytoplasm, where they are retained due to the lack of Pgp expression in cardiac tissue.[60] The limited uptake of G5-L(x)-DOX conjugates and negligible DOX release in the presence of rat cardiomyocyte cytoplasmic enzymes resulted in G5-L4-DOX conjugates being non-toxic towards plated rat cardiomyocytes fter 8 hours of incubation as determined by the LDH leakage cell viability assay, while an equivalent dose of free DOX was found to be toxic. These results highlight the ability of G5-L (x)-DOX to utilize the presence of the liver-specific azoreductase enzymes as a switch to control DOX release, and as a result achieve selectieve DOX delivery and cytotoxicity towards hepatic cancer cells. As a result G5-L(x)-DOX conjugates have the potential to achieve high anticancer activity towards hepatic cancer cells while limiting the delivery of free DOX to heart tissue and thereby reducing the cardiotoxicity associated with DOX administration in the clinic.[26]

Conclusions

G5-L(x)-DOX conjugates were synthesized incorporating four different azo-linkers (L1-L4) to achieve selective DOX release in the presence of the liver-specific azoreductase enzyme. By modulating the σ values of the engineered azo-linkers, and subsequently changing its affinity to azoreductase cleavage, G5-L(x)-DOX conjugates were able to achieve tunable DOX release in the presence of azoreductase enzymes and the cytoplasm of whole hepatic cancer cells. This resulted in effective hepatic cancer cell apoptosis upon incubation with G5-L(x)-DOX conjugates, with cytotoxicity profiles that followed a similar rank order of DOX release as observed during enzymatic reduction and in vitro drug release studies. Limited DOX release, uptake and non-specific toxicity of G5-L(x)-DOX conjugates towards isolated rat cardiomyocytes confirmed delivery of free DOX was selective for hepatic cancer cells upon activation by azoreductase enzymes. As a result G5-L(x)-DOX nano-conjugates show potential as a novel therapeutic alternative to loco-regional chemotherapy techniques in the treatment of unresectable HCC, which will preferentially accumulate in tumor tissue and selectively release the loaded DOX molecules to hepatic cancer cells to achieve high anticancer activity with reduced DOX-mediated cardiotoxicity in the clinic. Furthermore, the flexibility in the design of the described azo-linkers offers the opportunity to incorporate a variety of linker compositions into a single G5-L(x)-DOX molecule to achieve differential activation and DOX release rates in the presence of azoreductase enzymes to design personalized medicines for HCC therapy.

Example 13

The following materials and methods were utilized in the study described in Example 14.

Materials

G5-$(NH_2)_{128}$ dendrimers were purchased from Dendritic Nanotechnologies (Mount Pleasant, Mich.), N-acetylgalactosamine, hydrochloric acid solution (35%) and fluorescein isothiocyanate (Fl) were purchased from Sigma-Aldrich Inc. (St. Louis, Mo.). N-hydroxysuccinimide-activated m-poly (ethylene glycol) (2 kDa) (NHS-PEG) was purchased from NOF Corporation (Cibitung-Bekasi, Indonesia). [$^{14}$C]Iodoacetamide was purchased from American Radiolabeled Chemicals, Inc. (St. Louis, Mo.), and SOLVABLE™ digestion reagent and ULTIMA-FLO™ AP flow scintillation cocktail fluid purchased from Perkin-Elmer (Waltham, Mass.). EcoLume™ analytical liquid scintillation fluid was purchased from MP Biomedical (Solon, Ohio). SP94 peptide ($H_2$N-SFSIIHTPILPLGGC-COOH; SEQ ID NO: 1) was custom synthesized by GenScript Inc (Piscataway, N.J.) with a GGC spacer at the C-terminus. Minimum essential medium (MEM), OPTI-MEM reduced serum medium, Rosewell Park Memorial Institute-1640 (RPMI) medium, Hanks Balanced Salt Solution (HBSS), fetal bovine serum (FBS), 0.25% trypsin/0.20% ethylene diamine teraacetic acid (EDTA) solution, phosphate buffered saline (PBS), penicillin/streptomycin/amphotericin solution, sodium pyruvate and non-essential amino acid solutions were purchased from Invitrogen Corporation (Carlsbad, Calif.). Pronase from *Streptomyces griseus* and DNase I grade II from bovine pancreas were purchased from Roche, Inc. (Indianapolis, Ind.). Bovine Serum Albumin (BSA) and dialysis cassette (MWCO 1-10 kDa) were purchased from Thermo Fisher Scientific Inc. (Rockford, Ill.). Phagocytosis assay kit was purchased from Cayman Chemicals Co. (Ann Arbor, Mich.). Primary hepatocytes isolated from the livers of Sprague-Dawley rats plated in 24-well plates at $5 \times 10^5$ cells/well and complete hepatocyte culture media (K2300) were purchased from Xenotech LLC (Lenexa, Kans.).

Synthesis of $[^{14}C]G5-(NH_2)_{127}$, $[^{14}C]G5-(Ac)_{108}$-(NAcGal)$_{14}$, and $[^{14}C]G5-(Ac)_{73}$-(PEG)$_{10}$ Conjugates G5-(NH$_2$)$_{128}$ PAMAM dendrimers (113.1 mg, 0.0039 mmoles) were dissolved in 6 mL 0.1M sodium bicarbonate solution (pH 10) followed by addition of 1.2 molar equivalents of [$^{14}$C]Iodoacetamide dissolved in DI water, and the reaction was stirred in the dark at room temperature. Radiolabeling progress was monitored daily by removing 100 μL of reaction solution and analyzed by size exclusion chromatography using a Hewlett Packard Series II 1050 liquid chromatography system equipped with a Superdex™ 75 size exclusion column and Packard 500TR flow scintillation detector. Run conditions include a 20 minute analysis period at 1 mL/min flow rate of 0.1M sodium bicarbonate solution (pH 10) and 2 ml/min flow of scintillation cocktail into the detector. Once the chromatography peak area of [$^{14}$C]G5-(NH$_2$) conjugates was ≥90% of the total assayed radioactivity the reaction was stopped (~72 hours), purified by dialysis (MWCO 10 kDa) against sterile water and dried by lyophilization to yield 108.6 mg of [$^{14}$C]G5-(NH$_2$) (0.0038 mmoles, 97% yield). 1 mg of [$^{14}$C]G5-(NH$_2$) dendrimers was mixed with 5 mL EcoLume™ scintillation cocktail and analyzed by a LS6500 liquid scintillation counter (Beckman Coulter, Indianapolis, Ind.) to determine number of [$^{14}$C] labels attached per conjugate.

[$^{14}$C]G5-(Ac)$_{108}$-(NAcGal)$_{14}$ conjugates were synthesized by covalently coupling NAcGal moieties to the surface of [$^{14}$C]G5-(NH$_2$)$_{127}$ dendrimers through thiourea linkages and then acetylated following a published protocol to produce [$^{14}$C]G5-(Ac)$_{108}$-(NAcGal)$_{14}$ as a white solid (23.9 mg, 97% yield). MALDI-TOF analysis was performed on a non-radioactive, un-labeled G5-(Ac)$_{108}$-(NAcGal)$_{14}$ analogue synthesized at the same time and in an identical manner resulting in a mass of 38,180 gm/mole. [$^{14}$C]G5-(Ac)$_{73}$-(PEG)$_{10}$ conjugates were synthesized by dissolving [$^{14}$C]G5-(NH$_2$)$_{127}$ (47.8 mg, 0.0017 mmoles) dendrimers in 3 mL anhydrous MeOH and NHS-PEG (65.0 mg, 0.0306 mmoles) was added to the reaction mixture and stirred at room temperature for 24 hours. Solvents were removed under reduced pressure, and conjugates acetylated as previously described[26] before purification by dialysis (MWCO 10 kDa) against sterile water and dried by lyophilization to produce [$^{14}$C]G5-(PEG)$_{10}$ as a white solid (88.0 mg, 99% yield). MALDI-TOF analysis of un-labeled G5-(Ac)$_{73}$-(PEG)$_{10}$ conjugates shows a molecular weight of 51,962 gm/mole.

In Vivo Biodistribution of [$^{14}$C]G5-(NH$_2$)$_{127}$, [$^{14}$C]G5-(Ac)$_{108}$-(NAcGal)$_{14}$, and [$^{14}$C]G5-(Ac)$_{73}$-(PEG)$_{10}$ Conjugates in Tumor-Bearing Mice We developed an orthotopic hepatic cancer model by injection of HepG2 cells suspended in matrigel in the left lobe of the mouse model. Briefly, 4-5 week old female NCr nude mice were in UCUCA approved pathogen-free animal housing facility with unrestricted access to food and water. Mice received 100 mg/kg cyclophosphamide via intraperitoneal injection 24 hours prior to xenograft surgery, then 1 hour before surgery mice receive 0.24 mg/kg dexamethasone, and again 24 hours post-surgery. At the time of the surgery mice were anesthetized by injecting i.p. a mixture of ketamine:xylazine 70:10 mg/kg, followed by exposing of the liver via laparotomy and injecting $1 \times 10^7$ HepG2 cells suspended in 100 μL matrigel into the left median hepatic lobe. Each mouse received 15 mg/kg ampicillin by i.p. before suturing the incision. Dimensions of the implanted tumor was measured 4 weeks after implantation using a caliper to calculate the tumor volume using the ellipsoidal volume formula (V=π/6*W$^2$*L).[35] Once tumor volume reached 75-100 mm$^3$ mice were used in subsequent biodistribution studies.

[$^{14}$C]G5-(NH$_2$)$_{127}$, [$^{14}$C]G5-(Ac)$_{108}$-(NAcGal)$_{14}$ or [$^{14}$C]G5-(Ac)$_{73}$-(PEG)$_{10}$ conjugates were dissolved in 250 μl of sterile saline at a dose of 0.322 μmole/kg to achieve sufficient radioactivity to resolve up to a 1000 fold reduction in the injected dose. Animals were given 0.5 ml sterile saline administered i.p. 24 hours prior to treatment to maximize blood volume, and conjugates administered as a single bolus dose via tail-vein injection (n=3 per time point). 2, 24 and 48 hours post administration animal were anesthetized and euthanized by intra cardiac blood draw, with plasma immediately separated via centrifugation (9,000 rpm, 10 min). Tumor tissue and vital organs including the brain, heart, lungs, kidneys, liver, spleen, pancreas, intestine, lymph nodes (peyer's patches), bone marrow, and waste (feces and urine absorbed onto filter paper) were collected, weighed and snap frozen. Before processing samples were thawed and an equal volume of PBS was added, followed by extensive homogenization via a Polytron PT 1600 E homogenizer. 1 mL of SOLVABLE™ tissue digestion reagent was added per 100 mg of tissue (or a minimum of 3 mL), followed by extensive vortexing and incubation for 18 hours in a 60° C. shaking water bath. Samples were then re-homogenized and digested for an additional 8 hours in a 60° C. shaking water bath, before addition of 200 μl of glacial acetic acid followed by extensive vortexing and an additional 1 hour incubation at 60° C. to precipitate proteins. Samples were centrifuged (3,000 rpm, 5 minutes) to condense solid material and supernatant volume recorded, before mixing 2 mL of the supernatant with 5 mL of EcoLume™ and total radioactivity determined by liquid scintillation counting. Extraction efficiency of each conjugate from tissue samples was calculated in triplicate by spiking 0.0247 μmole of [$^{14}$C]-labeled conjugates with organs and waste harvested from untreated mice, and samples processed and assayed at the same time and in an identical fashion as biodistribution samples. All results were compared to a set of standards prepared in triplicate to determine concentration of [$^{14}$C]-labeled conjugate in each sample, and results normalized to extraction efficiency. Conjugate distribution is reported as percent of the injected dose accumulated per tissue as a function of time.

Synthesis of G5-(Fl)$_6$-(Ac)-(cPEG[NAcGal$_{\alpha/\beta}$]) Conjugates

Figure 34:
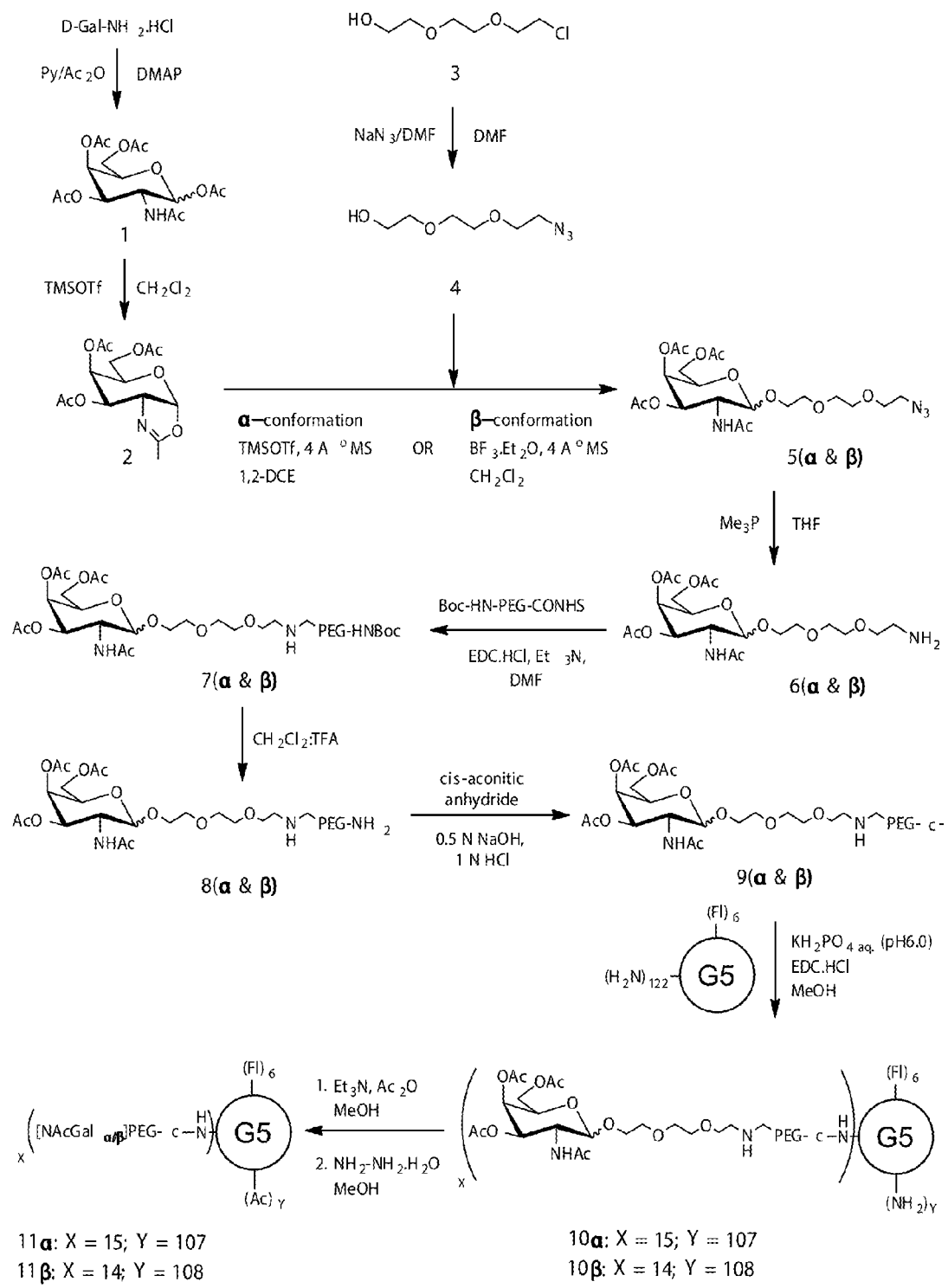
FIG. 34 represents a synthesis scheme of α- or β-conformation NAcGal-targeted G5-PEG carriers through cis-aconityl linkages to prepare $G5-(Fl)_6-(Ac)_{107}-(cPEG[NAcGal_\alpha])_{15}$ and $G5-(Fl)_6-(Ac)_{108}-(cPEG[NAcGal_\beta])_{14}$ conjugates.
Figure 35:
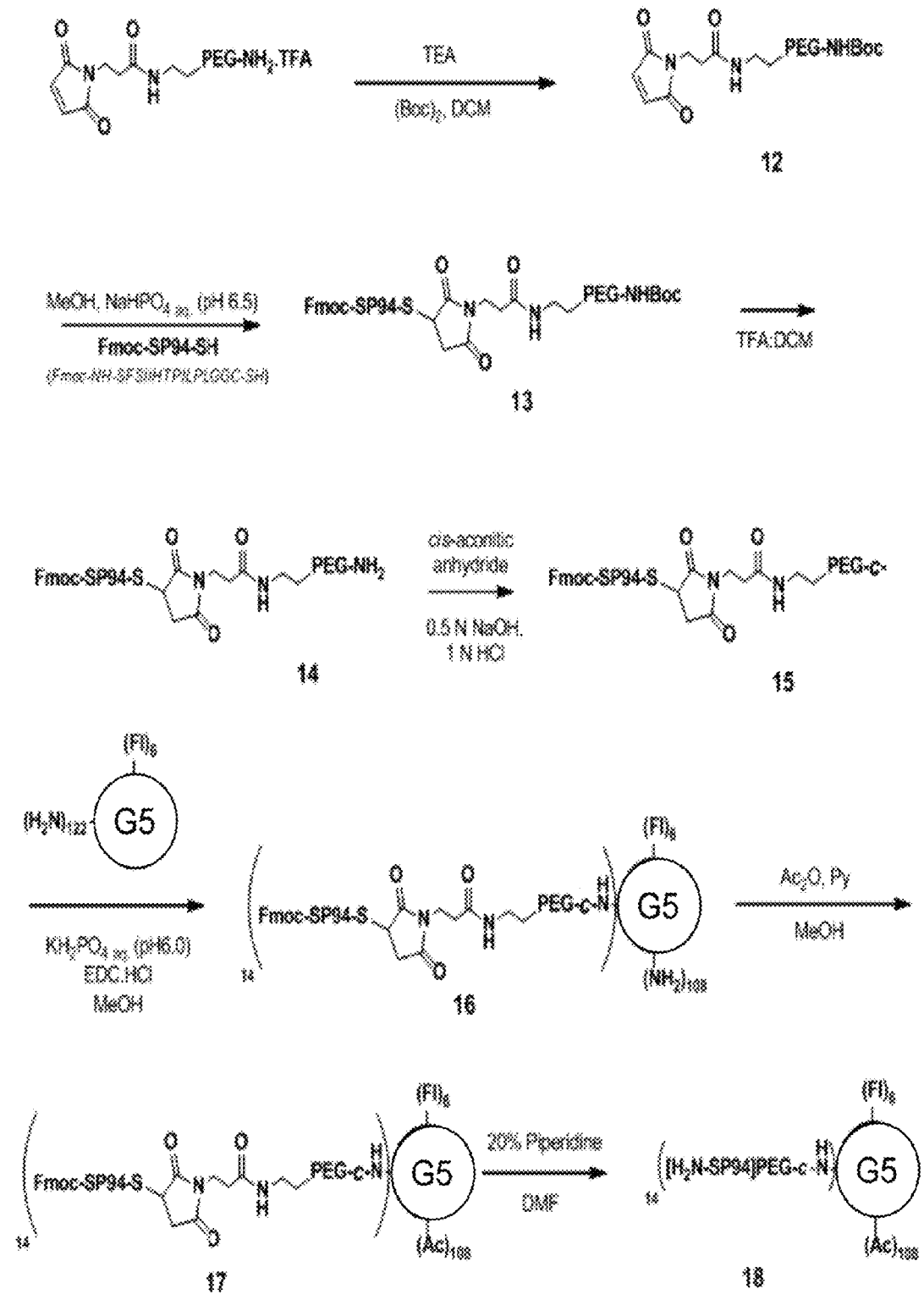
FIG. 35 represents a synthesis scheme of SP94 peptide-targeted G5-PEG carriers through cis-aconityl linkages to prepare $G5-(Fl)_6-(Ac)_{108}-(cPEG[SP94])_{14}$ conjugates.

In the following paragraphs directed to syntheses, compounds (1) to (11β) are illustrated in FIG. 34, while compounds (12) to (22) are illustrated in FIG. 35.

Synthesis of (3aR,5R,6R,7R,7aR)-5-(acetoxymethyl)-2-methyl-5,6,7,7a-tetrahydro-3aH-pyrano[3,2-d]oxazole-6,7-diyl diacetate (2)

D-Gal-NH$_2$.HCl (5.0 g, 23.24 mmol) was dissolved in pyridine (28.15 mL, 348.74 mmol) and acetic anhydride (26.35 mL, 278.88 mmol) was added slowly, followed by addition of DMAP (2.0 g) and reaction mixture stirred at 0° C. for 1 hour, then at room temperature for 24 hours. The reaction was then quenched with sat. NaHCO$_3$ solution and extracted into ethyl acetate, followed by washing with 1N HCl solution, water, brine and dried over Na$_2$SO$_4$. Solvents were evaporated under reduced pressure and the residue was purified by silica gel column chromatography using DCM:EA:MeOH (7.5:2.0:0.5) as an eluent to obtain compound 1 (7.25 g, 80% yield). $^1$H-NMR (500 MHz, CDCl$_3$): 1:0.33 β:α ratio. δ 1.82 (s, 3H, CH$_3$, OAc, (β)), 1.85 (s, 3H, CH$_3$, OAc, (α)), 1.88 (s, 3H, CH$_3$, OAc, (β)), 1.90 (s, 3H, CH$_3$, OAc, (β)), 1.92 (s, 3H, CH$_3$, OAc, (α)), 1.94 (s, 3H, CH$_3$, OAc, (α)), 1.98 (s, 3H, CH$_3$, OAc, (α)), 2.00 (s, 3H, CH$_3$, OAc, (α)), 2.03 (s, 3H, CH$_3$, OAc, (β)), 2.04 (s, 3H, CH$_3$, OAc, (β)), 3.90-4.04 (m, 3H, H$_3$ and 2×H$_6$), 4.06 (m, 3H, H$_6$, 2×H$_3$), 4.55 (dt, 1H, J=3.5 & 9.0 Hz, H$_5$), 4.61 (dt, 1H, J=4.5 & 9.0 Hz, H$_5$), 5.04-5.12 (m, 2H, 2×H$_2$), 5.22 (d, 1H, J=1.5 Hz, H$_4$), 5.30 (d, 1H, J=2.0 Hz, H$_4$), 6.10 (d, 1H, J=3.5 Hz, (α), H$_1$), 6.28 (d, 1H, J=8.5 Hz, (β), H$_1$); $^{13}$C-NMR (125 MHz, CDCl$_3$): δ 20.30 (OAc, 3CH$_3$, (β)), 20.33 (OAc, 3CH$_3$, (β)), 20.35 (OAc, 3CH$_3$, (β)), 20.40 (OAc, 3CH$_3$, (α)), 20.42 (OAc, 3CH$_3$, (α)), 20.52 (OAc, 3CH$_3$, (β)), 20.70 (OAc, 3CH$_3$, (α)), 20.75 (OAc, 3CH$_3$, (α)), 23.51 (OAc, 3CH$_3$, (α)), 23.53 (OAc, 3CH$_3$, (β)), 46.52 (β, C$_2$), 55.90 (α, C$_2$), 61.03 (β, C$_6$), 61.78 (α, C$_6$), 66.41 (β, C$_3$), 67.36 (β, C$_4$), 68.14 (β, C$_5$), 70.01 (α, C$_3$), 73.45 (α, C$_4$), 78.47 (α, C$_5$), 90.80 (β, C$_1$), 93.63 (α, C$_1$), 168.80 (β, CO), 169.01 (α, CO), 169.65 (α, CO), 169.98 (β, CO), 170.14 (β, CO), 170.20 (α, CO), 170.53 (α, CO), 170.56 (β, CO), 170.58 (β, CO), 173.87 (α, CO). EI-MS: [M+H]$^+$ C$_{16}$H$_{24}$NO$_{10}$ calcd 390.13, obsd 390.12, [M+Na]$^+$ C$_{16}$H$_{23}$NNaO$_{10}$ calcd 412.12, obsd 412.11

The crude mixture of compound 1 (2.0 g, 5.139 mmol) was dissolved in DCM (25 mL) and TMSOTf (1.85 mL, 10.27 mmol) was added and reaction mixture stirred at 40° C. for 24 hours. The reaction was quenched with Et$_3$N (0.4 mL, pH 7.5), diluted in DCM and extracted with sat. NaHCO$_3$ solution. The organic layer was washed with water, brine and dried over Na$_2$SO$_4$ before evaporation of solvents under reduced pressure and the residue purified by silica gel column chromatography using DCM:EA:MeOH (7.5:2.0:0.5) as an eluent to obtain compound 2 (1.35 g, 82% yield). $^1$H-NMR (500 MHz, CDCl$_3$): δ 2.03 (s, 3H, H$_7$), 2.064 (s, 3H, CH$_3$, OAc), 2.067 (s, 3H, CH$_3$, OAc), 2.08 (s, 3H, CH$_3$, OAc), 4.12 (dd, 1H, J=6.5 & 12.0 Hz, H$_6$), 4.18 (d, 1H, J=9.0 Hz, H$_3$), 4.32 (dd, 1H, J=3.5 & 12.0 Hz, H$_{6'}$), 4.52 (dd, 1H, J=1.5 & 5.5 Hz, H$_2$), 5.00 (m, 1H, H$_5$), 5.14 (s, 1H, H$_4$), 6.12 (d, 1H, J=6.5 Hz, H$_1$); $^{13}$C-NMR (125 MHz, CDCl$_3$): δ 14.30 (C$_7$), 20.6, 20.7, 20.75 (OAc, 3CH$_3$), 62.8 (C$_6$), 69.6 (C$_2$), 76.4 (C$_3$), 77.6 (C$_5$), 84.3 (C$_4$), 107.3 (C$_1$), 167.05 (C$_8$), 169.6, 169.8, 170.3 (OAc, CO). EI-MS: [M+H]$^+$ C$_{14}$H$_{20}$NO$_8$ calcd 330.12, obsd 330.11, [M+Na]$^+$ C$_{14}$H$_{19}$NNaO$_8$ calcd 352.10, obsd 352.11.

Synthesis of 2-(2-(2-azidoethoxy)ethoxy)ethanol (4)

Compound 3 (10.0 g, 59.50 mmol) was dissolved in anhydrous DMF (200 mL), to which NaN$_3$ (77.3 g, 119.00 mmol) was added and reaction mixture stirred at 80° C. or 48 hours. Solvents were removed under reduced pressure and residue dissolved in DCM (200 mL), washed with water (400 mL) and brine (100 mL) before being dried over Na$_2$SO$_4$. Solvent was evaporated under reduced pressures and residue purified by silica gel column chromatography using EA:hexane (6:4) to obtain 4 as a liquid (7.80 g, 75% yield). $^1$H-NMR (500 MHz, CDCl$_3$): δ 2.34 (d, 1H, J=5.5 Hz, OH), 3.93 (t, 2H, J=6.0 Hz, H$_a$), 3.61 (t, 2H, J=4.5 Hz, H$_b$), 3.65-3.68 (m, 6H, H$_c$, H$_e$, H$_f$), 3.73 (q, 2H, J=5.5 Hz, H$_d$); $^{13}$C-NMR (125 MHz, CDCl$_3$): δ 50.62 (C$_a$), 61.73 (C$_f$), 70.02 (C$_b$), 70.36 (C$_e$), 70.63 (C$_c$), 72.45 (C$_d$). EI-MS: [M+Na]$^+$ C$_6$H$_{13}$N$_3$NaO$_3$ calcd 198.08, obsd 198.07

Synthesis of (2R,3R,4R,5R,6R)-5-acetamido-2-(acetoxymethyl)-6-(2-(2-(2-azidoethoxy)ethoxy)ethoxy)tetrahydro-2H-pyran-3,4-diyl diacetate (5α & β)

(5α & 5β): Compound 2 (150 mg, 0.454 mmol) and alcohol 4 (95.5 mg, 0.545 mmol) was dissolved in 1,2-dichloroethane (3 mL), followed by the addition of 4 A° MS (0.3 g) and reaction mixture stirred at room temperature for 20 minutes under N$_2$. TMSOTf (50.5 mg, 0.227 mmol) was then added via syringe and mixture stirred at 50° C. for 24 hours, followed by cooling to room temperature and quenching with Et$_3$N (0.4 mL, pH 7.5). The reaction mixture was extracted twice with DCM (60 mL) and saturated NaHCO$_3$ solution (20 mL), and organic layer washed with water, brine and dried over Na$_2$SO$_4$. Solvents were evaporated under reduced pressure and the residue purified by silica gel column chromatography using DCM:MeOH (9.5:0.5) as an eluent to obtain compound 5α (40 mg, 15% yield) as the first eluted. 5α $^1$H NMR (400 MHz, CDCl$_3$): δ 1.97 (s, 3H, CH$_3$, OAc), 1.98 (s, 3H, CH$_3$, OAc), 2.03 (s, 3H, CH$_3$, OAc), 2.14 (s, 3H, CH$_3$, OAc), 3.46 (t, 2H, J=5.2 Hz, H$_a$), 3.62-3.76 (m, 8H, H$_{b,c,d,e}$), 3.81-3.92 (m, 2H, H$_f$), 4.09-4.25 (m, 3H, H$_5$, H$_6$), 4.76 (d, 1H, J=8.5 Hz, H$_3$); 5.04 (dd, 1H, J=3.0, 11.0 Hz, H$_4$), 5.29-5.31 (m, 2H, H$_2$, H$_6$), 6.18 (d, 1H, J=4.6 Hz, H$_1$); EI-MS: [M+Na]$^+$ C$_{20}$H$_{32}$N$_4$NaO$_{11}$ calcd 527.20, obsd 520.19. Second eluted was 5β: (1.15 g, 85% yield). 5β $^1$H NMR (500 MHz, CDCl$_3$): δ 1.98 (s, 3H, CH$_3$, OAc), 2.04 (s, 3H, CH$_3$, OAc), 2.06 (s, 3H, CH$_3$, OAc), 2.13 (s, 3H, CH$_3$, OAc), 3.38 (t, 2H, J=5.0 Hz, H$_a$), 3.61-3.67 (m, 8H, H$_{b,c,d,e}$), 3.75-3.82 (m, 1H, H$_f$), 4.18-4.22 (m, 2H, H$_f$, H$_6$), 4.32-4.38 (m, 2H, H$_2$, H$_6$), 4.75 (dd, 1H, J=2.5 & 5.5 Hz, H$_3$); 5.00 (s, 1H, H$_4$), 5.34 (m, 1H, H$_5$), 6.06 (d, 1H, J=8.0 Hz, H$_1$), 4.52 (dd, 1H, J=1.5 & 5.5 Hz, H$_2$), 5.00 (m, 1H, H$_5$), 5.14 (s, 1H, H$_4$), 6.12 (d, 1H, J=6.5 Hz, H$_1$); 5β $^{13}$C NMR (125 MHz, CDCl$_3$): δ 20.9 (OAc, CH$_3$), 21.12 (2 OAc, CH$_3$), 23.39 (OAc, CH$_3$), 50.87 Ca), 60.54 (C$_2$), 62.87 (C$_6$), 67.21 (C$_f$), 70.13 (C$_b$), 70.23 (C$_c$), 70.55 (C$_d$), 70.88 (C$_e$), 70.91 (C$_5$), 78.03 (C$_3$), 80.04 (C$_4$), 106.90 (C$_1$), 169.72, 170.25, 170.77, 170.82 (4OAc, CO). EI-MS: [M+Na]$^+$ C$_{20}$H$_{32}$N$_4$NaO$_{11}$ calcd 527.20, obsd 520.19.

This protocol was modified to synthesis 5β exclusively. Briefly, compound 2 (1.0 g, 3.03 mmol) and alcohol 4 (1.60 g, 9.11 mmol) were dissolved in anhydrous DCM (20 mL), followed by addition of dried 4 A° MS (0.4 g) and reaction mixture stirred at room temperature for 20 minutes under N$_2$. CSA (camphor sulphonic acid, 0.615 g, 9.0 mL, 9.1 mmol) was added at room temperature and 8 hours, followed by heating to 45° C. for 24 hours. The reaction mixture was cooled to room temperature, neutralized with Et$_3$N (0.2 mL, pH 7.5), diluted with DCM (100 mL) and extracted using saturated NaHCO$_3$ solution. The organic layer was washed with water, brine and dried over Na$_2$SO$_4$. Solvents were evaporated under reduced pressure and the residue purified by silica gel column chromatography using DCM:EtOAc:

MeOH (8.0:1.5:0.5) to obtain compound 5β (1.15 g, 85%). The spectral data matched with above compound 5β.

Synthesis of (2R,3R,4R,5R,6R)-5-acetamido-2-(acetoxymethyl)-6-(2-(2-(2-aminoethoxy)ethoxy)ethoxy)tetrahydro-2H-pyran-3,4-diyl diacetate (6α & β)

Compound 5 (5α: 100 mg, 0.574 mmol; 5β: 150 mg, 0.861 mmol) was dissolved in anhydrous THF (8 mL), followed by addition of Me$_3$P (6α: 180 mg, 0.689 mmol; 6β: 0.046 g, 0.59 mmol, as a 1M solution in 0.12 mL THF) and reaction mixture stirred at room temperature for 16 hours under N$_2$. Solvents were evaporated under reduced pressure to obtain compound 6α (240 mg, 83% yield) and 6β (0.125 g, 90% yield). No further purification was required and compound was used directly for next step. 6α $^1$H NMR (500 MHz, CDCl$_3$): δ 1.98 (s, 3H, CH$_3$, OAc), 2.02 (s, 3H, CH$_3$, OAc), 2.06 (s, 3H, CH$_3$, OAc), 2.14 (s, 3H, CH$_3$, OAc), 3.22-3.34 (m, 2H, —NH$_2$), 3.58-3.80 (m, 8H), 3.80-3.88 (m, 2H), 3.94-4.15 (m, 4H), 4.16-4.24 (m, 1H), 4.70 (d, 1H, J=8.5 Hz), 5.18 (dd, 1H, J=3.0 & 11.0 Hz), 5.40 (d, 1H, J=3.0 Hz, H$_1$); ESI-MS: [M+H]$^+$ C$_{20}$H$_{35}$N$_2$O$_{11}$ calcd 479.22, obsd 479.20. 6β $^1$H NMR (500 MHz, CD$_3$OD): δ 1.88 (s, 3H, CH$_3$, OAc), 1.92-1.98 (m, 6H, 2CH$_3$, OAc), 2.02 (s, 3H, CH$_3$, OAc), 2.98-3.07 (m, 2H, H$_a$), 3.32-3.35 (m, 1H, H$_c$), 3.48-3.74 (m, 8H), 3.75-3.96 (m, 2H), 4.02-4.42 (m, 4H), 4.96-4.07 (m, 1H), 5.30 (m, 1H, H$_1$); 6β $^{13}$C NMR (125 MHz, CD$_3$OD): δ 20.53 (OAc, $\underline{C}$H$_3$), 20.62 (2OAc, $\underline{C}$H$_3$), 20.66 (OAc, $\underline{C}$H$_3$), 50.51 Ca), 61.56 (C$_2$), 62.71 (C$_6$), 69.50 (C$_f$), 69.90 (C$_b$), 70.25 (C$_c$), 70.51 (C$_d$), 72.39 (C$_e$), 76.29 (C$_5$), 77.58 (C$_3$), 84.27 (C$_4$), 107.26 (C$_1$), 169.62, 169.74, 170.33, 170.46 (4OAc, $\underline{C}$O). ESI-MS: [M+H]$^+$ C$_{20}$H$_{35}$N$_2$O$_{11}$ calcd 479.22, obsd 479.20.

Synthesis of (2R,3R,4R,5R,6R)-5-acetamido-2-(acetoxymethyl)-6-(2-(2-(2-amino(Boc amino PEG-)ethoxy)ethoxy)ethoxy)tetrahydro-2H-pyran-3,4-diyl diacetate (7α & β)

7α: Compound 6α (30 mg, 0.063 mmol) and BocHN-PEG-CONHS (70 mg, 0.031 mmol) were dissolved in anhydrous DMF (3 mL), followed by addition of Et$_3$N (0.02 mL) and reaction mixture stirred at room temperature for 48 hours. The reaction mixture was precipitated by slow dropwise addition of ether (40 mL) at 0° C., and solution stored at −18° C. overnight to complete precipitation. The precipitated portion was filtered through a glass filter at 0° C., washed twice with DCM (25 mL) and concentrated under reduced pressure to produce compound 7α as an off-white solid (68 mg, 80% yield). 7α $^1$H NMR (500 MHz, CDCl$_3$): δ 1.43 (s, 9H, 3CH$_3$, Boc), 1.94 (s, 3H, CH$_3$, OAc), 1.98 (s, 3H, CH$_3$, OAc), 2.03 (s, 3H, CH$_3$, OAc), 2.14 (s, 3H, CH$_3$, OAc), 3.05-3.15 (m, 4H), 3.32-3.65 (m, 10H, H$_{a,b,c,d,e}$), 3.40-4.00 (m, 180H, PEG-H), (4.02-4.18 (m, 3H, H$_2$, H$_{6,6'}$), 4.78 (d, 1H, J=3.4 Hz, H$_3$); 5.02-5.16 (m, 2H), 5.34 (d, 1H, J=1.2 Hz), 6.54 (d, 1H, J=3.6 Hz H$_1$); EI-MS: [M+H]$^-$ C$_{20}$H$_{35}$N$_2$O$_{11}$+PEG-NHBoc calcd 2622.32, obsd 2622.20.

7β: Compound 6β (25 mg, 0.053 mmol) and BocHN-PEG-CONHS (0.04 g, 0.017 mmol) were dissolved in anhydrous DMF (3 mL), followed by addition of EDC.HCl (0.005 g, 0.026 mmol), HOBT (0.0035 mg, 0.026 mmol) in DMF (0.5 mL), Et$_3$N (0.02 mL) and stirred for 48 hours at room temperature. The reaction mixture was purified via dialysis (MWCO 1 kDa) against deionized water for 36 hours, followed by extraction of the dialysis contents twice with cold Et$_2$O (5 mL) and lyophilized to obtain compound 7β as an off-white solid (47 mg, 80% yield). 7β $^1$H NMR (500 MHz, D$_2$O): δ 1.28 (s, 9H, 3CH$_3$, Boc), 1.82 (s, 3H, CH$_3$, OAc), 1.88 (s, 3H, CH$_3$, OAc), 1.93 (s, 3H, CH$_3$, OAc), 2.00 (s, 3H, CH$_3$, OAc), 2.06-2.09 (m, 52H, PEG-H), 3.18 (t, 2H, J=5.0 Hz, Ha), 3.38-3.46 (m, 3H, H$_{2d,1e}$), 3.48-3.62 (m, 180H, PEG-H), 3.69 (t, 1H, J=4.5 Hz, H$_e$), 3.80 (s, 1H, H$_f$), 4.04-4.21 (m, 4H, H$_2$, H$_5$, H$_{6,6'}$), 5.06 (dd, 1H, J=3.0 & 11.0 Hz, H$_3$); 5.31 (d, 1H, J=3.5 Hz H$_4$), 5.66 (d, 1H, J=8.5 Hz H$_1$). EI-MS: [M+H]$^-$ C$_{20}$H$_{35}$N$_2$O$_{11}$+PEG-NHBoc calcd 2622.32, obsd 2622.20.

Synthesis of (2R,3R,4R,5R,6R)-5-acetamido-2-(acetoxymethyl)-6-(2-(2-(2-amino(amino PEG-)ethoxy)ethoxy)ethoxy)tetrahydro-2H-pyran-3,4-diyl diacetate (8α & β)

Compound 7 (7α: 83 mg, 0.033 mmol; 7β: 35 mg, 0.013 mmol) was dissolved in DCM:TFA (1.5:1, 4 mL) and stirred at room temperature for 12 hours, followed by evaporation under reduced pressure. Residue was washed three times with DCM (3 mL) and evaporated to remove all TFA, followed by washing twice with cold Et$_2$O (4 mL) and decanted before evaporation to obtain compound 8 (8α: 75 mg, 90% yield; 8β: 28 mg, 83% yield) as a crude mixture utilized for the next reaction. 8α $^1$H-NMR (400 MHz, CDCl$_3$): δ 1.97 (s, 3H, CH$_3$, OAc), 2.06 (s, 3H, CH$_3$, OAc), 2.10 (s, 3H, CH$_3$, OAc), 2.13 (s, 3H, CH$_3$, OAc), 3.17 (t, 2H, NH$_2$), 3.32-3.65 (m, 10H, H$_{a,b,c,d,e}$), 3.62 (m, 180H, PEG-H), 3.72-3.80 (m, 4H, H$_f$, H$_{a'}$), 3.89 (m, 2H, H$_a$) 4.05-4.17 (m, 3H, H$_2$, H$_{6,6'}$), 4.79 (d, 1H, J=4.4 Hz, H$_3$); 5.15 (d, 1H, J=5.4 Hz, H$_4$), 5.33 (d, 1H, J=5.8 Hz H$_5$), 6.54 (d, 1H, J=4.2 Hz H$_1$). 8β $^1$H-NMR (500 MH, CDCl$_3$): δ 1.98 (s, 3H, CH$_3$, OAc), 2.02 (s, 6H, 2CH$_3$, OAc), 2.03 (s, 3H, CH$_3$, OAc), 2.10-2.24 (m, 52H, PEG-H), 3.17 (s, 2H, Ha), 3.48-3.62 (m, 180H, PEG-H), 3.90-4.58 (m, 6H), 5.16-5.44 (m, 3H), 5.49 (s, 2H), 5.84 (d, 1H, J=9.0, H$_1$); 6.06-6.30 (m, 2H), 6.46 (s, 1H). EI-MS: [M+H]$^-$ C$_{20}$H$_{35}$N$_2$O11+PEG-NH$_2$ calcd 2522.3, obsd 2522.20.

Synthesis of (2R,3R,4R,5R,6R)-5-acetamido-2-(acetoxymethyl)-6-(2-(2-(2-amino(cis-aconityl-amino PEG-)ethoxy)ethoxy)ethoxy)tetrahydro-2H-pyran-3,4-diyl diacetate (9α & β)

Compound 8 (8α: 75 mg, 0.030 mmol; 8β: 28 mg, 0.011 mmol) was dissolved in DI water (4 mL) followed by addition of cis-aconitic anhydride (9α: 16 mg, 0.101 mmol; 9β: 6 mg, 0.038 mmol) in 1,4-dioxane (0.5 mL). The pH was adjusted to 8.5-8.7 by dropwise addition of 0.5 M NaOH and solution stirred for 10 minutes at room temperature. The pH was then adjusted to 7.4-7.5 via addition of ice-cold 1N HCl solution and reaction mixture stirred at 0° C. for 5 minutes before further acidification to pH 2.5-3.0 while stirring for 5 minutes at 0° C. The reaction mixture was purified by dialysis (MWCO 1 kDa) against sterile water for 36 hours and lyophilized to obtain compound 9 as an off-white solid (9α: 65 mg; 82% yield; 9β: 25 mg, 85% yield). 9α $^1$H-NMR (400 MHz, CDCl$_3$): δ 1.97 (s, 3H, CH$_3$, OAc), 2.06 (s, 3H, CH$_3$, OAc), 2.10 (s, 3H, CH$_3$, OAc), 2.13 (s, 3H, CH$_3$, OAc), 3.32-3.62 (m, 12H, CH$_2$—COOH, H$_{a,b,c,d,e}$), 3.62 (m, 180H, PEG-H), 3.72-3.80 (m, 4H, H$_f$, H$_{a'}$), 3.89 (m, 2H, H$_a$) 4.05-4.17 (m, 3H, H$_2$, H$_{6,6'}$), 4.81 (d, 1H, J=4.2 Hz, H$_3$); 5.15 (dd, 1H, J=1.6 & 1 Hz, H$_4$), 5.29 (d, 1H, J=1.4 Hz H$_5$), 6.33 (s, 1H, olefin), 6.44 (d, 1H, J=4.4 Hz H$_1$), 7.61 (bs, 2H, COOH). 9β $^1$H-NMR (500 MHz, CDCl$_3$): δ 1.10-2.60 (m, 64H, 4CH$_3$, PEG-H), 3.13 (s, 2H, H$_a$), 3.42-3.90 (m, 180H, PEG-H), 3.96-4.42 (m, 6H), 5.30-5.42 (m, 2H), 6.35 (s, 1H), 6.81 (d, 1H, J=7.0, olefin); 7.12 (d, 1H, J=7.0, olefin), 7.54 (dd, 1H, J=3.0 & 5.5 Hz, olefin), 7.71 (dd, 1H, J=3.5 & 6.0 Hz, olefin). EI-MS: [M+H]⁻ $C_{20}H_{35}N_2O11$+PEG-NH-cis-Ac calcd 2678.3, obsd 2678.20.

Synthesis of (2R,3R,4R,5R,6R)-5-acetamido-2-(acetoxymethyl)-6-(2-(2-(2-amino(Fl₆-G5-cis-aconityl-amino PEG-)ethoxy)ethoxy)ethoxy)tetrahydro-2H-pyran-3,4-diyl diacetate (10α & β)

Compound 9 (9α: 10.7 mg, 0.004 mmol; 9β: 5.3 mg, 0.002 mmol) was dissolved in 0.1 M potassium phosphate buffer (pH 6.0, 2.5 mL) followed by addition of EDC.HCl (10α: 4 mg, 0.016 mmol; 10β: 2 mg, 0.008 mmol; 1:4 with acid) and reaction mixture stirred at room temperature for 30 minutes. G5-(Fl)₆-(NH₂)₁₂₂ (10α: 12 mg, 0.00039 mmol; 10β: 5 mg, 0.00016 mmol) in MeOH (2 mL) was added and solution adjusted to pH 8.0 via dropwise addition of 0.5 M NaOH, followed by stirring at room temperature in the dark for 36 hours. The reaction was purified by dialysis (MWCO 10 kDa) against sterile water for 36 hours and lyophilized to obtain compound 10 as a light orange solid (10α: 20 mg; 88% yield; 10β: 10 mg, 97% yield). 10α ¹H-NMR (400 MHz, D₂O): δ 1.90 (s, 3H, CH₃, OAc), 1.96 (s, 3H, CH₃, OAc), 1.98 (s, 3H, CH₃, OAc), 2.09 (s, 3H, CH₃, OAc), 2.32-3.32 (m, G5-H) 3.32-3.56 (m, 10H, $H_{a,b,c,d,e}$), 3.56 (m, PEG-H), 3.60-3.63 (m, 4H, $H_f$ $H_{a'}$), 3.73-3.76 (m, 2H, $H_a$) 4.09-4.17 (m, 3H, H₂, $H_{6,6'}$), 4.98 (dd, 1H, J=1.6 & 1.8 Hz, H₄), 5.27 (d, 1H, J=1.6 Hz H₅), 6.42 (bd, 1H, H₁). 10β ¹H-NMR (500 MHz, D₂O): δ 0.40-2.72 (m, 184H, 4CH₃, G5-H, PEG-H), 3.13 (s, 2H, $H_a$), 3.22-3.66 (m, 420H, G5-H, PEG-H), 3.68 (s, 1H), 3.79 (s, 2H), 3.84-3.40 (m, 2H), 4.10 (s, 2H), 4.17 (s, 2H), 4.32 (d, 1H, J=7.5 Hz); 5.09 (s, 1H), 6.76 (d, 1H, J=7.0, olefin); 7.06 (d, 1H, J=7.0, olefin), 7.36 (dd, 1H, J=3.0 & 5.5 Hz, olefin), 7.91 (d, 1H, J=6.0 Hz, olefin).

Synthesis of (2R,3R,4R,5R,6R)-5-acetamido-2-(acetoxymethyl)-6-(2-(2-(2-amino(Fl₆-G5(Ac)-cis-aconityl-amino PEG-)ethoxy)ethoxy)ethoxy)tetrahydro-2H-pyran-3,4-diyl diacetate (11α & β)

Compound 10 (10α: 20 mg, 0.0006 mmol; 10β: 10 mg, 0.0003 mmol) was dissolved in anhydrous MeOH (2 mL), followed by addition of Et₃N (0.2 mL), excess of Ac₂O (0.15 mL) and reaction mixture stirred at room temperature for 48 hours. Solvents were removed under reduced pressure and residue purified by dialysis (MWCO 10 kDa) against sterile water for 48 hours and residue lyophilized. To remove the acetyl groups from the NAcGal sugar moiety the compound was dissolved in anhydrous MeOH (2 mL) containing hydrazine hydrate (0.4 mL) and reaction mixture stirred at room temperature for 48 hours. Solvents were removed under reduced pressure and residue purified by dialysis (MWCO 10 kDa) against deionized water for 48 hours and lyophilized to obtain compound 11 as a light orange solid (11α: 18.5 mg, 93% yield; 11β: 9 mg, 90% yield. 11α ¹H NMR (500 MHz, D₂O): δ 0.40-2.72 (m, 184H, 4CH₃, G5-H, PEG-H), 3.13 (s, 2H, Ha), 3.22-3.66 (m, 420H, G5-H, PEG-H), 3.68 (s, 1H), 3.79 (s, 2H), 3.84-3.40 (m, 2H), 4.10 (s, 2H), 4.17 (s, 2H), 4.34 (d, 1H, J=7.5 Hz); 5.12 (s, 1H), 6.65 (d, 1H, J=7.0, olefin); 7.12 (d, 1H, J=7.0, olefin), 7.34 (dd, 1H, J=3.0 & 5.8 Hz, olefin), 7.98 (d, 1H, J=6.4 Hz, olefin). 11β ¹H NMR (500 MHz, D₂O): δ 0.40-2.72 (m, 184H, 4CH₃, G5-H, PEG-H), 3.13 (s, 2H, Ha), 3.22-3.66 (m, 420H, G5-H, PEG-H), 3.68 (s, 1H), 3.79 (s, 2H), 3.84-3.40 (m, 2H), 4.10 (s, 2H), 4.17 (s, 2H), 4.32 (d, 1H, J=7.5 Hz); 5.09 (s, 1H), 6.76 (d, 1H, J=7.0, olefin); 7.06 (d, 1H, J=7.0, olefin), 7.36 (dd, 1H, J=3.0 & 5.5 Hz, olefin), 7.91 (d, 1H, J=6.0 Hz, olefin).

Synthesis of G5-(Fl)₆-(Ac)-(cPEG[SP94]) conjugates

Synthesis of Fmoc-SP94-Mal-tert-butyl(2-(3-(2,5-dioxo-2,5-dihydro-1H-pyrrol-1-yl)propanamido)(polyethylene glycol)ethyl)carbamate (13)

Commercially available MAL-PEG-NH₂.TFA (0.010 g, 0.005 mmol) was dissolved in anhydrous DCM and added (Boc)₂ (0.0015 g, 0.005 mmol) at room temperature and stirred for 16 hours. The reaction was quenched with water and extracted in DCM (2×25 mL). The organic layer was washed with water and dried over Na₂SO₄ and solvents removed under reduced pressure to obtain compound 12 (0.010 g, 95% yield). The compound was used for next step without further purification. ESI-MS: [M+H]⁺ MAL-PEG-$NH_{BOC}$ calcd 1892.10, obsd 1892.20

Compound 12 (0.0075 g, 0.0093 mmoles) and Fmoc-SP94-SH peptides (0.0065 g, 0.0093 mmoles) were dissolved in pH 6.5 sodium phosphate buffer:MeOH (1.5:0.5 mL) mixture and reaction solution stirred at room temperature for 36 hours. The solution was then purified by dialysis (MWCO 1 kDa) against deionized water for 36 hours to remove low molecular weight impurities, and lyophilized to obtain compound 13 (0.012 g, 80% yield). ¹H NMR (500 MHz, CDCl₃): δ 0.82-1.02 (m, 24H, 8-CH₃), 1.12-1.76 (m, 42H), 1.74-2.10 (m, 8H), 2.14-2.24 (m, 3H), 2.47 (t, 4H, J=6.5 Hz), 2.68 (bs, 1H), 2.81 (bs, 1H), 2.88-3.06 (m, 3H), 3.08-3.42 (m, 48H including PEG-H), 3.42-4.08 (m, 242H), 4.09-4.32 (m, 5H), 4.32-4.54 (m, 4H), 4.58-4.80 (m, 5H), 5.13 (bs, 1H), 5.22 (bs, 2H), 5.35 (t, 1H, J=6.0 Hz), 6.65 (d, 1H, J=8.0 Hz, —NH), 6.83 (s, 2H), 7.01 (d, 1H, J=8.5 Hz, —NH), 7.10-7.46 (m, 10H), 7.52-7.78 (m, 2H), 7.78-8.00 (m, 2H), 8.08 (d, 1H, J=8.5 Hz, —NH), 8.24-8.46 (m, 2H, —NH), 8.70-8.78 (m, 2H); ESI-MS: [M+H]⁺ FmocNH-SP94-S-MAL-PEG-NH-Boc calcd 3669.20, obsd 3669.11.

Synthesis of Fmoc-SP94-Mal-(2-(3-(2,5-dioxo-2,5-dihydro-1H-pyrrol-1-yl)propanamido)(polyethylene glycol)ethyl)carbamate (14)

Compound 13 (0.012 g, 0.013 mmoles) was dissolved in DCM:trifluoroacetic acid (TFA) (1.5:1, 2.5 mL) and stirred at room temperature for 24 hours, followed by removal of solvents under reduced pressure. The residue was repeatedly diluted in DCM (3 mL) and dried several times to completely remove residual TFA, followed by repeated washing and decanting with cold Et₂O (3×4 mL) to remove low molecular weight impurities. Solvents were removed under reduced pressure to obtain compound 14 (0.011 g, 85% yield) utilized as the crude mixture for the next reaction. ¹H NMR (500 MHz, CDCl₃): δ 0.73-1.02 (m, 24H, 8-CH₃), 1.10-1.72 (m, 26H), 1.74-2.10 (m, 8H), 2.12-2.24 (m, 3H), 2.42-2.54 (m, 4H), 3.00-3.44 (m, 38H, including PEG-H), 3.42-4.08 (m, 180H), 4.09-4.80 (m, 18H), 5.08 (bs, 1H), 5.30-5.55 (m, 2H), 6.64 (d, 1H, J=8.0 Hz, —NH), 6.99 (d, 1H, J=8.0 Hz, —NH), 7.10-7.44 (m, 10H), 7.58-7.84 (m, 2H), 8.22-8.32 (m, 1H), 8.66-8.88 (m, 1H); ESI-MS: [M+H]⁺ FmocNH-SP94-S-MAL-PEG-NH₂ calcd 3569.20, obsd 3569.00.

Synthesis of Fmoc-SP94-Mal-(2-(3-(2,5-dioxo-2,5-dihydro-1H-pyrrol-1-yl)propanamido)-2-amino(cis-aconityl-amino PEG-)-(polyethylene glycol)ethyl)carbamate (15)

Compound 14 (0.028 g, 0.011 mmoles) was dissolved in deionized water (4 mL) followed by addition of cis-aconitic anhydride (0.006 g, 0.038 mmoles) dissolved in 0.5 mL of 1,4-dioxane. The pH was adjusted to 8.5-8.7 by dropwise addition of 0.5 M NaOH and solution stirred for 10 minutes at room temperature. This was followed by adjustment of the pH to 7.4-7.5 via addition of ice-cold 1N HCl solution and reaction mixture stirred at 0° C. for 5 minutes before further acidification to pH 2.5-3.0 at 0° C. while stirring for 5 minutes. The reaction mixture was purified by dialysis (MWCO 1 kDa) against deionized water for 36 hours and lyophilized to obtain compound 15 as an off-white fluffy solid (0.011 g, 65% yield). $^1$H NMR (500 MHz, CDCl$_3$): δ 0.78-1.02 (m, 24H, 8-CH$_3$), 1.12-1.74 (m, 42H), 1.78-2.10 (m, 8H), 2.20 (t, 4H, J=7.5 Hz), 2.28 (t, 2H, J=7.5 Hz), 2.30-2.54 (m, 6H), 2.90-4.10 (m, 290H, including PEG-H), 4.10-4.24 (m, 8H), 4.28-4.52 (m, 6H), 4.54-4.80 (m, 5H), 5.35 (t, 1H, J=5.0 Hz), 5.38 (bs, 1H), 6.33 (bs, 1H), 6.62-7.00 (m, 4H, —NH), 7.00-7.42 (m, 9H), 7.60-7.84 (m, 5H), 8.11 (bs, 1H, —NH), 8.47 (bs, 1H, —NH), 8.52-8.60 (m, 2H); ESI-MS: [M+H]$^-$ FmocNH-SP94-S-MAL-PEG-NH-Cis-Ac-COOH calcd 3725.31, obsd 1862.20 as a doubly charged ion.

Synthesis of Fmoc-SP94-Mal-(2-(3-(2,5-dioxo-2,5-dihydro-1H-pyrrol-1-yl)propanamido)-2-amino(Fl$_6$-G5-cis-aconityl-amino PEG-)-(polyethylene glycol)ethyl)carbamate (16)

Compound 15 (0.0075 g, 0.002 mmoles, 18 eq.) was dissolved in 2.5 mL 0.1 M potassium phosphate buffer (pH 6.0) followed by addition of EDC.HCl (0.002 g, 0.008 mmoles, 1:4 with acid) and stirred at room temperature for 30 minutes. Fluorescently-labeled G5-(Fl)$_6$-(NH$_2$)$_{122}$ dendrimers (0.005 g, 0.0001 mmoles) were dissolved in 2 mL MeOH and the pH of the solution adjusted to 8.0 with 0.5 M Na$_2$CO$_3$ solution, followed by stirring of the reaction mixture for 48 hours in the dark. The reaction solution was purified by dialysis (MWCO 10 kDa) against sterile water for 36 hours, and lyophilized to obtain compound 16 as a light orange fluffy solid (0.010 g, 85% yield). $^1$H NMR (500 MHz, D$_2$O): δ 0.58-0.80 (m, 24H, 8-CH$_3$), 0.92-1.24 (m, 12H), 1.52-4.00 (m, 254H, including PEG-H), 4.50 (s, 2H), 4.58 (s, 2H), 4.74 (bs, 1H), 5.10 (bs, 1H), 5.15 (bs, 1H), 6.14 (d, 2H, J=12.0 Hz —NH), 6.30-6.52 (m, 4H), 6.84-7.23 (m, 4H), 7.35 (bs, 1H, —NH), 7.46 (bs, 1H, —NH), 7.72 (bs, 1H, —NH), 7.62-7.82 (m, 2H).

Synthesis of Fmoc-SP94-Mal-(2-(3-(2,5-dioxo-2,5-dihydro-1H-pyrrol-1-yl)propanamido)-2-amino(FT-G5-NHAc-cis-aconityl-amino PEG-)-(polyethylene glycol)ethyl)carbamate (17)

Compound 16 (0.001 g, 0.0003 mmoles) was dissolved in anhydrous MeOH (1.5 mL), followed by addition of Et$_3$N (0.2 mL) and Ac$_2$O (0.1 mL) before stirring of the reaction mixture at room temperature for 48 hours. Solvents were removed under reduced pressure and reside dissolved in water (4 mL) and purified by dialysis (MWCO 10 kDa) against deionized water for 24 hours before lyophilization to obtain compound 17 as a light orange color fluffy solid (0.008 g, 80% yield).

Synthesis of H$_2$N-SP94-Mal-(2-(3-(2,5-dioxo-2,5-dihydro-1H-pyrrol-1-yl)propanamido)-2-amino(FT-G5-NHAc-cis-aconityl-amino PEG-)-(polyethylene glycol)ethyl)carbamate (18)

Compound 17 (0.008 g, 0.0003 mmoles) was dissolved in 20% piperidine in DMF (1.5 mL) and mixture stirred at room temperature for 48 hours. Piperidine was removed under reduced pressure, residue dissolved in water and compound purified by dialysis (MWCO 10 kDa) against deionized water for 48 hours before lyophilization to obtain compound 18 as a light orange color fluffy solid (0.006 g, 80% yield). $^1$H NMR (500 MHz, D$_2$O): δ 0.58-0.80 (m, 24H, 8-CH$_3$), 0.92-1.26 (m, 12H), 1.39 (s, 3H), 1.42 (s, 3H), 1.56-1.94 (m, 12H), 2.12-2.42 (m, 12H), 2.50-3.60 (m, 252H, including PEG-H), 3.70-4.01 (m, 12H,), 4.10-4.34 (m, 8H), 4.38 (d, 2H, J=5.5 Hz), 4.50 (s, 2H), 4.52-4.62 (m, 5H), 5.04 (bs, 1H), 5.10 (bs, 1H), 5.15 (bs, 1H), 6.12 (d, 2H, J=12.0 Hz —NH), 6.10-6.52 (m, 4H), 6.84-7.30 (m, 5H), 7.14 (bs, 1H, —NH), 7.55 (bs, 1H, —NH), 7.70 (bs, 1H, —NH), 7.75 (bs, 1H, —NH), 7.88 (bs, 1H, —NH), 8.05 (bs, 1H, —NH), 8.20-8.40 (m, 2H).

Characterization of Targeted G5-(Fl)$_6$-(Ac)-(cPEG) Conjugates

The number of PEG chains attached per single G5-(Fl)$_6$-(Ac) dendrimer was determined by gravimetric analysis after sample acidification, dialysis and change in weight measured. Briefly, 2 mg of each targeted G5-(cPEG) conjugate was dissolved in 1 mL of HCl-acidified PBS (pH 1.0) and mixture stirred at room temperature for 24 hours, before dialysis (MWCO 5 kDa) against deionized water for 48 hours. The remaining G5-(Fl)$_6$-(Ac) dendrimers were lyophilized and dried sample weighed using a semi-micro analytical balance. The change in weight was divided by the molecular weight of the PEG-R (where R represents, methyl (non-targeted), NAc-Gal sugar or the SP94 peptide) to determine the number of targeted or non-targeted PEG chains attached per G5-(Fl)$_6$-(Ac) dendrimer carrier. This analysis was performed in triplicate for each conjugate with a nominal ±10% deviation in the mean number of calculated PEG-ligand chains. Results are reported as the average number of PEG chains with or without targeting attached per dendrimer±standard error of the mean SEM.

Size and surface charge of G5-(Fl)$_6$-(Ac)-(cPEG) carriers with and without targeting ligands was determined by dissolving each conjugate in 1 mL deionized water at a particle concentration of 1 μM and analyzed using a 90Plus particle size analyzer with ZetaPALS capability (Brookhaven Instruments Corporation, Holtsville, N.Y.). To investigate the acid-sensitive cleavage of the cis-aconityl linker and release of PEG chains from the G5-(Fl)$_6$-(Ac) carrier, 0.5 mg/mL of G5-(Fl)$_6$-(Ac)-(cPEG) conjugates was dissolved in 2 mL of 1 mM citrate buffer prepared at either pH 5.0 or pH 7.4 and samples incubated for 24 hours at 37° C. while shaking. We collected 100 μL of the G5-(Fl)$_6$-(Ac)-(cPEG) solution at selected time points (0-24 hours) and the concentration of free PEG analyzed using a Ultrahydroge1500 10 μm (7.8× 300 mm) column connected to a Viscotek GPCmax system equipped with a Water refractive index detector. Deionized water was used as a mobile phase at a 0.5 mL/min flow rate, and the concentration of free PEG released as a function of time quantified by measuring the change in solution refractive index versus elution time compared to a series of PEG standards, and results referenced to the calculated initial PEG concentration to determine % PEG release. Results are presented as the average % PEG release of triplicate experiments±SEM.

Culture of HepG2 and Rat Hepatocytes Cells

HepG2 cells (a gift from Dr. Donna Shewach, Department of Pharmacology, University of Michigan) were cultured in T-75 flasks using MEM supplemented with 10% FBS, and 1% penicillin/streptomycin/amphotericin, sodium pyruvate and non-essential amino acids following published protocols.[26] HepG2 cells (passages 28-32) were incubated at 37°

C., 5% CO2 and 95% relative humidity while changing the culture medium every 48 hours. Cells were passaged at 80-90% confluency using a 0.25% trypsin-EDTA solution. Primary hepatocytes freshly isolated from Sprague-Dawley rats were received 48 hours after isolation and cultured in fresh complete hepatocyte culture media (K2300) for 24 hours before their use in different uptake studies.

Uptake of G5-(Fl)$_6$-(Ac)$_{108}$-(NAcGal)$_{14}$ and NAc-Gal- or SP94-Targeted G5-(Fl)$_6$-(Ac)-(cPEG) Conjugates by HepG2 Cancer Cells and Primary Rat Hepatocytes HepG2 cells and rat hepatocytes were seeded in 24-well plates at a density of 5×10$^5$ cells/well. After adherence the culture medium was aspirated and the cells were incubated for 2 or 24 hours at regular culture conditions with non-targeted G5-(Fl)$_6$-(Ac)$_{107}$-(cPEG)$_{15}$, NAcGal-targeted G5-(Fl)$_6$-(Ac)$_{108}$-(NAcGal)$_{14}$, G5-(Fl)$_6$-(Ac)$_{107}$-(cPEG[NAc-Gal$_\alpha$])$_{15}$ and G5-(Fl)$_6$-(Ac)$_{108}$-(cPEG[NAcGal$_\beta$])$_{14}$, or SP94-targeted G5-(Fl)$_6$-(Ac)$_{108}$-(cPEG[SP94])$_{14}$ conjugates dissolved at 100-4,000 nM eq. ligand concentration in OPTI-MEM solution for HepG2 cells or hepatocyte culture media (K2300) for rat hepatocytes. After the selected incubation period cells were washed with cold PBS, trypsinized and centrifuged at 1000 rpm for 5 min to pellet the cells before suspending them in 1 ml of fresh PBS and analyzing them using flw cytometry as previously described. Uptake of each conjugate was evaluated as a function of conjugate's chemical composition, concentration, and incubation time via three independent experiments using four replicates for each experimental condition. Uptake of NAcGal-targeted G5-(Fl)$_6$-(Ac)$_{108}$-cPEG[NAcGal$_\beta$]))$_{14}$ conjugates into rat hepatocytes was evaluated as a function of incubation time at the highest ligand concentration (4,000 nM) upon co-incubation with 100 mM of free NAcGal ligands using flow cytometry to determine the confirm the role of the ASGPR in the internalization of NAcGal-targeted conjugates into rat hepatocytes. Internalization results are represented as the percentage of cells analyzed by flow cytometry showing FITC-fluorescence. In addition, the normalized relative fluorescence for each treatment was obtained by subtracting the average geometric mean fluorescence of untreated control cells from the geometric mean for each treatment group to obtain the relative fluorescence per cell as a function of treatment.

Isolation of Mouse Kupffer Cells

Isolation of primary mouse Kupffer cells was performed as previously described by Su et. al,[36] with minor modification. Briefly, two black-swiss mice were anesthetized via i.p injection of pentobarbital (50 µg/g), abdominal cavity exposed via 'U' shaped celiotomy and inferior vena cava cannulated with a 20 gauge angiocath. The livers were each perfused with 12 mL 37° C. heparin solution (1000 U/mL in HBSS) over 1 minute, followed by 12 mL 37° C. pronase solution (0.1% w/v in HBSS) perfused for 1 minute. The blanched livers were then excised, gall bladder removed and liver tissue finely minced before a 60 minute digestion in 150 mL pronase solution while spinning at 37° C. 1 mL of DNase solution (80 µg/mL in PBS) was added in 20 minute intervals during digestion to prevent cell clumping, and the slurry was filtered through gauze mesh and centrifuged at room temperature (1800 rpm, 5 minutes). The pellet was then resuspended in 10 mL DNase solution and filtered through a 70 µm cell strainer before centrifugation at 16° C. Cell pellet was suspended in 1 mL DNase solution and added to the top of a discontinuous Percoll gradient prepared by gently adding 3.75 mL 50% Percoll to 5 mL 25% Percoll (diluted in 10×PBS) in a 15 mL falcon tube over 5 minutes, ensuring a visible interface is formed before addition of cell solution. The gradient mixture was then centrifuged at 0° C. (1800 rpm, 15 minutes) using the lowest acceleration/deceleration settings so as to not disturb the gradient. The debris and 25% Percoll layer were discarded, and the 50% Percoll fraction was removed and washed twice 20 mL DNase solution to remove Percoll. Cells viability was assessed by trypan blue (>90% viable), diluted in serum-free RPMI and added at 5×10$^5$ cells/well in 24-well plates. Plates were incubated for 30 minutes at 37° C. and medium aspirated to remove non-adherent debris, followed by addition of 1 mL RPMI medium containing 5% FBS added to the adherent Kupffer cells. These cells were >80% pure for Kupffer cells as estimated by uptake of FITC-labeled IgG-latex beads using a phagocytosis assay kit (Cayman Chemicals, Ann Arbor, Mich.) following the manufacturer's guidelines. The remaining cells are primarily endothelial and stellate cells as previously described.[36]

Opsonization of Targeted G5-(cPEG) Conjugates and Phagocytosis by Kupffer Cells

Opsonization of G5-(Fl)$_6$-(NH$_2$)$_{122}$ dendrimers, G5-(Fl)$_6$-(Ac)$_{107}$-(cPEG)$_{15}$, G5-(Fl)$_6$-(Ac)$_{108}$-(NAcGal)$_{14}$, G5-(Fl)$_6$-(Ac)$_{108}$-(cPEG[NAcGal$_\beta$])$_{14}$ and G5-(Fl)$_6$-(Ac)$_{108}$-(cPEG[SP94])$_{14}$ conjugates was performed by diluting each conjugate in PBS (pH 7.4) at a 10 nM particle concentration in a quartz cuvette, opsonization initiated by addition of 0.2 mg/mL BSA. Intrinsic BSA tryptophan fluorescence quenching due to particle binding has been reported previously,[37] and was recorded using a QM4 fluorescence spectrophotometer (Perkin-Elmer, Waltham, Mass.). The sample was maintained at 37° C. using a heated cuvette holder, excitation wavelength set to 280 nm and emission scanned from 300-400 nm over a 60 minute incubation period. The fluorescence quenching efficiency is defined as I°/I, where I° and I are the peak fluorescence intensity at initiation of opsonization and as a function of time, respectively.

Uptake of non-targeted G5-(Fl)$_6$-(NH$_2$)$_{122}$ and G5-(Fl)$_6$-(Ac)$_{107}$-(cPEG)$_{15}$, NAcGal-targeted G5-(Fl)$_6$-(Ac)$_{108}$-(NAcGal)$_{14}$ and G5-(Fl)$_6$-(Ac)$_{108}$-(cPEG[NAcGal$_\beta$])$_{14}$, or SP94-targeted G5-(Fl)$_6$-(Ac)$_{108}$-(cPEG[SP94])$_{14}$ conjugate in isolated mouse Kupffer cells was evaluated after pre-incubation at 4,000 nM eq. ligand concentration in mouse serum for 1 hour at 37° C., followed by dilution to 1 mL total volume with RPMI medium and incubated with isolated Kupffer cells, plated at 5×10$^5$ cells/well in a 24-well plate, for 2 hours at normal culture conditions before analysis by flow cytometry.

Example 14

Synthesis of [$^{14}$C]G5-(NH$_2$)$_{127}$, [$^{14}$C]G5-(Ac)$_{108}$-(NAcGal)$_{14}$, and [$^{14}$C]G5-(Ac)$_{73}$-(PEG)$_{10}$ Conjugates

[$^{14}$C]G5-(NH$_2$)$_{127}$ dendrimers possessed an average of 1.02 [$^{14}$C] radio-labels as determined by liquid scintillation counting. [$^{14}$C]G5-(NH$_2$)$_{127}$ dendrimers were then utilized to prepare [$^{14}$C]G5-(Ac)$_{108}$-(NAcGal)$_{14}$ conjugates which contained 11 mole % NAcGal content, a ligand loading ratio previously shown to result in selective uptake of G5-NAcGal targeted carriers into hepatic cancer cells.[26] [$^{14}$]-(Ac)$_{73}$-(PEG)$_{10}$ conjugates were synthesized and possessed an average of 10 PEG chains per dendrimer by MALDI-TOF analysis.

Figure 36A:
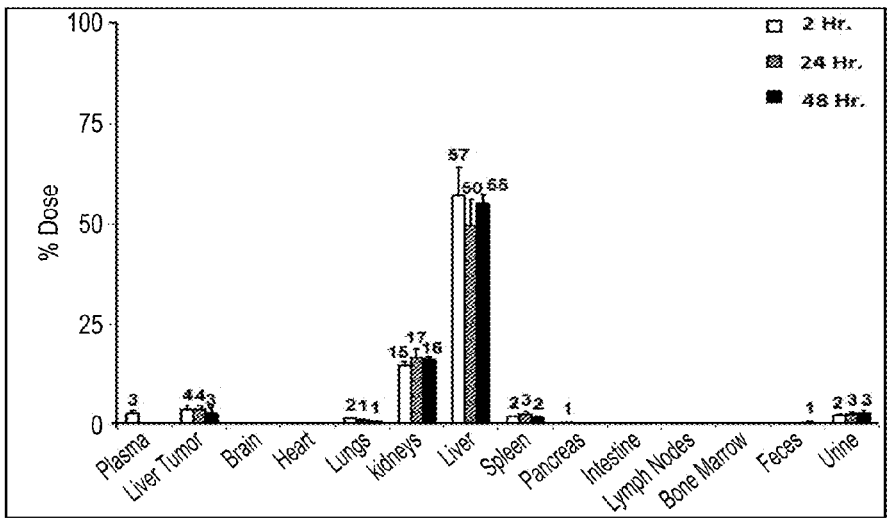
FIG. 36 represents a collection of graphs that demonstrate biodistribution of radio-labeled (A) $[^{14}C]G5-(NH_2)_{127}$, (B) $[^{14}C](Ac)_{108}-(NAcGal)_{14}$ and (C) $[^{14}C]G5-(Ac)_{73}-(PEG)_{10}$ conjugates after intravenous administration to HepG2 orthotopic liver-tumor bearing mouse models.
Figure 36B:
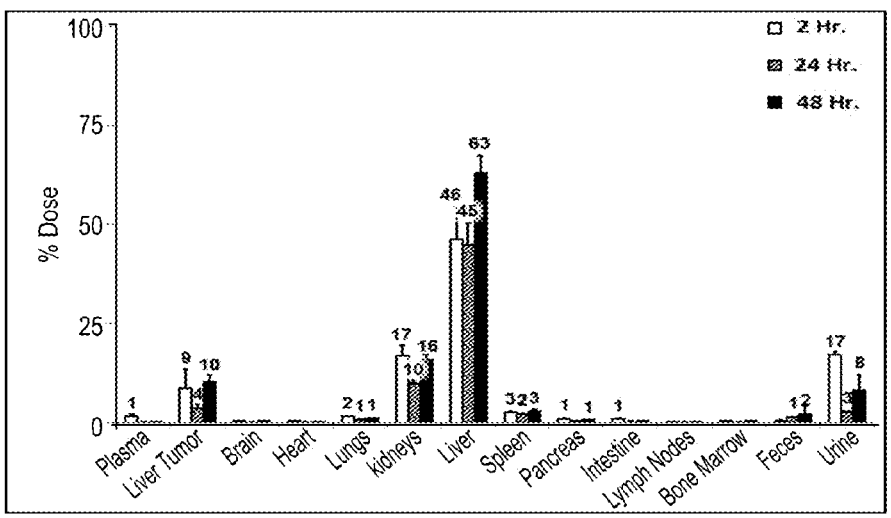
Figure 36C:
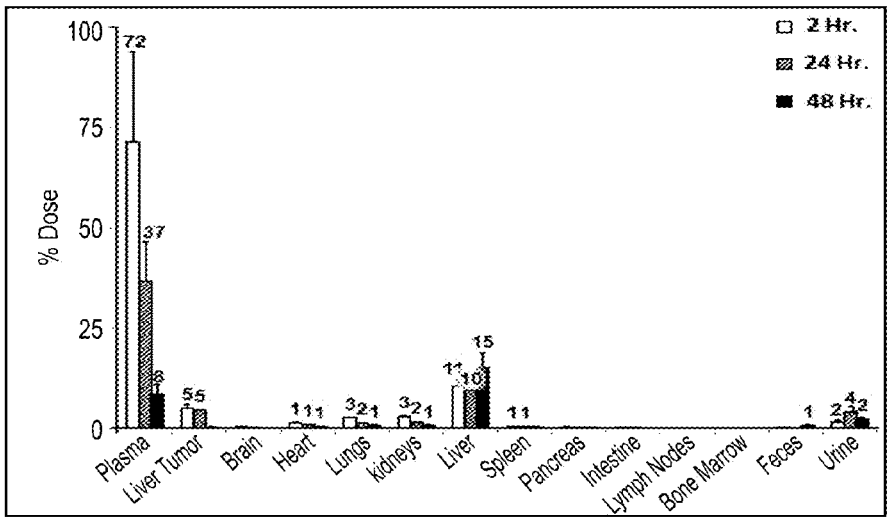

In Vivo Biodistribution of [$^{14}$C]G5-(NH$_2$)$_{127}$, [$^{14}$C]G5-(Ac)$_{108}$-(NAcGal)$_{14}$, and [$^{14}$C]G5-(Ac)$_{73}$-(PEG)$_{10}$ Conjugates in Tumor-Bearing Mice Administration of [$^{14}$C]G5-(NH$_2$)$_{127}$ to the orthotopic liver tumor-bearing mouse models resulted in rapid clearance of particles from the systemic circulation with only 3% ID assayed in the plasma 2 hours after administration, resulting in a plasma half-life (t$_{1/2}$) of 1.03 hours (FIG. 36; Panel A). 4% ID of [$^{14}$C]G5-(NH$_2$)$_{127}$ distributed to liver tumor tissue 2 hours after administration and was retained there up to 48 hours. Intravenous injection of [$^{14}$C]G5-(NH$_2$)$_{127}$ dendrimers to the mouse model also resulted in 50-57% ID of the carrier distributed to normal liver tissue between 2 and 48 hours after administration. In addition, 16% ID of the administered [$^{14}$C]G5-(NH$_2$)$_{127}$ dendrimers accumulated in kidney tissue 48 hours after i.v. injection. Finally, <1% ID distributed to both heart and bone marrow tissue after 48 hours.

[$^{14}$C]G5-(Ac)$_{108}$-(NAcGal)$_{14}$ conjugates also showed rapid clearance from the systemic circulation similar to that of the non-targeted [$^{14}$C]G5-(NH$_2$)$_{127}$ dendrimers with 1% ID remaining in the plasma 2 hours after administration (t$_{1/2}$ = 1.01 hours) (FIG. 36; Panel B). 9% ID of the [$^{14}$C]G5-(Ac)$_{108}$-(NAcGal)$_{14}$ conjugates distributed to tumor tisue 2 hours after i.v. administration, and slightly increased to 10% ID after 48 hours. 45-46% ID was cleared by the normal liver tissue between 2 and 24 hours after injection, and increased to 63% ID after 48 hours of distribution. Finally, kidney distribution of [$^{14}$C]G5-(Ac)$_{108}$-(NAcGal)$_{14}$ conjugates was similar to non-targeted [$^{14}$C]G5-(NH$_2$)$_{127}$ dendrimers with 16% ID 48 hours after administration.

Attachment of 2 kDa PEG chains to the dendrimer surface resulted in 72% ID of [$^{14}$C]G5(Ac)$_{73}$-(PEG)$_{10}$ conjugates remaining in the plasma 2 hour after administration, decreasing to 8% ID at 48 hours (t$_{1/2}$=16.7 hours). 11-15% ID of [$^{14}$C]G5-(Ac)$_{73}$-(PEG)$_{10}$ conjugates distributed to normal liver tissue between 2 and 48 hours after administration (FIG. 36; Panel C). Renal accumulation of [$^{14}$C]G5-(Ac)$_{73}$-(PEG)$_{10}$ conjugates was ≤3% ID between the 2 and 48 hour time points studied. There was no significant improvement in tumor specific delivery compared to the previous [$^{14}$C]G5-(NH$_2$)$_{127}$ dendrimers and [$^{14}$C]G5-(Ac)$_{108}$-(NAcGal)$_{14}$ conjugates, with 5% of injected [$^{14}$C]G5-(Ac)$_{73}$-(PEG)$_{10}$ conjugates accumulating in the liver tumor 2 and 24 hours after administration and <1% ID at 48 hours.

Characterization of Targeted G5-(Fl)$_6$-(Ac)-(cPEG) Conjugates

Based on these biodistribution results we synthesized targeted G5-(cPEG) carriers in which NAcGal or SP94 targeting ligands are displayed at the terminal end of the PEG chains. NAcGal-(FIG. 34) or SP94-targeted (FIG. 35) G5-(Fl)$_6$-(Ac)-(cPEG) conjugates were synthesized as described resulting in 14-15 targeting groups attached per dendrimer. Particle size results showed 7.37 nm for G5-(Fl)$_6$-(Ac)$_{107}$-(cPEG)$_{15}$ conjugates, which increased to 7.61 nm for G5-(Fl)$_6$-(Ac)$_{107}$-(cPEG[NAcGal$_\alpha$])$_{15}$, 8.30 nm for G5-(Fl)$_6$-(Ac)$_{108}$-(cPEG[NAcGal$_\beta$])$_{14}$ and 9.91 nm for G5-(Fl)$_6$-(Ac)$_{108}$-(cPEG[SP94])$_{14}$ (Table 1). G5-(Fl)$_6$-(Ac)$_{107}$-(cPEG)$_{15}$, G5-(Fl)$_6$-(Ac)$_{107}$-(cPEG[NAcGal$_\alpha$])$_{15}$ and G5-(Fl)$_6$-(Ac)$_{108}$-(cPEG[NAcGal$_\beta$])$_{14}$ conjugates possessed an approximate neutral charge, while G5-(Fl)$_6$-(Ac)$_{108}$-(cPEG[SP94])$_{14}$ had a slightly negative charge as indicated by zeta potential measurements.

TABLE 1

Composition and characterization of targeted G5-(cPEG) conjugates

| Particle Composition | Molecular Weight [kDa] | Targeting ligands per dendrimer (x) | Size [nm] | Zeta Potential [mV] |
|---|---|---|---|---|
| G5-(Fl)$_6$-(Ac)$_{107}$-(cPEG)$_x$ | 68.6 | 15 | 7.37 ± 0.78 | −0.03 ± 0.01 |
| G5-(Fl)$_6$-(Ac)$_{107}$-(cPEG[NAcGaL$_\alpha$])$_x$ | 75.7 | 15 | 7.61 ± 0.29 | −0.01 ± 0.01 |
| G5-(Fl)$_6$-(Ac)$_{108}$-(cPEG[NAcGal$_\beta$])$_x$ | 73.1 | 14 | 8.03 ± 1.03 | −0.03 ± 0.02 |
| G5-(Fl)$_6$-(Ac)$_{108}$-(cPEG[SP94])$_x$ | 95.2 | 14 | 9.91 ± 1.08 | −0.38 ± 0.22 |

Figure 41:
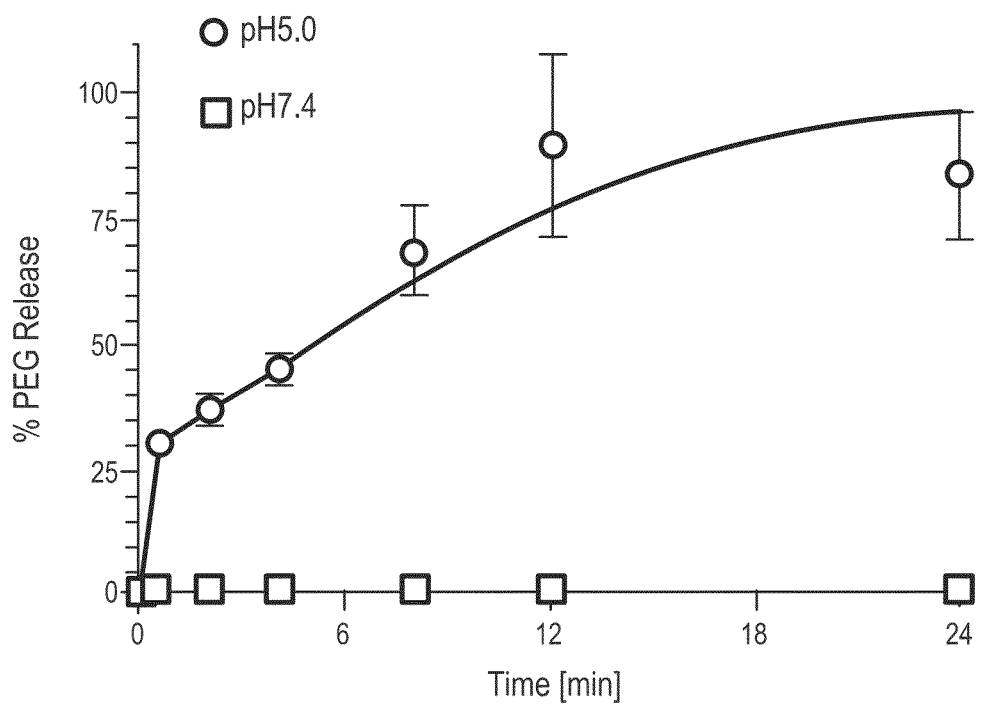
FIG. 41 represents a graph of % PEG release from G5-(cPEG) conjugates as a function of pH over a 24 hour incubation period at 37° C.

To confirm pH-sensitive PEG release from cis-aconityl linked G5-(Fl)$_6$-(Ac)$_{107}$-(cPEG)$_{15}$ conjugates the carriers were dissolved in pH 5.0 citrate buffer resulting in approximately 96% PEG release after 24 hours of incubation at 37° C. (t$_{1/2}$=5.20 hours) (FIG. 41). No free PEG was detected by GPC analysis during the 24 hour incubation at pH 7.4.

Uptake of NAcGal- or SP94-Targeted G5-(Fl)$_6$-(Ac)-(cPEG) Conjugates by HepG2 Cancer Cells Internalization of targeted G5-(Fl)$_6$-(Ac)-(cPEG) conjugates into HepG2 hepatic cancer cells was expressed as the % of fluorescent cells after incubation with each particle composition (FIG. 37; Panels A & B). Limited internalization of G5-(Fl)$_6$-(Ac)$_{107}$-(cPEG)$_{15}$ conjugates was observed for all concentrations and time points tested, with 11% and 9% of treated cells showing fluorescence after a 2 and 24 hour incubation period, respectively. 2 hour uptake of G5-(Fl)$_6$-(Ac)$_{108}$-(cPEG[SP94])$_{14}$ conjugates showed a similar profile with 2-14% of treated HepG2 cells internalizing the conjugates for the 250-4000 nM tested ligand concentrations. However, uptake of G5-(Fl)$_6$-(Ac)$_{108}$-(cPEG[SP94])$_{14}$ conjugates improved after 24 hours of incubation with a linear increase in the % of fluorescently-labeled cells from 4% to 82% for the 250 nM and 4000 nM ligand concentrations, respectively. Uptake of G5-(Fl)$_6$-(Ac)$_{107}$-(cPEG[NAcGal$_\alpha$])$_{15}$ and G5-(Fl)$_6$-(Ac)$_{108}$-(cPEG[NAcGal$_\beta$])$_{14}$ conjugates into HepG2 cells showed a significant effect of sugar conformation on binding affinity to the ASGPR and subsequent receptor-mediated endocytosis into HepG2 cells. ≤3% of treated cells showed fluorescence after a 2 hour incubation with the NAcGal$_\alpha$-targeted G5-(Fl)$_6$-(Ac)$_{107}$-(cPEG[NAcGal$_\alpha$])$_{15}$ conjugates across the 100-4000 nM tested ligand concentrations. A 2 hour incubation of G5-(Fl)$_6$-(Ac)$_{108}$-(cPEG[NAcGal$_\beta$])$_{14}$ conjugates with HepG2 cells however showed a linear increase in the % of labeled cells from 5% to 93% between the 250 nM and 4000 nM tested ligand concentrations. After a 24 hour incubation period 34%-81% of HepG2 cells treated with the G5-(Fl)$_6$-(Ac)$_{108}$-(cPEG[NAcGal$_\beta$])$_{14}$ conjugates internalized the particles at the 100-500 nM ligand concentrations, respectively, while ≥1000 nM concentrations saturated the treated cells.

Uptake of each conjugate into HepG2 cells was also represented as normalized relative fluorescence from the flow cytometry signal, which provides a comparison of the intracellular particle concentrations per cell as a function of treatment and incubation time (FIG. 37; Panels C & D). After a 2 hour incubation there was a 16-fold increase in G5-(Fl)$_6$-(Ac)$_{108}$-(cPEG[NAcGal$_\beta$])$_{14}$ intracellular concentration in HepG2 cells treated with a 4000 nM ligand concentration of the particles compared to G5-(Fl)$_6$-(Ac)$_{107}$-(cPEG)$_{15}$ and G5-(Fl)$_6$-(Ac)$_{108}$-(cPEG[SP94])$_{14}$ conjugates. The intracellular concentration of G5-(Fl)$_6$-(Ac)$_{108}$-(cPEG[NAcGal$_\beta$])$_{14}$ particles in HepG2 cells after a 2 hour incubation period was also 8-fold higher versus cells treated with G5-(Fl)$_6$-(Ac)$_{107}$-(cPEG[NAcGal$_\alpha$])$_{15}$. At 24 hours of treatment intracellular particle concentrations were 5-14 fold higher for G5-(Fl)$_6$-(Ac)$_{108}$-(cPEG[NAcGal$_\beta$])$_{14}$ treated HepG2 cells versus G5-(Fl)$_6$-(Ac)$_{108}$-(cPEG[SP94])$_{14}$ treated cells at the 1000-4000 nM tested ligand concentrations. In addition, the intracellular particle concentration of G5-(Fl)$_6$-(Ac)$_{108}$-(cPEG[NAcGal$_\beta$])$_{14}$ conjugates in HepG2 cells were up to 67-fold greater compared to G5-(Fl)$_6$-(Ac)$_{107}$-(cPEG)$_{15}$ and G5-(Fl)$_6$-(Ac)$_{107}$-(cPEG[NAcGal$_\alpha$])$_{15}$ conjugates at a 24 hour incubation time and 4000 nM ligand concentration.

Opsonization of Targeted G5-(cPEG) Conjugates and Phagocytosis by Kupffer Cells

Figure 38:
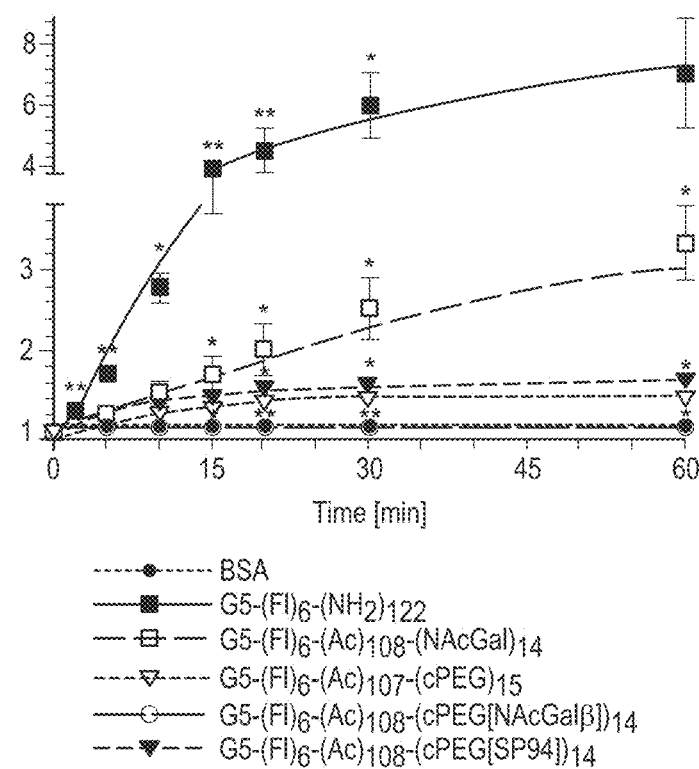
FIG. 38 represents a graph demonstrating the opsonization of $G5-(Fl)_6-(NH_2)_{122}$, $G5-(Fl)_6-(Ac)_{108}-(NAcGal)_{14}$, $G5-(Fl)_6-(Ac)_{107}-(cPEG)_{15}$, $G5-(Fl)_6-(Ac)_{108}-(cPEG[NAcGal_\beta])_{14}$ and $G5-(Fl)_6-(Ac)_{108}-(cPEG[SP94])_{14}$ conjugates incubated at a 20 nM particle concentration with 0.2 mg/mL BSA for 1 hour. Data presented as average (n=3)+S.E.M.

Opsonization of the tested particle formulations was studied using a published BSA binding assay to determine the quenching of the proteins tryptophan fluorescent signal due upon particle complexation.[37] The quenching efficiency ($I_o/I$) for each particle composition was calculated by dividing the initial BSA fluorescence signal ($I_o$) by the change in fluorescence intensity (I) as a function of time (FIG. 38). G5-(Fl)$_6$-(NH$_2$)122 dendrimers, tested as the polymer control, showed a strong BSA fluorescence quenching efficiency which plateaued after 15 minutes of incubation. This quenching efficiency was reduced 2-fold by neutralizing the dendrimer surface with neutral acetyl groups and NAcGal-sugar moieties to prepare G5-(Fl)$_6$-(Ac)$_{108}$-(NAcGal)$_{14}$ conjugates. PEGylation of G5 dendrimers further inhibited opsonization, with G5-(Fl)$_6$-(Ac)$_{107}$-(cPEG)$_{15}$ carriers reducing BSA binding >5-folds compared to the cationic G5-(Fl)$_6$-(NH$_2$)$_{122}$ dendrimers and >2-fold compared to G5-(Fl)$_6$-(Ac)$_{108}$-(NAcGal)$_{14}$ conjugates. Finally, no statistical difference in BSA fluorescence quenching was observed for proteins incubated with G5-(Fl)$_6$-(Ac)$_{108}$-(cPEG[NAcGal$_\beta$])$_{14}$ conjugates compared to the control BSA solution absent of particles. Conversely, attachment of SP94 peptides ligands to the terminal end of the PEG chains increased the fluorescence quenching efficiency for G5-(Fl)$_6$-(Ac)$_{108}$-(cPEG[SP94])$_{14}$ conjugates by roughly 11% compared to G5-(Fl)$_6$-(Ac)$_{107}$-(cPEG)$_{15}$ conjugates after a 1 hour incubation with BSA proteins.

Figure 39:
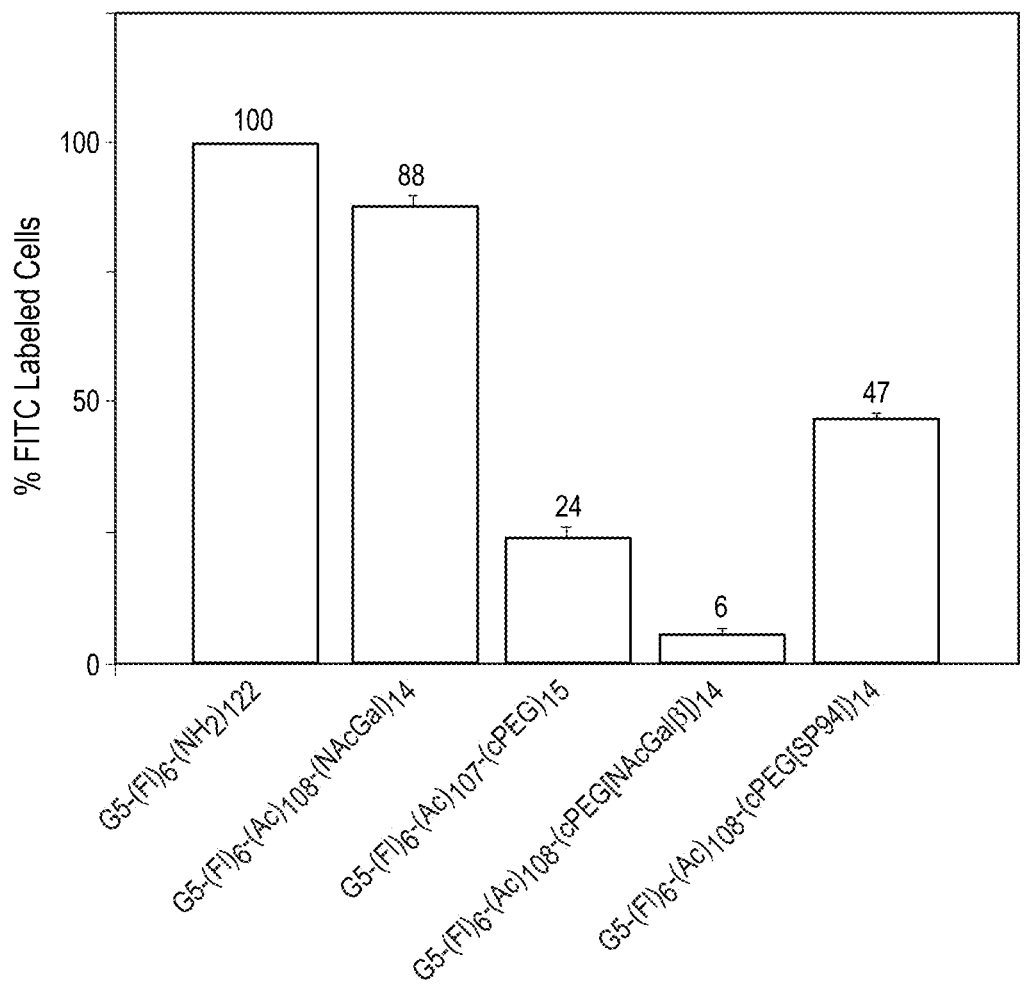
FIG. 39 represents a graph that demonstrate the uptake of $G5-(Fl)_6-(NH_2)_{122}$, $G5-(Fl)_6-(Ac)_{108}-(NAcGal)_{14}$, $G5-(Fl)_6-(Ac)_{107}-(cPEG)_{15}$, $G5-(Fl)_6-(Ac)_{108}-(cPEG[NAcGal_\beta])_{14}$ and $G5-(Fl)_6-(Ac)_{108}-(cPEG[SP94])_{14}$ conjugates incubated with mouse Kupffer cells at 4000 nM targeting ligand concentrations for 2 hours. Data presented as mean (n=4)+S.E.M. of the % labeled cells.

These opsonization profiles for the tested particle compositions correlated to recognition and phagocytosis by mouse Kupffer cells during a 2 hour incubation period after pre-incubation of each conjugate in mouse serum (FIG. 39). G5-(Fl)$_6$-(NH$_2$)$_{122}$ dendrimers were internalized into 100% of treated Kupffer cells due to their rapid opsonization after 2 hours of incubation. G5-(Fl)$_6$-(Ac)$_{108}$-(NAcGal)$_{14}$ conjugates were also rapidly phagocytized by Kupffer cells resulting in 88% of treated cells showing fluorescence during flow cytometry analysis. PEGylation of G5 dendrimers to prepare G5-(Fl)$_6$-(Ac)$_{107}$-(cPEG)$_{15}$ resulted in 24% of treated cells internalizing the conjugates after a 2 hour incubation period (FIG. 39). The enhanced hydrophilicity of NAcGal-targeted G5-(Fl)$_6$-(Ac)$_{108}$-(cPEG[NAcGal$_\beta$])$_{14}$ conjugates led to only 6% of treated Kupffer cells internalizing these particles after a 2 hour incubation. Finally, incubation of Kupffer cells with SP94-targeted of G5-(Fl)$_6$-(Ac)$_{108}$-(cPEG[SP94])$_{14}$ conjugates resulted in 47% of the treated cells showing fluorescence.

Uptake of G5-(Fl)$_6$-(Ac)$_{108}$-(NAcGal)$_{14}$ and NAcGal- or SP94-Targeted G5-(Fl)$_6$-(Ac)-(cPEG) Conjugates by Primary Rat Hepatocytes To confirm these targeted G5-(cPEG) conjugates selectively target hepatic cancer cells G5-(Fl)$_6$-(Ac)$_{108}$-(cPEG[SP94])$_{14}$ and G5-(Fl)$_6$-(Ac)$_{108}$-(cPEG[NAcGal$_\beta$])$_{14}$ conjugates were incubated with primary rat hepatocytes, and particle uptake results compared to the G5-(Fl)$_6$-(Ac)$_{108}$-(NAcGal)$_{14}$ control (FIG. 40). Between 2 and 24 hours of incubation ≤5% of treated hepatocytes displayed intracellular fluorescence after exposure to G5-(Fl)$_6$-(Ac)$_{108}$-(cPEG[SP94])$_{14}$ or G5-(Fl)$_6$-(Ac)$_{108}$-(cPEG[NAcGal$_\beta$])$_{14}$ conjugates across the 100-4000 nM ligand concentrations tested (FIG. 40; Panels A & B). These results were compared to the uptake of G5-(Fl)$_6$-(Ac)$_{108}$-(NAcGal)$_{14}$ controls into hepatocytes which showed a roughly 2-fold increase in the % of labeled cells compared to the G5-(Fl)$_6$-(Ac)$_{108}$-(cPEG[SP94])$_{14}$ or G5-(Fl)$_6$-(Ac)$_{108}$-(cPEG[NAcGal$_\beta$])$_{14}$ conjugates after 2 hours of incubation. At 24 hours the percentage of fluorescently labeled hepatocytes after incubation with the G5-(Fl)$_6$-(Ac)$_{108}$-(NAcGal)$_{14}$ controls increased from 5%-22% between 500-4000 nM ligand concentration.

Similarly, intracellular particle concentration increased >20-folds for hepatocytes treated with G5-(Fl)$_6$-(Ac)$_{108}$-(NAcGal)$_{14}$ controls versus G5-(Fl)$_6$-(Ac)$_{108}$-(cPEG[NAcGal$_\beta$])$_{14}$ conjugates after a 2 hour incubation period at the 4000 nM ligand concentration (FIG. 40; Panel C). Intracellular concentrations of G5-(Fl)$_6$-(Ac)$_{108}$-(NAcGal)$_{14}$ conjugates after internalization into hepatocytes decreased by 8%-15% between 2 and 24 hours across the 100-4000 nM ligand concentrations tested (FIG. 40; Panels C & D). In contrast G5-(Fl)$_6$-(Ac)$_{108}$-(cPEG[NAcGal$_\beta$])$_{14}$ conjugates showed a doubling of the intracellular particle concentration in hepatocytes between the 2 and 24 hour incubation periods. Intracellular concentrations of peptide-targeted G5-(Fl)$_6$-(Ac)$_{108}$-(cPEG[SP94])$_{14}$ conjugates in hepatocytes showed a static 2-8 RFU across all the tested incubation times and ligand concentrations.

Discussion

In Vivo Biodistribution of [$^{14}$C]G5-(NH$_2$)$_{127}$, [$^{14}$C]G5-(Ac)$_{108}$-(NAcGal)$_{14}$, and [$^{14}$C]G5-(Ac)$_{73}$-(PEG)$_{10}$ Conjugates in Tumor-Bearing Mice Administration of [$^{14}$C]G5-(NH$_2$)$_{127}$ conjugates to liver tumor-bearing animal models showed approximately 4% ID accumulating in tumor tissue 2 hours after administration due to EPR-mediated passive targeting,[30,38] and were retained there up to 48 hours. However, [$^{14}$C]G5-(NH$_2$)$_{127}$ dendrimers were rapidly cleared by the healthy liver tissue due to rapid opsonization of cationic PAMAM dendrimers by serum albumin[39] leading to recognition and uptake by liver macrophage Kupffer cells. In addition, a substantial fraction (16% ID) of the administered [$^{14}$C]G5-(NH$_2$)$_{127}$ dendrimers accumulated in kidney tissue after 48 hours, which is similar to other published studies on the in vivo biodistribution of cationic dendrimers.[40-42] This is in contrast to linear polymers which do not readily accumulate in renal tissue indicating the hyper-branched conformation of dendrimer carriers affects renal reabsorption and retention.[42] Previous studies have reported that G4 PAMAM-Gd complexes accumulate in the proximal straight tubules in the outer medulla stripe of the kidneys, and are localized to the lysosomes of proximal tubule cells which is only possible upon dendrimer filtration.[43] Finally, administration of [$^{14}$C]G5-(NH$_2$)$_{127}$ dendrimers to the mouse model resulted in negligible carrier distribution to the heart and bone marrow tissue for up to 48 hours after injection, which is advantageous as these are common sites of non-specific toxicity during clinical therapy using chemotherapeutic agents (e.g. Doxorubicin).[44]

Administration of [$^{14}$C]G5-(Ac)$_{108}$-(NAcGal)$_{14}$ conjugates to the tumor-bearing mouse model also showed rapid systemic clearance of particles similar to the [$^{14}$C]G5-(NH$_2$)$_{127}$ dendrimer control. Similarly, cardiac, bone marrow and renal distribution was similar between [$^{14}$C]G5-(Ac)$_{108}$-(NAcGal)$_{14}$ conjugates and the non-targeted [$^{14}$C]G5-(NH$_2$)$_{127}$ dendrimer control. However, there was a 2-3 fold increase in the accumulation of [$^{14}$C]G5-(Ac)$_{108}$-(NAcGal)$_{14}$ conjugates in tumor tissue between 2 and 48 hours after administration to liver tumor bearing mice compared to [$^{14}$C]G5-(NH$_2$)$_{127}$ dendrimers. This is due to recognition of the displayed NAcGal ligands on the [$^{14}$C]G5-(Ac)$_{108}$-(NAcGal)$_{14}$ conjugates by the ASGPR of hepatic cancer cells leading to enhanced tumor-specific delivery. However, NAcGal-targeting also increased distribution of [$^{14}$C]G5-(Ac)$_{108}$-(NAcGal)$_{14}$ conjugates to normal liver tissue 48 hours after administration by nearly 10% ID compared to the [$^{14}$C]G5-(NH$_2$)$_{127}$ controls due to expression of the ASGPR on normal hepatocytes.[45] Despite the selective targeting of G5-NAcGal conjugates to hepatic cancer cells in vitro, galactosamine (Gal) targeted polymer nanoparticles have been reported to display significant distribution to normal liver tissue after i.v. administration to in vivo tumor models.[46,47] Specifically, Gal-targeted poly(γ-glutamic acid) and poly(lactide) co-polymer nanoparticles displayed a >3-fold increase in particle concentration in normal liver compared to tumor tissue between 1-24 hours after i.v. administration to a hepatoma-bearing nude mouse model.[46] Similarly, i.v. injection of $^{123}$I-labeled Gal-functionalized HPMA-DOX conjugates to a liver-tumor bearing mouse metastatic model resulted in a roughly 8-fold increase in the % ID of the particle accumulating per gram of normal liver tissue versus the tumor 1 hour after injection.[47] This led to Gal-targeted HPMA-DOX conjugates displaying a 5-fold increase in distribution to the healthy liver compared to tumor tissue in three hepatoma patients during phase I clinical trials.[48]

This non-specific distribution of nanoparticles to healthy liver tissue can be minimized via attachment of PEG chains ≥2 kDa in size to the carrier surface, resulting in reduced opsonization of the particles in the systemic circulation and subsequently limiting clearance by hepatic macrophages.[24,49-51] This stealth effect of PEGylation led to a >4-fold reduction in hepatic clearance of [$^{14}$C]G5-(Ac)$_{73}$-(PEG)$_{10}$ conjugates between 2 and 48 hours after administration to the tumor model compared to [$^{14}$C]G5-(NH$_2$)$_{127}$ and [$^{14}$C]G5(Ac)$_{108}$-(NAcGal)$_{14}$ carriers. This reduced RES clearance, and a >5-fold reduction in kidney distribution of [$^{14}$C]G5-(Ac)$_{73}$-(PEG)$_{10}$ conjugates between 2 and 48 hours compared to the other tested conjugates, resulted in a 16-fold increase in plasma circulation time compared to [$^{14}$C]G5-(Ac)$_{108}$-(NAcGal)$_{14}$ and [$^{14}$C]G5-(NH$_2$)$_{127}$ conjugates. This is a result of increased MW weight and particle hydrodynamic radius of the carrier due to PEGylation which leads to decreased renal filtration and as a result longer residence in the systemic circulation.[52] This supports previous studies which found that attachment of 2 kDa PEG to G4 PAMAM-NH$_2$ dendrimers resulted in a >8-fold reduction of the % ID distributing to kidney per gram of tissue weight compared to the non-PEGylated carrier 24 hours after administration.[53] Interestingly, this increase in plasma circulation time and limited distribution to non-specific RES organs for [$^{14}$C]G5-(Ac)$_{73}$-(PEG)$_{10}$ conjugates did not significantly improve tumor specific delivery compared to [$^{14}$C]G5-(Ac)$_{108}$-(NAcGal)$_{14}$ and [$^{14}$C]G5-(NH$_2$)$_{127}$ between 2 and 24 hours after administration. Okuda et al. previously showed that G6 lysine dendrimers (with a similar size and number of surface NH$_2$ groups to G5 PAMAM dendrimers utilized in this study) functionalized with 76 PEG groups (5 kDa MW) showed a 2-6 fold increase in tumor distribution compared to the non-PEGylated parent dendrimers between 3 and 24 hours after intravenous administration to a colon carcinoma xenograft mouse model.[54] This was due to the large increase in MW as a result of coupling 76 PEG groups to the carrier surface increasing its MW by 380 kDa. The [$^{14}$C]G5-(Ac)$_{73}$-(PEG)$_{10}$ conjugates utilized in this study were prepared with 10 PEG groups, resulting in a gain of 20 kDa which may not have been sufficient to enhance tumor-specific accumulation. However, this PEGylation density was designed to ensure the conjugates were below the renal excretion limit (~50 kDa) in order to prevent long term residence of the carrier in the body leading to systemic toxicity.[52,55] In addition, it is advantageous to limit the number of PEG groups attached to the surface of dendrimer carriers for the delivery of chemotherapeutic agents to limit steric crowding and maximize the payload of conjugated anticancer drugs.[56] Finally, at 48 hours <1% ID was detected in the tumor indicating that [$^{14}$C]G5-(Ac)$_{73}$-(PEG)$_{10}$ conjugates are washed out of tumor tissue at long biodistribution times.

These results suggest that while PEGylation of G5 dendrimers decreases non-specific distribution to normal liver tissue and increases plasma-residence time of the carrier, display of the NAcGal targeting ligand is necessary for long term carrier residence in tumor tissue. This is supported by previous reports which show that display of folate-ligands at the terminal end of a PEGylated Gd nanoparticle resulted in improved tumor retention of the targeted imaging agents compared to non-targeted Gd-PEG particles 8 and 24 hours after administration to a folate-receptor positive tumor xenograft mouse model.[57]

Characterization of Targeted G5-(Fl)$_6$-(Ac)-(cPEG) Conjugates

The development of targeted G5-(cPEG) carriers is intended to minimize opsonization of the G5 carrier due to PEGylation, and subsequently avoid internalization into Kupffer cells, while retaining selective receptor-mediated endocytosis of the carrier into hepatic cancer cells through display of the targeting ligand. Particle size analysis found a 0.36-0.66 nm increase in particle size for G5-(Fl)$_6$-(Ac)$_{107}$-(cPEG[NAcGal$_\alpha$])$_{15}$ and G5-(Fl)$_6$-(Ac)$_{108}$-(cPEG[NAcGal$_\beta$])$_{14}$ conjugates compared to the G5-(Fl)$_6$-(Ac)$_{107}$-(cPEG)$_{15}$ control due to the addition of the NAcGal targeting ligand. Similarly, G5-(Fl)$_6$-(Ac)$_{108}$-(cPEG[SP94])$_{14}$ particles had a 2.54 nm increase in particle size compared to the G5-(Fl)$_6$-(Ac)$_{107}$-(cPEG)$_{15}$ control due to the addition of the large 12-amino acid SP94-peptide. Zeta potential measurements indicated G5-(Fl)$_6$-(Ac)$_{107}$-(cPEG)$_{15}$, G5-(Fl)$_6$-(Ac)$_{107}$-(cPEG[NAcGal$_\alpha$])$_{15}$ and G5-(Fl)$_6$-(Ac)$_{108}$-(cPEG[NAcGal$_\beta$])$_{14}$ conjugates had neutral surface charge due to the complete functionalization of the dendrimer surface amine groups by neutral PEG and acetyl moieties, while G5-(Fl)$_6$-(Ac)$_{108}$-(cPEG[SP94])$_{14}$ conjugates had a slightly negative charge due to the carboxylic acid groups on the SP94 cysteine residue.

pH-sensitive PEG release from G5-(Fl)$_6$-(Ac)$_{107}$-(cPEG)$_{15}$ conjugates was assessed in acidic and neutral conditions. Incubation of the conjugates at pH 5.0 and 37° C. resulted in almost complete PEG liberation after 24 hours, with a half-life of $t_{1/2}$=5.20 hours. This profile is similar to release kinetics from DOX-poly($_L$-lactic acid)-PEG micelles in which DOX molecules were conjugated to the polymer backbone via cis-aconityl linkages, resulting in a drug release half-life of 5 hours in pH 5.0 PBS.[58] No free PEG was detected by GPC analysis during the 24 hour incubation period of G5-(Fl)$_6$-(Ac)$_{107}$-(cPEG)$_{15}$ at pH 7.4, demonstrating the stability of these conjugates in normal physiologic conditions while achieving pH-sensitive PEG release after delivery to the endosome.

Uptake of NAcGal- or SP94-Targeted G5-(Fl)$_6$-(Ac)-(cPEG) Conjugates by HepG2 Cancer Cells Incubation of HepG2 cells with G5-(Fl)$_6$-(Ac)$_{107}$-(cPEG)$_{15}$ conjugates for 2 and 24 hours resulted in limited particle internalization (≤11% labeled cell) for all tested ligand concentrations. This is due to the reported steric inhibition of PEGylated carriers from interacting with the cell membrane and therefore reduces carrier internalization; an effect described as the 'PEG dilemma'.[59] To address this we displayed the NAcGal or SP94 targeting ligand at the terminal end of the PEG chains to achieve receptor-mediated endocytosis of the targeted G5-(cPEG) conjugates into hepatic cancer cells. Interestingly, G5-(Fl)$_6$-(Ac)$_{108}$-(cPEG[SP94])$_{14}$ conjugates showed a 2 hour uptake profile into HepG2 cells that was comparable to the non-targeted G5-(Fl)$_6$-(Ac)$_{107}$-(cPEG)$_{15}$ controls across all tested ligand concentrations. However, internalization of G5-(Fl)$_6$-(Ac)$_{108}$-(cPEG[SP94])$_{14}$ conjugates into HepG2 cells increased by >9-folds compared to G5-(Fl)$_6$-(Ac)$_{107}$-(cPEG)$_{15}$ controls after a 24 hour incubation period indicating a delayed internalization profile for SP94-targeted conjugates into hepatic cancer cells. These results contrast published hyperspectral confocal fluorescent microscopy data for fluorescent SP94-targeted nanoporous particles which were found to bind and be internalized into the endosome of treated Hep3B human hepatic cancer cells within 15 minutes at 37° C.[60] This difference is due to reduced expression or affinity of the SP94-target receptor (which currently has not been identified) of HepG2 versus the Hep3B cell lines.[28] Specifically, a previous study by Lo et al. reported a 25% reduction of labeled HepG2 cells compared to the Hep3B cell line as determined by flow cytometry after incubation of SP94 peptides with a library of hepatocellular carcinoma cell lines for 1 hour, followed by staining with fluorescent anti-mouse IgG.

As expected there was a significant difference in the internalization of G5-(Fl)$_6$-(Ac)$_{107}$-(cPEG[NAcGal$_\alpha$])$_{15}$ and G5-(Fl)$_6$-(Ac)$_{108}$-(cPEG[NAcGal$_\beta$])$_{14}$ conjugates into HepG2 cells due to NAcGal sugar conformation. Attachment of NAcGal$_p$-sugar molecules to prepare G5-(Fl)$_6$-(Ac)$_{108}$-(cPEG[NAcGal$_\beta$])$_{14}$ conjugates resulted in a 31-fold increase in HepG2 uptake over NAcGal$_\alpha$-targeted conjugates after 2 hours of incubation at the 1000-4000 nM ligand concentrations tested. Similarly, normalized relative fluorescence of HepG2 cells treated with G5-(Fl)$_6$-(Ac)$_{108}$-(cPEG[NAcGal$_\beta$])$_{14}$ showed a significant increase in intracellular particle concentration at the highest ligand concentration (4000 nM) compared to G5-(Fl)$_6$-(Ac)$_{107}$-(cPEG)$_{15}$, G5-(Fl)$_6$-(Ac)$_{108}$-(cPEG[SP94])$_{14}$ and G5-(Fl)$_6$-(Ac)$_{107}$-(cPEG[NAcGal$_\alpha$])$_{15}$ conjugates after 2 and 24 hours of incubation. These results are due to the specific recognition of sugars in the β-conformation by the ASGPR expressed on hepatic cells as previously reported.[29] In addition, the limited internalization of G5-(Fl)$_6$-(Ac)$_{107}$-(cPEG[NAcGal$_\alpha$])$_{15}$ conjugates confirms that uptake of G5-(Fl)$_6$-(Ac)$_{108}$-(cPEG[NAcGal$_\beta$])$_{14}$ into hepatic cancer cells is mediated by binding of the NAcGal-ligands to the ASGPR despite being displayed at the terminal end of the PEG chains. Finally, it is also clear that internalization of NAcGal-targeted dendrimer conjugates via the ASGPR is more rapid than SP94-receptor mediated internalization for the HepG2 hepatic cancer cell line.

Opsonization of Targeted G5-(cPEG) Conjugates and Phagocytosis by Kupffer Cells

Incubation of BSA proteins with cationic G5-(Fl)$_6$-(NH$_2$)$_{122}$ dendrimers resulted in a strong and rapid fluorescence quenching of the proteins tryptophan residues. This has been previously reported to be a result of hydrophilic complexation of the protein with the polycationic PAMAM dendrimers, as well as interaction of the dendrimers aliphatic chains with BSA hydrophobic pockets.[61] This quenching efficiency was moderately reduced by neutralizing the dendrimer surface with hydrophilic acetyl groups and NAcGal-sugar moieties, while PEGylation reduced BSA binding to G5-(Fl)$_6$-(Ac)$_{107}$-(cPEG)$_{15}$ particles >5-folds compared to the cationic G5-(Fl)$_6$-(NH$_2$)$_{122}$ dendrimers. This ability of PEG to reduce opsonization of polymeric nano-particles is well established, resulting from a steric repulsion of proteins from the polymer surface by the hydrophilic PEG corona.[49] Moreover, display of hydrophilic NAcGal sugar residues on the terminus of PEG chains for G5-(Fl)$_6$-(Ac)$_{108}$-(cPEG[NAcGal$_\beta$])$_{14}$ conjugates virtually eliminated protein binding by further reducing any remaining hydrophobic interaction of the PAMAM dendrimer carrier with BSA proteins. Conversely, attachment of hydrophobic SP94 peptides increased G5-(Fl)$_6$-(Ac)$_{108}$-(cPEG[SP94])$_{14}$ opsonization with BSA proteins compared to the G5-(Fl)$_6$-(Ac)$_{107}$-(cPEG)$_{15}$ control due to the hydrophobic nature of the leucine- and isoleucine-rich peptide.

These opsonization profiles correlated to recognition and phagocytosis by mouse Kupffer cells, with saturation of the treated cells upon a 2 hour exposure with the cationic G5-(Fl)$_6$-(NH$_2$)$_{122}$ dendrimers. G5-(Fl)$_6$-(Ac)$_{108}$-(NAcGal)$_{14}$ conjugates were also rapidly phagocytized by Kupffer cells due to both particle opsonization observed during the BSA fluorescence quenching assay, as well as the recognition of NAcGal-moieties by the galactose receptor present on Kupffer cells.[62] Specifically, previous reports have demonstrated that short chemical spacers (~4 Å) separating the sugar moiety from its branching point resulted in targeting of galactose-containing constructs to the related macrophage receptor on liver Kupffer cells.[62,63] Long spacers (>20 Å), however, results in selectivity of the glycoside towards the hepatocyte-specific ASGPR. The distance between NAcGal-ligands and the dendrimer surface for the G5-(Fl)$_6$-(Ac)$_{108}$-(NAcGal)$_{14}$ conjugates was calculated to be roughly 8-9 Å in length, suggesting significant contribution of receptor-mediated endocytosis in the internalization of these particles into Kupffer cells. PEGylation of G5 dendrimers to prepare G5-(Fl)$_6$-(Ac)$_{107}$-(cPEG)$_{15}$ conjugates resulted in nearly a 4-fold reduction in Kupffer cell phagocytosis versus G5-(Fl)$_6$-(NH$_2$)$_{122}$ dendrimers confirming the ability of carrier PEGylation to avoid particle uptake into liver macrophages. The enhanced hydropholicity of NAcGal-targeted G5-(Fl)$_6$-(Ac)$_{108}$-(cPEG[NAcGal$_\beta$])$_{14}$ conjugates led to reduced opsonization and as a result further inhibited carrier phagocytosis by Kupffer cells. Additionally, the extension of the displayed NAcGal-ligands well beyond 20 Å from the dendrimer surface due to the PEG spacer prevented its recognition by the galactose-receptor on liver Kupffer cells and enhanced its selectivity for the ASGPR. Finally, incubation of Kupffer cells with G5-(Fl)$_6$-(Ac)$_{108}$-(cPEG[SP94])$_{14}$ conjugates showed a roughly 2-fold increase in Kupffer cells phagocytosis compared to G5-(Fl)$_6$-(Ac)$_{107}$-(cPEG)$_{15}$ conjugates, despite only a 12% increase in protein binding during BSA opsonization experiments. This observation is likely due to either a receptor-mediated internalization pathway for SP94-peptides in Kupffer cells that is not yet identified, or hydrophobic interaction of G5-(Fl)$_6$-(Ac)$_{108}$-(cPEG[SP94])$_{14}$ conjugates with the Kupffer cell membrane.

Uptake of G5-(Fl)$_6$-(Ac)$_{108}$-(NAcGal)$_{14}$ and NAcGal- or SP94-Targeted G5-(Fl)$_6$-(Ac)-(cPEG) Conjugates by Primary Rat Hepatocytes The selectivity of targeted G5-(cPEG) conjugates for hepatic cancer cells was determined by incubating G5-(Fl)$_6$-(Ac)$_{108}$-(cPEG[SP94])$_{14}$ and G5-(Fl)$_6$-(Ac)$_{108}$-(cPEG[NAcGal$_\beta$])$_{14}$ conjugates with primary rat hepatocytes, and particle uptake results compared to HepG2 hepatic cancer cells. Between 2 and 24 hours of incubation ≤5% of treated hepatocytes displayed intracellular fluorescence after exposure with G5-(Fl)$_6$-(Ac)$_{108}$-(cPEG[SP94])$_{14}$ and G5-(Fl)$_6$-(Ac)$_{108}$-(cPEG[NAcGal$_\beta$])$_{14}$ conjugates at 100-4000 nM ligand concentrations. For G5-(Fl)$_6$-(Ac)$_{108}$-(cPEG[NAcGal$_\beta$])$_{14}$ conjugates this represents a 20-30 fold reduction in affinity for internalization into hepatocytes as compared to HepG2 hepatic cancer cells. These results are in spite of reports indicating that cell surface expression of ASGPR, and its binding kinetics to sugar ligands, is similar between HepG2 hepatic cancer cells and isolated rat hepatocytes.[27] However, the recycle time of extracellular displayed ASGPR on HepG2 cells is reported to occur every 15.9 minutes after ligand binding,[64] while the receptor turnover rate for rat hepatocytes is approximately 20 hours.[65] As a result the ASGPR expressed on the surface of HepG2 cells are able to recycle bound receptors 75-times faster than hepatocytes, resulting in enhanced uptake of G5-(Fl)$_6$-(Ac)$_{108}$-(cPEG[NAcGal$_\beta$])$_{14}$ conjugates in hepatic cancer cells as a function of time. Compared to G5-(Fl)$_6$-(Ac)$_{108}$-(cPEG[NAcGal$_\beta$])$_{14}$ conjugates the % of labeled hepatocytes after incubation with G5-(Fl)$_6$-(Ac)$_{108}$-(NAcGal)$_{14}$ for 2 and 24 hours increased by 3- and 4-folds, respectively. Similarly, intracellular particle concentration increased >20-folds for hepatocytes treated with G5-(Fl)$_6$-(Ac)$_{108}$-(NAcGal)$_{14}$ versus G5-(Fl)$_6$-(Ac)$_{108}$-(cPEG[NAcGal$_\beta$])$_{14}$ conjugates after a 2 hour incubation period at the 4000 nM ligand concentration. This difference in conjugate uptake is likely due to the large size and molecular weight of PEGylated G5-(Fl)$_6$-(Ac)$_{108}$-(cPEG[NAcGal$_\beta$])$_{14}$ conjugates which were 8.03 nm and 73.1 kDa, respectively. While G5-(Fl)$_6$-(Ac)$_{108}$-(NAcGal)$_{14}$ conjugates were previously reported to have an average particle size of 6.02 nm and molecular weight of 39.5 kDa.[26] The reduction in cancer cell internalization of polymeric nanoparticles as a function of increasing particle size and molecular weight is well established in the literature.[66,67]

Interestingly, there was a slight decline in the intracellular G5-(Fl)$_6$-(Ac)$_{108}$-(NAcGal)$_{14}$ concentration observed in hepatocytes between the 2 and 24 hour incubation time despite a >2-fold increase in the % of labeled hepatocytes between the same time periods. G5-(Fl)$_6$-(Ac)$_{108}$-(cPEG[NAcGal$_\beta$])$_{14}$ conjugates, however, showed a doubling of the intracellular particle concentration in hepatocytes between the 2 and 24 hour incubation periods. This suggests that at long incubation times internalized G5-(Fl)$_6$-(Ac)$_{108}$-(NAcGal)$_{14}$ conjugates may be exocytosed out of the hepatocytes, while the large molecular weight of G5-(Fl)$_6$-(Ac)$_{108}$-(cPEG[NAcGal$_\beta$])$_{14}$ conjugates inhibited their exocytosis out of hepatocytes after internalization. Intracellular concentrations of peptide-targeted G5-(Fl)$_6$-(Ac)$_{108}$-(cPEG[SP94])$_{14}$ conjugates in hepatocytes showed similar values across all tested ligand concentration and incubation times, indicating no affinity of these conjugates for receptor-mediated endocytosis into hepatocytes.

CONCLUSION

We have successfully developed targeted G5-(cPEG) conjugates based on in vivo biodistribution results for G5-NAcGal and G5-PEG conjugates in an orthotopic liver tumor mouse model. These studies G5-NAcGal dendrimers achieve enhanced liver tumor-specific delivery over the non-targeted carrier, but also led to significant accumulation in normal liver. PEGylation of the G5 dendrimer carrier enhanced systemic circulation time, and limited liver and kidney distribution of the carrier, however the lack of targeting resulted in washing out of carrier in tumor tissue 48 hours after administration. Based on these results we synthesized targeted G5-(cPEG) conjugates which displayed the NAcGal sugar or SP94 peptide targeting ligand at the terminal end of the attached PEG. These PEG chains were attached to the G5 carriers through acid-sensitive cis-aconityl linkages which were stable at normal physiologic conditions but were rapidly reduced at acidic pH resulting in PEG 'shedding' from the surface of the dendrimer carrier. Targeting of G5-(cPEG[NAcGal]) conjugates to the ASGPR displayed on hepatic cancer cells showed >30-fold higher affinity for the β sugar conformation over a during uptake experiments into HepG2 human hepatic cancer cells. Conjugation of the SP94 hepatoma cell-specific peptide to prepare G5-(cPEG[SP94]) conjugates resulted in their selective affinity towards hepatic cancer cells, however their internalization into HepG2 cells was found to be much slower in comparison to ASGPR-mediated endocytosis. This targeting strategy was found to limit particle opsonization and subsequently reduced non-specific internalization of the dendrimer carrier into liver macrophage Kupffer cells. Finally, G5-(cPEG[NAcGal$_\beta$]) conjugates were found to have as much as a 50-fold lower affinity for normal hepatocytes compared to HepG2 cells indicating the selective targeting of these carriers to hepatic cancer cells over normal liver parenchymal cells. These results clearly show that NAcGal$_\beta$-targeted G5-(cPEG) dendrimers present a highly efficient carrier for selective delivery of therapeutic molecules into the cytoplasm of hepatic cancer cells while avoiding distribution to healthy liver tissue to achieve high anticancer activity with minimal systemic toxicity.

The following list represents the references cited in Examples 11 and 12:

1 ACS. Vol. Cancer Facts & Figures. 2011. (American Cancer Society, Atlanta, 2011).
2 Vol. (American Cancer Society, Atlanta, 2011).
3 Bosch, F. X., Ribes, J., Díaz, M. & Cléries, R. Primary liver cancer: worldwide incidence and trends. *Gastroenterology* 127, S5-S16 (2004).
4 El-Serag, H. B., Marrero, J. A., Rudolph, L. & Reddy, K. R. Diagnosis and treatment of hepatocellular carcinoma. *Gastroenterology* 134, 1752-1763 (2008).
5 Poon, R. T.-P., Fan, S.-T. F., Tsang, F. H.-F. & Wong, J. Locoregional therapies for hepatocellular carcinoma: a critical review from the surgeon's perspective. *Ann. Surg.* 235, 466-486 (2002).
6 Yamada, R. et al. Transcatheter arterial chemoembolization (TACE) in the treatment of unresectable liver cancer. *World Journal of Surgery* 19, 795-800, doi:10.1007/bf00299773 (1995).
7 Skitzki, J. J. & Chang, A. E. Hepatic artery chemotherapy for colorectal liver metastases: technical considerations and review of clinical trials. *Surgical Oncology* 11, 123-135, doi:10.1016/s0960-7404(02)00032-4 (2002).
8 Li, L. et al. In vivo delivery of silica nanorattle encapsulated docetaxel for liver cancer therapy with low toxicity and high efficacy. *ACS Nano* 4, 6874-6882 (2010).
9 Liu, S.-Y., Liang, Z.-S., Gao, F., Luo, S.-F. & Lu, G.-Q. In vitro photothermal study of gold nanoshells functionalized with small targeting peptides to liver cancer cells. *J. Mater. Sci.-Mater.* M. 21, 665-674 (2010).
10 Maeng, J. H. et al. Multifunctional doxorubicin loaded superparamagnetic iron oxide nanoparticles for chemotherapy and magnetic resonance imaging in liver cancer. *Biomaterials* 31, 4995-5006 (2010).

11 Na, K., Park, K.-H., Kim, S. W. & Bae, Y. H. Self-assembled hydrogel nanoparticles from curdlan derivatives: characterization, anti-cancer drug release and interaction with a hepatoma cell line (HepG2). *J. Control. Release* 69, 225-236 (2000).

12 Maeda, H. SMANCS and polymer-conjugated macromolecular drugs: advantages in cancer chemotherapy. *Adv. Drug Deliver. Rev.* 46, 169-185 (2001).

13 Duncan, R. et al. Preclinical evaluation of polymer-bound doxorubicin. *J. Control. Release* 19, 331-346 (1992).

14 Kopeček, J., Kopečková, P., Minko, T. & Lu, Z.-R. HPMA copolymer-anticancer drug conjugates: design, activity, and mechanism of action. *European Journal of Pharmaceutics and Biopharmaceutics* 50, 61-81, doi:10.1016/s0939-6411(00)00075-8 (2000).

15 Tang, A., Kopečková, P. & Kopeček, J. Binding and cytotoxicity of HPMA copolymer conjugates to lymphocytes mediated by receptor-binding epitopes. *Pharm. Res.* 20, 360-367 (2003).

16 David, A., Kopečková, P., Rubinstein, A. & Kopeček, J. Enhanced biorecognition and internalization of HPMA copolymers containing multiple or multivalent carbohydrate side-chains by human hepatocarcinoma cells. *Bioconjugate Chem.* 12, 890-899, doi:10.1021/bc010026v (2001).

17 Lammers, T. et al. Effect of physicochemical modification on the biodistribution and tumor accumulation of HPMA copolymers. *Journal of Controlled Release* 110, 103-118, doi:10.1016/j.jconrel.2005.09.010 (2005).

18 Gao, S.-Q., Lu, Z.-R., Petri, B., Kopečková, P. & Kopeček, J. Colon-specific 9-aminocamptothecin-HPMA copolymer conjugates containing a 1,6-elimination spacer. *Journal of Controlled Release* 110, 323-331, doi:10.1016/j.jconrel.2005.10.004 (2006).

19 Zbaida, S. in *Enzyme Systems that Metabolise Drugs and Other Xenobiotics* 555-566 (John Wiley & Sons, Ltd, 2002).

20 Zbaida, S., Brewer, C. F. & Levine, W. G. Substrates for microsomal azoreductase. Hammett substituent effects, NMR studies, and response to inhibitors. *Drug Metabolism and Disposition* 20, 902-908 (1992).

21 Zbaida, S., Brewer, C. F. & Levine, W. G. Hepatic microsomal azoreductase activity. Reactivity of azo dye substrates is determined by their electron densities and redox potentials. *Drug Metabolism and Disposition* 22, 412-418 (1994).

22 Hammett, L. P. The effect of structure upon the reactions of organic compounds. Benzene derivatives. *J. Am. Chem. Soc.* 59, 96-103 (1937).

23 McDaniel, D. H. & Brown, H. C. An extended table of hammett substitutent constants based on the ionization of substituted benzoic acids. *J. Org. Chem.* 23, 420-427 (1958).

24 de Groot, F. M. H. et al. Elongated Multiple Electronic Cascade and Cyclization Spacer Systems in Activatible Anticancer Prodrugs for Enhanced Drug Release. *The Journal of Organic Chemistry* 66, 8815-8830, doi:10.1021/jo0158884 (2001).

25 Franken, N. A. P., Rodermond, H. M., Stap, J., Haveman, J. & van Bree, C. Clonogenic assay of cells in vitro. *Nat. Protoc.* 1, 2315-2319 (2006).

26 Saltiel, E. & McGuire, W. Doxorubicin (adriamycin) cardiomyopathy—a critical review. *Western J. Med.* 139, 332-341 (1983).

27 Kim, J.-H., El-Khouly, M. E., Araki, Y., Ito, O. & Kay, K.-Y. Photoinduced processes of subphthalocyanine-diazobenzene-fullerene triad as an efficient excited energy transfer system. *Chem. Lett.* 37, 544-545 (2008).

28 Zbaida, S. & Levine, W. G. A novel application of cyclic voltammetry for direct investigation of metabolic intermediates in microsomal azo reduction. *Chemical Research in Toxicology* 4, 82-88, doi:10.1021/tx00019a011 (1991).

29 Fuwa, K. & Valle, B. L. The Physical Basis of Analytical Atomic Absorption Spectrometry. The Pertinence of the Beer-Lambert Law. *Analytical Chemistry* 35, 942-946, doi:10.1021/ac60201a006 (1963).

30 Westfall, M. V., Rust, E. M., Albayya, F. & Metzger, J. M. in *Methods in Cell Biology* Vol. Volume 52 (eds P. Emerson Charles & H. Lee Sweeney) Ch. 15, 307-322 (Academic Press, 1997).

31 Wahr, P. A., Michele, D. E. & Metzger, J. M. Effects of aging on single cardiac myocyte function in Fischer 344× Brown Norway rats. *Am. J. Physiol.-Heart C.* 279, H559-H565 (2000).

32 van de Kerkhof, E. G., de Graaf, I. A. M. & Groothuis, G. M. M. In Vitro Methods to Study Intestinal Drug Metabolism. *Current Drug Metabolism* 8, 658-675 (2007).

33 Medina, S. H. et al. N-acetylgalactosamine-functionalized dendrimers as hepatic cancer cell-targeted carriers. *Biomaterials* 32, 4118-4129, doi:10.1016/j.biomaterials.2010.11.068 (2011).

34 Yoo, H. S. & Park, T. G. Biodegradable polymeric micelles composed of doxorubicin conjugated PLGA-PEG block copolymer. *Journal of Controlled Release* 70, 63-70, doi:10.1016/s0168-3659(00)00340-0 (2001).

35 Medina, S. H. & El-Sayed, M. E. H. Dendrimers as Carriers for Delivery of Chemotherapeutic Agents. *Chemical Reviews* 109, 3141-3157, doi:10.1021/cr900174j (2009).

36 Svenson, S. & Tomalia, D. A. Dendrimers in biomedical applications—reflections on the field. *Adv. Drug Deliver. Rev.* 57, 2106-2129 (2005).

37 Tomalia, D. A., Reyna, L. A. & Svenson, S. Dendrimers as multi-purpose nanodevices for oncology drug delivery and diagnostic imaging. *Biochem. Soc. T.* 035, 61-67 (2007).

38 Nowak, A. K., Chow, P. K. H. & Findlay, M. Systemic therapy for advanced hepatocellular carcinoma: a review. *European Journal of Cancer* 40, 1474-1484, doi:10.1016/j.ejca.2004.02.027 (2004).

39 Kalva, S. P. et al. Transarterial cemoembolization with doxorubicin-eluting microspheres for inoperable hepatocellular carcinoma. *Gastrointest. Cancer Res.* 4, 2-8 (2011).

40 Langowski, J. & Long, A. Computer systems for the prediction of xenobiotic metabolism. *Advanced Drug Delivery Reviews* 54, 407-415, doi:10.1016/s0169-409x(02)00011-x (2002).

41 He, C., Hu, Y., Yin, L., Tang, C. & Yin, C. Effects of particle size and surface charge on cellular uptake and biodistribution of polymeric nanoparticles. *Biomaterials* 31, 3657-3666, doi:10.1016/j.biomaterials.2010.01.065 (2010).

42 Sadekar, S. & Ghandehari, H. Transepithelial transport and toxicity of PAMAM dendrimers: Implications for oral drug delivery. *Advanced Drug Delivery Reviews* 64, 571-588, doi:10.1016/j.addr.2011.09.010 (2012).

43 Greish, K. et al. Size and surface charge significantly influence the toxicity of silica and dendritic nanoparticles. *Nanotoxicology* 0, 1-11, doi:doi:10.3109/17435390.2011.604442.

44 Fox, M. E., Szoka, F. C. & Fréchet, J. M. J. Soluble Polymer Carriers for the Treatment of Cancer: The Importance of Molecular Architecture. *Accounts of Chemical Research* 42, 1141-1151, doi:10.1021/ar900035f (2009).

45 Alexis, F., Pridgen, E., Molnar, L. K. & Farokhzad, O. C. Factors Affecting the Clearance and Biodistribution of Polymeric Nanoparticles. *Molecular Pharmaceutics* 5, 505-515, doi:10.1021/mp800051m (2008).

46 Wilkening, S., Stahl, F. & Bader, A. Comparison of primary human hepatocytes and hepatoma cell line HepG2 with regard to their biotransformation properties. *Drug Metab. Dispos.* 31, 1035-1042 (2003).

47 Aninat, C. et al. Expression of cytochromes P450, conjugated enzymes and nuclear receptors in human hepatoma HepaRG cells. *Drug Metab. Dispos.* 34, 75-83 (2006).

48 Wilkening, S. & Bader, A. Influence of culture time on the expression of drug-metabolizing enzymes in primary human hepatocytes and hepatoma cell line HepG2. *J. Biochem. Mol. Toxic.* 17, 207-213 (2003).

49 Bao, L. et al. Increased expression of P-glycoprotein is associated with doxorubicin chemoresistance in the metastatic 4T1 breast cancer model. *Am. J. Pathol.* 178, 838-852 (2011).

50 Duncan, R. Polymer conjugates as anticancer nanomedicines. *Nat Rev Cancer* 6, 688-701 (2006).

51 Shen, F. et al. Quantitation of doxorubicin uptake, efflux, and modulation of multidrug resistance (MDR) in MDR human cancer cells. *J. Pharmacol. Exp. Ther.* 324, 95-102 (2008).

52 Verma, A. & Stellacci, F. Effect of surface properties on nanoparticle-cell interactions. *Small* 6, 12-21 (2010).

53 Guo, L. et al. Similarities and differences in the expression of drug-metabolizing enzymes between human hepatic cell lines and primary human hepatocytes. *Drug Metab. Dispos.* 39, 528-538 (2011).

54 Majer, B. J. et al. Genotoxic effects of dietary and lifestyle related carcinogens in human derived hepatoma (HepG2, Hep3B) cells. *Mutat. Res.-Fund. Mol. M.* 551, 153-166 (2004).

55 Lee, T. K.-W., Lau, T. C.-M. & Ng, I. O.-L. Doxorubicin-induced apoptosis and chemosensitivity in hepatoma cell lines. *Cancer Chemoth. Pharm.* 49, 78-86 (2002).

56 Greco, F. & Vicent, M. J. Polymer-drug conjugates: current status and future trends. *Frontiers in bioscience: a journal and virtual library* 13, 2744-2756 (2008).

57 Maeda, H. The enhanced permeability and retention (EPR) effect in tumor vasculature: the key role of tumor-selective macromolecular drug targeting. *Adv. Enzyme Regul.* 41, 189-207 (2001).

58 Maeda, H., Bharate, G. Y. & Daruwalla, J. Polymeric drugs for efficient tumor-targeted drug delivery based on EPR-effect. *Eur. J. Pharm. Biopharm.* 71, 409-419 (2009).

59 Anzenbacher, P. & Anzenbacherová, E. Cytochromes P450 and metabolism of xenobiotics. *Cellular and Molecular Life Sciences* 58, 737-747, doi:10.1007/pl00000897 (2001).

60 Cordon-Cardo, C. et al. Expression of the multidrug resistance gene product (P-glycoprotein) in human normal and tumor tissues. *J. Histochem. Cytochem.* 38, 1277-1287 (1990).

The following list represents the references cited in Examples 13 and 14:

1 Tomalia, D. A., Reyna, L. A. & Svenson, S. Dendrimers as multi-purpose nanodevices for oncology drug delivery and diagnostic imaging. *Biochem. Soc. T.* 35, 61-67 (2007).

2 Gillies, E. R. & Fréchet, J. M. J. Dendrimers and dendritic polymers in drug delivery. *Drug Discov. Today* 10, 35-43 (2005).

3 Medina, S. H. & El-Sayed, M. E. H. Dendrimers as carriers for delivery of chemotherapeutic agents. *Chem. Rev.* 109, 3141-3157 (2009).

4 Chang, Y. et al. Novel water-soluble and pH-responsive anticancer drug nanocarriers: Doxorubicin-PAMAM dendrimer conjugates attached to superparamagnetic iron oxide nanoparticles (IONPs). *Journal of Colloid and Interface Science* 363, 403-409, doi:10.1016/j.jcis.2011.06.086 (2011).

5 Ki Choi, S. et al. Light-controlled release of caged doxorubicin from folate receptor-targeting PAMAM dendrimer nanoconjugate. *Chemical Communications* 46, 2632-2634 (2010).

6 Kono, K. et al. Preparation and cytotoxic activity of poly (ethylene glycol)-modified poly(amidoamine) dendrimers bearing adriamycin. *Biomaterials* 29, 1664-1675, doi:10.1016/j.biomaterials.2007.12.017 (2008).

7 Majoros, I. J., Myc, A., Thomas, T., Mehta, C. B. & Baker, J. R. PAMAM dendrimer-based multifunctional conjugate for cancer therapy: synthesis, characterization, and functionality. *Biomacromolecules* 7, 572-579 (2006).

8 Gurdag, S., Khandare, J., Stapels, S., Matherly, L. H. & Kannan, R. M. Activity of Dendrimer-Methotrexate Conjugates on Methotrexate-Sensitive and -Resistant Cell Lines. *Bioconjugate Chemistry* 17, 275-283, doi:10.1021/bc0501855 (2006).

9 Quintana, A. et al. Design and Function of a Dendrimer-Based Therapeutic Nanodevice Targeted to Tumor Cells Through the Folate Receptor. *Pharmaceutical Research* 19, 1310-1316, doi:10.1023/a:1020398624602 (2002).

10 Quintana, A. et al. Design and function of a dendrimer-based therapeutic nanodevice targeted to tumor cells through the folate receptor. *Pharm. Res.* 19, 1310-1316 (2002).

11 Wang, Y. et al. Targeted delivery of doxorubicin into cancer cells using a folic acid-dendrimer conjugate. *Polym. Chem.* 2 (2011).

12 Patri, A. K. et al. Synthesis and in vitro testing of J591 antibody-dendrimer conjugates for targeted prostate cancer therapy. *Bioconjugate Chem.* 15, 1174-1181 (2004).

13 Shukla, R. et al. HER2 specific tumor targeting with dendrimer conjugated anti-HER2 mAb. *Bioconjugate Chem.* 17, 1109-1115 (2006).

14 Thomas, T. P. et al. In vitro targeting of synthesized antibody-conjugated dendrimer nanoparticles. *Biomacromolecules* 5, 2269-2274 (2004).

15 Boswell, C. A. et al. Synthesis, characterization, and biological evaluation of integrin $\alpha v\beta 3$-targeted PAMAM dendrimers. *Mol. Pharm.* 5, 527-539 (2008).

16 Lesniak, W. G. et al. Synthesis and characterization of PAMAM dendrimer-based multifunctional nanodevices for targeting $\alpha v\beta 3$ integrins. *Bioconjugate Chem.* 18, 1148-1154 (2007).

17 Shukla, R. et al. Tumor angiogenic vasculature targeting with PAMAM dendrimer-RGD conjugates. *Chem. Commun.*, 5739-5741 (2005).

18 Boswell, C. A. et al. Synthesis, Characterization, and Biological Evaluation of Integrin $\alpha v\beta 3$-Targeted PAMAM Dendrimers. *Molecular Pharmaceutics* 5, 527-539, doi:10.1021/mp800022a (2008).

19 Shukla, S. et al. Synthesis and Biological Evaluation of Folate Receptor-Targeted Boronated PAMAM Dendrimers as Potential Agents for Neutron Capture Therapy. *Bioconjugate Chemistry* 14, 158-167, doi:10.1021/bc025586o (2002).

20 Aillon, K. L., Xie, Y., El-Gendy, N., Berkland, C. J. & Forrest, M. L. Effects of nanomaterial physicochemical properties on in vivo toxicity. *Advanced Drug Delivery Reviews* 61, 457-466, doi:10.1016/j.addr.2009.03.010 (2009).

21 Chauhan, A. S., Jain, N. K. & Diwan, P. V. Pre-clinical and behavioural toxicity profile of PAMAM dendrimers in mice. *Proceedings of the Royal Society A: Mathematical, Physical and Engineering Science*, doi:10.1098/rspa.2009.0448 (2009).

22 Klajnert, B. & Bryszewska, M. Fluorescence studies on PAMAM dendrimers interactions with bovine serum albumin. *Bioelectrochemistry* 55, 33-35, doi:10.1016/s1567-5394(01)00170-0 (2002).

23 Greish, K. et al. Size and surface charge significantly influence the toxicity of silica and dendritic nanoparticles. *Nanotoxicology* 0, 1-11, doi:doi:10.3109/17435390.2011.604442.

24 Kaminskas, L. M. & Boyd, B. J. in *Intracellular Delivery* Vol. 5 (ed Aleš Prokop) 155-178 (Springer Netherlands, 2011).

25 Jain, K., Kesharwani, P., Gupta, U. & Jain, N. K. Dendrimer toxicity: Let's meet the challenge. *International Journal of Pharmaceutics* 394, 122-142, doi:10.1016/j.ijpharm.2010.04.027 (2010).

26 Medina, S. H. et al. N-acetylgalactosamine-functionalized dendrimers as hepatic cancer cell-targeted carriers. *Biomaterials* 32, 4118-4129 (2011).

27 Schwartz, A., Fridovich, S., Knowles, B. & Lodish, H. Characterization of the asialoglycoprotein receptor in a continuous hepatoma line. *J. Biol. Chem.* 256, 8878-8881 (1981).

28 Lo, A., Lin, C.-T. & Wu, H.-C. Hepatocellular carcinoma cell-specific peptide ligand for targeted drug delivery. *Mol. Cancer Ther.* 7, 579-589 (2008).

29 Khorev, O., Stokmaier, D., Schwardt, O., Cutting, B. & Ernst, B. Trivalent, Gal/GalNAc-containing ligands designed for the asialoglycoprotein receptor. *Bioorgan. Med. Chem* 16, 5216-5231 (2008).

30 Maeda, H., Bharate, G. Y. & Daruwalla, J. Polymeric drugs for efficient tumor-targeted drug delivery based on EPR-effect. *Eur. J. Pharm. Biopharm.* 71, 409-419 (2009).

31 Torchilin, V. P. Recent advances with liposomes as pharmaceutical carriers. *Nat. Rev. Drug Discov.* 4, 145-160 (2005).

32 Cerritelli, S., Velluto, D. & Hubbell, J. A. PEG-SS-PPS: reduction-sensitive disulfide block copolymer vesicles for intracellular drug delivery. *Biomacromolecules* 8, 1966-1972 (2007).

33 Takae, S. et al. PEG-detachable polyplex micelles based on disulfide-linked block catiomers as bioresponsive non-viral gene vectors. *J. Am. Chem. Soc.* 130, 6001-6009 (2008).

34 Romberg, B., Hennink, W. & Storm, G. Sheddable coatings for long-circulating nanoparticles. *Pharm. Res.* 25, 55-71 (2008).

35 Tomayko, M. M. & Reynolds, C. P. Determination of subcutaneous tumor size in athymic (nude) mice. *Cancer Chemother. Pharmacol.* 24, 148-154 (1989).

36 Su, G. L. et al. Activation of human and mouse Kupffer cells by lipopolysaccharide is mediated by CD14. *Am. J. Physiol.-Gastr. L.* 283, G640-G645 (2002).

37 Amida, Janát-Amsbury, M. M., Ray, A., Peterson, C. M. & Ghandehari, H. Geometry and surface characteristics of gold nanoparticles influence their biodistribution and uptake by macrophages. *Eur. J. Pharm. Biopharm.* 77, 417-423 (2011).

38 Maeda, H., Wu, J., Sawa, T., Matsumura, Y. & Hori, K. Tumor vascular permeability and the EPR effect in macromolecular therapeutics: a review. *J. Control. Release* 65, 271-284 (2000).

39 Pan, G., Lemmouchi, Y., Akala, E. O. & Bakare, O, Studies on PEGylated and Drug-Loaded PAMAM Dendrimers. *Journal of Bioactive and Compatible Polymers* 20, 113-128, doi:10.1177/0883911505049656 (2005).

40 Kobayashi, H. & Brechbiel, M. W. Nano-sized MRI contrast agents with dendrimer cores. *Adv. Drug Deliv. Rev.* 57, 2271-2286, doi:DOI: 10.1016/j.addr.2005.09.016 (2005).

41 Malik, N. et al. Dendrimers: Relationship between structure and biocompatibility in vitro, and preliminary studies on the biodistribution of 125I-labelled polyamidoamine dendrimers in vivo. *J Control Release* 65, 133-148, doi: Doi: 10.1016/s0168-3659(99)00246-1 (2000).

42 Sadekar, S., Ray, A., Janàt-Amsbury, M., Peterson, C. M. & Ghandehari, H. Comparative Biodistribution of PAMAM Dendrimers and HPMA Copolymers in Ovarian-Tumor-Bearing Mice. *Biomacromolecules* 12, 88-96, doi: 10.1021/bm101046d (2010).

43 Kobayashi, H. et al. Renal tubular damage detected by dynamic micro-MRI with a dendrimer-based magnetic resonance contrast agent. *Kidney Int* 61, 1980-1985 (2002).

44 Blum, R. H. & Carter, S. K. Adriamcyin: a new anticancer drug with significant clinical activity. *Ann. Intern. Med.* 80, 249-259 (1974).

45 Stockert, R. J. The asialoglycoprotein receptor: relationships between structure, function, and expression. *Physiological Reviews* 75, 591-609 (1995).

46 Liang, H.-F. et al. Paclitaxel-Loaded Poly(γ-glutamic acid)-poly(lactide) Nanoparticles as a Targeted Drug Delivery System against Cultured HepG2 Cells. *Bioconjugate Chemistry* 17, 291-299, doi:10.1021/bc0502107 (2006).

47 Pimm, M. V., Perkins, A. C., Strohalm, J., Ulbrich, K. & Duncan, R. Gamma Scintigraphy of a 123I-Labelled N-(2-Hydroxypropyl)Methacrylamide Copolymer-Doxorubicin Conjugate Containing Galactosamine Following Intravenous Administration to Nude Mice Bearing Hepatic Human Colon Carcinoma. *Journal of Drug Targeting* 3, 385-390, doi:doi:10.3109/10611869608996829 (1996).

48 Seymour, L. W. et al. Hepatic Drug Targeting: Phase I Evaluation of Polymer-Bound Doxorubicin. *Journal of Clinical Oncology* 20, 1668-1676, doi:10.1200/jco.20.6.1668 (2002).

49 Owens III, D. E. & Peppas, N. A. Opsonization, biodistribution, and pharmacokinetics of polymeric nanoparticles. *Int. J. Pharm.* 307, 93-102 (2006).

50 Wijagkanalan, W., Kawakami, S. & Hashida, M. Designing dendrimers for drug delivery and imaging: pharmacokinetic considerations. *Pharm. Res.* 28, 1500-1519 (2011).

51 van Vlerken, L., Vyas, T. & Amiji, M. Poly(ethylene glycol)-modified nanocarriers for tumor-targeted and intracellular delivery. *Pharm. Res.* 24, 1405-1414 (2007).

52 Fox, M. E., Szoka, F. C. & Fréchet, J. M. J. Soluble polymer carriers for the treatment of cancer: the importance of molecular architecture. *Accounts Chem. Res.* 42, 1141-1151 (2009).

53 Kojima, C., Regino, C., Umeda, Y., Kobayashi, H. & Kono, K. Influence of dendrimer generation and polyethylene glycol length on the biodistribution of PEGylated dendrimers. *International Journal of Pharmaceutics* 383, 293-296, doi:10.1016/j.ijpharm.2009.09.015 (2010).

54 Okuda, T. et al. PEGylated lysine dendrimers for tumor-selective targeting after intravenous injection in tumor-bearing mice. *Journal of Controlled Release* 116, 330-336, doi:10.1016/j.jconrel.2006.09.012 (2006).
55 Duncan, R. The dawning era of polymer therapeutics. *Nat. Rev. Drug. Discov.* 2, 347-360 (2003).
56 Yang, H., Lopina, S., DiPersio, L. & Schmidt, S. Stealth dendrimers for drug delivery: correlation between PEGylation, cytocompatibility, and drug payload. *Journal of Materials Science: Materials in Medicine* 19, 1991-1997, doi:10.1007/s10856-007-3278-0 (2008).
57 Oyewumi, M. O., Yokel, R. A., Jay, M., Coakley, T. & Mumper, R. J. Comparison of cell uptake, biodistribution and tumor retention of folate-coated and PEG-coated gadolinium nanoparticles in tumor-bearing mice. *Journal of Controlled Release* 95, 613-626, doi:10.1016/j.jconrel.2004.01.002 (2004).
58 Yoo, H. S., Lee, E. A. & Park, T. G. Doxorubicin-conjugated biodegradable polymeric micelles having acid-cleavable linkages. *J. Control. Release* 82, 17-27 (2002).
59 Dufort, S., Sancey, L. & Coll, J.-L. Physico-chemical parameters that govern nanoparticles fate also dictate rules for their molecular evolution. *Adv. Drug Deliver. Rev.* 64, 179-189 (2012).
60 Ashley, C. E. et al. The targeted delivery of multicomponent cargos to cancer cells by nanoporous particle-supported lipid bilayers. *Nat. Mater.* 10, 389-397 (2011).
61 Mandeville, J. S. & Tajmir-Riahi, H. A. Complexes of Dendrimers with Bovine Serum Albumin. *Biomacromolecules* 11, 465-472, doi:10.1021/bm9011979 (2010).
62 van Berkel, T. J. et al. The effect of a water-soluble trisgalactoside-terminated cholesterol derivative on the fate of low density lipoproteins and liposomes. *J. Biol. Chem.* 260, 2694-2699 (1985).
63 Westerlind, U. et al. Ligands of the asialoglycoprotein receptor for targeted gene delivery, part 1: synthesis of and binding studies with biotinylated cluster glycosides containing N-acetylgalactosamine. *Glycoconjugate J.* 21, 227-241 (2004).
64 Schwartz, A. L., Fridovich, S. E. & Lodish, H. F. Kinetics of internalization and recycling of the asialoglycoprotein receptor in a hepatoma cell line. *J. Biol. Chem.* 257, 4230-4237 (1982).
65 Warren, R. & Doyle, D. Turnover of the surface proteins and the receptor for serum asialoglycoproteins in primary cultures of rat hepatocytes. *J. Biol. Chem.* 256, 1346-1355 (1981).
66 Zauner, W., Farrow, N. A. & Haines, A. M. R. In vitro uptake of polystyrene microspheres: effect of particle size, cell line and cell density. *J. Control. Release* 71, 39-51 (2001).
67 Jiang, W., KimBetty, Y. S., Rutka, J. T. & ChanWarren, C. W. Nanoparticle-mediated cellular response is size-dependent. *Nat. Nano.* 3, 145-150 (2008).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A dendrimer conjugate comprising a structure of

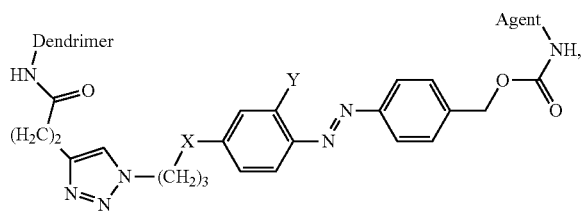

wherein X is NCH₃ and Y is H or OCH₃, or a structure of

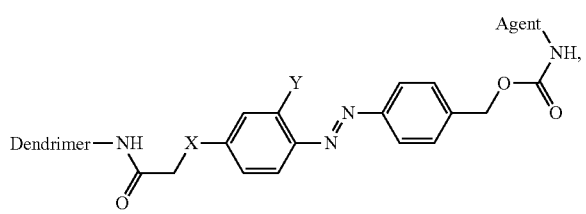

wherein X is O and Y is OCH₃ wherein the agent is a therapeutic agent or an imaging agent.

2. A pharmaceutical composition comprising a dendrimer conjugate of claim 1 and a pharmaceutically acceptable carrier.

3. A method of delivering a therapeutic agent to liver cells of a subject comprising contacting liver cells with a dendrimer conjugate of claim 1, or a composition or pharmaceutical composition comprising the same under conditions sufficient to deliver the therapeutic agent to the liver cells wherein the dendrimer conjugate comprises a therapeutic agent.

4. A method of imaging a liver cell of a liver tissue, comprising administering to the subject a dendrimer conjugate of claim 1, or a composition or pharmaceutical composition comprising the same, in an amount effective to image the liver cell, wherein the dendrimer conjugate comprises an imaging agent.

5. The dendrimer conjugate of claim 1, further comprising a hepatocyte-specific targeting molecule, a PEG chain, or a combination thereof.

6. The dendrimer conjugate of claim 5, wherein the hepatocyte-specific targeting molecule is a ligand of the asialoglycoprotein receptor (ASGPR).

7. The dendrimer conjugate of claim 6, wherein the ligand of the ASGPR is N-acetyl-galactosamine.

8. The dendrimer conjugate of claim 5, wherein the hepatocyte-specific targeting molecule is attached to the dendrimer through a thiourea moiety, a urea moiety, a carbamate moiety, a linkage from terminal epoxide opening, an amide linkage through peptide coupling, a linkage by formation of the Shiff base, a linkage formed by reduction of Shiff base, a linkage generated by "click" chemistry, or is attached to the dendrimer through linkage to a PEG chain which is linked to the dendrimer.

9. The dendrimer conjugate of claim 5, wherein the PEG chain is attached to the dendrimer through an acid hydrolysable linkage.

10. The dendrimer of claim 5, wherein a first end of the PEG chain is attached the dendrimer and a second end of the PEG chain is attached to one or more hepatocyte-specific targeting molecules.

11. The dendrimer conjugate of claim 1, wherein the dendrimer is a poly(amidoamine) (PAMAM) polymer.

12. The dendrimer conjugate of claim 11, wherein the dendrimer is acetylated, labeled, or both acetylated and labeled.

13. The dendrimer conjugate of claim 1, wherein the therapeutic agent is an anti-cancer therapeutic agent.

14. The dendrimer conjugate of claim 13, wherein the anti-cancer therapeutic agent is doxirubicin.

15. The dendrimer conjugate of claim 1, wherein the dendrimer is a G5 dendrimer.

* * * * *